(12) United States Patent
Blättler et al.

(10) Patent No.: US 9,163,044 B2
(45) Date of Patent: Oct. 20, 2015

(54) CARBON MONOXIDE RELEASING MOLECULES AND USES THEREOF

(75) Inventors: Walter Anton Blättler, Brookline, MA (US); Carlos J. R. C. Romão, Cascais (PT); Sandra Sofia Pereira Rodrigues, Moscavide - Lisboa (PT); Lukas Adrian Kromer, Winterthur (CH); Leo Edmond Otterbein, Beverly, MA (US); David John Gallo, Salem, MA (US)

(73) Assignee: Alfama, Inc., Cambridge, MA (US)

( * ) Notice: Subject to any disclaimer, the term of this patent is extended or adjusted under 35 U.S.C. 154(b) by 0 days.

(21) Appl. No.: 14/112,786

(22) PCT Filed: Apr. 19, 2012

(86) PCT No.: PCT/US2012/034264
§ 371 (c)(1),
(2), (4) Date: Jan. 29, 2014

(87) PCT Pub. No.: WO2012/145520
PCT Pub. Date: Oct. 26, 2012

(65) Prior Publication Data
US 2014/0142176 A1    May 22, 2014

Related U.S. Application Data

(60) Provisional application No. 61/477,036, filed on Apr. 19, 2011.

(51) Int. Cl.
*A01N 55/02* (2006.01)
*A61K 31/28* (2006.01)
*C07F 11/00* (2006.01)

(52) U.S. Cl.
CPC .................... *C07F 11/00* (2013.01)

(58) Field of Classification Search
CPC ............ C07F 11/00; C07F 1/00; A61K 31/28
See application file for complete search history.

(56) References Cited

U.S. PATENT DOCUMENTS

| | | |
|---|---|---|
| 2,870,180 A | 1/1959 | Kozikowski et al. |
| 3,065,250 A | 11/1962 | Levering |
| 3,278,570 A | 10/1966 | Wilkinson et al. |
| 3,694,232 A | 9/1972 | Hall et al. |
| 3,812,166 A | 5/1974 | Wiechert |
| 3,829,504 A | 8/1974 | Hall et al. |
| 3,980,583 A | 9/1976 | Mitchell et al. |
| 4,189,487 A | 2/1980 | Klosa |
| 4,312,989 A | 1/1982 | Spielvogel et al. |
| 4,322,411 A | 3/1982 | Vinegar et al. |
| 4,535,167 A | 8/1985 | Freidinger |
| 4,613,621 A | 9/1986 | Horrmann |
| 4,649,151 A | 3/1987 | Dougherty et al. |
| 4,657,902 A | 4/1987 | Kappas et al. |
| 4,668,670 A | 5/1987 | Rideout et al. |
| 4,699,903 A | 10/1987 | Rideout et al. |
| 4,709,083 A | 11/1987 | Spielvogel |
| 4,792,452 A | 12/1988 | Howard et al. |
| 4,910,211 A | 3/1990 | Imamura et al. |
| 4,938,949 A | 7/1990 | Borch et al. |
| 5,010,073 A | 4/1991 | Kappas et al. |
| 5,086,060 A | 2/1992 | Haley et al. |
| 5,102,670 A | 4/1992 | Abraham et al. |
| 5,254,706 A | 10/1993 | Spielvogel et al. |
| 5,312,816 A | 5/1994 | Spielvogel et al. |
| 5,350,767 A | 9/1994 | Hallberg et al. |
| 5,447,939 A | 9/1995 | Glasky et al. |
| 5,621,000 A | 4/1997 | Arena et al. |
| 5,631,284 A | 5/1997 | Legzdins et al. |
| 5,659,027 A | 8/1997 | Spielvogel et al. |

(Continued)

FOREIGN PATENT DOCUMENTS

DE    4014762 A1    11/1991
EP    0 034 238      8/1981

(Continued)

OTHER PUBLICATIONS

Achatz et al, Z. Anorg. Allg. Chem. 2005, 631, 2339-2346.*
Abel et al., Transition-metal complexes of seven-membered ring systems. Part I: the cycloHeptatriene-Metal Complexes and Related Compounds. J. Chem. Soc. 1958:4559-63.
Albers et al., The use of supported transition metals and metal oxides as catalysts for the metal carbonyl substitution reaction. J Chem Soc, Chem Commun. 1982:96-7.
Herrmann et al., Synthetic Methods of Organometallic and Inorganic Chemistry, vol. 1, Chapter 3 Commonly Used Starting Materials. Georg Thieme Verlag, New York, 1996, p. 129.
Kirtley, Molybdenum Compounds with nu$^1$-Carbon Ligands in Comprehensive Organometallic Chemistry I. Pergamon, Oxford. Sections 27.1.2.5 and 27.1.3.2. 1982; vol. 3:1120-26 and 1134-45.
Tamm et al., Isocyanide Complexes of Molybdenum. Comprehensive Organometallic Chemistry III Elsevier, Oxford. 2007;5:486-96.
Volkl et al., Fixation of Metallo Nitrile Ylides and Metallo Nitrile Imines as Ligands in Transition Metal Complexes. Z. Anorg. Allg. Chem. 2010;636:1339-46.

(Continued)

*Primary Examiner* — Wu-Cheng Winston Shen
*Assistant Examiner* — Jean Cornet
(74) *Attorney, Agent, or Firm* — Wolf, Greenfield & Sacks, P.C.

(57) ABSTRACT

Provided herein are novel carbon-monoxide releasing molecules (CO-RMs) of the Formula (I): and esters, amides, salts, solvates and hydrates thereof; wherein $R^1$ and $R^2$ are as described herein. Also provided are pharmaceutical compositions comprising these compounds, methods of their preparation, and their use in the treatment of liver disease and inflammation.

5 Claims, 41 Drawing Sheets

(56) References Cited

U.S. PATENT DOCUMENTS

| | | |
|---|---|---|
| 5,664,563 A | 9/1997 | Schroeder et al. |
| 5,670,664 A | 9/1997 | Kao et al. |
| 5,700,947 A | 12/1997 | Soldato |
| 5,756,492 A | 5/1998 | Buelow et al. |
| 5,767,157 A | 6/1998 | Van Moerkerken |
| 5,801,184 A | 9/1998 | Glasky et al. |
| 5,811,463 A | 9/1998 | Legzdins et al. |
| 5,824,673 A | 10/1998 | Abrams et al. |
| 5,861,426 A | 1/1999 | del Soldato et al. |
| 5,882,674 A | 3/1999 | Herrmann et al. |
| 5,885,621 A | 3/1999 | Head et al. |
| 5,888,982 A | 3/1999 | Perrella et al. |
| 5,891,689 A | 4/1999 | Takle et al. |
| 6,025,376 A | 2/2000 | Laurent et al. |
| 6,025,394 A | 2/2000 | Menander et al. |
| 6,027,936 A | 2/2000 | Glasky |
| 6,040,341 A | 3/2000 | del Soldato et al. |
| 6,051,576 A | 4/2000 | Ashton et al. |
| 6,060,467 A | 5/2000 | Buelow et al. |
| 6,066,333 A | 5/2000 | Willis et al. |
| 6,177,471 B1 | 1/2001 | Menander et al. |
| 6,203,991 B1 | 3/2001 | Nabel et al. |
| 6,211,233 B1 | 4/2001 | del Soldato |
| 6,218,417 B1 | 4/2001 | del Soldato |
| 6,242,432 B1 | 6/2001 | del Soldato |
| 6,251,927 B1 | 6/2001 | Lai et al. |
| 6,284,752 B1 | 9/2001 | Abrams et al. |
| 6,331,564 B1 | 12/2001 | Brugnara et al. |
| 6,338,963 B1 | 1/2002 | Glasky et al. |
| 6,344,178 B1 | 2/2002 | Alberto et al. |
| 6,350,752 B1 | 2/2002 | Glasky et al. |
| 6,417,182 B1 | 7/2002 | Abrams et al. |
| 6,518,269 B1 | 2/2003 | Camden et al. |
| 6,645,938 B2 | 11/2003 | Oeltgen et al. |
| 6,673,908 B1 | 1/2004 | Stanton |
| 7,011,854 B2 | 3/2006 | Haas et al. |
| 7,045,140 B2 | 5/2006 | Motterlini et al. |
| 7,053,242 B1 | 5/2006 | Alberto et al. |
| 7,569,214 B2 | 8/2009 | Kozlowski |
| 7,964,220 B2 | 6/2011 | Haas et al. |
| 7,968,605 B2 | 6/2011 | de Matos et al. |
| 7,989,650 B2 | 8/2011 | Motterlini et al. |
| 8,236,339 B2 | 8/2012 | Motterlini et al. |
| 8,389,572 B2 | 3/2013 | Motterlini et al. |
| 9,023,402 B2 | 5/2015 | Haas et al. |
| 2002/0043595 A1 | 4/2002 | Bridgers |
| 2002/0045611 A1 | 4/2002 | Abrams et al. |
| 2002/0049190 A1 | 4/2002 | Bridger et al. |
| 2002/0155166 A1 | 10/2002 | Choi et al. |
| 2002/0165242 A1 | 11/2002 | Glasky et al. |
| 2002/0193363 A1 | 12/2002 | Bridger et al. |
| 2003/0039638 A1 | 2/2003 | Bach et al. |
| 2003/0064114 A1 | 4/2003 | Motterlini et al. |
| 2003/0068387 A1 | 4/2003 | Buelow et al. |
| 2003/0124157 A1 | 7/2003 | Engles et al. |
| 2003/0157154 A1 | 8/2003 | Fuller et al. |
| 2003/0207786 A1 | 11/2003 | Miracle et al. |
| 2003/0219496 A1 | 11/2003 | Otterbein et al. |
| 2003/0219497 A1 | 11/2003 | Otterbein et al. |
| 2004/0052866 A1 | 3/2004 | Otterbein et al. |
| 2004/0067261 A1 | 4/2004 | Haas et al. |
| 2004/0122091 A1 | 6/2004 | Dasseux et al. |
| 2004/0131602 A1 | 7/2004 | Buelow et al. |
| 2004/0131703 A1 | 7/2004 | Bach et al. |
| 2004/0143025 A1 | 7/2004 | Buelow et al. |
| 2004/0214900 A1 | 10/2004 | Forbes et al. |
| 2004/0228930 A1 | 11/2004 | Billiar et al. |
| 2004/0258772 A1 | 12/2004 | Otterbein et al. |
| 2005/0048133 A1 | 3/2005 | Pinksy et al. |
| 2005/0175555 A1 | 8/2005 | Stradi et al. |
| 2006/0115542 A1 | 6/2006 | Motterlini et al. |
| 2006/0127501 A1 | 6/2006 | Motterlini et al. |
| 2006/0147548 A1 | 7/2006 | Motterlini et al. |
| 2006/0148900 A1 | 7/2006 | Haas et al. |
| 2006/0233890 A1 | 10/2006 | Haas et al. |
| 2007/0049640 A1 | 3/2007 | Pavliv |
| 2007/0065485 A1 | 3/2007 | Motterlini et al. |
| 2007/0207217 A1 | 9/2007 | Haas et al. |
| 2007/0207993 A1 | 9/2007 | Haas et al. |
| 2007/0219120 A1 | 9/2007 | de Matos et al. |
| 2008/0026984 A1 | 1/2008 | de Matos et al. |
| 2010/0105770 A1 | 4/2010 | Motterlini et al. |
| 2010/0196516 A1 | 8/2010 | Nobre et al. |
| 2011/0015263 A1 | 1/2011 | Motterlini et al. |
| 2011/0038955 A1 | 2/2011 | Rodrigues et al. |
| 2011/0237546 A1 | 9/2011 | Haas et al. |
| 2014/0212514 A1 | 7/2014 | Rodrigues et al. |
| 2014/0219996 A1 | 8/2014 | Pamplona et al. |

FOREIGN PATENT DOCUMENTS

| | | |
|---|---|---|
| EP | 0076493 | 4/1983 |
| EP | 0 181 721 | 5/1986 |
| EP | 0 632 026 | 1/1995 |
| FR | 2816212 | 5/2002 |
| GB | 1107510 | 6/1965 |
| GB | 0111872.8 | 7/2001 |
| GB | 0227135.1 | 12/2002 |
| GB | 0227138.5 | 12/2002 |
| GB | 2395431 | 5/2004 |
| GB | 2395432 A | 5/2004 |
| HU | 57595 | 12/1991 |
| HU | 211 084 | 10/1995 |
| WO | WO 85/04326 A1 | 10/1985 |
| WO | WO 91/01128 | 2/1991 |
| WO | WO 91/01301 | 2/1991 |
| WO | WO 92/03402 | 3/1992 |
| WO | WO 92/04905 | 4/1992 |
| WO | WO 93/05795 | 4/1993 |
| WO | WO 94/01413 | 1/1994 |
| WO | WO 94/22482 | 10/1994 |
| WO | WO 95/05814 | 3/1995 |
| WO | WO 95/09831 | 4/1995 |
| WO | WO 95/35105 A1 | 12/1995 |
| WO | WO 96/03125 | 2/1996 |
| WO | WO 96/09038 | 3/1996 |
| WO | WO 97/16405 | 5/1997 |
| WO | WO 97/36615 | 10/1997 |
| WO | WO 97/37644 | 3/1998 |
| WO | WO 98/09618 | 3/1998 |
| WO | WO 98/13058 A1 | 4/1998 |
| WO | WO 98/29115 | 7/1998 |
| WO | WO 98/38179 | 9/1998 |
| WO | WO 98/48848 | 11/1998 |
| WO | WO 99/67231 | 12/1999 |
| WO | WO 00/10613 | 3/2000 |
| WO | WO 00/21965 A1 | 4/2000 |
| WO | WO 00/36113 | 6/2000 |
| WO | WO 00/56145 | 9/2000 |
| WO | WO 00/56743 | 9/2000 |
| WO | WO 00/61537 | 10/2000 |
| WO | WO 01/12584 | 2/2001 |
| WO | WO 01/16359 | 3/2001 |
| WO | WO 01/25243 | 4/2001 |
| WO | WO 01/28545 | 4/2001 |
| WO | WO 02/078684 | 10/2002 |
| WO | WO 02/080923 | 10/2002 |
| WO | WO 02/092072 | 11/2002 |
| WO | WO 02/092075 A2 | 11/2002 |
| WO | WO 02/092075 A3 | 11/2002 |
| WO | WO 03/000114 | 1/2003 |
| WO | WO 03/066067 | 8/2003 |
| WO | WO 03/067598 | 8/2003 |
| WO | WO 03/072024 | 9/2003 |
| WO | WO 03/082850 A2 | 10/2003 |
| WO | WO 03/088923 | 10/2003 |
| WO | WO 03/088981 | 10/2003 |
| WO | WO 03/094932 | 11/2003 |
| WO | WO 03/096977 | 11/2003 |
| WO | WO 03/103585 | 12/2003 |
| WO | WO 2004/029033 | 4/2004 |
| WO | WO 2004/043341 | 5/2004 |
| WO | WO 2004/045598 | 6/2004 |
| WO | WO 2004/045599 | 6/2004 |

(56) References Cited

FOREIGN PATENT DOCUMENTS

| WO | WO 2004/080420 | 9/2004 |
|---|---|---|
| WO | WO 2005/013691 A1 | 2/2005 |
| WO | WO 2005/090400 | 9/2005 |
| WO | WO 2006/012215 | 2/2006 |
| WO | WO 2007/073226 | 6/2007 |
| WO | WO 2007/085806 A2 | 8/2007 |
| WO | WO 2008/003953 A2 | 1/2008 |
| WO | WO 2008/069688 | 6/2008 |
| WO | WO 2008/130261 A1 | 10/2008 |
| WO | WO 2009/013612 A1 | 1/2009 |

OTHER PUBLICATIONS

Winter, Hexacorbonyls and carbonyl complexes of carbon sigma-bonded ligands of chromium, molybdenum and tungsten in Comprehensive Organometallic Chemistry II. Pergamon, Oxford. Section 3.6. 1995; vol. 5:161-5.
Foresti et al., Use of carbon monoxide as a therapeutic agent: promises and challenges. Intensive Care Med. Apr. 2008;34(4):649-58.
Achatz et al., Carbonyl complexes of chromium, molybdenum and tungsten with isocyano acetate. Reactions of coordinated isocyanoacetate. Stabilization of isocyanoacetic acid and isocyanacetyl chloride at the metal atom. Isocyanopeptides. Z Angorg Allg Chem. 2005;631:2339-46.
King et al, CAS Database Accession No. 1974:83184. 1 page.
Wang et al., Syntheses and evaluation of drug-like properties of CO-releasing molecules containing ruthenium and group 6 metal. Eur J Med Chem. Mar. 3, 2014;74:199-215. Epub Jan. 9, 2014.
[No Author Listed] "supramolecule" IUPAC compendium of chemical terminology. 2nd Edition. 1997. Retrieved from the internet at www.iupac.org/goldbook/SO6153.pdf on May 8, 2006.
[No Author Listed] Biosis Chem Abstracts Database. Accession No. PREV200600414130. 2005. Otterbein et al., Cell Mol Biol (Noisy-le-grand). Oct. 3, 2005;51(5):433-40. Abstract.
[No Author Listed] Chemical Abstracts. 2002;137:119662. (FR2816212).
[No Author Listed] Chemical Abstracts. 2004;140:400075. (WO2004/043341).
[No Author Listed] Chemical Abstracts. 2004;141:270758. (Ryter et al.).
[No Author Listed] Chemical Abstracts. 2004;142:211995. (Stein et al.).
[No Author Listed], Solutions, emulsions, suspensions, and extractives. Remington's Pharmaceutical Science. 1985; 17th edition. Gennaro, ed. Ch. 84. p. 1511-2.
Abe et al., The effects of prostacyclin analog OP-41483 on normothermic liver ischemia and reperfusion injury in rats. Prostaglandins Leukot Essent Fatty Acids. Jun. 1993;48(6):417-22.
Abel et al., Anionic halogenopentacarbonyls of chromium, molybdenum, and tungsten. J Chem Soc. Apr. 16, 1963:2068-70.
Abel et al., Carbonyl halides of manganese and some related compounds. J Chem Soc. 1959;Part 2:1501-5.
Abel et al., Reaction of molybdenum carbonyl with various halides: a potassium etherate salt. Chem Indust. 1960;442.
Abraham et al., The biological significance and physiological role of heme oxygenase. Cell Physiol Biochem. 1996;6:129-68.
Aburaya et al., Heme oxygenase-1 protects gastric mucosal cells against non-steroidal anti-inflammatory drugs. J Biol Chem. Nov. 3, 2006;281(44):33422-32. Epub Aug. 31, 2006.
Adkison et al., Semicarbazone-based inhibitors of cathepsin K, are they prodrugs for aldehyde inhibitors? Bioorg Med Chem Lett. Feb. 15, 2006;16(4):978-83. Epub Nov. 15, 2005. Abstract only.
Akamatsu et al., Heme oxygenase-1-derived carbon monoxide protects hearts from transplant associated ischemia reperfusion injury. FASEB J. Apr. 2004;18(6):771-2. Epub Feb. 20, 2004.
Alberto et al., A novel organometallic aqua complex of technetium for the labeling of biomolecules: synthesis of [99mTc(OH2)3(CO)3]+ from [99mTcO4]− in aqueous solution and its reaction with a bifunctional ligand. J Am Chem Soc. 1998;120:7987-8. Epub Jul. 24, 1998.
Alberto et al., Synthesis and properties of boranocarbonate: a convenient in situ CO source for the aqueous preparation of [(99m)Tc(OH(2))3(CO)3]+. J Am Chem Soc. Apr. 4, 2001;123(13):31356. Epub Mar. 13, 2001.
Alessio et al., Carbonyl Derivatives of Chloride-Dimethyl Sulfoxide-Ruthenium(II) Complexes: Synthesis, Structural Characterization, and Reactivity of Ru(CO)x(DMSO)4-xC12 Complexes (x = 1-3). Inorg Chem. 1995;34(19):4722-34.
Alessio et al., Carbonyl Derivatives of Chloride-Dimethyl Sulfoxide-Ruthenium(III) Complexes: Synthesis, Crystal Structure, and Reactivity of [(DMSO)2H][trans-RuC14(DMSO-O)(CO)] and mer,cis-RuC13(DMSO-O)2(CO). Inorg Chem. 1995;34(19):4716-21.
Allanson et al., Ultraviolet A (320-400 nm) modulation of ultraviolet B (290-320 nm)-induced immune suppression is mediated by carbon monoxide. J Invest Dermatol. Mar. 3, 2005;124(3):644-50.
Allardyce et al., Development of organometallic (organo-transition metal) pharmaceuticals. Appl Organomet Chem. Jan. 2005;19:1-10.
Amersi et al., Ex vivo exposure to carbon monoxide prevents hepatic ischemia/reperfusion injury through p38 MAP kinase pathway. Hepatology, Apr. 2002;35(4):815-23.
Andreadis et al., Oxidative and nitrosative events in asthma. Free Radic Biol Med. Aug. 1, 2003;35(3):213-25. Review. Abstract only.
Angelici et al., Carboxamido carbonyl complexes of manganese(I). Inorg Chim Acta. Mar. 1968;2:3-7. Abstract only.
Angelici, Preparation, characterization, and reactions of the cis-Dihalotetracarbonylmanganate(I) anions. Inorg Chem. Aug. 1964;3(8):1099-1102.
Aujard et al., Tridemethylisovelleral, a potent cytotoxic agent. Bioorg Med Chem. Nov. 15, 2005;13(22):6145-50. Epub Aug. 1, 2005. Abstract only.
Bagul et al., Carbon monoxide protects against ischemia-reperfusion injury in an experimental model of controlled nonheartbeating donor kidney. Transplantation. Feb. 27, 2008;85(4):576-81.
Bani-Hani et al., Modulation of thrombin-induced neuroinflammation in BV-2 microglia by carbon monoxide-releasing molecule 3. J Pharmacol Exp Ther. Sep. 2006;318(3):1315-22. Epub Jun. 13, 2006.
Bannenberg et al., Therapeutic applications of the gaseous mediators carbon monoxide and hydrogen sulfide. Expert Opin Ther Pat. May 2009;19(5):663-82. Review.
Barkoudah et al., The permissive role of endothelial NO in CO-induced cerebrovascular dilation. Am J Ph siol Heart Circ Physiol. Oct. 2004;287(4):H1459-65. Epub Jun. 10, 2004.
Bauer et al., Evidence for a functional link between stress response and vascular control in hepatic portal circulation. Am J Physiol. Nov. 1996;271(5 Pt 1):G929-35.
Bauerová et al., Role of reactive oxygen and nitrogen species in etiopathogenesis of rheumatoid arthritis. Gen Physiol Biophys. Oct. 1999;18 Spec No. 15-20. Review. Abstract only.
Beal, Oxidatively modified proteins in aging and disease. Free Radic Biol Med. May 1, 2002;32(9):797-803. Review. Abstract only.
Beaty et al., An in vitro model for the in vivo mobilization of cadmium by chelating agents using 113Cd-NMR spectroscopy Chem Res Toxicol. Jul.-Aug. 1992;5(4):568-75. Abstract only.
Beck et al., Metallkomplexe mit biologisch wichtigen liganden: XVIII. Histidinato-carbonyl-komplexe von molybdän und wolfram. J Organometallic Chemistry. May 27, 1980;191(1):73-7.
Becker et al., Age-related changes in antibody-dependent cell-mediated cytotoxicity in mouse spleen. Isr J Med Sci. Feb. 1979;15(2):147-50.
Becker et al., NO-independent regulatory site of direct sGC stimulators like YC-1 and BAY 41-2272. BMC Pharmacol. 2001;1:13. Epub Dec. 28, 2001.
Berman et al., Sensitization and catalysis of light-induced decarbonylation of aldehydes. J Am Chem Soc. 1963;85(24):4010-4013.
Beutler, The effect of carbon monoxide on red cell life span in sickle cell disease. Blood. Aug. 1975;46(2):253-9.
Boissiere et al., Exercise and vasorelaxing effects of CO-releasing molecules in hypertensive rats. Med Sci Sports Exerc. Apr. 2006;38(4):652-9.

(56) References Cited

OTHER PUBLICATIONS

Botros et al., Interaction between endogenously produced carbon monoxide and nitric oxide in regulation of renal afferent arterioles. Am J Physiol Heart Circ Physiol. Dec. 2006;291(6):H2772-8. Epub Jul. 14, 2006.
Brashears et al., Effect of meat packaging technologies on the safety and spoilage-indicating characteristics of ground beef—Phase 1: safety characteristics. Jun.-Jul. 2006. National Cattleman's Beef Asscoiation. 22 pages. Available at www.fda.gov/ohrms/dockets/dockets/05p0459/05p-0459-c000009-01-vol2.pdf.
Brisdon et al., The preparation and charactisation of tri-μ-halogenohexacarbonyl-dimetallate(I) anions of manganese and rhenium. J Organometallic Chem. 1978;161:233-43.
Brooks et al., The spoilage characteristics of ground beef packaged in high-oxygen and low-oxygen modified atmosphere packages. Proc. Reciprocal Meat Conference. University of Illinois at Urbana-Champaign. Jun. 18-21, 2006:61-5.
Brouard et al., Carbon monoxide generated by heme oxygenase 1 suppresses endothelial cell apoptosis. J Exp Med. Oct. 2, 2000;192(7):1015-25.
Brüne et al., Inhibition of platelet aggregation by carbon monoxide is mediated by activation of guanylate cyclase. Mol Pharmacol. Oct. 1987;32(4):497-504.
Bundgaard et al., Pro-drugs as delivery systems. Pharm Int. 1981;2:136-40.
Bundgaard et al., Pro-drugs as drug delivery systems XX. Oxazolidines as potential pro-drug types for β-aminoalcohols, aldehydes or ketones. Intl J Pharm. Feb. 1982;10(2):165-75. Abstract only.
Burgmayer et al., Synthesis and structure of a 7-coordinate molybdenum carbonyl fluoride derivative—Et4n Mo(Co)2(S2cnet2)2f. Inorganic Chem. 1985;24:2224-30.
Burleson et al., The effect of dyes used to evaluate the in situ, ex-vivo, and perfused kidney. Invest Urol. Nov. 1981;19(3):165-8. Abstract only. Accession No. PREV198273058212.
Campbell et al., Molecular targets in immune-mediated diseases: the case of tumour necrosis factor and rheumatoid arthritis. Immunol Cell Biol. Oct. 2003;81(5):354-66.
Carroll et al., Ligand abstraction in the reaction of aryldiazonium ions with some iron complexes containing coordinated cysteine, maleonitriledithiol, or triarylphosphine. Can J Chem. 1974;52:1914-22.
Cepinskas et al., Carbon monoxide liberated from carbon monoxide-releasing molecule CORM-2 attenuates inflammation in the liver of septic mice. Am J Physiol Gastrointest Liver Physiol, Jan. 2008; 294:G184-G191. Epub Nov. 8, 2007.
Chakravortty et al., Inducible nitric oxide synthase and control of intracellular bacterial pathogens. Microbes Infect. Jun. 2003;5(7):621-7. Review. Abstract only.
Chatterjee, Water-soluble carbon monoxide-releasing molecules: helping to elucidate the vascular activity of the 'silent killer'. Br J Pharmacol. Jun. 2004;142(3):391-3. Epub May 17, 2004.
Chauveau et al., Gene transfer of heme oxygenase-1 and carbon monoxide delivery inhibit chronic rejection. Am J Transplant. Aug. 2002;2(7):581-92.
Chlopicki et al., Carbon monoxide released by CORM-3 inhibits human platelets by a mechanism independent of soluble guanylate cyclase. Cardiovasc Res. Jul. 15, 2006;71(2):393-401. Epub Mar. 22, 2006.
Cihonski et al., Crown ethers in inorganic chemistry—preparation and characterization of group 6 pentacarbonyl hydroxides and fluorides. Inorganic Chem. 1975;14(7):1717-20.
Clark et al., Cardioprotective actions by a water-soluble carbon monoxide-releasing molecule. Circ Res. Jul. 25, 2003;93(2):e2-8. Epub Jul. 3, 2003.
Clark et al., Heme oxygenase-l-derived bilirubin ameliorates postischemic myocardial dysfunction. Am J Physiol Heart Circ Physiol. Feb. 2000;278(2):H643-51.
Clark et al., Measuring left ventricular function in the normal, infarcted and CORM-3-preconditioned mouse heart using complex admittance-derived pressure volume loops. J Pharmacol Methods Toxicol. Mar.-Apr. 2009;59(2):94-9.
Coburn et al., Endogenous carbon monoxide production in man. J Clin Invest. Jul. 1963;42(7):1172-8.
Coceani et al., Carbon monoxide formation in the ductus arteriosus in the lamb: implications for the regulation of muscle tone. Br J Pharmacol. Feb. 1997;120(4):599-608.
Coceani, Carbon monoxide in vasoregulation: the promise and the challenge. Circ Res. Jun. 23, 2000;86(12):1184-6. Review.
Cohen et al., Dithiobenzoatotetracarbonylmanganese(I). Inorg Chem. 1964;3(11):1641-42.
Conant et al., Trimethylacetaldehyde and dimethylethylacetaldehyde. J Am Chem Soc. Apr. 1929;51(4):1246-55.
Cotton et al., Dimethyl- and diethyldithiocarbamate complexes of some metal carbonyl compounds. Inorg Chem. Jun. 2, 1964;3:1398-1402.
Cotton et al., X-ray molecular structures of Mn(CO)5(O2CCF3) and Mn(CO)3(C5H5N)2(O2CCF3). Inorg Chem. 1981;20(4):1287-91.
Coville et al., Steric measurement of substituted cyclopentadiene ligands and the synthesis and proton NMR spectral analysis of [(.eta.5-C5H4R)Fe(CO)(L)I] complexes with variable R. Organometallics. 1992;11(3):1082-90.
Crabtree, Immune and inflammatory responses to *Helicobacter pylori* infection. Scandinavian J Gastroenterology. 1996;31(s215):3-10. Abstract only.
De Backer et al., Mechanisms of relaxation by carbon monoxide-releasing molecule-2 in murine gastric fundus and jejunum. Eur J Pharmacol. Oct. 31, 2007;572(2-3):197-206. Epub Jun. 13, 2007.
De Backer et al., Role of the soluble guanylyl cyclase alpha1/alpha2 subunits in the relaxant effect of CO and CORM-2 in murine gastric fundus. Naunyn Schmiedebergs Arch Pharmacol. Nov. 2008;378(5):493-502. Epub Jun. 18, 2008.
De Backer et al., Water-soluble CO-releasing molecules reduce the development of postoperative ileus via modulation of MAPK/HO-1 signalling and reduction of oxidative stress. Gut. Mar. 2009;58(3):347-56. Epub Nov. 20, 2008.
De Filippo et al., Inductive effect in dithiocarbanate decomposition mechanism. J Org Chem. 1973;38(3):560-3.
Desmard et al., A carbon monoxide-releasing molecule (CORM-3) exerts bactericidal activity against *Pseudomonas aeruginosa* and improves survival in an animal model of bacteraemia. FASEB J. Apr. 2009;23(4):1023-31. Epub Dec. 18, 2008.
Desmard et al., Carbon monoxide reduces the expression and activity of matrix metalloproteinases 1 and 2 in alveolar epithelial cells. Cell Mol Biol (Noisy-le-grand). Sep. 30, 2005;51(4):403-8.
Dharmaraj, Ruthenium (II) complexes containing bidentate Schiff bases and their antifungal activity. Transition Metal Chemistry. 2001; 26(1-2): 105-109.
Di Pascoli et al., Chronic CO levels have [corrected] a beneficial effect on vascular relaxation in diabetes. Biochem Biophys Res Commun. Feb. 17, 2006;340(3):935-43. Epub Dec. 27, 2005. Erratum in: Biochem Biophys Res Commun. Mar. 14, 2006;342(3):1003.
Diamantis et al., Preparation and structure of ethylenediaminetetraacetate complexes of ruthenium(II) with dinitrogen, carbon monoxide, and other π-acceptor ligands. Inorg Chem. 1981;20:1142-50.
Douglas et al., Preparation of some group Vi fluorometal carbonyl derivatives. J Organometal Chem. 1974;65:65-9.
Drew et al., Synthesis, spectral properties, and reactions of manganese and rhenium pentacarbonyl phosphine and phosphite cation derivatives and related complexes. Inorg. Chem. 1975;14(7):1579-84.
Dröge, Free radicals in the physiological control of cell function. Physiol Rev. Jan. 2002;82(1):47-95. Review.
Duchêne et al., Cyclodextrins in targeting. Application to nanoparticles. Adv Drug Deliv Rev. Mar. 1, 1999;36(1):29-40.
Duckers et al., Heme oxygenase-1 protects against vascular constriction and proliferation. Nat Med. Jun. 2001;7(6):693-8.
Durante, Heme oxygenase-1 in growth control and its clinical application to vascular disease. J Cell Physiol. Jun. 2003;195(3):373-82. Review.

(56) References Cited

OTHER PUBLICATIONS

Egli et al., Organometallic 99mTc-aquaion labels peptide to an unprecedented high specific activity. J Nucl Med. Nov. 1999;40(11):1913-7.
El-Kholy, Catalysis by crown ether complexes—part III effect of cation on the catalytic activity of crown ether—alkali metal halide complexes in the liquid phase oxidation of ethylbenzene. Egypt J Chem. 1979;22(1):23-8.
Elliott et al., Nitric oxide: a regulator of mucosal defense and injury. J Gastroenterol. Dec. 1998;33(6):792-803. Review. Abstract only.
Fairlamb et al., η4-pyrone iron(0)carbonyl complexes as effective CO-releasing molecules (CO-RMs). Bioorg Med Chem Lett. Feb. 15, 2006;16 (4):995-8. Epub Nov. 11, 2005.
Fang, Antimicrobial reactive oxygen and nitrogen species: concepts and controversies. Nat Rev Microbiol. Oct. 2004;2(10):820-32. Review. Abstract only.
Feldmann et al., Anti-TNF alpha therapy of rheumatoid arthritis: what have we learned? Annu Rev Immunol. 2001;19:163-96. Review.
Ferrándiz et al., Treatment with a CO-releasing molecule (CORM-3) reduces joint inflammation and erosion in murine collagen-induced arthritis. Ann Rheum Dis. Sep. 2008;67(9):1211-7. Epub Dec. 6, 2007.
Ferrier et al., FTIR spectrometric study of geometrical isomers of dicarbonyl ferrobiscyteinate influence of the counter cation.J Molec Struct. 1995;344(3):189-93.
Fischer et al., Methylpyridin-Chrom(O)-Tricarbonyl. Zeitschrift Fur Naturforschung Part-B—Chemie Biochemie Biophysik Biologie Und Verwandten Gebiete. 1959;14:736-7. English translation provided.
Fischer et al., Uber aromatenkomplexe von metallen .37. zur aromatenkomplexebildung des pyridins mit chromhexacarbonyl. Chemische berichte-recueil. 1960;93:1156-61. English abstract provided.
Fischer, Crystal structure of 1,4,7,10,13-pentaoxacylcopentadecane sodium bromide, C10H20BrNaO5. Zeitschrift fur kristallographie. 1996;211:827-8. English translation provided.
Fiumana et al., Carbon monoxide mediates vasodilator effects of glutamate in isolated pressurized cerebral arterioles of newborn pigs. Am J Physiol Heart Circ Physiol. Apr. 2003;284(4):H1073-9.
Flemstrom et al., Gastroduodenal HCO3(−) transport: characteristics and proposed role in acidity regulation and mucosal protection. Am J Physiol. Mar. 1982;242(3):G183-93.
Foresti et al., Reviewing the use of carbon monoxide-releasing molecules (CO-RMs) in biology: implications in endotoxin-mediated vascular dysfunction. Cell Mol Biol (Noisy-le-grand). Sep. 30, 2005;51(4):409-23.
Foresti et al., The heme oxygenase pathway and its interaction with nitric oxide in the control of cellular homeostasis. Free Radic Res. Dec. 1999;31(6):459-75. Review.
Foresti et al., Vasoactive properties of CORM-3, a novel water-soluble carbon monoxide-releasing molecule. Br J Pharmacol. Jun. 2004;142(3):453-60. Epub May 17, 2004.
Frangogiannis et al., The inflammatory response in myocardial infarction. Cardiovasc Res. Jan. 2002;53(1):31-47. Review.
Friebe et al., Sensitizing soluble guanylyl cyclase to become a highly CO-sensitive enzyme. EMBO J. Dec. 16, 1996;15(24):6863-8.
Friebe et al., YC-1 potentiates nitric oxide- and carbon monoxide-induced cyclic GMP effects in human platelets. Mol Pharmacol. Dec. 1998;54(6):962-7.
Fujita et al., Paradoxical rescue from ischemic lung injury by inhaled carbon monoxide driven by derepression of fibrinolysis. Nat Med. May 2001;7(5):598-604.
Fukuda et al., Induction of heme oxygenase-1 (HO-1) after traumatic brain injury in the rat. Neurosci Lett. Oct. 20, 1995;199(2):127-30.
Furchgott et al., Endothelium-dependent and -independent vasodilation involving cyclic GMP: relaxation induced by nitric oxide, carbon monoxide and light. Blood Vessels. 1991;28(1-3):52-61.
Giboreau et al., Procedure for the preparation of pure dithiocarbamates. J Org Chem. 1994;59:1205-7.
Girolami et al., Reaction of binuclear carboxylate complexes of molybdenum, rhenium, ruthenium, and rhodium with tert-Butyl Isocyanide: metal-metal bond cleavage vs. bond retention. Inorganic Chemistry. Jul. 1981;20(7):2040-4.
Gordeuk et al., Carbonyl iron therapy for iron deficiency anemia. Blood. Mar. 1986;67(3):745-52.
Gottschaldt et al., Sugar-selective enrichment of a D-glucose-substituted ruthenium bipyridyl complex inside HepG2 cancer cells. Chembiochem. Mar. 22, 2010;11(5):649-52. Epub Feb. 15, 2010.
Greener et al., Now you're signaling, with gas: gasotransmitters open a window on biology and drill development. The Scientist. Sep. 13, 2004;18(17):20-2.
Günther et al., Carbon monoxide protects pancreatic beta-cells from apoptosis and improves islet function/survival after transplantation. Diabetes. Apr. 2002;51(4):994-9. MEDLINE Abstract. Accession No. NLM11916917.
Guo et al., Administration of a CO-releasing molecule at the time of reperfusion reduces infarct size in vivo. Am J Physiol Heart Circ Physiol. May 2004;286(5):H1649-53. Epub Jan. 2, 2004.
Haag et al., Polymer therapeutics: concepts and applications. Angew Chem Int Ed Engl. Feb. 13, 2006;45(8):1198-215. Review. Abstract only.
Haddleton et al., [N-Alkyl-(2-pyridyl)methanimine]copper(I) complexes: characterisation and application as catalysts for atom-transfer polymerisation. Eur J Inorg Chem. Dec. 7, 1998;1998(11):1799-1806. Abstract only.
Haddleton et al., Atom transfer polymerization of methyl methacrylate mediated by alkylpyridylmethanimine type ligands, copper(I) bromide, and alkyl halides in hydrocarbon solution. Macromolecules. 1999;32(7):2110-19. Abstract only.
Hadjigogos, The role of free radicals in the pathogenesis of rheumatoid arthritis. Panminerva Med. Mar. 2003;45(1):7-13. Review. Abstract only.
Hall et al., DNA interaction with metal complexes and salts of substituted boranes and hydroborates in murine and human tumor cell lines. Anticancer Drugs. Aug. 1991;2(4):389-99.
Hall et al., The anti-inflammatory activity of boron derivatives in rodents. Met Based Drugs. 1995;2(1):1-12.
Hall et al., The anti-inflammatory activity of metal complexes and salts of amine carboxyboranes. Appl Organomett Chem. 1994;8:473-80.
Hall et al., The hypolipidemic activity of metal complexes of amine carboxyboranes in rodents. Met Based Drugs. 1994;1(4):329-36.
Hancock et al., Antibody-induced transplant arteriosclerosis is prevented by graft expression of anti-oxidant and anti-apoptotic genes. Nat Med. Dec. 1998;4(12):1392-6.
Henricks et al., Reactive oxygen species as mediators in asthma. Pulm Pharmacol Ther. 2001;14(6):409-20. Review. Abstract only.
Herrick et al., Flash photolytic investigation of photoinduced carbon monoxide dissociation from dinuclear manganese carbonyl compounds. Inorg Chem. 1984;23:4550-3.
Hieber et al., Derivate des Mangancarbonyls mit schwefelorganischen Liganden. Chemische Berichte. 1966;99(7):2312-21. English abstract provided.
Hitchon et al., Oxidation in rheumatoid arthritis. Arthritis Res Ther. 2004;6(6):265-78. Epub Oct. 13, 2004. Review.
Hogg, Free radicals in disease. Semin Reprod Endocrinol. 1998;16(4):241-8. Review. Abstract only.
Holmuhamedov et al., Mitochondrial ATP-sensitive K+ channels modulate cardiac mitochondrial function. Am J Physiol. Nov. 1998;275(5 Pt 2):H1567-76.
Hosgood et al., Application of nitric oxide and carbon monoxide in a model of renal preservation. Br J Surg. Aug. 2008;95(8):1060-7.
Huang et al., Photolysis of the histidine-heme-CO complex. J Am Chem Soc. Nov. 1, 1991;113:9141-4.
Huebers et al., Absorption of carbonyl iron. J Lab Clin Med. Nov. 1986;108(5):473-8.
Ignat'ev et al., Reactivity of perfluoroakyl halides towards nucleophiles. Russ J Electrochem. Dec. 1995;31(12):1235-9. Translated from Elektrokhimiya. 1995:31(12):1337-42.
Jander et al., Neutralisationenanaloge reaktionen in essigaureanhybrid. Zietschrift fur anorganische chemie. 1948;255:238-52. English abstract provided.

(56) References Cited

OTHER PUBLICATIONS

Jellum et al., Quantitative determination of biologically important thiols and disulfides by gas-liquid chromatography Analyt Biochem. 1969;31:339-47. Abstract only.

Johansen et al., Spectrophotometric determination of the rates of hydrolysis of aldehyde-releasing pro-drugs in aqueous solution and plasma. Intl J Pharma. Dec. 1982;13(1):89-98. Abstract only.

Johnson et al., Metal carbonyls as pharmaceuticals? [Ru(CO)3Cl(glycinate)], a CO-releasing molecule with an extensive aqueous solution chemistry. Dalton Trans. Apr. 21, 2007;(15):1500-8. Epub Mar. 8, 2007.

Johnson et al., Metal carbonyls: a new class of pharmaceuticals? Angew Chem Int Ed Engl. Aug. 18, 2003;42(32):3722-9.

Johnson et al., Role of endogenous carbon monoxide in central regulation of arterial pressure. Hypertension. Oct. 1997;30(4):962-7.

Józkowicz et al., Heme oxygenase and angiogenic activity of endothelial cells: stimulation by carbon monoxide and inhibition by tin protoporphyrin-IX. Antioxid Redox Signal. Apr. 2003;5(2):155-62.

Kamimura et al., The protective effect of carbon monoxide on the ischemia-induced cell death. The J Biochem. Aug. 2002;74(8):926. Japanese abstract. English translation provided.

Kharitonov et al., Basis of guanylate cyclase activation by carbon monoxide. Proc Natl Acad Sci U S A. Mar. 28, 1995;92(7):2568-71.

Kharitonov et al., Kinetics and equilibria of soluble guanylate cyclase ligation by CO: effect of YC-1. Biochemistry. Aug. 17, 1999;38(33):10699-706.

Krueger et al., Potential of tumor necrosis factor inhibitors in psoriasis and psoriatic arthritis. Arch Dermatol. Feb. 2004;140(2):218-25. Review.

Kubic et al., Metabolism of dihalomethanes to carbon monoxide. I. In vivo studies. Drug Metab Dispos. Jan.-Feb. 1974;2(1):53-7. Abstract only.

Kuiate et al., Composition of the essential oil from leaves and flowers of *Dichrocephala integrifolia* (L.) O. Kuntze Chev. From Cameroon. Flavour and Fragrance J. Nov./Dec. 1999;14(6):419-20. Abstract only.

Lambert et al., O,O'-Diphenyldithiophosphatotetracarbonylmanganese(I) and related compounds. Inorg Chem. 1966;5(7):1287-9.

Lawton et al., Myocardial oxygen consumption in the rabbit heart after ischemia: hyperpolarized arrest with pinacidil versus depolarized hyperkalemic arrest. Circulation. Nov. 4, 1997;96(9 Suppl):II-247-52.

Ledger, Carbon monoxide-releasing metal carbonyls: a new class of pharmaceuticals? Drug Disc Today. Dec. 2003;8(23):1096.

Lee et al., Heme oxygenase-1 mediates the anti-inflammatory effect of interleukin-10 in mice. Nat Med. Mar. 2002;8(3):240-6.

Levrand et al., Controlled release of volatile aldehydes and ketones by reversible hydrazone formation—classical profragrances are getting dynamic. Chem. Commun. 2006;28:2965-7. Epub Apr. 3, 2006.

Li et al., Carbon monoxide protects PC12 cells from peroxynitrite-induced apoptotic death by preventing the depolarization of mitochondrial transmembrane potential. Biochem Biophys Res Commun. Apr. 14, 2006;342(3):984-90. Epub Feb. 20, 2006.

Lipmann et al., Organometallic Lewis Acids. LI. Reactivity of organometallic Lewis Acids (OC)4Re(OEt2)FBF3 and (OC)2(PPh3)2Ru(FBF3)2. Journal of Organometallic Chemistry. 1994;466(1-2):167-174. English abstract provided.

Loftsson et al., Cyclodextrins in topical drug formulations: theory and practice. Int J Pharm. Aug. 28, 2001;225(1-2):15-30. Review.

Loganson et al., Metal carbonyl complexes with ligands of biological origin. Russ Chem Rev. 1985;54(3):277-92.

Lovell et al., Biologic agents for the treatment of juvenile rheumatoid arthritis: current status. Paediatr Drugs. 2004;6(3):137-46.

Mahmoud et al., Potential anticancer agents. XVI. Isolation of bicyclofarnesane sesquiterpenoids from *Capsicodendron dinisii*. J Nat Prod. May-Jun. 1980;43(3):365-71. Abstract only.

Mai et al., Soluble surface proteins from *Helicobacter pylori* activate monocytes/macrophages by lipopolysaccharide-independent mechanism. J Clin Invest. Mar. 1991;87(3):894-900.

Maines, Heme oxygenase: function, multiplicity, regulatory mechanisms, and clinical applications. FASEB J. Jul. 1988;2(10):2557-68. Review.

Maines, The heme oxygenase system: a regulator of second messenger gases. Annu Rev Pharmacol Toxicol. 1997;37:517-54. Review.

Marks et al., Does carbon monoxide have a physiological function? Trends Pharmacol Sci. May 1991;12(5):185-8. Review.

Martins et al., Induction of carbon monoxide in the donor reduces graft immunogenicity and chronic graft deterioration. Transplant Proc. Jan.-Feb. 2005;37(1):379-81.

Matsuda et al., Mediators of non-adrenergic non-cholinergic inhibitory neurotransmission in porcine jejunum. Neurogastroenterol Motil. Oct. 2004;16(5):605-12.

Mattes et al., Triply bridged thiobenzoato carbonyl manganates(I) and rhenates(I). The crystal and molecular structure of caesium tris(μ-thiobenzoatos(S))bis(tricarbonyl rhenate). J Organometall Chem. Sep. 25, 1979; 178(1):191-6.

McLaughlin et al., Potentiation of carbon monoxide-induced relaxation of rat aorta by YC-1 [3- (5'-hydroxymethyl-2'-furyl)-1-benzylindazole]. Can J Physiol Pharmacol. Apr. 2000;78(4):343-9.

McMillen et al., Hydrocarbon bond dissociation energies. Ann Rev Phys Chem. Oct. 1982;33:493-532.

Meder et al., Metallkomplexe mit biologisch wichtigen liganden, XLII [1] carbonylmetallkomplexe mit anionen von mehrfunktionellen alpha-aminosaeuren [Metal complexes with biologically important ligands], XLII [1] carbonyl metal complexes with anions of polyfunctional alpha-amino acids]. Zeitschrift fur Naturforschung;1986:1247-54. German language reference. English abstract provided.

Megías et al., The carbon monoxide-releasing molecule tricarbonyldichlororuthenium(II) dimer protects human osteoarthritic chondrocytes and cartilage from the catabolic actions of interleukin1-beta. J Pharmacol Exp Ther. Apr. 2008;325(1):56-61. Epub Jan. 14, 2008.

Miguel et al., Manganese(I) complexes with (tricyclohexylphosphonio)dithiocarboxylate as chelate and unidentate ligand. X-Ray crystal structure of fac-[Mn(C0)3{S2CP(C6H11)3}2]ClO4•H2O. J Chem Soc, Dalton Trans. 1987;12:2875-80.

Mikuls et al., Benefit-risk assessment of infliximab in the treatment of rheumatoid arthritis. Drug Saf. 2003;26(1):23-32. Review. Abstract only.

Miller et al., The pharmacological activities of the metabolites of N-[(trimethylamineboryl)-carbonyl]-L-phenylalanine methyl ester. Met Based Drugs. 1996;3(5):219-26.

Moncada et al., Nitric oxide: physiology, pathophysiology, and pharmacology. Pharmacol Rev. Jun. 1991;43(2):109-42.

Moncada et al., The discovery of nitric oxide and its role in vascular biology. Br J Pharmacol. Jan. 2006;147 Suppl 1:S193-201.

Moore et al., Brief inhalation of low-dose carbon monoxide protects rodents and swine from postoperative ileus. Crit Care Med. Jun. 2005;33(6):1317-26.

Morita et al., Carbon monoxide controls the proliferation of hypoxic vascular smooth muscle cells. J Biol Chem. Dec. 26, 1997;272(52):32804-9.

Morita et al., Endothelial cell expression of vasoconstrictors and growth factors is regulated by smooth muscle cell-derived carbon monoxide. J Clin Invest. Dec. 1995;96(6):2676-82.

Morita et al., Smooth muscle cell-derived carbon monoxide is a regulator of vascular cGMP. Proc Natl Acad Sci U S A. Feb. 28, 1995;92(5):1475-9.

Morse et al., Suppression of inflammatory cytokine production by carbon monoxide involves the JNK pathway and AP-1. J Biol Chem. Sep. 26, 2003;278(39):36993-8. Epsub Jul. 11, 2003.

Motterlini et al., Bioactivity and pharmacological actions of carbon monoxide-releasing molecules. Curr Pharm Des. 2003;9(30):2525-39.

Motterlini et al., Carbon monoxide-releasing molecules: characterization of biochemical and vascular activities. Circ Res. Feb. 8, 2002;90(2):E17-24.

(56) References Cited

OTHER PUBLICATIONS

Motterlini et al., Chapter 16: Studies on the development of carbon-monoxide-releasing molecules: potential applications for the treatment of cardiovascular dysfunction. Ed., Rui Wang. CRC Press, New York. 2002:249-72.
Motterlini et al., Characterization of vasoactive effects elicited by carbon monoxide-releasing molecules. Abstracts 8th Intl Symposium on Mechanisms of Vasodilation. J Vasc Res. May 31-Jun. 3, 2001;055.
Motterlini et al., CORM-A1: a new pharmacologically active carbon monoxide-releasing molecule. FASEB J. Feb. 2005;19(2):284-6. Epub Nov. 19, 2004.
Motterlini et al., Functional and metabolic effects of propionyl-L-camitine in the isolated perfused hypertrophied rat heart. Mol Cell Biochem. Oct. 21, 1992;116(1-2):139-45.
Motterlini et al., Heme oxygenase-l-derived carbon monoxide contributes to the suppression of acute hypertensive responses in vivo. Circ Res. Sep. 7, 1998;83(5):568-77. Correction included.
Motterlini et al., Therapeutic applications of carbon monoxide-releasing molecules. Expert Opin Investig Drugs. Nov. 2005;14(11):1305-18. Review.
Motterlini, Vasoactive properties of carbon monoxide-releasing molecules. Biomed Pharmacother. 2002;56(7):349-50.
Moya et al., Metal carbonyl complexes containing heterocyclic nitrogen ligands: Part IX. MnBr(CO)3(3,3'-R-2,2'-biquinoline) compounds. Polyhedron. Mar. 1, 2002; 21(4):439-44. Abstract only.
Mungrue et al., From molecules to mammals: what's NOS got to do with it? Acta Physiol Scand. Oct. 2003;179(2):123-35. Review. Abstract only.
Musameh et al., Improved myocardial function after cold storage with preservation solution supplemented with a carbon monoxide-releasing molecule (CORM-3). J Heart Lung Transplant. Nov. 2007;26(11):1192-8.
Musameh et al., Positive inotropic effects of carbon monoxide-releasing molecules (CO-RMs) in the isolated perfused rat heart. Br J Pharmacol. Dec. 2006;149(8):1104-12. Epub Oct. 23, 2006.
Nagai et al., Unusual CO bonding geometry in abnormal subunits of hemoglobin M Boston and hemoglobin M Saskatoon. Biochemistry. Jul. 2, 1991;30(26):6495-503.
Nakao et al., Carbon monoxide inhalation protects rat intestinal grafts from ischemia/reperfusion injury. Am J Pathol. Oct. 2003;163(4):1587-98.
Nakao et al., Protective effect of carbon monoxide in transplantation. J Cell Mol Med. Jul.-Sep. 2006;10(3):650-71. Review.
Nathan, Points of control in inflammation. Nature. Dec. 19-26, 2002;420(6917):846-52. Review.
Ndisang et al., Modulation of the immunological response of guinea pig mast cells by carbon monoxide. Immunopharmacology. Jun. 1999;43(1):65-73.
Neto et al., Protection of transplant-induced renal ischemia-reperfusion injury with carbon monoxide. Am J Physiol Renal Physiol. Nov. 2004;287(5):F979-89. Epub Aug. 3, 2004.
Nitschke et al., Properties of (trifluoromethanesulfonato)pentacarbonylmanganese(I) and -rhenium(I). Reactions in superacid solvents. Inorg Chem. 1985;24(13):1972-8.
Nobre et al., Antimicrobial action of carbon monoxide-releasing compounds. Antimicrob Agents Chemother. Dec. 2007;51(12):4303-7. Epub Oct. 8, 2007.
Nudelman et al., Prodrugs of butyric acid. Novel derivatives possessing increased aqueous solubility and potential for treating cancer and blood diseases. Eur J Med Chem. Jan. 2001;36(1):63-74. Abstract only.
Nudelman et al., The role of intracellularly released formaldehyde and butyric acid in the anticancer activity of acyloxyalkyl esters. J. Med. Chem. Feb. 24, 2005. 2005;48(4):1042-54. Epub Jan. 22, 2005. Abstract only.
Nydegger et al., New concepts in organ preservation. Transpl Immunol. May 2002;9(2-4):215-25.
O'Brien et al., Aldehyde sources, metabolism, molecular toxicity mechanisms, and possible effects on human health. Crit Rev Toxicol. Aug. 2005;35(7):609-62. Review.
Otterbein et al., Carbon monoxide has anti-inflammatory effects involving the mitogen-activated protein kinase pathway. Nat Med. Apr. 2000;6(4):422-8.
Otterbein et al., Carbon monoxide provides protection against hyperoxic lung injury. Am J Physiol. Apr. 1999;276(4 Pt 1):L688-94.
Otterbein et al., Carbon monoxide suppresses arteriosclerotic lesions associated with chronic graft rejection and with balloon injury. Nat Med. Feb. 2003;9(2):183-90. Epub Jan. 21, 2003.
Otterbein et al., Exogenous administration of heme oxygenase-1 by gene transfer provides protection against hyperoxia-induced lung injury. J Clin Invest. Apr. 1999;103(7):1047-54.
Otterbein et al., Heme oxygenase-1: unleashing the protective properties of heme. Trends Immunol. Aug. 2003;24(8):449-55. Review.
Otterbein, Carbon monoxide: innovative anti-inflammatory properties of an age-old gas molecule. Antioxid Redox Signal. Apr. 2002;4(2):309-19. Review.
Ozawa et al., Leydig cell-derived heme oxygenase-1 regulates apoptosis of premeiotic germ cells in response to stress. J Clin Invest. Feb. 2002;109(4):457-67.
Pae et al., Carbon monoxide produced by heme oxygenase-1 suppresses T cell proliferation via inhibition of IL-2 production. J Immunol. Apr. 15, 2004;172(8):4744-51.
Paintner et al., Synthesis and antimicrobial activity of tetrodecamycin partial structures. Bioorg Med Chem. Jul. 3, 2003;11(13):2823-33. Abstract only.
Pankey et al., Clinical relevance of bacteriostatic versus bactericidal mechanisms of action in the treatment of Gram-positive bacterial infections. Clin Infect Dis. Mar. 15, 2004;38(6):864-70. Epub Mar. 1, 2004. Review.
Patel et al., Preparation of ($\eta$5-cyclopentadienyl) and ($\eta$5-Methylcyclopentadienyl)Fe(CO)2Me cyclodextrin inclusion compounds and their subsequent ligand substitution reactions. Attempts at cyclodextrin mediated enantioselective ligand substitution. J Organometal Chem. 1997;547:103-112.
Peloso et al., Expanding the armamentarium for the spondyloarthropathies. Arthritis Res Ther. 2004;6 Suppl 2:S36-43. Epub Jun. 21, 2004.
Pena et al., A novel carbon monoxide-releasing molecule fully protects mice from severe malaria. Antimicrob Agents Chemother. Mar. 2012;56(3):1281-90. Epub Dec. 12, 2011.
Piantadosi, Biological chemistry of carbon monoxide. Antioxid Redox Signal. Apr. 2002;4(2):259-70. Review.
Pneumatikakis et al., Interactions of bis-[$\mu$-chloro-chlorotricarbonylruthenium(II) and poly-[$\mu$-dichloro-dicarbonylruthenium (II)] with nucleotides. Inorg Chimica Acta. 1988;151:243-8.
Quick et al., Pentacarbonylmanganese halides. In Inorganic Syntheses, vol. 19. Duward F. Shriver., Ed. Inorganic Syntheses, Inc. 1979:158-63.
Rattan et al., Mechanism of internal anal sphincter relaxation by CORM-1, authentic CO, and NANC nerve stimulation. Am J Physiol Gastrointest Liver Physiol. Sep. 2004;287(3):G605-11.
Rehder et al., 55Mn NMR characteristics of carbonylmanganese complexes with hetero-substituted dithioformato-, thioformamido- and thioformamide ligands [1]. Inorg Chim Acta. 1983;73:243-7. Abstract only.
Reimann et al., Reactions of metal carbonyls. Part III. Steric and stereochemical limitations of higher substitution of manganese carbonyl bromide. J Chem Soc Dalton Trans. 1973;841-6. Abstract only.
Rodella et al., Carbon monoxide and biliverdin prevent endothelial cell sloughing in rats with type I diabetes. Free Radic Biol Med. Jun. 15, 2006;40(12):2198-205. Epub Mar. 20, 2006.
Rutkowska-Zbik et al., Theoretical density functional theory studies on interactions of small biologically active molecules with isolated heme group. J Comput Chem. Mar. 2007;28(4):825-31.
Ryan et al., Renal vascular responses to CORM-A1 in the mouse. Pharmacol Res. Jul. 2006;54(1):24-9. Epub Mar. 9, 2006.
Ryter et al., Carbon monoxide in biology and medicine. Bioessays. Mar. 2004;26(3):270-80.

(56) References Cited

OTHER PUBLICATIONS

Ryter et al., Carbon monoxide: to boldly go where NO has gone before. Sci STKE. Apr. 20, 2004;2004(230):RE6. Review.

Ryter et al., Heme oxygenase/carbon monoxide signaling pathways: regulation and functional significance. Mol Cell Biochem. May-Jun. 2002;234-235(1-2):249-63. Review.

Ryter et al., Heme oxygenase-1/carbon monoxide: from basic science to therapeutic applications. Physiol Rev. Apr. 2006;86(2):583-650. Review.

Sacerdoti et al., Treatment with tin prevents the development of hypertension in spontaneously hypertensive rats. Science. Jan. 20, 1989;243(4889):388-90.

Sacks et al., Comparative bioavailability of elemental iron powders for repair of iron deficiency anemia in rats. Studies of efficacy and toxicity of carbonyl iron. Am J Clin Nutr. Apr. 1978;31(4):566-71.

Salazar-Salinas et al., Molecular biosensor based on a coordinated iron complex. J Chem Phys. Mar. 14, 2009;130(10):105101.

Sammut et al., Carbon monoxide is a major contributor to the regulation of vascular tone in aortas expressing high levels of haeme oxygenase-1. Br J Pharmacol. Dec. 1998;125(7):1437-44.

Sandborn, Strategies for targeting tumour necrosis factor in IBD.Best Pract Res Clin Gastroenterol. Feb. 2003;17(1):105-17. Review.

Sandouka et al., Carbon monoxide-releasing molecules (CO-RMs) modulate respiration in isolated mitochondria. Cell Mol Biol (Noisy-le-grand). Sep. 30, 2005;51(4):425-32.

Sandouka et al., Treatment with CO-RMs during cold storage improves renal function at reperfusion. Kidney Int. Jan. 2006;69(2):239-47.

Santucci et al., Pentoxifylline prevents indomethacin induced acute gastric mucosal damage in rats: role of tumour necrosis factor alpha. Gut. Jul. 1994;35(7):909-15.

Sarady et al., Carbon monoxide protection against endotoxic shock involves reciprocal effects on iNOS in the lung and liver. FASEB J. May 2004;18(7):854-6. Epub Mar. 4, 2004.

Sato et al., Carbon monoxide generated by heme oxygenase-1 suppresses the rejection of mouse-to-rat cardiac transplants. J Immunol. Mar. 15, 2001;166(6):4185-94.

Sato et al., Heme oxygenase-1 or carbon monoxide prevents the inflammatory response associated with xenograft rejection. Acta Haematologica. 13th Symposium on Mol Biol Hematopoiesis and Treatment of Leukemia and Cancer. New York, NY. Jul. 14-18, 2000. Released Jul. 2000;103(Suppl1): Abstract 345, p. 87.

Sawle et al., Carbon monoxide-releasing molecules (CO-RMs) attenuate the inflammatory response elicited by lipopolysaccharide in RAW264.7 murine macrophages. Br J Pharmacol. Jul. 2005;145(6):800-10.

Sawle et al., Homocysteine attenuates endothelial haem oxygenase-1 induction by nitric oxide (NO) and hypoxia. FEBS Lett. Nov. 23, 2001;508(3):403-6.

Schmidt et al., Manganese(I) and rhenium(I) pentacarbonyl(Trifluoromethanesulfatonato) complexes. In Inorganic Syntheses, Ed. Herbert D. Kaesz. Inorganic Syntheses, Inc. vol. 26. 1989:113-17.

Schubert, The action of carbon monoxide on iron and cobalt complexes of cysteine. Carbon Monixide on Iron and Cobalt Cysteine Complexes. 1933;55:4563-70.

Severin et al., Metal complexes of biologically important ligands. LXX. Synthesis, stereochemistry and reactions of ruthenium (II) and osmium (II) complexes with .alpha.-amino carboxylates. 1994; 127(4): 615-620. English abstract provided.

Shapiro, Carbonyl-trapping therapeutic strategies. Am J Ther. Sep. 1998;5(5):323-53. Review.

Shiohira et al., Protective effect of carbon monoxide donor compounds in endotoxin-induced acute renal failure. Am J Nephrol. 2007;27(5):441-6. Epub Jul. 12, 2007.

Silver et al., Mossbauer studies on protoprophyrin IX iron (II) solutions containing sulphur ligands and their carbonyl adducts. Inorg Chimica Acta. 1984;9:279-83.

Siow et al., Heme oxygenase-carbon monoxide signalling pathway in atherosclerosis: anti-atherogenic actions of bilirubin and carbon monoxide? Cardiovasc Res. Feb. 1999;41(2):385-94.

Sjöstrand, Endogenous formation of carbon monoxide in man under normal and pathological conditions. Scan J Clin Lab Invest. 1949;1:201-14.

Skattebøl et al., Synthesis of (±)-Lineatin, an aggregation pheromone component of *Trypodendron lineatum*. Acta Chem Scand B. 1985;39:291-304.

Soares et al., Expression of heme oxygenase-1 can determine cardiac xenograft survival. Nat Med. Sep. 1998;4(9):1073-7.

Song et al., Carbon monoxide inhibits human airway smooth muscle cell proliferation via mitogen-activated protein kinase pathway Am J Res Bir Cell Mol Biol. Nov. 2002;27(5):603-10.

Song et al., Carbon monoxide inhibits T lymphocyte proliferation via caspase-dependent pathway. J Immunol. Jan. 15, 2004;172(2):1220-6.

Spector, Review: Oxidative stress and disease. J Ocul Pharmacol Ther. Apr. 2000;16(2):193-201. Review. Abstract only.

Srisook et al., CO from enhanced HO activity or from CORM-2 inhibits both O2- and NO production and downregulates HO-1 expression in LPS-stimulated macrophages. Biochem Pharmacol. Jan. 12, 2006;71(3):307-18. Epub Dec. 2, 2005.

Srisook et al., Role of NO in enhancing the expression of HO-1 in LPS-stimulated macrophages. Methods Enzymol. 2005;396:368-77.

Staal et al., The syntheses and coordination properties of $M(CO)_3X(DAB)$ (M = Mn, Re; X = Cl, Br, I; DAB = 1,4-diazabutadiene). J Organometal Chem. May 1, 1979:170( 2):235-45. Abstract only.

Stagni et al., A water-soluble carbon monoxide-releasing molecule (CORM-3) lowers intraocular pressure in rabbits. Br J Ophthalmol. Feb. 2009;93(2):254-7. Epub Oct. 31, 2008.

Stanford et al., Carbon monoxide inhibits endothelin-1 release by human pulmonary artery smooth muscle cells. Eur J Pharmacol. Feb. 23, 2004;486(3):349-52.

Stanford et al., Heme oxygenase is expressed in human pulmonary artery smooth muscle where carbon monoxide has an anti-proliferative role. Eur J Pharmacol. Jul. 25, 2003;473(2-3):135-41.

Stec et al., Heme oxygenase-1 induction does not improve vascular relaxation in angiotensin II hypertensive mice. Am J Hypertens. Feb. 2008;21(2):189-93. Epub Jan. 3, 2008.

Stein et al., Administration of a CO-releasing molecule induces late preconditioning against myocardial infarction. J Mol Cell Cardiol. Jan. 2005;38(1):127-34. Epub Dec. 8, 2004.

Stone et al., Soluble guanylate cyclase from bovine lung: activation with nitric oxide and carbon monoxide and spectral characterization of the ferrous and ferric states. Biochemistry. May 10, 1994;33(18):5636-40.

Stone et al., Synergistic activation of soluble guanylate cyclase by YC-1 and carbon monoxide: implications for the role of cleavage of the iron-histidine bond during activation by nitric oxide. Chem Biol. May 1998;5(5):255-61.

Suematsu et al., Carbon monoxide: an endogenous modulator of sinusoidal tone in the perfused rat liver. J Clin Invest. Nov. 1995;96(5):2431-7.

Sun et al., Attenuation of leukocytes sequestration by carbon monoxide-releasing molecules: liberated carbon monoxide in the liver of thermally injured mice. J Burn Care Res. Jan.-Feb. 2007;28(1):173-81.

Sun et al., CO-releasing molecules (CORM-2)-liberated CO attenuates leukocytes infiltration in the renal tissue of thermally injured mice. Int J Biol Sci. Jun. 16, 2008;4(3):176-83.

Sun et al., Preconditioning of carbon monoxide releasing molecule-derived CO attenuates LPS-induced activation of HUVEC. Int J Biol Sci. Aug. 22, 2008;4(5):270-8.

Sun et al., Role of CO-releasing molecules liberated CO in attenuating leukocytes sequestration and inflammatory responses in the lung of thermally injured mice. J Surg Res. May 1, 2007;139(1):128-35. Epub Feb. 9, 2007.

Suzuki et al., Activated platelets in ulcerative colitis enhance the production of reactive oxygen species by polymorphonuclear leukocytes. Scand J Gastroenterol. Dec. 2001;36(12):1301-6. Abstract only.

(56) References Cited

OTHER PUBLICATIONS

Szakács-Schmidt et al., Iron (II) thiolates as reversible carbon monoxide carriers. Inorg Chimica Acta. 1992;198-200:401-5.

Szallasi et al., Dialdehyde sesquiterpenes and other terpenoids as vanilloids. Eur J Pharmacol. Aug. 28, 1998;356(1):81-9. Abstract only.

Taillé et al., Mitochondrial respiratory chain and NAD(P)H oxidase are targets for the antiproliferative effect of carbon monoxide in human airway smooth muscle. J Biol Chem. Jul. 8, 2005;280(27):25350-60. Epub Apr. 29, 2005.

Takács et al., Synthesis and molecular structure of carbonyl derivatives of Iron (II) thiolates containing nitrogen-donor ligands. Inorg Chemica Acta. 1989;166:39-46.

Tamaki, Role of second messenger gases in ischemia and reperfusion injury. Low Temp Med. 2001;27(1):1-5. English abstract provided.

Tayem et al., Protection against cisplatin-induced nephrotoxicity by a carbon monoxide-releasing molecule. Am J Physiol Renal Physiol. Apr. 2006;290(4):F789-94. Epub Nov. 15, 2005.

Tenhunen et al., Microsomal heme oxygenase. Characterization of the enzyme. J Biol Chem. Dec. 10, 1969;244(23):6388-94.

Tilg et al., Antitumour necrosis factor therapy in Crohn's disease. Expert Opin Biol Ther. Oct. 2002;2(7):715-21. Review. Abstract only.

Togane et al., Protective roles of endogenous carbon monoxide in neointimal development elicited by arterial injury. Am J Physiol Heart Circ Physiol. Feb. 2000;278(2):H623-32.

Tomita et al., Structure and reaction of bis(L-cysteinato)dicarbonyliron(II). Inorg Nucl Chem Lett. 1968;4:715-8.

Treichel et al., Synthesis and reactivity of bridging thiolato-manganese carbonyl complexes, $Et_4N[Mn_2(\mu\text{-}SR)_3(CO)_6]$. J Organometall Chem. Sep. 10, 1985;292(3):385-93.

Tsuburai et al., The role of heme oxygenase in pulmonary circulation. Low Temp Med. 2001;27(1):28-35. English abstract provided.

Urban et al., Metal complexes of biologically important ligands, LXXXVII α-amino carboxylate complexes of palladium(II), iridium(III) and ruthenium (II) from chloro-bridged ortho-metallated metal compounds and $[(OC)_3Ru(C1)(\mu\text{-}C1)]_2$. J Organomett Chem. 1996;517:191-200.

Urwyler et al., Positive allosteric modulation of native and recombinant gamma-aminobutyric acid(B) receptors by 2,6-Di-tert-butyl-4-(3-hydroxy-2,2-dimethyl-propyl)-phenol (CGP7930) and its aldehyde analog CGP13501. Mol Pharmacol. Nov. 2001;60(5):963-71.

Van Staveren et al., Spectroscopic Properties, Electrochemistry, and Reactivity of Mo0, MoI, and MoII Complexes with the [Mo(bpa)(CO)3] Unit [bpa = bis(2-picolyl)amine] and Their Application for the Labelling of Peptides. Eur J Inorg Chem. 2002;6:1518-29.

Vannacci et al., Evaluation of the effects of a novel carbon monoxide releasing molecule (CORM-3) in an in vitro model of cardiovascular inflammation. 1. Histamine in allergy, inflammation, tissue growth and repair. Inflamm Res. Apr. 2006;55 Suppl 1:S05-6.

Vannacci et al., The effect of a carbon monoxide-releasing molecule on the immunological activation of guinea-pig mast cells and human basophils. Inflamm Res. 2004;53 Suppl 1:S09-10.

Varadi et al., Beneficial effects of carbon monoxide-releasing molecules on post-ischemic myocardial recovey. Life Sci. Apr. 3, 2007;80(17):1619-26. Epub Feb. 2, 2007.

Vera et al., Protective effect of carbon monoxide-releasing compounds in ischemia-induced acute renal failure. J Am Soc Nephrol. Apr. 2005;16(4):950-8. Epub Feb. 23, 2005.

Verma et al., Carbon monoxide: a putative neural messenger. Science. Jan. 15, 1993;259(5093):381-4.

Verona et al., Regioselectivity in the nucleophilic functionalization of xanthene complexes of Mn(CO)3. J Organelle Chem. Nov. 1, 1996;524(1-2)71-80.

Viswanathamurthi et al., Synthesis, characterization and biocidal studies of ruthenium (II) carbonyl complexes containing tetradentate Schiff bases. Transition Metal Chemistry. 1999; 24(6):638-641.

Volti et al., Carbon monoxide signaling in promoting angiogenesis in human microvessel endothelial cells. Antiox Redox Signal. May 2005;7(5-6):704-10.

Vreman et al., Determination of carbon monoxide (CO) in rodent tissue: effect of heme administration and environmental CO exposure. Anal Biochem. Jun. 15, 2005;341(2):280-9. Abstract only.

Vulapalli et al., Cardioselective overexpression of HO-1 prevents I/R-induced cardiac dysfunction and apoptosis. Am J Physiol Heart Circ Physiol. Aug. 2002;283(2):H688-94.

Waibel et al., Stable one-step technetium-99m labeling of His-tagged recombinant proteins with a novel Tc(I)-carbonyl complex. Nat Biotechnol. Sep. 1999;17(9):897-901.

Wang et al., A correlation of the visible and Soret spectra of dioxygen- and carbon monoxide-heme complexes and five-coordinate heme complexes with the spectra of oxy-, carboxy-, and deoxyhemoglobins. Biochemistry. Oct. 30, 1979;18(22):4960-77.

Wang et al., Carbon monoxide-induced vasorelaxation and the underlying mechanisms. Br J Pharmacol. Jul. 1997;121(5):927-34.

Wang et al., Preconditioning limits mitochondrial Ca(2+) during ischemia in rat hearts: role of K(ATP) channels. Am J Physiol Heart Circ Physiol. May 2001;280(5):H2321-8.

Wang et al., The chemical modification of KCa channels by carbon monoxide in vascular smooth muscle cells. J Biol Chem. Mar. 28, 1997;272(13):8222-6.

Weigel et al., Inhibition of DNA replication in *Escherichia coli* by cyanide and carbon monoxide. J Biol Chem. Nov. 10, 1975;250(21):8536-42.

Willis et al., Heme oxygenase: a novel target for the modulation of the inflammatory response. Nat Med. Jan. 1996;2(1):87-90.

Wu et al., Carbon monoxide: endogenous production, physiological functions, and pharmacological applications. Pharmacol Rev. Dec. 2005;57(4):585-630. Review.

Wu et al., Different mechanisms underlying the stimulation of K(Ca) channels by nitric oxide and carbon monoxide. J Clin Invest. Sep. 2002;110(5):691-700.

Xi et al., Carbon monoxide activates KCa channels in newborn arteriole smooth muscle cells by increasing apparent Ca2+ sensitivity of alpha-subunits. Am J Physiol Heart Circ Physiol. Feb. 2004;286(2):H6.10-8. Epub Oct. 16, 2003.

Xu et al., A facile method for synthesis of (R)-(−)- and (S)-(+)-homocitric acid lactones and related α-hydroxy dicarboxylic acids from d- or l-malic acid. Tetrahedron Lett. May 30, 2005;46(22):3815-18. Abstract only.

Yachie et al., Oxidative stress causes enhanced endothelial cell injury in human heme oxygenase-1 deficiency. J Clin Invest. Jan. 1999;103(1):129-35.

Yan et al., Cytotoxicity of rhenium(I) alkoxo and hydroxo carbonyl complexes in murine and human tumor cells. Pharmazie. Apr. 2000;55(4):307-13.

Yet et al., Cardiac-specific expression of heme oxygenase-1 protects against ischemia and reperfusion injury in transgenic mice. Circ Res. Jul. 20, 2001;89(2):168-73.

Yet et al., Induction of heme oxygenase-1 expression in vascular smooth muscle cells. A link to endotoxic shock. J Biol Chem. Feb. 14, 1997;272(7):4295-301.

Zhang et al., Carbon monoxide inhibition of apoptosis during ischemia-reperfusion lung injury is dependent on the p38 mitogen-activated protein kinase pathway and involves caspase 3. J Biol Chem. Jan. 10, 2003;278(2):1248-58. Epub Oct. 23, 2002.

Zimmerman et al., Cerebroprotective effects of the CO-releasing molecule CORM-A1 against seizure-induced neonatal vascular injury. Am J Physiol Heart Circ Physiol. Oct. 2007;293:H2501-H2507.

Zuckerbraun et al., Carbon monoxide protects against the development of experimental necrotizing enterocolitis. Am J Physiol Gastrointest Liver Physiol. Sep. 2005;289(3):G607-13. Epub May 12, 2005.

Zuckerbraun et al., Carbon monoxide reverses established pulmonary hypertension. J Exp Med. Sep. 4, 2006;203(9):2109-19. Epub Aug. 14, 2006.

\* cited by examiner

US 9,163,044 B2

CARBON MONOXIDE RELEASING MOLECULES AND USES THEREOF

RELATED APPLICATIONS

The present application is a national stage filing under 35 U.S.C. §371 of international PCT application, PCT/US2012/034264, filed Apr. 19, 2012, and entitled "CARBON MONOXIDE RELEASING MOLECULES AND USES THEREOF," which claims priority under 35 U.S.C. §119(e) to U.S. Provisional Patent Application Ser. No. 61/477,036, filed Apr. 19, 2011, and entitled "CARBON MONOXIDE RELEASING MOLECULES AND USES THEREOF," which are incorporated herein by reference in their entireties for all purposes.

FIELD OF THE INVENTION

The instant disclosure relates to carbon monoxide releasing molecules (CO-RMs) and uses thereof to treat liver diseases and inflammatory conditions.

BACKGROUND OF THE INVENTION

Carbon monoxide (CO) is the most commonly encountered environmental poison. Paradoxically, more than half a century ago, it was found that carbon monoxide is constantly formed in humans in small quantities, and that under certain pathophysiological conditions this endogenous production of carbon monoxide may be increased (Sjostrand, *Scan J Clin Lab Invest*. (1949) 1: 201-214). Thus, although it has been known for a long time that carbon monoxide is generated in the human body, only in recent years have scientists begun to explore the possible biological activities of this gaseous molecule. The main endogenous source of carbon monoxide is heme oxygenase, which exists in constitutive (HO-2 and HO-3) and inducible (HO-1) isoforms. Heme serves as substrate for HO-1 and HO-2 in the formation of carbon monoxide, free ferrous iron, and biliverdin, the latter being rapidly converted to bilirubin by biliverdin reductase (see, e.g., Maines, *Annu Rev Pharmacol Toxicol*. (1997) 37:517-554). It is generally believed that HO-1 represents a pivotal inducible defensive system against stressful stimuli, including UVA radiation, carcinogens, ischemia-reperfusion damage, endotoxic shock, and several other conditions characterized by production of oxygen-derived free radicals (see, e.g., Abraham et al., *Cell Physiol Biochem*. (1996) 6: 129-168). As part of its physiological and cytoprotective actions, heme oxygenase-derived carbon monoxide appears to play a major role as neurotransmitter, regulator of sinusoidal tone, inhibitor of platelet aggregation, and suppressor of acute hypertensive responses. Exogenously applied carbon monoxide has been a very useful experimental procedure to reveal the beneficial effects of carbon monoxide in animal disease models (see, e.g., US 2002155166, US 2003039638, US 2003219496, US 2003219497, US 2004052866, WO 03/103585, WO 04/043341). Thus, consistent findings reveal a series of important cellular functions that support a versatile role for carbon monoxide.

Carbon monoxide administration by inhalation is not practical for clinical applications, as it requires special delivery devices such as ventilators, face masks, tents, or portable inhalers. Moreover, carbon monoxide delivery to therapeutic targets by inhalation is inefficient, because it involves transport of carbon monoxide by hemoglobin. Hemoglobin binds carbon monoxide reversibly, but with very high affinity. Therefore, the doses required to deliver carbon monoxide to therapeutic targets in diseased tissues are likely to be associated with adverse effects. Carbon monoxide releasing molecules (CO-RMs) is a potential therapeutic alternative that can deliver carbon monoxide directly to therapeutic targets without the formation of intermediate CO-hemoglobin complexes (see, e.g., Johnson et al., *Angew Chem Int Ed Engl* (2003) 42:3722-3729). The advantages of carbon monoxide delivery by CO-RMs over carbon monoxide delivery by inhalation is generally recognized. However, CO-RMs should be able to deliver carbon monoxide selectively to diseased tissues. The identification of CO-RMs that are best suited for the treatment of a particular disease remains a major challenge of CO-RM development. Thus, there continues to remain a need for CO-RMs which, upon administration in vivo, selectively target a particular disease or organ with therapeutic benefit.

SUMMARY OF THE INVENTION

The present application provides inventive molybdenum CO-RM compounds, pharmaceutical compositions thereof, and methods of preparation, use, and treatment.

In one aspect, provided is a compound of the Formula (I):

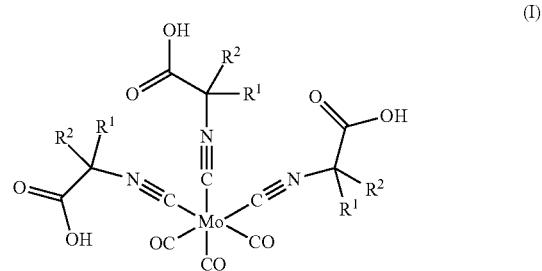

wherein:

each instance of $R^1$ is independently hydrogen, an unsubstituted $C_{1-3}$alkyl, or a $C_{1-3}$alkyl substituted with —$CO_2R^{A1}$ or —$C(=O)N(R^{A1})_2$, wherein each instance of $R^{A1}$ is independently hydrogen or $C_{1-10}$alkyl;

each instance of $R^2$ are independently hydrogen, an unsubstituted $C_{1-3}$alkyl, or a $C_{1-3}$alkyl substituted with —$CO_2R^{A2}$ or —$C(=O)N(R^{A2})_2$, wherein each instance of $R^{A2}$ is independently hydrogen or $C_{1-10}$alkyl;

or $R^1$ and $R^2$ and the carbon to which they are both attached are independently joined to form a $C_{3-4}$ carbocyclyl;

provided that each instance of $R^1$ and $R^2$ attached to the same carbon are not both hydrogen.

In certain embodiments, each instance of $R^2$ is hydrogen. In certain embodiments, each instance of $R^2$ is hydrogen and each instance of $R^1$ is independently an unsubstituted $C_{1-3}$alkyl or a $C_{1-3}$alkyl substituted with —$CO_2R^{A1}$ or —$C(=O)N(R^{A1})_2$. In certain embodiments, each instance of $R^1$ is independently an unsubstituted $C_{1-3}$alkyl. In certain embodiments, each instance of $R^1$ is $C_{1-3}$alkyl substituted with —$CO_2R^A$.

In certain embodiments, each instance of $R^2$ is independently an unsubstituted $C_{1-3}$alkyl or a $C_{1-3}$alkyl substituted with —$CO_2R^{A2}$ or —$C(=O)N(R^{12})_2$, and each instance of $R^1$ is independently an unsubstituted $C_{1-3}$alkyl or a $C_{1-3}$alkyl substituted with —$CO_2R^{A1}$ or —$C(=O)N(R^{A1})_2$.

In certain embodiments, each instance of $R^1$ is independently an unsubstituted $C_{1-3}$ alkyl; and each instance of $R^2$ is independently an unsubstituted $C_{1-3}$alkyl.

In certain embodiments, each instance of $R^1$ is independently an unsubstituted $C_{1-3}$alkyl; and each instance of $R^2$ is independently a $C_{1-3}$alkyl substituted with —$CO_2R^{42}$.

In certain embodiments, each instance of $R^1$ is independently a $C_{1-3}$alkyl substituted with —$CO_2R^{41}$; and each instance of $R^2$ is independently a $C_{1-3}$alkyl substituted with —$CO_2R^{42}$.

In certain embodiments, $R^1$ and $R^2$ and the carbon to which they are both attached are independently joined to form a $C_{3-4}$ carbocyclyl.

Exemplary compounds of the Formula (I) include, but are not limited to:

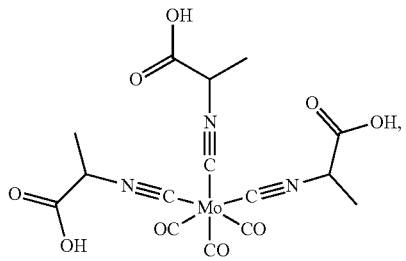

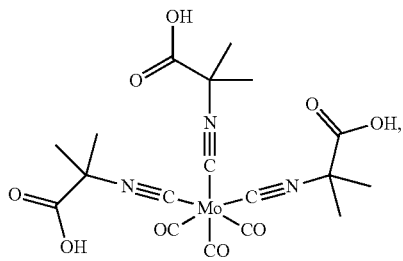

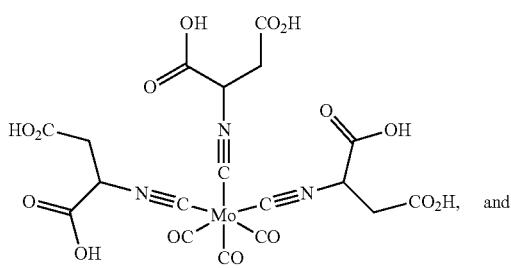

and

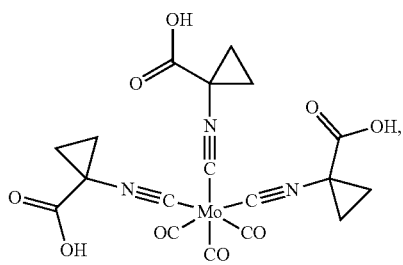

and salts, esters, amides, solvates, and hydrates thereof, and combinations thereof.

Also provided are pharmaceutical compositions comprising a compound of the Formula (I), or a salt, ester, amide, solvate, or hydrate thereof, or a combination thereof, and a pharmaceutically acceptable excipient.

In another aspect, provided are esters of the Formula (I), e.g., of the Formula (II):

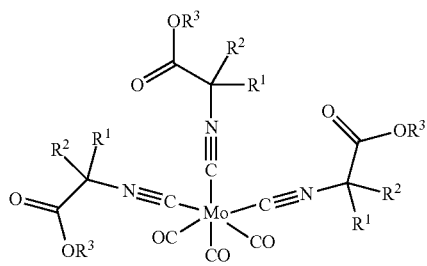

or a salt, solvate or hydrate thereof, or a combination thereof; wherein $R^1$ and $R^2$ are as defined herein; and each instance of $R^3$ is independently $C_{1-6}$alkyl.

In yet another aspect, provided are amides of the Formula (I), e.g., of the Formula (III):

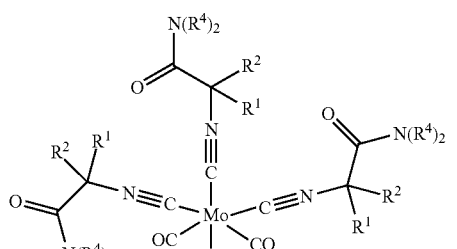

or a salt, solvate or hydrate thereof, or a combination thereof; wherein $R^1$ and $R^2$ are as defined herein; and each instance of $R^4$ is independently hydrogen or $C_{1-6}$alkyl.

In still yet another aspect, provided are methods or use of treating liver disease and/or an inflammatory disease in a subject. In certain embodiments, the method comprises administering an effective amount of a compound of Formula (I), or a salt, ester, amide, solvate, or hydrate thereof, or a combination thereof. In other embodiments, the method comprises instructing the subject to take an effective amount of a compound of Formula (I), or a salt, ester, amide, solvate, or hydrate thereof, or a combination thereof. In certain embodiments, the effective amount is a therapeutically effective amount. In certain embodiments, the effective amount is a prophylactically effective amount.

Also provided are methods of preparing compounds of the present invention.

The details of one or more embodiments of the disclosure are set forth in the accompanying Figures and the Detailed Description. Other features, objects, and advantages of the disclosure will be apparent from the description and from the claims.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A depicts the CO release from Compound 1b (50 μM) in 50 mM HEPES buffer (pH 7.4) in the dark or under light. FIG. 1B depicts the CO released from Compound 1b (10 µM) in 0.5 M K-phosphate buffer (pH 7.4) in the presence or absence of rat liver microsomes. FIG. 1C depicts the tissue CO distribution experiments performed in CD-1 female mice. Compound 1b was administered i.v. (50 mg/kg in 150 µL PBS pH 7.5). 25 minutes after dosing, the animal was euthanized, the heart, kidneys, liver and lung were collected, and CO quantization was done. Samples of the freshly collected blood were transferred to AVOXimeter 4000 cuvettes (ITC) to measure the levels of carboxyhemoglobin (COHb), oxyhemoglobin (O2Hb) and methemoglobin (MetHb) using a portable AVOXimeter 4000 CO-oximeter. The results are shown as mean percentage of total hemoglobin species in circulation.

FIG. 2A depicts the CO release from Compound 2b (50 µM) in 50 mM HEPES buffer (pH 7.4) in the dark or under light. FIG. 2B depicts the CO released from Compound 2b (10 µM) in 0.5 M K-phosphate buffer (pH 7.4) in the presence or absence of rat liver microsomes. FIGS. 2C-2E depict three identical tissue CO distribution experiments performed in CD-1 female mice. Compound 2b was administered i.v. (50 mg/kg in 150 µL PBS pH 7.5). 25 minutes after dosing, the animal was euthanized, the heart, kidneys, liver and lung were collected, and CO quantization was done. Samples of the freshly collected blood were transferred to AVOXimeter 4000 cuvettes (ITC) to measure the levels of carboxyhemoglobin (COHb), oxyhemoglobin (O2Hb) and methemoglobin (MetHb) using a portable AVOXimeter 4000 CO-oximeter. The results are shown as mean percentage of total hemoglobin species in circulation.

FIG. 3A depicts the ORTEP drawing of Compound 3a; the labeling scheme for all non-hydrogen atoms is shown. Thermal elipsoids are at the 30% probability level. FIG. 3B depicts the x-ray powder diffraction (XRPD) pattern of Compound 3a.

FIG. 4A depicts the ORTEP drawing of Compound 3b; the labeling scheme for all non-hydrogen atoms is shown. Thermal elipsoids are at the 30% probability level. FIG. 4B depicts the x-ray powder diffraction (XRPD) pattern of Compound 3b, Type I product. FIG. 4C depicts the x-ray powder diffraction (XRPD) pattern of Compound 3b, Type II product. FIG. 4D depicts CO release from Compound 3b (50 µM) in 50 mM HEPES buffer (pH 7.4) in the dark or under light. FIG. 4E depicts CO release from Compound 3b (10 µM) in 0.5 M K-phosphate buffer (pH 7.4) in the presence or absence of rat liver microsomes. FIGS. 4F-4G depict two identical tissue CO distribution experiments performed in CD-1 female mice. Compound 3b was administered i.v. (50 mg/kg in 150 µL PBS pH 7.5). 25 minutes after dosing, the animal was euthanized, the heart, kidneys, liver and lung were collected, and CO quantization was done. Samples of the freshly collected blood were transferred to AVOXimeter 4000 cuvettes (ITC) to measure the levels of carboxyhemoglobin (COHb), oxyhemoglobin (O2Hb) and methemoglobin (MetHb) using a portable AVOXimeter 4000 CO-oximeter. The results are shown as mean percentage of total hemoglobin species in circulation.

FIG. 5A depicts the CO released from Compound 4b (10 µM) in 0.5 M K-phosphate buffer (pH 7.4) in the presence or absence of rat liver microsomes. FIG. 5B depicts the tissue CO distribution experiments performed in CD-1 female mice. Compound 4b was administered i.v. (50 mg/kg in 150 µL PBS pH 7.5). 25 minutes after dosing, the animal was euthanized, the heart, kidneys, liver and lung were collected, and CO quantization was done. Samples of the freshly collected blood were transferred to AVOXimeter 4000 cuvettes (ITC) to measure the levels of carboxyhemoglobin (COHb), oxyhemoglobin (O2Hb) and methemoglobin (MetHb) using a portable AVOXimeter 4000 CO-oximeter. The results are shown as mean percentage of total hemoglobin species in circulation.

FIG. 6A depicts the CO released from Compound 5b (10 M) in 0.5 M K-phosphate buffer (pH 7.4) in the presence or absence of rat liver microsomes. FIG. 6B depicts the tissue CO distribution experiments performed in CD-1 female mice. Compound 5b was administered i.v. (50 mg/kg in 150 µL PBS pH 7.5). 25 minutes after dosing, the animal was euthanized, the heart, kidneys, liver and lung were collected, and CO quantization was done. Samples of the freshly collected blood were transferred to AVOXimeter 4000 cuvettes (ITC) to measure the levels of carboxyhemoglobin (COHb), oxyhemoglobin (O2Hb) and methemoglobin (MetHb) using a portable AVOXimeter 4000 CO-oximeter. The results are shown as mean percentage of total hemoglobin species in circulation.

FIG. 10A depicts the kinetics of ALT production after 300 mg/kg administration of acetaminophen (APAP) by intraperitoneal (i.p.) injection. ALT is expressed in U/L over time (hours). FIG. 10B depicts the kinetics of APAP clearance after administration of 300 mg/kg by i.p. injection. APAP is expressed in g/L over time (hours).

FIG. 11A depicts the effect of treatment with Compound 3b on serum ALT in an APAP-induced acute liver failure (ALF) model. ALF was induced in C57Bl/6 male mice with a single dose of acetaminophen (300 mg/kg) by i.p. injection. One hour after APAP injection, the animals were treated with 0.3, 3, 30 or 60 mg/kg doses of Compound 3b. ALT was measured 22 h after APAP injection (n=5 mice for each group). FIG. 11B depicts the effect of Compound 3b in the liver damage induced by APAP. ALF was induced in C57Bl/6 male mice with a single dose of acetaminophen (300 mg/kg) by i.p. injection. Compound 3b (0.3, 3, 30, 60 mg/kg) or Compound 1b (60 mg/kg) were administered to mice 1 h after APAP. Twenty-two hours after APAP injection, serum ALT was measured (results in FIG. 11A), centrilobular sections of mouse livers were cut and stained with hematoxylin and eosin, and the percentage of liver necrosis was determined (FIG. 11B).

FIGS. 12A-12B depict the effect of treatment with NAC or Compound 3b on serum ALT in an ALF model. ALF was induced in C57Bl/6 male mice with a single dose of acetaminophen (300 mg/kg) by i.p. injection. Animals were treated with NAC (N-acetyl-cysteine; 300 mg/kg) or Compound 3b (60 or 120 mg/kg) administered at one and three hours after APAP injection. ALT was measured 22 h after APAP injection (n=4 or n=5 mice for each group). FIG. 12B is a zoom of FIG. 12A to help visualize the differences in the treated groups. FIG. 12C confirms the results obtained with ALT serum determinations (FIGS. 12A-12B), and depicts the effect of treatment with NAC or Compound 3b on liver damage in an APAP-induced ALF model. ALF was induced in C57Bl/6 male mice with a single dose of acetaminophen (300 mg/kg) by i.p. injection. Animals were treated with NAC (300 mg/kg) or Compound 3b (60 or 120 mg/kg) administered at one and three hours after APAP injection. Twenty-two hours after APAP injection, serum ALT was measured (indicated in FIGS. 12A-12B), centrilobular sections of mouse livers were cut and stained with hematoxylin and eosin, and the percentage of liver necrosis was determined.

FIG. 21A: Percentage of increase in survival ActD/TNF-α treated cells in the presence of Compound 3b, relative to cells treated with only the apoptosis inducers. FIG. 21B: Toxicity of the Compound 3b doses on murine hepatocytes (not treated with apoptosis inducers). Data are the mean±S.D. of 3-5 independent experiments (3-5 livers from different mice).

DETAILED DESCRIPTION OF CERTAIN EMBODIMENTS OF THE INVENTION

Figure 1A:
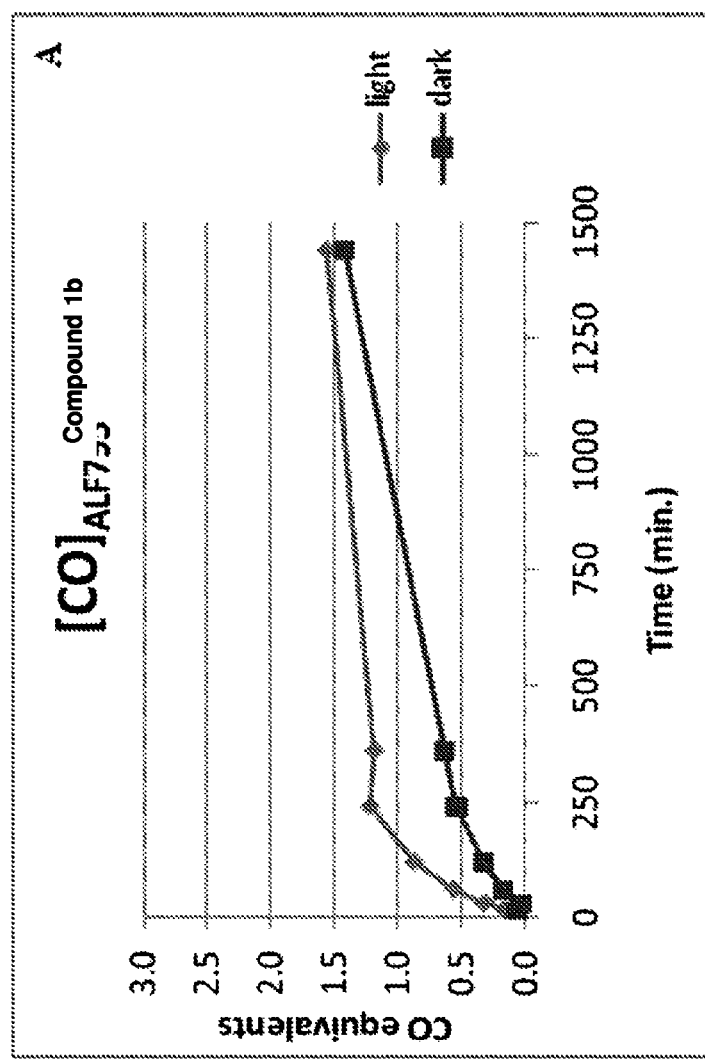
FIGS. 1A-1C.

The present disclosure is based, at least in part, on the surprising discovery that particular carbon monoxide releasing molecules (CO-RMs) compounds of the Formula (I):

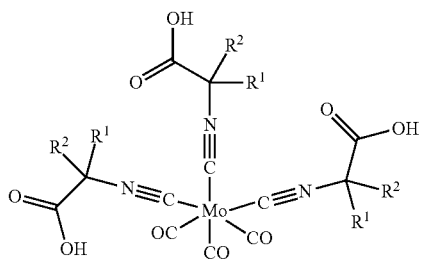

are therapeutic CO-releasing molecules with specificity for the liver, and have been found to reduce liver necrosis stimulate liver regeneration, and reduce inflammation.

As is understood from the following disclosure, compounds of the Formula (I) require that each instance of $R^1$ and $R^2$ attached to the same carbon are not both hydrogen. That requirement is important aspect of the present discovery. For example, a structurally similar CO-releasing molecule wherein each instance of $R^1$ and $R^2$ is hydrogen is inactive in an in vivo model of liver failure.

Thus, the compounds of the present disclosure are considered particularly useful for the treatment of diseases of the liver, but are also generally contemplated for use in the treatment of inflammatory diseases.

Compounds

In one aspect, the present disclosure provides a compound of the Formula (I):

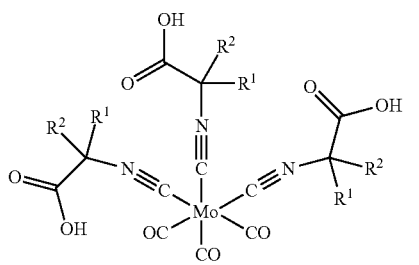

or a salt, ester, amide, solvate, or hydrate thereof, or a combination thereof;
wherein:
each instance of $R^1$ is independently hydrogen, an unsubstituted $C_{1-3}$alkyl, or a $C_{1-3}$alkyl substituted with $-CO_2R^{41}$ or $-C(=O)N(R^{41})_2$, wherein each instance of $R^{41}$ is independently hydrogen or $C_{1-10}$alkyl;
each instance of $R^2$ are independently hydrogen, an unsubstituted $C_{1-3}$alkyl, or a $C_{1-3}$alkyl substituted with $-CO_2R^{42}$ or $-C(=O)N(R^{42})_2$, wherein each instance of $R^{42}$ is independently hydrogen or $C_{1-10}$alkyl;
or $R^1$ and $R^2$ and the carbon to which they are both attached are independently joined to form a $C_{3-4}$ carbocyclyl;
provided that each instance of $R^1$ and $R^2$ attached to the same carbon are not both hydrogen.

The specific chemical terms are described below. General principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. General principles of organometallic chemistry is described in S. W. Kirtley in *Comprehensive Organometallic Chemistry I* (G. Wilkinson, F. G. A. Stone, W. Abel Eds, Vol 3, 1080, Pergamon, Oxford 1982; M. J. Winter in *Comprehensive Organometallic Chemistry II* (W. Abel, F. G. A. Stone, G. Wilkinson Eds), Vol 5, 163, Pergamon, Oxford 1995; and M. Tamm, R. J. Baker, in *Comprehensive Organometallic Chemistry III* (R. H. Crabtree and D. M. P. Mingos Eds), Vol 5, 391, Elsevier, Oxford 2007.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$), n-nonyl ($C_9$), n-decyl ($C_{10}$), and the like.

"Carbocyclyl" refers to a radical of a non-aromatic cyclic hydrocarbon group having from 3 to 4 ring carbon atoms ("$C_{3-4}$ carbocyclyl") and zero heteroatoms in the non-aromatic ring system. Exemplary $C_{3-4}$ carbocyclyl groups include, without limitation, cyclopropyl ($C_3$), cyclopropenyl ($C_3$), cyclobutyl ($C_4$), and cyclobutenyl ($C_4$). In some embodiments, "carbocyclyl" is a monocyclic, saturated carbocyclyl group having from 3 to 4 ring carbon atoms ("$C_{3-4}$ cycloalkyl").

"Alkenyl" refers to a radical of a straight-chain or branched hydrocarbon group having from 2 to 10 carbon atoms and one or more carbon-carbon double bonds ("$C_{2-10}$ alkenyl"). In some embodiments, an alkenyl group has 2 to 9 carbon atoms ("$C_{2-9}$alkenyl"). In some embodiments, an alkenyl group has 2 to 8 carbon atoms ("$C_{2-8}$alkenyl"). In some embodiments, an alkenyl group has 2 to 7 carbon atoms ("$C_{2-7}$alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$—alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

"Alkynyl" refers to a radical of a straight-chain or branched hydrocarbon group having from 2 to 10 carbon atoms and one or more carbon-carbon triple bonds ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_2$—alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_2$—alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

"Heterocyclyl" refers to a radical of a 5- to 10-membered non-aromatic ring system having ring carbon atoms and 1 to 4 ring heteroatoms, wherein each heteroatom is independently selected from nitrogen, oxygen, and sulfur ("5-10 membered heterocyclyl"). In heterocyclyl groups that contain one or more nitrogen atoms, the point of attachment can be a carbon or nitrogen atom, as valency permits. A heterocyclyl group can either be monocyclic or bicyclic, and can be saturated or can contain one or more carbon-carbon double or triple bonds. Heterocyclyl bicyclic ring systems can include one or more heteroatoms in one or both rings. Heterocyclyl also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, and the like.

"Aryl" refers to a radical of a monocyclic or bicyclic 4n+2 aromatic ring system (e.g., having 6 or 10π electrons shared in a cyclic array) having 6-10 ring carbon atoms and zero heteroatoms provided in the aromatic ring system ("$C_{6-10}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). Aryl also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

"Heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. Heteroaryl includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. Heteroaryl also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Alkyl, carbocyclyl, heterocyclyl, aryl, and heteroaryl groups, as defined herein, may be optionally substituted (e.g., "substituted" or "unsubstituted" alkyl, "substituted" or "unsubstituted" carbocyclyl, "substituted" or "unsubstituted" heterocyclyl, "substituted" or "unsubstituted" aryl or "substituted" or "unsubstituted" heteroaryl). In general, the term "substituted", whether preceded by the term "optionally" or not, means that at least one hydrogen present on a group (e.g., a carbon or nitrogen atom) is replaced with a permissible substituent, i.e., a non-hydrogen substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds that results in the formation of a stable compound. Exemplary substituents include, but are not limited to, alkyl, alkenyl, alkynyl, carbocyclyl, heterocyclyl, aryl, heteroaryl, substituted or unsubstituted hydroxyl (e.g., —OH, alkoxy), substituted or unsubstituted thiol (e.g., —SH, alkylthiooxy), substituted or unsubstituted amino (e.g., —NH$_2$, alkyl amino, dialkyl amino), cyano, nitro, halo (i.e., —F, Br, —Cl, —I), ester, amide, imino, —CO$_2$H, —CHO, and the like.

The term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, see Berge et al., describes pharmaceutically acceptable salts in detail in *J. Pharmaceutical Sciences* (1977) 66:1-19, and P. Heinrich Stahl and Camille G. Wermuth, Handbook of Pharmaceutical Salts: Properties, Selection and Use. International Union of Pure and Applied Chemistry, Wiley-VCH 2002. Pharmaceutically acceptable salts include pharmaceutically acceptable acid addition salts (i.e., a salt formed from the compound upon addition of an acid) and pharmaceutically acceptable base addition salts (i.e., a salt formed from the compound upon addition of a base). Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate salts. Pharmaceutically acceptable base addition salts include, but are not limited to, aluminum, calcium, lithium, magnesium, potassium, sodium, zinc, and quaternary amine salts.

An "ester" of a compound of the present disclosure refers to that compound wherein one or more of the acidic hydrogens of the carboxylic acid (—CO$_2$H) groups provided in the molecule are replaced with a non-hydrogen group (e.g., an alkyl group). Exemplary esters of compounds of the present disclosure include, but are not limited to, compounds which comprise one or more of the following groups:

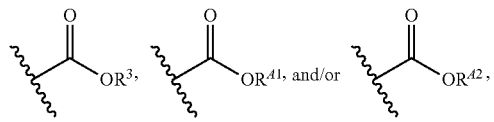

wherein $R^3$, $R^{A1}$, and $R^{A2}$ are as described herein, provided that $R^3$, $R^{A1}$, and $R^{A2}$ are not hydrogen.

An "amide" of a compound of the present disclosure refers to that compound wherein one or more of the —OH groups of the carboxylic acid (—CO$_2$H) provided in the molecule are replaced with a substituted or unsubstituted amino group. Exemplary amides of compounds of the present disclosure include, but are not limited to, compounds which comprise one or more of the following groups:

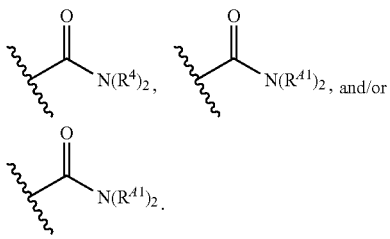

wherein $R^4$, $R^{A1}$, and $R^{A2}$ are as described herein.

The term "hydrate" refers to a compound of the present disclosure non-covalently associated with one or more molecules of water. Likewise, a "solvate" refers to a compound of the present disclosure non-covalently associated with one or more molecules of an organic solvent.

(i) Various Embodiments of $R^1$ and $R^2$

In certain embodiments, at least one instance of $R^1$ and $R^2$ and the carbon to which they are both attached are joined to form a $C_3$ carbocyclyl. In certain embodiments, at least one instance of $R^1$ and $R^2$ and the carbon to which they are both attached are joined to form a cyclopropanyl ($C_3$) ring. In certain embodiments, at least one instance of $R^1$ and $R^2$ and the carbon to which they are both attached are joined to form a cyclobutanyl ($C_4$) ring.

In certain embodiments, at least two instances of $R^1$ and $R^2$ and the carbon to which they are both attached are independently joined to form a $C_{3-4}$ carbocyclyl. In certain embodiments, at least two instances of $R^1$ and $R^2$ and the carbon to which they are both attached are joined to form a cyclopropanyl ($C_3$) ring. In certain embodiments, at least two instances of $R^1$ and $R^2$ and the carbon to which they are both attached are joined to form a cyclobutanyl ($C_4$) ring.

In certain embodiments, each instance of $R^1$ and $R^2$ and the carbon to which they are both attached are independently joined to form a $C_{3-4}$ carbocyclyl. In certain embodiments, each instance of $R^1$ and $R^2$ and the carbon to which they are both attached are joined to form a cyclopropanyl ($C_3$) ring. In certain embodiments, each instance of $R^1$ and $R^2$ and the carbon to which they are both attached are joined to form a cyclobutanyl ($C_4$) ring.

In certain embodiments, at least one instance of $R^1$ and $R^2$, wherein $R^1$ and $R^2$ are attached to the same carbon, comprise $R^1$ independently selected from hydrogen, an unsubstituted $C_{1-3}$alkyl, and a $C_{1-3}$alkyl substituted with —$CO_2R^{A1}$ or —C(—O)N($R^{A1}$)$_2$, wherein each instance of $R^{A1}$ is independently hydrogen or $C_{1-10}$ alkyl; and $R^2$ independently selected from hydrogen, an unsubstituted $C_{1-3}$alkyl, and a $C_{1-3}$alkyl substituted with —$CO_2R^{A2}$ or —C(=O)N($R^{A2}$)$_2$, wherein each instance of $R^{A2}$ is independently hydrogen or $C_{1-10}$alkyl.

In certain embodiments, at least two instances of $R^1$ and $R^2$, wherein $R^1$ and $R^2$ are attached to the same carbon, comprise $R^1$ independently selected from hydrogen, an unsubstituted $C_{1-3}$alkyl, and a $C_{1-3}$alkyl substituted with —$CO_2R^{A1}$ or —C(—O)N($R^{A1}$)$_2$, wherein each instance of $R^{A1}$ is independently hydrogen or $C_{1-10}$alkyl; and $R^2$ independently selected from hydrogen, an unsubstituted $C_{1-3}$alkyl, and a $C_{1-3}$alkyl substituted with —$CO_2R^{A2}$ or —C(=O)N($R^{A2}$)$_2$, wherein each instance of $R^{A2}$ is independently hydrogen or $C_{1-10}$alkyl.

In certain embodiments, each instance of $R^1$ and $R^2$, wherein $R^1$ and $R^2$ are attached to the same carbon, comprise $R^1$ independently selected from hydrogen, an unsubstituted $C_{1-3}$alkyl, and a $C_{1-3}$alkyl substituted with —$CO_2R^{A1}$ or —C(=O)N($R^{A1}$)$_2$, wherein each instance of $R^{A1}$ is independently hydrogen or $C_{1-10}$ alkyl; and $R^2$ independently selected from hydrogen, an unsubstituted $C_{1-3}$alkyl, and a $C_{1-3}$alkyl substituted with —$CO_2R^{A2}$ or —C(=O)N($R^{A2}$)$_2$, wherein each instance of $R^{A2}$ is independently hydrogen or $C_{1-10}$alkyl.

As used herein, wherein $R^1$ is an unsubstituted $C_{1-3}$alkyl or a $C_{1-3}$alkyl substituted with —$CO_2R^{A1}$ or —C(—O)N($R^{A1}$)$_2$, it is understood that each instance of $R^1$ may encompass a variety of different groups, e.g., for example, each instance of $R^1$ may be independently selected from unsubstituted $C_{1-2}$alkyl, $C_{1-2}$alkyl substituted with —$CO_2R^{A1}$, $C_{1-2}$alkyl substituted with —C(=O)N($R^{A1}$)$_2$, unsubstituted $C_{2-3}$alkyl, $C_{2-3}$alkyl substituted with —$CO_2R^{A1}$, $C_{2-3}$alkyl substituted with —C(—O)N($R^{A1}$)$_2$, unsubstituted $C_1$alkyl, $C_1$alkyl substituted with —$CO_2R^{A1}$, $C_1$alkyl substituted with —C(=O)N($R^{A1}$)$_2$, unsubstituted $C_2$alkyl, $C_2$alkyl substituted with —$CO_2R^{A1}$, $C_2$alkyl substituted with —C(=O)N($R^{A1}$)$_2$, unsubstituted $C_3$alkyl, $C_3$alkyl substituted with —$CO_2R^{A1}$, or $C_3$alkyl substituted with —C(=O)N($R^{A1}$)$_2$. For example, in certain embodiments, each instance of $R^1$ is independently selected from —$CH_3$, —$CH_2CH_3$, —$CH_2CH_2CH_3$, —CH($CH_3$)$_2$, —$CH_2CO_2R^{A1}$, —$CH_2CH_2CO_2R^{A1}$, —CH($CO_2R^{A1}$)$CH_3$, —$CH_2CH_2CH_2CO_2R^{A1}$, —$CH_2$CH($CO_2R^{A1}$)$CH_3$, —CH($CO_2R^{A1}$)$CH_2CH_3$, —CH($CH_3$)(CH$CO_2R^{A1}$), —C($CO_2R^{A1}$)($CH_3$)$_2$, —$CH_2$C(=O)N($R^{A1}$)$_2$, —$CH_2CH_2$C(=O)N($R^{A1}$)$_2$, —CH(C(=O)N($R^{A1}$)$_2$)$CH_3$, —$CH_2CH_2CH_2$C(=O)N($R^{A1}$)$_2$, —$CH_2$CH(C(=O)N($R^{A1}$)$_2$)$CH_3$, —CH(C(=O)N($R^{A1}$)$_2$)$CH_2CH_3$, —CH($CH_3$)(CHC(=O)N($R^{A1}$)$_2$), and —C(C(=O)N($R^{A1}$)$_2$)($CH_3$)$_2$.

As generally described above, each instance of $R^{A1}$ is independently hydrogen or $C_{1-10}$alkyl. In certain embodiments, each instance of $R^{A1}$ is independently hydrogen or $C_{1-8}$alkyl. In certain embodiments, each instance of $R^{A1}$ is independently hydrogen or $C_{1-6}$alkyl. In certain embodiments, each instance of $R^{A1}$ is independently hydrogen or $C_{1-4}$alkyl. In certain embodiments, each instance of $R^{A1}$ is independently hydrogen or $C_{1-3}$alkyl. In certain embodiments, each instance of $R^{A1}$ is independently hydrogen or $C_{1-2}$alkyl. In certain embodiments, each instance of $R^{A1}$ is independently hydrogen or $C_1$alkyl. In certain embodiments, each instance of $R^{A1}$ is independently hydrogen.

Furthermore, as used herein, wherein $R^2$ is an unsubstituted $C_{1-3}$alkyl or a $C_{1-3}$alkyl substituted with —$CO_2R^{A2}$ or —C(=O)N($R^{A2}$)$_2$, it is understood that each instance of $R^2$ may encompass a variety of different groups, e.g., for example, each instance of $R^2$ may be independently selected from unsubstituted $C_{1-2}$alkyl, $C_{1-2}$alkyl substituted with —$CO_2R^{A2}$, $C_{1-2}$alkyl substituted with —C(=O)N($R^{A2}$)$_2$, unsubstituted $C_{2-3}$alkyl, $C_{2-3}$alkyl substituted with —$CO_2R^{A2}$, $C_{2-3}$alkyl substituted with —C(=O)N($R^{A2}$)$_2$, unsubstituted $C_1$alkyl, $C_1$alkyl substituted with —$CO_2R^{A2}$, $C_1$alkyl substituted with —C(=O)N($R^{A2}$)$_2$, unsubstituted $C_2$alkyl, $C_2$alkyl substituted with —$CO_2R^{A2}$, $C_2$alkyl substituted with —C(=O)N($R^{A2}$)$_2$, unsubstituted $C_3$alkyl, $C_3$alkyl substituted with —$CO_2R^{A2}$, or $C_3$alkyl substituted with —C(=O)N($R^{A2}$)$_2$. For example, in certain embodiments, each instance of $R^2$ is independently selected from —$CH_3$, —$CH_2CH_3$, —$CH_2CH_2CH_3$, —CH($CH_3$)$_2$, —$CH_2CO_2R^{A2}$, —$CH_2CH_2CO_2R^2$, —CH($CO_2R^{A2}$)$CH_3$, —$CH_2CH_2CH_2CO_2R^{A2}$, —$CH_2$CH($CO_2R^{A2}$)$CH_3$, —CH($CO_2R^{A2}$)$CH_2CH_3$, —CH($CH_3$)(CH$CO_2R^{A2}$), —C($CO_2R^{A2}$)($CH_3$)$_2$, —$CH_2$C(=O)N($R^{A2}$)$_2$, —$CH_2CH_2CH_2$C(=O)N($R^{A2}$)$_2$, —CH(C(=O)N(R)$_2$)$CH_3$, —$CH_2CH_2$C(=O)N($R^{A2}$)$_2$, —$CH_2$CH(C(=O)N($R^{A2}$)$_2$)$CH_3$, —CH(C(=O)N($R^{A2}$)$_2$)$CH_2CH_3$, —CH($CH_3$)(CHC(=O)N($R^2$)$_2$), and —C(C(=O)N($R^{A2}$)$_2$)($CH_3$)$_2$.

As generally described above, each instance of $R^{A2}$ is independently hydrogen or $C_{1-10}$alkyl. In certain embodiments, each instance of $R^{A2}$ is independently hydrogen or $C_{1-8}$alkyl. In certain embodiments, each instance of $R^{A2}$ is independently hydrogen or $C_{1-6}$alkyl. In certain embodiments, each instance of $R^{A2}$ is independently hydrogen or $C_{1-4}$alkyl. In certain embodiments, each instance of $R^{A2}$ is independently hydrogen or $C_{1-3}$alkyl. In certain embodiments, each instance of $R^{A2}$ is independently hydrogen or $C_{1-2}$alkyl. In certain embodiments, each instance of $R^{A2}$ is independently hydrogen or $C_1$alkyl. In certain embodiments, each instance of $R^{A2}$ is independently hydrogen.

(ii) Embodiments Wherein One of $R^1$ and $R^2$ is Hydrogen

In certain embodiments, each instance of $R^2$ is hydrogen. In this instance, in certain embodiments, each instance of $R^1$ is independently an unsubstituted $C_{1-3}$alkyl or a $C_{1-3}$alkyl substituted with $-CO_2R^{A1}$ or $-C(=O)N(R^{A1})_2$. In certain embodiments, at least one instance of $R^1$ is a $C_{1-3}$alkyl substituted with $-CO_2R^{A1}$. In certain embodiments, at least one instance of $R^1$ is a $C_{1-3}$alkyl substituted with $-C(=O)N(R^{A1})_2$. In certain embodiments, at least one instance of $R^1$ is an unsubstituted $C_{1-3}$alkyl. In certain embodiments, at least two instances of $R^1$ is an unsubstituted $C_{1-3}$alkyl or a $C_{1-3}$alkyl substituted with $-CO_2R^{A1}$. In certain embodiments, at least two instances of $R^1$ is a $C_{1-3}$alkyl substituted with $-CO_2R^{A1}$. In certain embodiments, at least two instances of $R^1$ is a $C_{1-3}$alkyl substituted with $-C(=O)N(R^{A1})_2$. In certain embodiments, at least two instances of $R^1$ is an unsubstituted $C_{1-3}$alkyl.

In certain embodiments, $R^2$ is hydrogen and each instance of $R^1$ is independently unsubstituted $C_{1-3}$alkyl or $C_{1-3}$alkyl substituted with $-CO_2R^{A1}$ or $-C(=O)N(R^{A1})_2$. In certain embodiments, each instance of $R^1$ is independently unsubstituted $C_{1-2}$alkyl or $C_{1-2}$alkyl substituted with $-CO_2R^{A1}$ or $-C(=O)N(R^{A1})_2$. In certain embodiments, each instance of $R^1$ is independently unsubstituted $C_{2-3}$alkyl or $C_{2-3}$alkyl substituted with $-CO_2R^{A1}$ or $-C(=O)N(R^{A1})_2$. In certain embodiments, each instance of $R^1$ is independently unsubstituted $C_1$alkyl or $C_1$alkyl substituted with $-CO_2R^{A1}$ or $-C(=O)N(R^{A1})_2$. In certain embodiments, each instance of $R^1$ is independently unsubstituted $C_2$alkyl or $C_2$alkyl substituted with $-CO_2R^{A1}$ or $-C(=O)N(R^{A1})_2$. In certain embodiments, each instance of $R^1$ is independently unsubstituted $C_3$alkyl or $C_3$alkyl substituted with $-CO_2R^{A1}$ or $-C(=O)N(R^{A1})_2$. In certain embodiments, each instance of $R^1$ is independently $-CH_3$, $-CH_2CH_3$, $-CH_2CH_2CH_3$, $-CH(CH_3)_2$, $-CH_2CO_2R^{A1}$, $-CH_2CH_2CO_2R^{A1}$, $-CH(CO_2R^{A1})CH_3$, $-CH_2CH_2CH_2CO_2R^{A1}$, $-CH_2CH(CO_2R^{A1})CH_3$, $-CH(CO_2R^{A1})CH_2CH_3$, $-CH(CH_3)(CHCO_2R^{A1})$, $-C(CO_2R^{A1})(CH_3)_2$, $-CH_2C(=O)N(R^{A1})_2$, $-CH_2CH_2C(=O)N(R^{A1})_2$, $-CH(C(=O)N(R^{A1})_2)CH_3$, $-CH_2CH_2CH_2C(=O)N(R^{A1})_2$, $-CH_2CH(C(=O)N(R^{A1})_2)CH_3$, $-CH(C(=O)N(R^{A1})_2)CH_2CH_3$, $-CH(CH_3)(CHC(=O)N(R^{A1})_2)$, and $-C(C(=O)N(R^{A1})_2)(CH_3)_2$. In certain embodiments, each instance of $R^1$ is independently $-CH_3$, $-CH_2CO_2R^{A1}$ or $-CH_2C(=O)N(R^{A1})_2$. In certain embodiments, each instance of $R^1$ is $-CH_3$. In certain embodiments, each instance of $R^1$ is independently $-CH_2CO_2R^{A1}$. In certain embodiments, each instance of $R^1$ is $-CH_2CO_2H$. In certain embodiments, each instance of $R^1$ is independently $-CH_2C(=O)N(R^{A1})_2$.

In certain embodiments, each instance of $R^2$ is hydrogen and each instance of $R^1$ is independently $C_{1-3}$alkyl substituted with $-CO_2R^{A1}$. In this instance, in certain embodiments, each instance of $R^1$ is independently $C_{1-2}$alkyl substituted with $-CO_2R^{A1}$. In certain embodiments, each instance of $R^1$ is independently $C_{2-3}$alkyl substituted with $-CO_2R^{A1}$. In certain embodiments, each instance of $R^1$ is independently $C_1$alkyl substituted with $-CO_2R^{A1}$. In certain embodiments, each instance of $R^1$ is independently $C_2$alkyl substituted with $-CO_2R^{A1}$. In certain embodiments, each instance of $R^1$ is independently $C_3$alkyl substituted with $-CO_2R^{A1}$. In certain embodiments, each instance of $R^1$ is independently $-CH_2CO_2R^{A1}$, $-CH_2CH_2CO_2R^{A1}$, $-CH(CO_2R^{A1})CH_3$, $-CH_2CH_2CH_2CO_2R^{A1}$, $-CH_2CH(CO_2R^{A1})CH_3$, $-CH(CO_2R^{A1})CH_2CH_3$, $-CH(CH_3)(CHCO_2R^{A1})$, or $-C(CO_2R^{A1})(CH_3)_2$. In certain embodiments, each instance of $R^1$ is independently $-CH_2CO_2R^{A1}$. In certain embodiments, each instance of $R^1$ is $-CH_2CO_2H$.

In certain embodiments, each instance of $R^2$ is hydrogen and each instance of $R^1$ is independently $C_{1-3}$alkyl substituted with $-C(=O)N(R^{A1})_2$. In this instance, in certain embodiments, each instance of $R^1$ is independently $C_{1-2}$alkyl substituted with $-C(=O)N(R^{A1})_2$. In certain embodiments, each instance of $R^1$ is independently $C_{2-3}$alkyl substituted with $-C(=O)N(R^{A1})_2$. In certain embodiments, each instance of $R^1$ is independently $C_1$alkyl substituted with $-C(=O)N(R^{A1})_2$. In certain embodiments, each instance of $R^1$ is independently $C_2$alkyl substituted with $-C(=O)N(R^{A1})_2$. In certain embodiments, each instance of $R^1$ is independently $C_3$alkyl substituted with $-C(=O)N(R^{A1})_2$. In certain embodiments, each instance of $R^1$ is independently $-CH_2C(=O)N(R^{A1})_2$, $-CH_2CH_2C(=O)N(R^{A1})_2$, $-CH(C(=O)N(R^{A1})_2)CH_3$, $-CH_2CH_2CH_2C(=O)N(R^{A1})_2$, $-CH_2CH(C(=O)N(R^{A1})_2)CH_3$, $-CH(C(=O)N(R^{A1})_2)CH_2CH_3$, $-CH(CH_3)(CHC(=O)N(R^{A1})_2)$, and $-C(=O)N(R^{A1})_2)(CH_3)_2$. In certain embodiments, each instance of $R^1$ is independently $-CH_2C(=O)N(R^{A1})_2$. In certain embodiments, each instance of $R^1$ is $-CH_2C(=O)NH_2$.

In certain embodiments, each instance of $R^2$ is hydrogen and each instance of $R^1$ is independently unsubstituted $C_{1-3}$alkyl. In this instance, in certain embodiments, each instance of $R^1$ is independently unsubstituted $C_{1-2}$alkyl. In certain embodiments, each instance of $R^1$ is independently unsubstituted $C_{2-3}$alkyl. In certain embodiments, each instance of $R^1$ is independently unsubstituted $C_1$alkyl. In certain embodiments, each instance of $R^1$ is independently unsubstituted $C_2$alkyl. In certain embodiments, each instance of $R^1$ is independently unsubstituted $C_3$alkyl. In certain embodiments, each instance of $R^1$ is independently $-CH_3$, $-CH_2CH_3$, $-CH_2CH_2CH_3$, or $-CH(CH_3)_2$. In certain embodiments, each instance of $R^1$ is $-CH_3$.

(iii) Embodiments Wherein Neither $R^1$ Nor $R^2$ are Hydrogen

In certain embodiments, each instance of $R^2$ is independently an unsubstituted $C_{1-3}$alkyl or a $C_{1-3}$alkyl substituted with $-CO_2R^{A2}$ or $-C(=O)N(R^{A2})_2$, and each instance of $R^1$ is independently an unsubstituted $C_{1-3}$alkyl or a $C_{1-3}$alkyl substituted with $-CO_2R^{A1}$ or $-C(=O)N(R^{A1})_2$. In this instance, in certain embodiments, at least one instance of $R^1$ is a $C_{1-3}$alkyl substituted with $-CO_2R^{A1}$. In certain embodiments, at least one instance of $R^1$ is a $C_{1-3}$alkyl substituted with $-C(=O)N(R^{A1})_2$. In certain embodiments, at least one instance of $R^1$ is an unsubstituted $C_{1-3}$alkyl. In certain embodiments, at least two instances of $R^1$ is a $C_{1-3}$alkyl substituted with $-CO_2R^{A1}$. In certain embodiments, each instance of $R^1$ is an unsubstituted $C_{1-3}$alkyl. In certain embodiments, each instance of $R^1$ is a $C_{1-3}$alkyl substituted with $-CO_2R^{A1}$. In certain embodiments, each instance of $R^1$ is a $C_{1-3}$alkyl substituted with $-C(=O)N(R^{A1})_2$. In certain embodiments, each instance of $R^1$ is independently unsubstituted $C_{1-2}$alkyl or $C_{1-2}$alkyl substituted with $-CO_2R^{A1}$ or $-C(=O)N(R^{A1})_2$. In certain embodiments, each instance of $R^1$ is independently unsubstituted $C_{2-3}$alkyl or $C_{2-3}$alkyl substituted with $-CO_2R^{A1}$ or $-C(=O)N(R^{A1})_2$. In certain embodiments, each instance of $R^1$ is independently unsubstituted $C_1$alkyl or $C_1$alkyl substituted with $-CO_2R^{A1}$ or $-C(=O)N(R^{A1})_2$. In certain embodiments, each instance of $R^1$ is independently unsubstituted $C_2$alkyl or $C_2$alkyl substituted with $-CO_2R^{A1}$ or $-C(=O)N(R^{A1})_2$. In certain embodiments, each instance of $R^1$ is independently unsubstituted $C_3$alkyl or $C_3$alkyl substituted with $-CO_2R^{A1}$ or $-C(=O)N(R^{A1})_2$. In certain embodiments, each instance of $R^1$ is independently $-CH_3$, $-CH_2CH_3$, $-CH_2CH_2CH_3$, $-CH(CH_3)_2$, $-CH_2CO_2R^{A1}$, $-CH_2CH_2CO_2R^{A1}$, $-CH(CO_2R^{A1})CH_3$, $-CH_2CH_2CH_2CO_2R^{A1}$, $-CH_2CH(CO_2R^{A1})CH_3$, $-CH(CO_2R^{A1})CH_2CH_3$, $-CH(CH_3)(CHCO_2R^{A1})$, $-C(CO_2R^{A1})(CH_3)_2$, $-CH_2C(=O)N(R^{A1})_2$, $-CH_2CH_2C(=O)N(R^{A1})_2$, $-CH(C(=O)N(R^{A1})_2)CH_3$, $-CH_2CH_2CH_2C(=O)N(R^{A1})_2$, $-CH_2CH(C(=O)N(R^{A1})_2)CH_3$, $-CH(C(=O)N(R^{A1})_2)CH_2CH_3$, $-CH(CH_3)(CHC(=O)N(R^{A1})_2)$, and $-C(C(=O)N(R^{A1})_2)(CH_3)_2$. In certain embodiments, each instance of $R^1$ is independently $-CH_3$, $-CH_2CO_2R^{A1}$ or $-CH_2C(=O)N(R^{A1})_2$. In certain embodiments, each instance of $R^1$ is $-CH_3$. In certain embodiments, each instance of $R^1$ is independently $-CH_2CO_2R^{A1}$. In certain embodiments, each instance of $R^1$ is $-CH_2CO_2H$. In certain embodiments, each instance of $R^1$ is independently $-CH_2C(=O)N(R^{A1})_2$. In certain embodiments, each instance of $R^1$ is independently $-CH_2C(=O)NH_2$.

In certain embodiments, each instance of $R^2$ is independently an unsubstituted $C_{1-3}$alkyl, and each instance of $R^1$ is independently an unsubstituted $C_{1-3}$alkyl or a $C_{1-3}$alkyl substituted with $-CO_2R^{A1}$ or $-C(=O)N(R^{A1})_2$. In this instance, in certain embodiments, at least one instance of $R^1$ is a $C_{1-3}$alkyl substituted with $-CO_2R^{A1}$. In certain embodiments, at least one instance of $R^1$ is a $C_{1-3}$alkyl substituted with $-C(=O)N(R^{A1})_2$. In certain embodiments, at least one instance of $R^1$ is an unsubstituted $C_{1-3}$alkyl. In certain embodiments, at least two instances of $R^1$ is a $C_{1-3}$alkyl substituted with $-CO_2R^{A1}$. In certain embodiments, each instance of $R^1$ is a $C_{1-3}$alkyl substituted with $-C(=O)N(R^{A1})_2$. In certain embodiments, each instance of $R^1$ is an unsubstituted $C_{1-3}$alkyl. In certain embodiments, each instance of $R^1$ is a $C_{1-3}$alkyl substituted with $-CO_2R^{A1}$. In certain embodiments, each instance of $R^1$ is a $C_{1-3}$alkyl substituted with $-C(=O)N(R^{A1})_2$. In certain embodiments, each instance of $R^1$ is independently unsubstituted $C_{1-2}$alkyl or $C_{1-2}$alkyl substituted with $-CO_2R^{A1}$ or $-C(=O)N(R^{A1})_2$. In certain embodiments, each instance of $R^1$ is independently unsubstituted $C_{2-3}$alkyl or $C_{2-3}$alkyl substituted with $-CO_2R^{A1}$ or $-C(=O)N(R^{A1})_2$. In certain embodiments, each instance of $R^1$ is independently unsubstituted $C_1$alkyl or $C_1$alkyl substituted with $-CO_2R^{A1}$ or $-C(=O)N(R^{A1})_2$. In certain embodiments, each instance of $R^1$ is independently unsubstituted $C_2$alkyl or $C_2$alkyl substituted with $-CO_2R^{A1}$ or $-C(=O)N(R^{A1})_2$. In certain embodiments, each instance of $R^1$ is independently unsubstituted $C_3$alkyl or $C_3$alkyl substituted with $-CO_2R^{A1}$ or $-C(=O)N(R^{A1})_2$. In certain embodiments, each instance of $R^1$ is independently $-CH_3$, $-CH_2CH_3$, $-CH_2CH_2CH_3$, $-CH(CH_3)_2$, $-CH_2CO_2R^{A1}$, $-CH_2CH_2CO_2R^{A1}$, $CH(CO_2R^{A1})CH_3$, $-CH_2CH_2CH_2CO_2R^{A1}$, $CH_2CH(CO_2R^{A1})CH_3$, $-CH(CO_2R^{A1})CH_2CH_3$, $-CH(CH_3)(CHCO_2R^{A1})$, $-C(CO_2R^{A1})(CH_3)_2$, $-CH_2C(=O)N(R^{A1})_2$, $-CH_2CH_2C(=O)N(R^{A1})_2$, $-CH(C(=O)N(R^{A1})_2)CH_3$, $-CH_2CH_2CH_2C(=O)N(R^{A1})_2$, $-CH_2CH(C(=O)N(R^{A1})_2)CH_3$, $-CH(C(=O)N(R^{A1})_2)CH_2CH_3$, $-CH(CH_3)(CHC(=O)N(R^{A1})_2)$, and $-C(C(=O)N(R^{A1})_2)(CH_3)_2$. In certain embodiments, each instance of $R^1$ is independently $-CH_3$, $-CH_2CO_2R^{A1}$ or $-CH_2C(=O)N(R^{A1})_2$. In certain embodiments, each instance of $R^1$ is $-CH_3$. In certain embodiments, each instance of $R^1$ is independently $-CH_2CO_2R^{A1}$. In certain embodiments, each instance of $R^1$ is $-CH_2CO_2H$. In certain embodiments, each instance of $R^1$ is independently $-CH_2C(=O)N(R^{A1})_2$. In certain embodiments, each instance of $R^1$ is independently $-CH_2C(=O)NH_2$.

In certain embodiments, each instance of $R^2$ is independently a $C_{1-3}$alkyl substituted with $-CO_2R^{12}$, and each instance of $R^1$ is independently an unsubstituted $C_{1-3}$ alkyl or a $C_{1-3}$alkyl substituted with $-CO_2R^{A1}$ or $-C(=O)N(R^{A1})_2$. In this instance, in certain embodiments, at least one instance of $R^1$ is a $C_{1-3}$alkyl substituted with $-CO_2R^{A1}$. In certain embodiments, at least one instance of $R^1$ is a $C_{1-3}$alkyl substituted with $-C(=O)N(R^{A1})_2$. In certain embodiments, at least one instance of $R^1$ is an unsubstituted $C_{1-3}$alkyl. In certain embodiments, at least two instances of $R^1$ is a $C_{1-3}$alkyl substituted with $-CO_2R^{A1}$. In certain embodiments, each instance of $R^1$ is a $C_{1-3}$alkyl substituted with $-C(O)N(R^{A1})_2$. In certain embodiments, each instance of $R^1$ is an unsubstituted $C_{1-3}$alkyl. In certain embodiments, each instance of $R^1$ is a $C_{1-3}$alkyl substituted with $-CO_2R^{A1}$. In certain embodiments, each instance of $R^1$ is a $C_{1-3}$alkyl substituted with $-C(=O)N(R^{A1})_2$. In certain embodiments, each instance of $R^1$ is an unsubstituted $C_{1-3}$alkyl. In certain embodiments, each instance of $R^1$ is independently unsubstituted $C_{1-2}$alkyl or $C_{1-2}$alkyl substituted with $-CO_2R^{A1}$ or $-C(=O)N(R^{A1})_2$. In certain embodiments, each instance of $R^1$ is independently unsubstituted $C_{2-3}$alkyl or $C_{2-3}$alkyl substituted with $-CO_2R^{A1}$ or $-C(=O)N(R^{A1})_2$. In certain embodiments, each instance of $R^1$ is independently unsubstituted $C_1$alkyl or $C_1$alkyl substituted with $-CO_2R^{A1}$ or $-C(=O)N(R^{A1})_2$. In certain embodiments, each instance of $R^1$ is independently unsubstituted $C_2$alkyl or $C_2$alkyl substituted with $-CO_2R^{A1}$ or $-C(=O)N(R^{A1})_2$. In certain embodiments, each instance of $R^1$ is independently unsubstituted $C_3$alkyl or $C_3$alkyl substituted with $-CO_2R^{A1}$ or $-C(=O)N(R^{A1})_2$. In certain embodiments, each instance of $R^1$ is independently $-CH_3$, $-CH_2CH_3$, $-CH_2CH_2CH_3$, $-CH(CH_3)_2$, $-CH_2CO_2R^{A1}$, $-CH_2CH_2CO_2R^{A1}$, $CH(CO_2R^{A1})CH_3$, $-CH_2CH_2CH_2CO_2R^{A1}$, $CH_2CH(CO_2R^{A1})CH_3$, $-CH(CO_2R^{A1})CH_2CH_3$, $-CH(CH_3)(CHCO_2R^{A1})$, $-C(CO_2R^{A1})(CH_3)_2$, $-CH_2C(=O)N(R^{A1})_2$, $-CH_2CH_2C(=O)N(R^{A1})_2$, $-CH(C(=O)N(R^{A1})_2)CH_3$, $-CH_2CH_2CH_2C(=O)N(R^{A1})_2$, $-CH_2CH(C(=O)N(R^{A1})_2)CH_3$, $-CH(C(=O)N(R^{A1})_2)CH_2CH_3$, $-CH(CH_3)(CHC(=O)N(R^{A1})_2)$, and $-C(C(=O)N(R^{A1})_2)(CH_3)_2$. In certain embodiments, each instance of $R^1$ is independently $-CH_3$, $-CH_2CO_2R^{A1}$ or $-CH_2C(=O)N(R^{A1})_2$. In certain embodiments, each instance of $R^1$ is $-CH_3$. In certain embodiments, each instance of $R^1$ is independently $-CH_2CO_2R^{A1}$. In certain embodiments, each instance of $R^1$ is $-CH_2CO_2H$. In certain embodiments, each instance of $R^1$ is independently $-CH_2C(=O)N(R^{A1})_2$. In certain embodiments, each instance of $R^1$ is independently $-CH_2C(=O)NH_2$.

In certain embodiments, each instance of $R^2$ is independently a $C_{1-3}$alkyl substituted with $-C(=O)N(R^{A2})_2$, and each instance of $R^1$ is independently an unsubstituted $C_{1-3}$alkyl or a $C_{1-3}$alkyl substituted with $-CO_2R^{A1}$ or $-C(=O)N(R^{A1})_2$. In this instance, in certain embodiments, at least one instance of $R^1$ is a $C_{1-3}$alkyl substituted with $-CO_2R^{A1}$. In certain embodiments, at least one instance of $R^1$ is a $C_{1-3}$alkyl substituted with —C(=O)N($R^{41}$)$_2$. In certain embodiments, at least one instance of $R^1$ is an unsubstituted $C_{1-3}$alkyl. In certain embodiments, at least two instances of $R^1$ is a $C_{1-3}$alkyl substituted with —CO$_2R^{41}$. In certain embodiments, each instance of $R^1$ is a $C_{1-3}$alkyl substituted with —C(=O)N($R^{41}$)$_2$. In certain embodiments, each instance of $R^1$ is an unsubstituted $C_{1-3}$alkyl. In certain embodiments, each instance of $R^1$ is a $C_{1-3}$alkyl substituted with —CO$_2R^{41}$. In certain embodiments, each instance of $R^1$ is a $C_{1-3}$alkyl substituted with —C(=O)N($R^{41}$)$_2$. In certain embodiments, each instance of $R^1$ is an unsubstituted $C_{1-3}$alkyl. In certain embodiments, each instance of $R^1$ is independently unsubstituted $C_{1-2}$alkyl or $C_{1-2}$alkyl substituted with —CO$_2R^{41}$ or —C(=O)N($R^{41}$)$_2$. In certain embodiments, each instance of $R^1$ is independently unsubstituted $C_{2-3}$alkyl or $C_{2-3}$alkyl substituted with —CO$_2R^{41}$ or —C(=O)N($R^{41}$)$_2$. In certain embodiments, each instance of $R^1$ is independently unsubstituted $C_1$alkyl or $C_1$alkyl substituted with —CO$_2R^{41}$ or —C(=O)N($R^{41}$)$_2$. In certain embodiments, each instance of $R^1$ is independently unsubstituted $C_2$alkyl or $C_2$alkyl substituted with —CO$_2R^{41}$ or —C(=O)N($R^{41}$)$_2$. In certain embodiments, each instance of $R^1$ is independently unsubstituted $C_3$alkyl or $C_3$alkyl substituted with —CO$_2R^{41}$ or —C(=O)N($R^{41}$)$_2$. In certain embodiments, each instance of $R^1$ is independently —CH$_3$, —CH$_2$CH$_3$, —CH$_2$CH$_2$CH$_3$, —CH(CH$_3$)$_2$, —CH$_2$CO$_2R^{41}$, —CH$_2$CH$_2$CO$_2R^{41}$, —CH(CO$_2R^{41}$)CH$_3$, —CH$_2$CH$_2$CH$_2$CO$_2R^{41}$, —CH$_2$CH(CO$_2R^{41}$)CH$_3$, —CH(CO$_2R^{41}$)CH$_2$CH$_3$, —CH(CH$_3$)(CHCO$_2R^{41}$), —C(CO$_2R^{41}$)(CH$_3$)$_2$, —CH$_2$C(=O)N($R^{41}$)$_2$, —CH$_2$CH$_2$C(=O)N($R^{41}$)$_2$, —CH(C(=O)N($R^{41}$)$_2$)CH$_3$, —CH$_2$CH$_2$CH$_2$C(=O)N($R^{41}$)$_2$, —CH$_2$CH(C(=O)N($R^{41}$)$_2$)CH$_3$, —CH(C(=O)N($R^{41}$)$_2$)CH$_2$CH$_3$, —CH(CH$_3$)(CHC(=O)N($R^{41}$)$_2$), and —C(C(=O)N($R^{41}$)$_2$)(CH$_3$)$_2$. In certain embodiments, each instance of $R^1$ is independently —CH$_3$, —CH$_2$CO$_2R^{41}$ or —CH$_2$C(=O)N($R^{41}$)$_2$. In certain embodiments, each instance of $R^1$ is —CH$_3$. In certain embodiments, each instance of $R^1$ is independently —CH$_2$CO$_2R^{41}$. In certain embodiments, each instance of $R^1$ is —CH$_2$CO$_2$H. In certain embodiments, each instance of $R^1$ is independently —CH$_2$C(=O)N($R^{41}$)$_2$.

In any of the above embodiments, $R^2$ is independently an unsubstituted $C_{1-3}$alkyl or a $C_{1-3}$alkyl substituted with —CO$_2R^{42}$ or —C(=O)N($R^{42}$)$_2$.

In any of the above embodiments, each instance of $R^2$ is independently $C_{1-3}$alkyl substituted with —CO$_2R^{42}$. In this instance, in certain embodiments, each instance of $R^2$ is independently $C_{1-2}$alkyl substituted with —CO$_2R^{42}$. In certain embodiments, each instance of $R^2$ is independently $C_{2-3}$alkyl substituted with —CO$_2R^{41}$. In certain embodiments, each instance of $R^2$ is independently $C_1$alkyl substituted with —CO$_2R^{42}$. In certain embodiments, each instance of $R^2$ is independently $C_2$alkyl substituted with —CO$_2R^{42}$. In certain embodiments, each instance of $R^2$ is independently $C_3$alkyl substituted with —CO$_2R^{42}$. In certain embodiments, each instance of $R^2$ is independently —CH$_2$CO$_2R^{42}$, —CH$_2$CH$_2$CO$_2R^{42}$, —CH(CO$_2R^{42}$)CH$_3$, —CH$_2$CH$_2$CH$_2$CO$_2R^{42}$, —CH$_2$CH(CO$_2R^{42}$)CH$_3$, —CH(CO$_2R^{42}$)CH$_2$CH$_3$, —CH(CH$_3$)(CHCO$_2R^{42}$), or —C(CO$_2R^{42}$)(CH$_3$)$_2$. In certain embodiments, each instance of $R^2$ is independently —CH$_2$CO$_2R^2$. In certain embodiments, each instance of $R^2$ is —CH$_2$CO$_2$H.

In any of the above embodiments, each instance of $R^2$ is independently $C_{1-3}$alkyl substituted with —C(=O)N($R^{42}$)$_2$. In certain embodiments, each instance of $R^2$ is independently $C_{1-2}$alkyl substituted with —C(=O)N($R^{42}$)$_2$. In certain embodiments, each instance of $R^2$ is independently $C_{2-3}$alkyl substituted with —C(=O)N($R^{42}$)$_2$. In certain embodiments, each instance of $R^2$ is independently $C_1$alkyl substituted with —C(=O)N($R^{42}$)$_2$. In certain embodiments, each instance of $R^2$ is independently $C_2$alkyl substituted with —C(=O)N($R^{42}$)$_2$. In certain embodiments, each instance of $R^2$ is independently $C_3$alkyl substituted with —C(=O)N($R^{42}$)$_2$. In certain embodiments, each instance of $R^2$ is independently —CH$_2$C(=O)N($R^{42}$)$_2$, —CH$_2$CH$_2$C(=O)N($R^{42}$)$_2$, —CH(C(=O)N($R^{42}$)$_2$)CH$_3$, —CH$_2$CH$_2$CH$_2$C(=O)N($R^{42}$)$_2$, —CH$_2$CH(C(=O)N($R^{42}$)$_2$)CH$_3$, —CH(C(=O)N($R^{42}$)$_2$)CH$_2$CH$_3$, —CH(CH$_3$)(CHC(=O)N($R^{42}$)$_2$), and —C(C(=O)N($R^{42}$)$_2$)(CH$_3$)$_2$. In certain embodiments, each instance of $R^2$ is independently —CH$_2$C(=O)N($R^{42}$)$_2$. In certain embodiments, each instance of $R^2$ is —CH$_2$C(=O)NH$_2$.

In any of the above embodiments, each instance of $R^2$ is independently unsubstituted $C_{1-3}$alkyl. In this instance, in certain embodiments, each instance of $R^2$ is independently unsubstituted $C_{1-2}$alkyl. In certain embodiments, each instance of $R^2$ is independently unsubstituted $C_{2-3}$alkyl. In certain embodiments, each instance of $R^2$ is independently unsubstituted $C_1$alkyl. In certain embodiments, each instance of $R^2$ is independently unsubstituted $C_2$alkyl. In certain embodiments, each instance of $R^2$ is independently unsubstituted $C_3$alkyl. In certain embodiments, each instance of $R^2$ is independently —CH$_3$, —CH$_2$CH$_3$, —CH$_2$CH$_2$CH$_3$, or —CH(CH$_3$)$_2$. In certain embodiments, each instance of $R^2$ is —CH$_3$.

(iv) Additional Embodiments

It should be understood from the above discussion that the compound of Formula (I), as described above, and subsets thereof (e.g., compounds of Formula (II)), encompass compounds wherein each instance of the ligand (i):

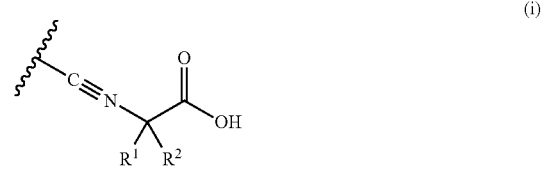

(i)

may be the same or different. For example, in certain embodiments, each instance of the ligand (i) is the same. In certain embodiments, at least one instance of the ligand (i) is different.

In certain embodiments, each instance of $R^1$ is the same. In certain embodiments, each instance of $R^2$ is the same. For example, in certain embodiments, $R^1$ and $R^2$ attached to the same carbon are the same. In certain embodiments, each instance of $R^1$ and $R^2$ is —CH$_3$. In certain embodiments, each instance of $R^1$ and $R^2$ is —CH$_2$CH$_3$. In certain embodiments, each instance of $R^1$ and $R^2$ is —CH$_2$CH$_2$CH$_3$. In certain embodiments, each instance of $R^1$ and $R^2$ is —CH$_2$CO$_2$H. In certain embodiments, each instance of $R^1$ and $R^2$ is —CH$_2$CO$_2$CH$_3$.

However, in certain embodiments, at least one instance of $R^1$ is different from $R^2$ attached to the same carbon or from another instance of $R^1$. In certain embodiments, at least one instance of $R^2$ is different from $R^1$ attached to the same carbon or from another instance of $R^2$. In certain embodiments, $R^1$ and $R^2$ attached to the same carbon are different groups. For example, in certain embodiments, $R^2$ is hydrogen and $R^1$ is —CH$_3$. In certain embodiments, $R^2$ is hydrogen and $R^1$ is —CH$_2$CH$_3$. In certain embodiments, R$^2$ is hydrogen and R$^1$ is —CH$_2$CH$_2$CH$_3$. In certain embodiments, R$^2$ is hydrogen and R$^1$ is —CH$_2$CO$_2$H. In certain embodiments, R$^2$ is hydrogen and R$^1$ is —CH$_2$CO$_2$CH$_3$.

As understood from the above discussion, the groups R$^1$ and R$^2$ attached to the same carbon each may be different, e.g., for example wherein R$^2$ is hydrogen and R$^1$ is not hydrogen. In this instance, the ligand of the formula (I) is a chiral ligand, i.e., having (R) or (S) stereochemistry. In certain embodiments, the chiral ligand has (R) stereochemistry. In certain embodiments, the chiral ligand has (S) stereochemistry.

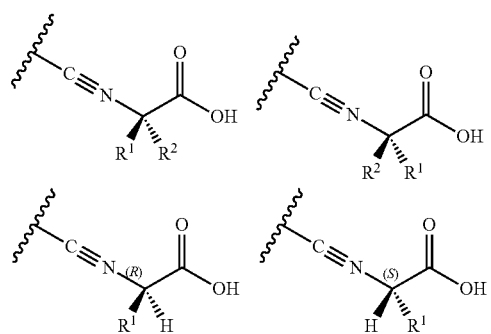

Various combinations of the above described embodiments are further contemplated herein.

For example, in certain embodiments of Formula (I), neither R$^1$ nor R$^2$ is hydrogen.

In other embodiments of Formula (I), each instance of R$^2$ is hydrogen, i.e., to provide a compound of the Formula (I-a):

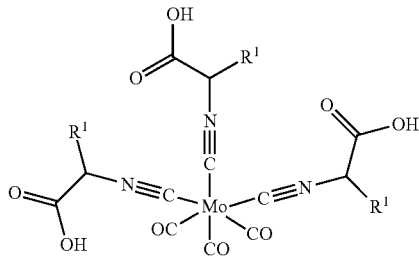

or a salt, ester, amide, solvate, or hydrate thereof, or a combination thereof; wherein R$^1$ is as described herein.

In other embodiments, wherein R$^1$ is an unsubstituted C$_{1-3}$alkyl, the compound of Formula (I) is a compound of the Formula (I-b):

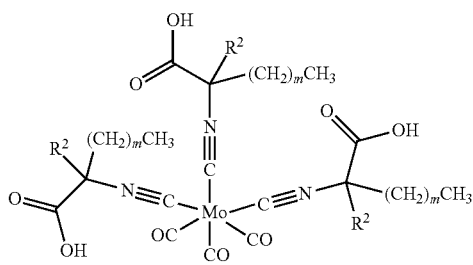

or a salt, ester, amide, solvate, or hydrate thereof, or a combination thereof; wherein R$^2$ is as described herein and each instance of m is independently 0, 1, or 2. In certain embodiments, m is 0. In certain embodiments, m is 1. In certain embodiments, m is 2. In certain embodiments, R$^2$ is hydrogen. In certain embodiments R$^2$ is not hydrogen.

For example, in certain embodiments of Formula (I-b), wherein R$^2$ is hydrogen, the compound of the Formula (I) is a compound of the Formula (I-c):

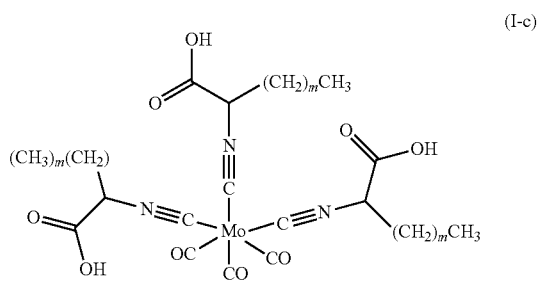

or a salt, ester, amide, solvate, or hydrate thereof, or a combination thereof; wherein each instance of m is independently 0, 1, or 2. In certain embodiments, m is 0. In certain embodiments, m is 1. In certain embodiments, m is 2.

In certain embodiments of Formula (I-b), wherein R$^2$ is an unsubstituted C$_{1-3}$alkyl, the compound is of the Formula (I-d):

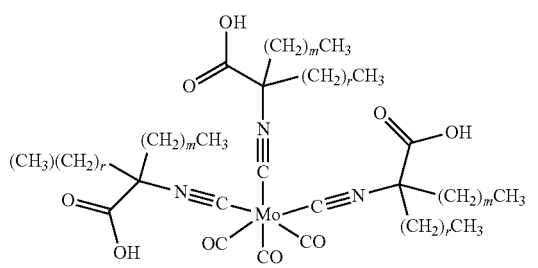

or a salt, ester, amide, solvate, or hydrate thereof, or a combination thereof; wherein each instance of r is independently 0, 1, or 2. In certain embodiments, r is 0. In certain embodiments, r is 1. In certain embodiments, r is 2.

In yet other embodiments, wherein R$^1$ is a C$_{1-3}$alkyl substituted by —CO$_2$R$^{41}$, the compound of Formula (I) is a compound of the Formula (I-e):

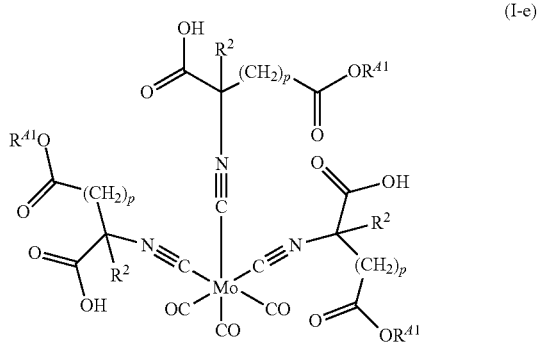

or a salt, ester, amide, solvate, or hydrate thereof, or a combination thereof; wherein $R^2$ and $R^{41}$ are as described herein, and each instance of p is independently 1, 2, or 3. In certain embodiments, p is 1. In certain embodiments, p is 2. In certain embodiments, p is 3. In certain embodiments, $R^2$ is hydrogen. In certain embodiments, $R^2$ is not hydrogen. In certain embodiments, $R^{41}$ is hydrogen.

For example, in certain embodiments of Formula (I-e), wherein $R^2$ is hydrogen, the compound is of the Formula (I-f):

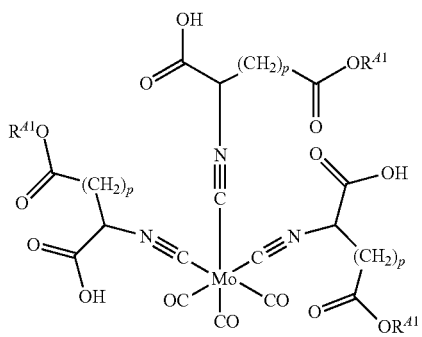

(I-f)

or a salt, ester, amide, solvate, or hydrate thereof, or a combination thereof; wherein $R^{41}$ is as described herein, and each instance of p is independently 1, 2, or 3. In certain embodiments, p is 1. In certain embodiments, p is 2. In certain embodiments, p is 3. In certain embodiments, $R^{41}$ is hydrogen.

In yet other embodiments, wherein $R^1$ is a $C_{1-3}$alkyl substituted by $-CO_2N(R^{41})_2$, the compound of Formula (I) is a compound of the Formula (I-g):

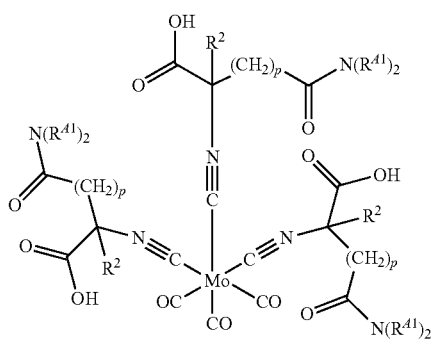

(I-g)

or a salt, ester, amide, solvate, or hydrate thereof, or a combination thereof; wherein $R^{41}$ is as described herein, and each instance of p is independently 1, 2, or 3. In certain embodiments, p is 1. In certain embodiments, p is 2. In certain embodiments, p is 3. In certain embodiments, $R^{41}$ is hydrogen.

For example, in certain embodiments of Formula (I-g), wherein $R^2$ is hydrogen, the compound is of the Formula (I-h):

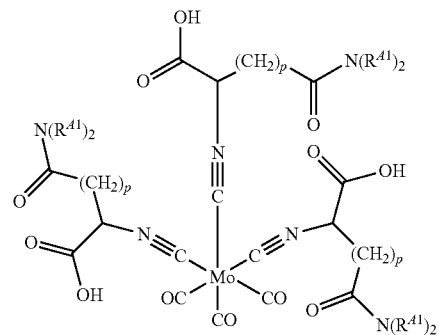

(I-h)

or a salt, ester, amide, solvate, or hydrate thereof, or a combination thereof; wherein $R^{41}$ is as described herein, and each instance of p is independently 1, 2, or 3. In certain embodiments, p is 1. In certain embodiments, p is 2. In certain embodiments, p is 3. In certain embodiments, $R^{41}$ is hydrogen.

In still yet other embodiments of Formula (I), wherein each instance of $R^1$ and $R^2$ and the carbon to which they are both attached are independently joined to form a $C_{3-4}$ carbocyclyl, the compound is of the Formula (I-i):

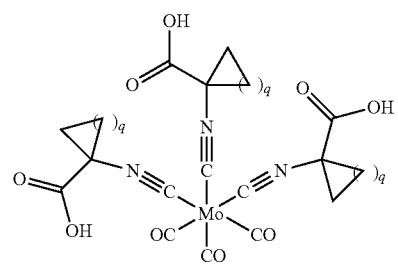

(I-i)

or a salt, ester, amide, solvate, or hydrate thereof, or a combination thereof; wherein each instance of q is independently 1 or 2. In certain embodiments, q is 1. In certain embodiments, q is 2.

Exemplary compounds of Formula (I) include, but are not limited to:

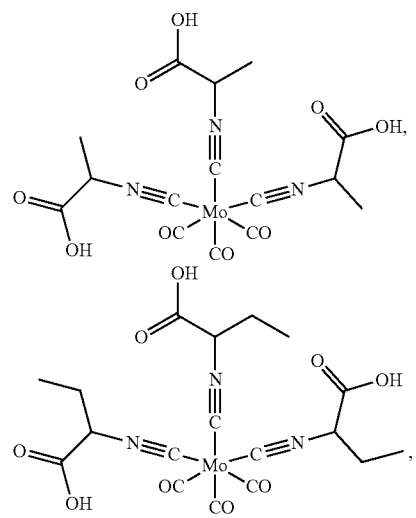

-continued
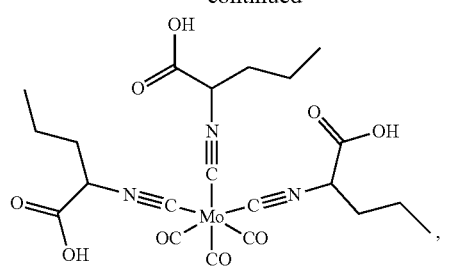
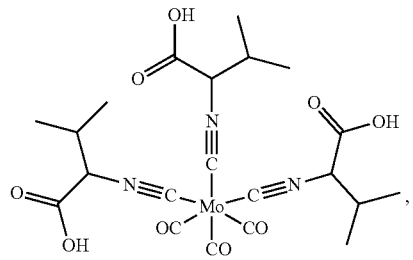
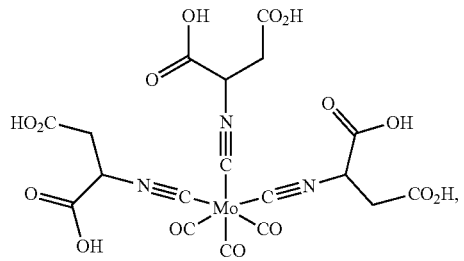
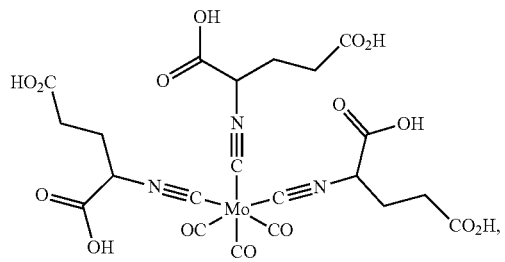
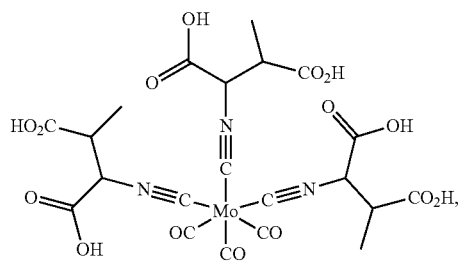
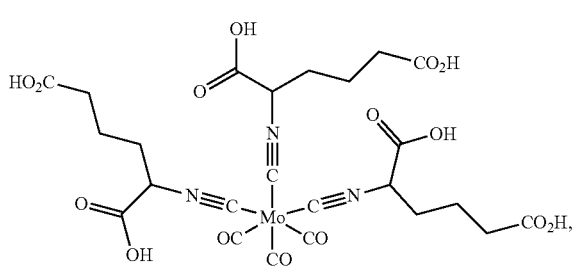
-continued
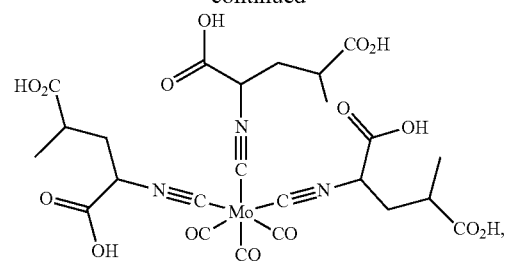
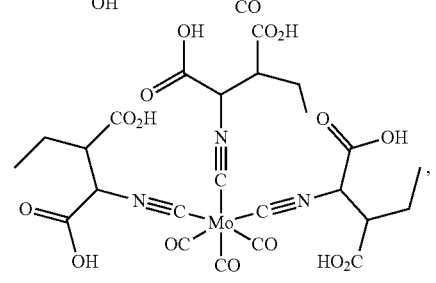
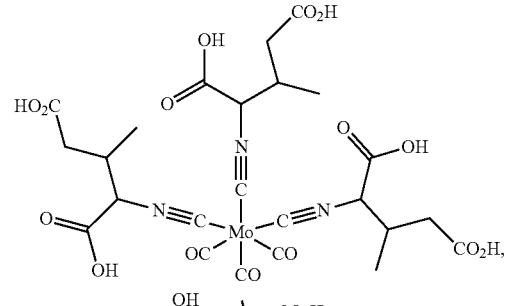
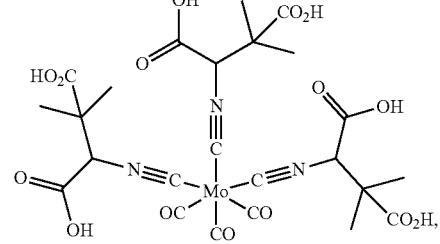
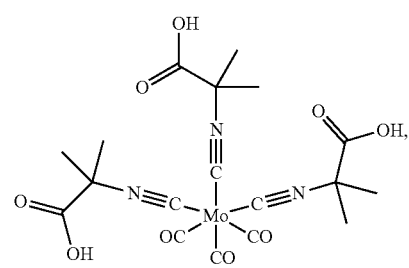
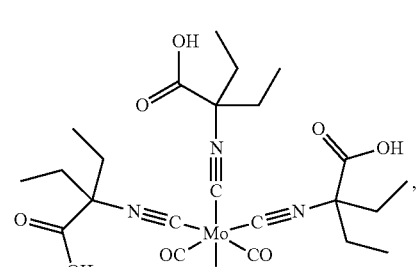

-continued
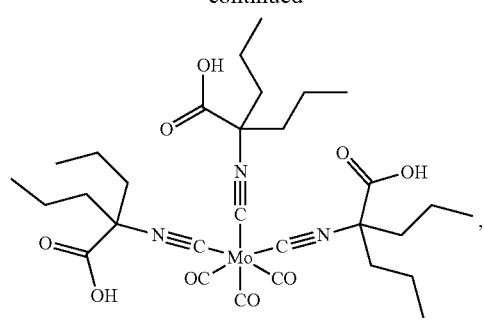
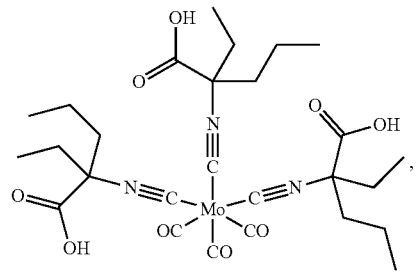
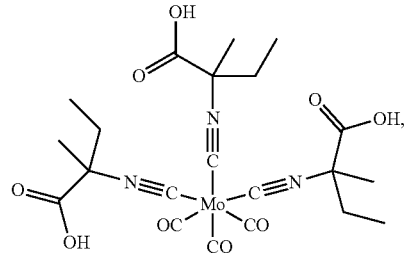
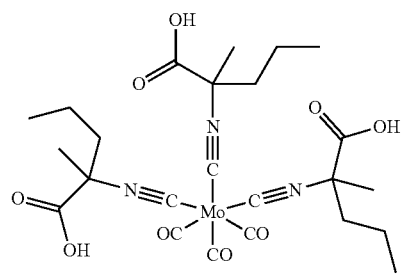
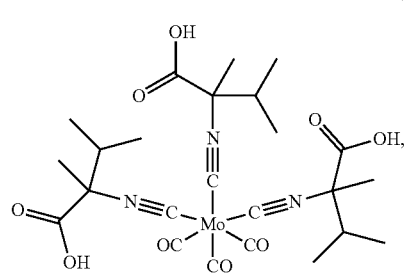
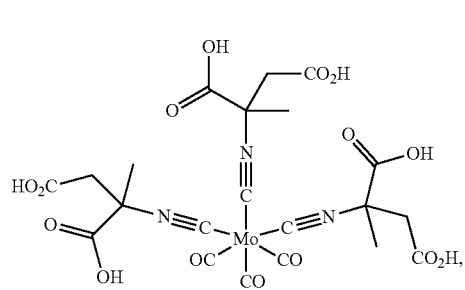
-continued
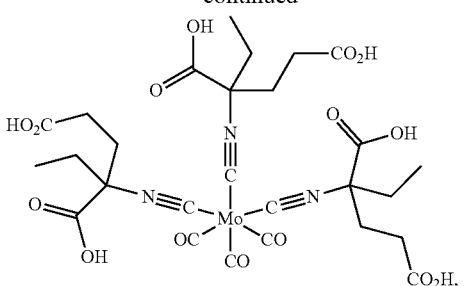
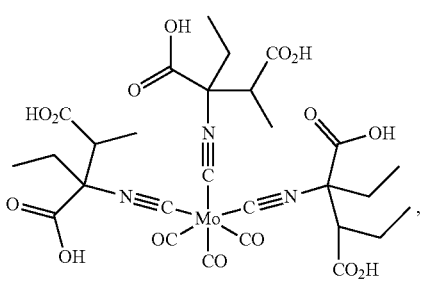
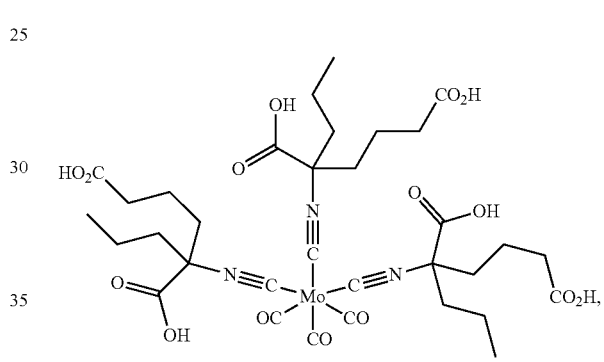
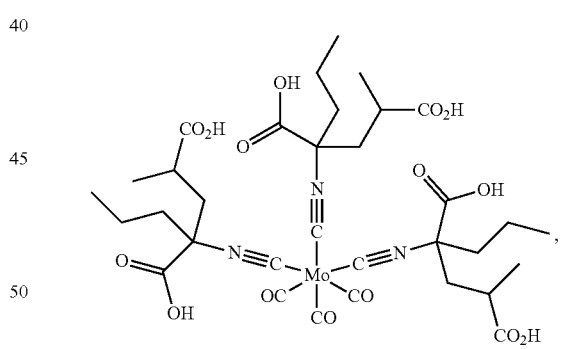
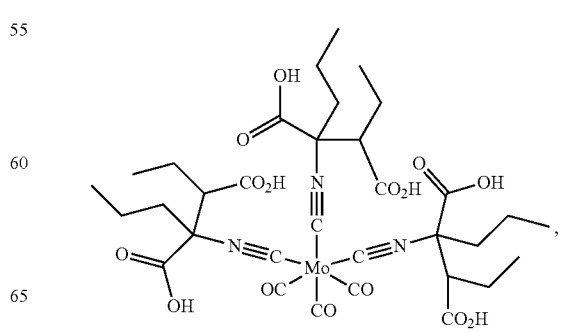

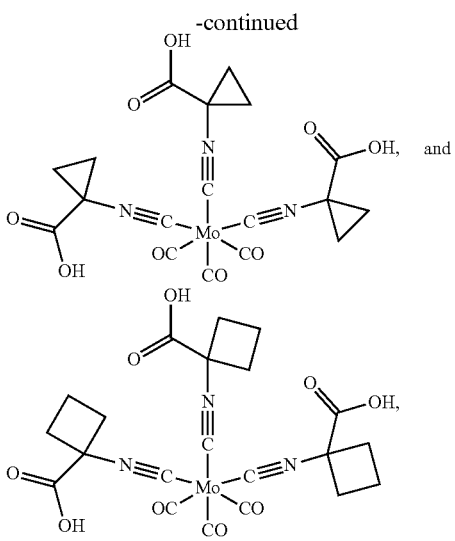

and salts, esters, amides, solvates, and hydrates thereof, and combinations thereof.

In certain embodiments, the compound of Formula (I) is compound (2-b):

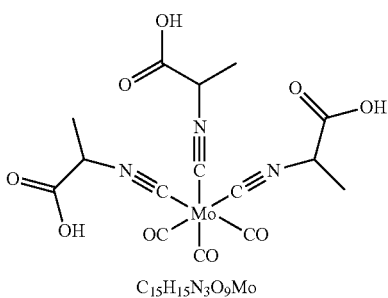

or a salt, ester, amide, solvate, or hydrate thereof, or a combination thereof.

The present disclosure further provides a compound of the molecular formula $C_{15}H_{15}N_3O_9Mo$ or a salt, ester, amide, solvate, or hydrate thereof, or a combination thereof.

In certain embodiments, the compound of Formula (I) is compound (3-b):

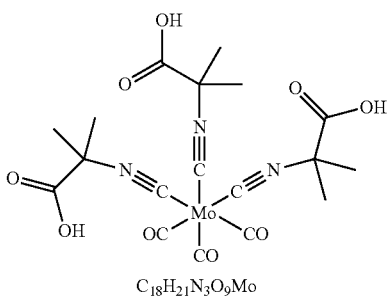

or a salt, ester, amide, solvate, or hydrate thereof, or a combination thereof.

The present disclosure further provides a compound of the molecular formula $C18H_{21}N_3O_9Mo$ or a salt, ester, amide, solvate, or hydrate thereof, or a combination thereof.

In certain embodiments, the compound of Formula (I) is compound (4-b):

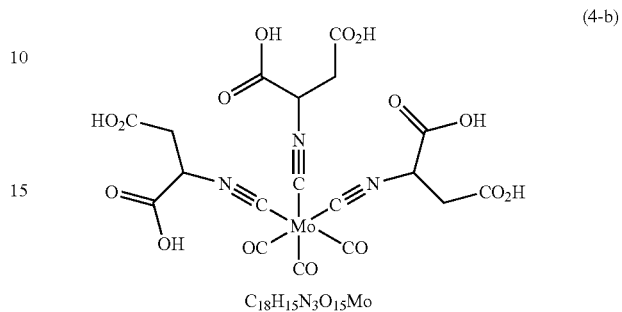

or a salt, ester, amide, solvate, or hydrate thereof, or a combination thereof.

The present disclosure further provides a compound of the molecular formula $C18H_{15}N_3O_{15}Mo$ or a salt, ester, amide, solvate, or hydrate thereof, or a combination thereof.

In certain embodiments, the compound of Formula (I) is compound (5-b):

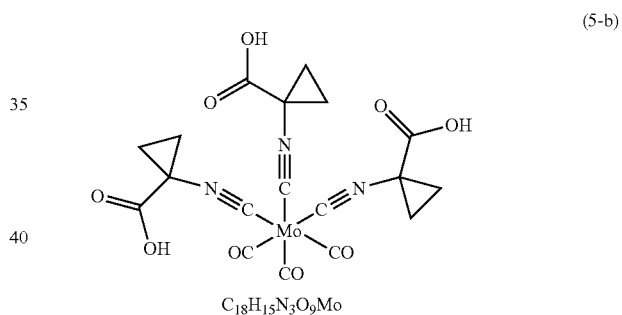

or a salt, ester, amide, solvate, or hydrate thereof, or a combination thereof.

The present disclosure further provides a compound of the molecular formula $C18H_{15}N_3O_9Mo$ or a salt, ester, amide, solvate, or hydrate thereof, or a combination thereof.

It is understood that the compound of Formula (I) encompasses salts, esters, amides, solvates, hydrates and any combination thereof, of the compound. Salts, esters, amides, solvates, and hydrates are described herein.

In certain embodiments, the compound of Formula (I) comprises a salt. In certain embodiments, the compound of Formula (I) comprises a mixture of the fully protonated compound and one or more salts. Specific salt forms of the compound of Formula (I) are contemplated herein since the compound contains multiple acidic groups which may form a salt upon contact with a base ("base addition salt").

For example, in certain embodiments, the salt of the compound of Formula (I) is a salt provided from the deprotonation of one, two, three, or more carboxylic acids groups attached thereto, e.g., such as the salts depicted in Formula (I-j), (I-k), (I-l), or (I-m):

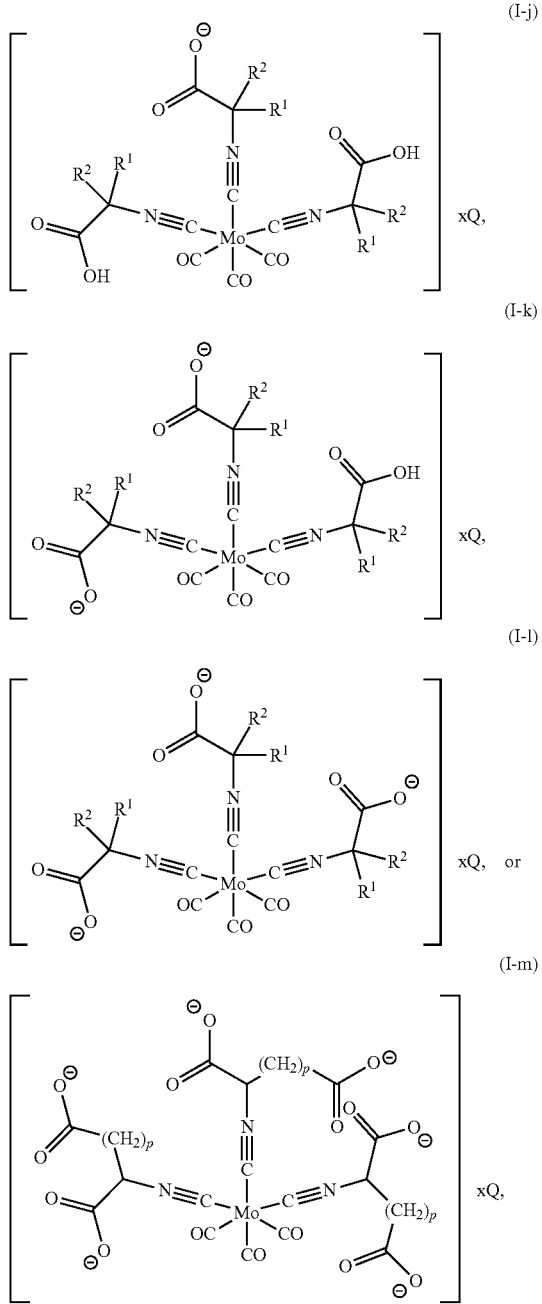

or a solvate or hydrate thereof, or a combination thereof, wherein x is 1, 2, 3, 4, 5, or 6, and Q is a cation, i.e., which renders the compound neutral.

It is clear from the depiction of the compound of Formula (I-m) that the present disclosure contemplates salt formation from the deprotonation of one or more —CO$_2$H substituents attached to the ligand (i). For the sake of brevity, the compound of Formula (I-m) is depicted as fully deprotonated. However, all intermediate salt forms, wherein 1, 2, 3, 4, or 5 of the carboxylic acid groups are deprotonated, are also contemplated.

Furthermore, as understood from the above, Q can be any cation, i.e., any atom or group of atoms that bears a positive charge. In certain embodiments, each instance of the cation Q is independently Na$^+$, K$^+$, Li$^+$, Mg$^{2+}$, Ca$^{2+}$, Zn$^{2+}$, Al$^{3+}$, or a quaternary amine of the formula [NR$^B_4$]$^+$, wherein each R$^B$ is independently hydrogen or substituted or unsubstituted C$_{1-10}$alkyl, or two R$^B$ groups are joined to form a substituted or unsubstituted 5-10 membered heteroaryl or substituted or unsubstituted 5-10 membered heterocyclyl ring.

In certain embodiments, at least one instance of Q is Na$^+$, K$^+$, Li$^+$, Mg$^{2+}$, Ca$^{2+}$, Zn$^{2+}$, or Al$^{3+}$. In certain embodiments, at least one instance of Q is Na$^+$, K$^+$, or Li$^+$. In certain embodiments, at least one instance of Q is Na$^+$. In certain embodiments, at least one instance of Q is K$^+$. In certain embodiments, at least one instance of Q is Li$^+$. In certain embodiments, each instance of the cation Q is independently Na$^+$, K$^+$, or Li$^+$. In certain embodiments, each instance of the cation Q is Na$^+$ (i.e., to provide a sodium salt). In certain embodiments, each instance of the cation Q is K$^+$ (i.e., to provide a potassium salt). In certain embodiments, each instance of the cation Q is Li$^+$ (i.e., to provide a lithium salt).

In certain embodiments, at least one instance of the cation Q is a quaternary amine of the formula [NR$^B_4$]$^+$ or [(R$^B$)$_2$N=R$^C$]$^+$ wherein R$^C$ is substituted or unsubstituted C$_{1-10}$alkyl (e.g., substituted or unsubstituted C$_{1-8}$alkyl, substituted or unsubstituted C$_{1-6}$alkyl, substituted or unsubstituted C$_{1-4}$alkyl, substituted or unsubstituted C$_{1-3}$alkyl, or substituted or unsubstituted C$_{1-2}$alkyl), or R$^C$ and R$^B$ are joined to form a substituted or unsubstituted 5-10 membered heteroaryl or substituted or unsubstituted 5-10 membered heterocyclyl ring; and each instance of R$^B$ is independently hydrogen or substituted or unsubstituted C$_{1-10}$alkyl (e.g., substituted or unsubstituted C$_{1-8}$alkyl, substituted or unsubstituted C$_{1-6}$alkyl, substituted or unsubstituted C$_{1-4}$alkyl, substituted or unsubstituted C$_{1-3}$alkyl, or substituted or unsubstituted C$_{1-2}$alkyl), or two R$^B$ groups and the nitrogen to which they are attached are joined to form a substituted or unsubstituted 5-10 membered heteroaryl, a substituted or unsubstituted 5-10 membered heterocyclyl ring.

Exemplary quaternary amines of the formula [NR$^B_4$]$^+$ include, but are not limited to, choline, histidine, lysine, and arginine:

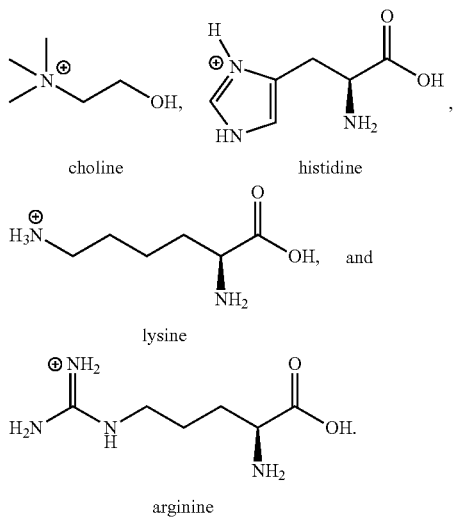

In certain embodiments, a salt of the compound (2-b) is selected from any one of the following mono-, di-, or tri-salt forms:

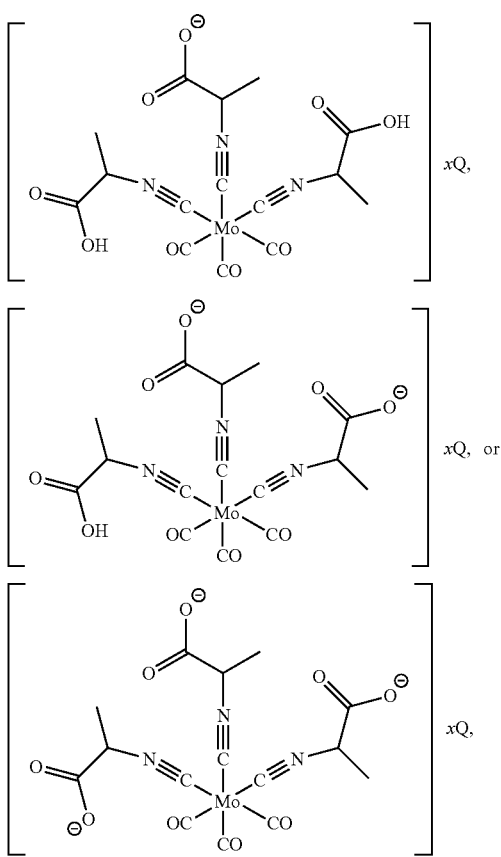

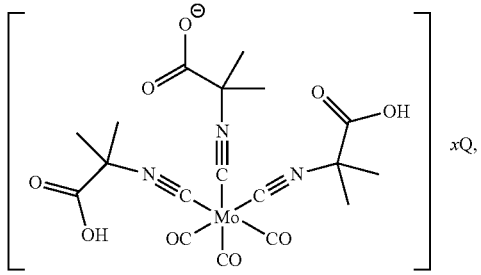

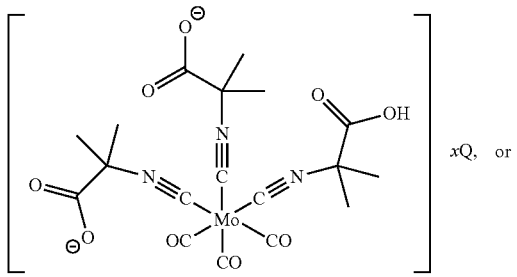

or a solvate or hydrate thereof, or a combination thereof, wherein x is 1, 2, or 3, and Q is a cation, as described herein.

In certain embodiments, a salt of the compound (3-b) is selected from any one of the following mono-, di-, or tri-salt forms:

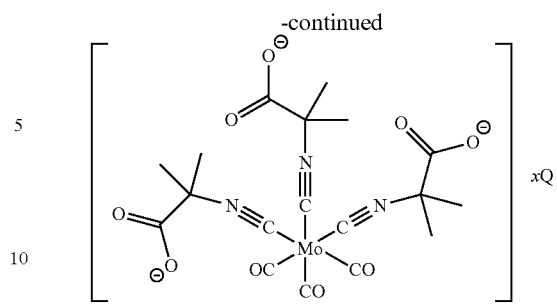

-continued or a solvate or hydrate thereof, or a combination thereof, wherein x is 1, 2, or 3, and Q is a cation as described herein.

In certain embodiments, the compound of Formula (I) is an ester and/or an amide, as described herein. In certain embodiments, the ester and/or the amide hydrolyzes in vivo to the carboxylic acid compound of the Formula (I). In certain embodiments, the ester and/or the amide is a prodrug. A "prodrug" refers to an ester and/or an amide of a compound of Formula (I) that can react under biological conditions (e.g., in vitro or in vivo enzymatic conditions) to provide the parent carboxylic acid compound. In certain embodiments, a prodrug has improved physical and/or delivery properties over the parent compound. Prodrugs are typically designed to enhance pharmacologically, pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may have enhanced stability for long-term storage.

In certain embodiments, the ester is a prodrug, i.e., hydrolyzes in vivo to the carboxylic acid compound of the Formula (I).

In certain embodiments, the ester of the compound of Formula (I) is a compound of Formula (II):

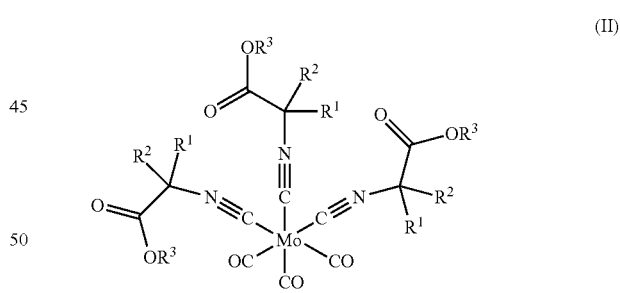

(II)

or a salt, solvate, or hydrate thereof, or a combination thereof; wherein $R^1$ and $R^2$ are as described herein; and each instance of $R^3$ is independently $C_{1-6}$alkyl, provided that each instance of $R^1$ and $R^2$ attached to the same carbon are not both hydrogen.

In certain embodiments, each instance of $R^3$ is independently $C_{1-5}$alkyl, $C_{1-4}$alkyl, $C_{1-3}$alkyl, $C_{1-2}$alkyl, $C_{2-6}$alkyl, $C_{2-5}$alkyl, $C_{2-4}$alkyl, $C_{2-3}$alkyl, $C_{3-6}$alkyl, $C_{3-5}$alkyl, $C_{3-4}$alkyl, $C_{4-6}$alkyl, $C_{5-6}$alkyl, $C_6$alkyl, $C_5$alkyl, $C_4$alkyl, $C_3$alkyl, $C_2$alkyl, or $C_1$alkyl. In certain embodiments, each instance of $R^3$ is independently —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2CH_2CH_2CH_2CH_3$, —$CH_2CH_2CH(CH_3)_2$, or —$CH_2CH_2CH_2CH_2CH_2CH_3$. In certain embodiments, each instance of $R^3$ is —$CH_3$. In certain embodiments, each instance of $R^3$ is —$CH_2CH_3$.

Exemplary compounds of Formula (II) include, but are not limited to:

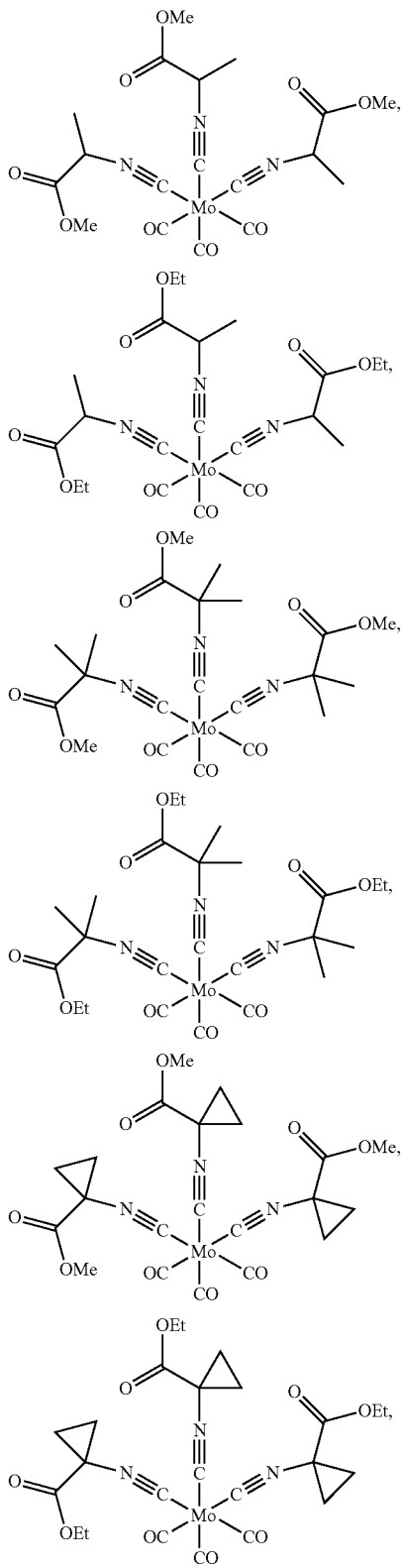

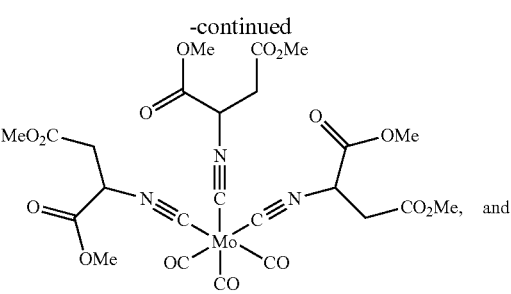

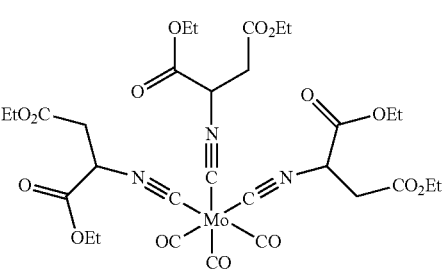

and salts, solvates, and hydrates thereof, and combinations thereof.

In certain embodiments, the compound of Formula (I) is an amide, as described herein. In certain embodiments, the amide is a prodrug, i.e., hydrolyzes in vivo to the carboxylic acid compound of the Formula (I).

In certain embodiments, the amide of the compound of Formula (I) is a compound of Formula (III):

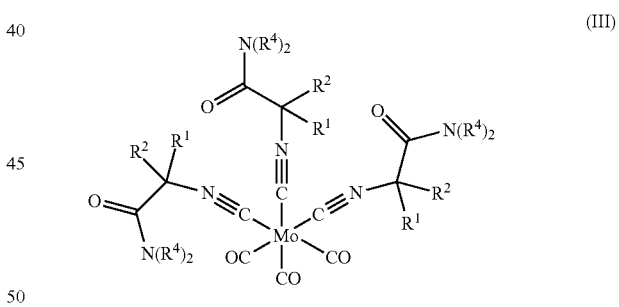

(III)

or a salt, solvate, or hydrate thereof, or a combination thereof; wherein $R^1$ and $R^2$ are as described herein; and each instance of $R^4$ is independently hydrogen or $C_{1-6}$alkyl, provided that each instance of $R^1$ and $R^2$ attached to the same carbon are not both hydrogen.

In certain embodiments, $R^4$ is $C_{1-5}$alkyl, $C_{1-4}$alkyl, $C_{1-3}$alkyl, $C_{1-2}$alkyl, $C_{2-6}$alkyl, $C_{2-5}$alkyl, $C_{2-4}$alkyl, $C_{2-3}$alkyl, $C_{3-6}$alkyl, $C_{3-5}$alkyl, $C_{3-4}$alkyl, $C_{4-6}$alkyl, $C_{5-6}$alkyl, $C_6$alkyl, $C_5$alkyl, $C_4$alkyl, $C_3$alkyl, $C_2$alkyl, or $C_1$alkyl. In certain embodiments, $R^4$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$C(CH_3)_3$, —$CH_2CH_2CH_2CH_3$, —$CH_2CH_2CH(CH_3)_2$, or —$CH_2CH_2CH_2CH_2CH_2CH_3$. In certain embodiments, each instance of $R^4$ is —$CH_3$. In certain embodiments, each instance of $R^4$ is —$CH_2CH_3$.

Exemplary compounds of Formula (III) include, but are not limited to:

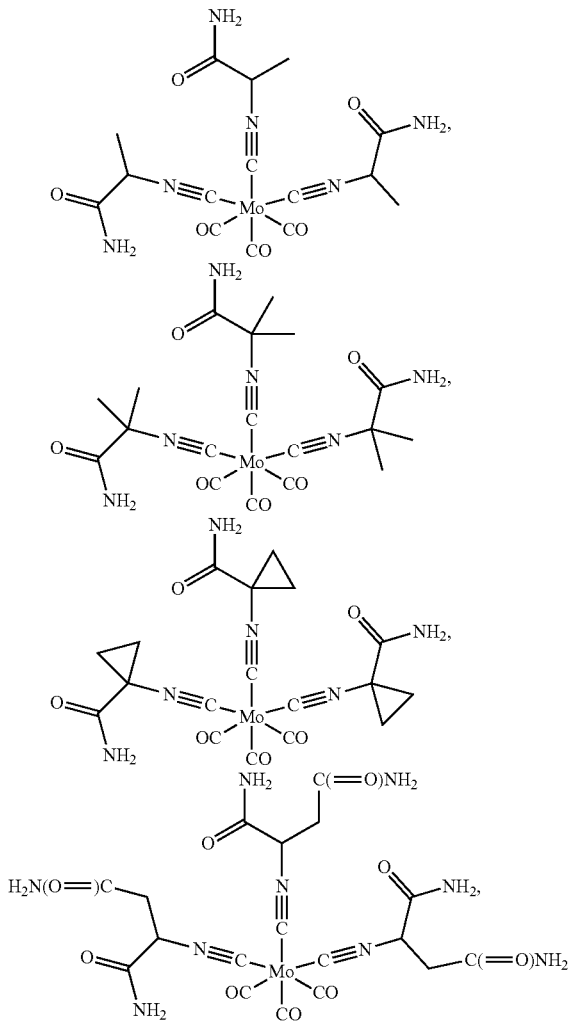

and salts, solvates, and hydrates thereof, and combinations thereof.

Methods of Preparation

Provided are methods of making compounds of the present disclosure, i.e., compounds of the Formula (I), (II), and (III).

For example, in one aspect, provided is a method of preparing a compound of the Formula (II):

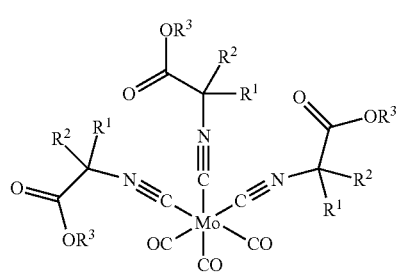
(II)

or a salt, solvate, or hydrate thereof, or a combination thereof; wherein $R^1$, $R^2$, and $R^3$ are as defined herein;

the method comprising reacting a molybdenum tri-CO complex with an isocyanide of the formula:

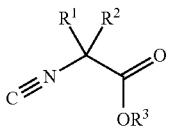

wherein $R^1$, $R^2$, and $R^3$ are as described herein; to provide a compound of the Formula (II).

In certain embodiments, the molybdenum tri-CO complex is of the formula:

$$Mo(CO)_3L_3$$

wherein $L_3$ represents either three monodentate ligands, one bidentate ligand and one monodentate ligand, or one tridentate ligand.

Exemplary monodentate ligands include, but are not limited to, CO, organonitriles (e.g., $CH_3CN$, $CH_3CH_2CN$), monosubstituted amines, disubstituted amines, trisubstituted amines, heterocyclyls (e.g., pyridine, piperidine), dialkylcyanamides, triphenylphosphine oxide, THF, DMF, or NMF.

Exemplary bidentate ligands include, but are not limited to, 1,5-cyclooctadiene, norbornadiene, 1,2-ethylenediamine, tetramethylethylenediamine, 1,2-dimethoxyethane, diglyme, or 2,5-dithiahexane.

Exemplary tridentate ligands include, but are not limited to, conjugated cyclic triene (e.g., cycloheptatriene), conjugated acyclic triene, arenes (e.g., benzene, toluene, xylene, mesitylene, naphthalene), tetraazamacrocyles (e.g., tetraazacyclododecane), polyamines (e.g., diethylenetriamine), and trithiocylononane.

In certain embodiments, the molybdenum tri-CO complex is of the formula:

$$Mo(CO)_3L_3$$

wherein $L_3$ represents either three monodentate ligands. In certain embodiments, the three monodentate ligands are CO ligands. In certain embodiments, the three monodentate ligands are organonitrile ligands.

In certain embodiments, the molybdenum tri-CO complex is of the formula:

$$Mo(CO)_3L_3$$

wherein $L_3$ represents one bidentate ligand and one monodentate ligand.

In certain embodiments, the molybdenum tri-CO complex is of the formula:

$$Mo(CO)_3L_3$$

wherein $L_3$ represents one tridentate ligand. In certain embodiments, the tridentate ligand is a cyclic triene. In certain embodiments, the cyclic triene is cycloheptatriene.

In certain embodiments, the molybdenum tri-CO complex is:

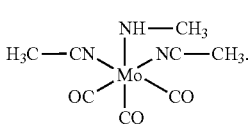

In certain embodiments, the molybdenum tri-CO complex is:

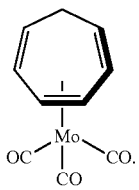

In yet another aspect, provided is a method of preparing a compound of the Formula (I):

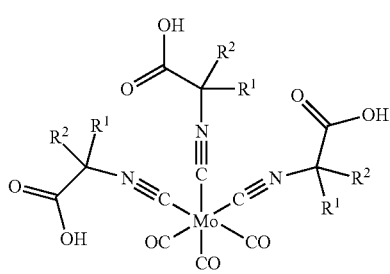

or a solvate or hydrate thereof, or a combination thereof; wherein $R^1$ and $R^2$ are as defined herein; the method comprising hydrolyzing a compound of Formula (II) to provide a compound of the Formula (I).

In certain embodiments, the step of hydrolyzing comprises an acid. In certain embodiments, the acid is an acid catalyst.

In certain embodiments, the step of hydrolyzing comprises a base. In certain embodiments, the base is a base catalyst. In certain embodiments, the base is an inorganic base. In certain embodiments, the base is a hydroxide. Exemplary hydroxides include NaOH, KOH, and LiOH.

In certain embodiments the step of hydrolyzing comprises an enzyme. In certain embodiments the enzyme is a carboxyesterase. In certain embodiments the enzyme is a lipase.

Chemically coupling the carboxylic acid with an amine (e.g., of the formula $HN(R^4)_2$) or alcohol (e.g., of the formula $HOR^3$) may employ methods well-known in the art; see, e.g., Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3th Edition, Cambridge University Press, Cambridge, 1987, for examples of reaction conditions useful in these types of chemical conversions.

For example, in one aspect, provided is a method of preparing a compound of the Formula (III):

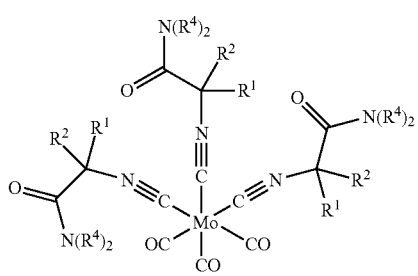

or a solvate or hydrate thereof, or a combination thereof; wherein $R^1$, $R^2$, and $R^4$ are as defined herein; the method comprising coupling an amine of the formula $HN(R^4)_2$ and a compound of Formula (I) to provide a compound of the Formula (III).

In certain embodiments, the step of coupling comprises contacting the compound of the Formula (I) and the amine of the formula $HN(R^4)_2$ with a peptide coupling agent.

Pharmaceutical Compositions

In certain embodiments, the present disclosure provides a pharmaceutical composition comprising a compound of the present disclosure or a salt, ester, amide, solvate, or hydrate thereof, or combination thereof, and a pharmaceutically acceptable excipient. In certain embodiments, the compound of the present disclosure or a pharmaceutically acceptable salt thereof is provided in an effective amount in the pharmaceutical composition.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present disclosure (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the disclosure will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the compounds of the disclosure are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the compounds of the instant disclosure with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of the instant disclosure may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the disclosure can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the disclosure formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the disclosure. Another formulation suitable for intranasal administration is a coarse powder comprising the active ingredient and having an average particle size from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the disclosure can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the disclosure can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this disclosure.

Compounds provided herein are typically formulated in dosage unit form for ease of administration and uniformity of dosage. It will be understood, however, that the total daily usage of the compositions of the present disclosure will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, the compounds of the disclosure may be administered orally or parenterally at dosage levels sufficient to deliver from about 0.001 mg/kg to about 200 mg/kg, 0.001 mg/kg to about 150 mg/kg, 0.001 mg/kg to about 100 mg/kg, 0.001 mg/kg to about 50 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Still further encompassed by the disclosure are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Optionally, a single container may comprise one or more compartments for containing an inventive pharmaceutical composition or compound, and/or a pharmaceutically acceptable excipient for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A kit may thus comprise such multi-compartment containers providing an inventive pharmaceutical composition or compound and one or more pharmaceutically acceptable excipients.

Optionally, instructions for use are additionally provided in such kits of the disclosure. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with an additional therapeutic agent.

Methods of Treatment and Use

The present disclosure is based at least in part on the discovery that compounds of the Formula (I) release an effective amount of carbon monoxide (CO) preferentially in the liver. These compounds also display anti-inflammatory activity and regenerative activity in the liver.

Thus, in one aspect, provided is a method of treating liver disease in a subject in need thereof, the method comprising administering an effective amount of a compound of Formula (I), or a salt, ester, amide, solvate, or a hydrate thereof, or a combination thereof, to treat the liver disease.

In another aspect, provided is a method of treating liver disease in a subject in need thereof, the method comprising instructing the subject to take an effective amount of a compound of Formula (I), or a salt, ester, amide, solvate, or a hydrate thereof, or a combination thereof, to treat the liver disease.

In another aspect, provided is a compound of Formula (I) for use in treating liver disease.

In certain embodiments, the method or use is a therapeutic treatment, and the effective amount is a therapeutically effective amount. In other embodiments, the method or use is a prophylactic treatment, and the effective amount is a prophylactically effective amount.

Exemplary liver diseases include, but are not limited to, drug-induced liver injury (e.g., acetaminophen-induced liver injury), hepatitis (e.g., chronic hepatitis, viral hepatitis, alcohol-induced hepatitis, autoimmune hepatitis, steatohepatitis), non-alcoholic fatty liver disease, alcohol-induced liver disease (e.g., alcoholic fatty liver, alcoholic hepatitis, alcohol-related cirrhosis), liver cirrhosis, liver cancer, primary biliary cirrhosis, cholestatis, cystic disease of the liver, and primary sclerosing cholangitis.

In certain embodiments, the liver disease is drug-induced liver injury. In certain embodiments, the drug induced liver injury is acetaminophen-induced liver injury.

In certain embodiments, the liver disease causes liver cell death in the subject. In certain embodiments, the administration of the compound stimulates liver cell regeneration in the subject.

In certain embodiments, the method further comprises administering an additional therapeutic agent. In certain embodiments, the additional therapeutic agent is N-acetyl-cysteine (NAC).

In certain embodiments the liver disease is associated with inflammation.

In another aspect, provided is a method of treating an inflammatory disease in a subject in need thereof, the method comprising administering an effective amount of a compound of Formula (I), or a salt, ester, amide, solvate, or a hydrate thereof, or a combination thereof, to treat the inflammatory disease.

In another aspect, provided is a method of treating an inflammatory disease in a subject in need thereof, the method comprising instructing the subject to take an effective amount of a compound of Formula (I), or a salt, ester, amide, solvate, or a hydrate thereof, or a combination thereof, to treat the inflammatory disease.

In another aspect, provided is a compound of Formula (I) for use in treating an inflammatory disease.

In certain embodiments, the method or use is a therapeutic treatment, and the effective amount is a therapeutically effective amount. In other embodiments, the method or use is a prophylactic treatment, and the effective amount is a prophylactically effective amount.

Exemplary inflammatory diseases include, but are not limited to, inflammation associated with asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder [e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD), Crohn's disease, Behcet's syndrome, colitis (e.g., ulcerative colitis, collagenous colitis, lymphocytic colitis, ischaemic colitis, diversion colitis, indeterminate colitis, microscopic colitis, chemical colitis, infectious colitis, fulminant colitis), and inflammatory bowel syndrome (IBS)], lupus, multiple sclerosis, morphea, myeasthenia gravis, myocardial ischemia, nephrotic syndrome, pemphigus vulgaris, pernicious anaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In some preferred embodiments, the inflammatory disorder is colitis.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

The terms "treat," "treating" and "treatment" contemplate an action that occurs while a subject is suffering from a disease, disorder or condition which reduces the severity of the disease, disorder or condition or retards or slows the progression of the disease, disorder or condition ("therapeutic treatment"), and also contemplates an action that occurs before a subject begins to suffer from the disease, disorder or condition and which inhibits or reduces the severity of the disease, disorder or condition ("prophylactic treatment").

In general, the "effective amount" of a compound refers to an amount sufficient to elicit the desired biological response, i.e., treating the disease, disorder or condition. As will be appreciated by those of ordinary skill in this art, the effective amount of a compound of the disclosure may vary depending on such factors as the desired biological endpoint, the pharmacokinetics of the compound, the disease being treated, the mode of administration, and the age, health, and condition of the subject. An effective amount encompasses therapeutic and prophylactic treatment.

A "therapeutically effective amount" of a compound is an amount sufficient to provide a therapeutic benefit in the treatment of disease, disorder or condition or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

A "prophylactically effective amount" of a compound is an amount sufficient to prevent the disease, disorder or condition, or one or more symptoms associated with the disease, disorder or condition or prevent its recurrence. A prophylactically effective amount of a compound means an amount of the compound, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

EXAMPLES

In order that the disclosure described herein may be more fully understood, the following examples are set forth. It should be understood that these examples are for illustrative purposes only and are not to be construed as limiting this disclosure in any manner.

Example 1

Preparation of Mo Complexes

Synthesis of $Mo(CO)_3(\eta^6\text{-}C_7H_8)$

The preparation of the molybdenum tri-CO complex $Mo(CO)_3(\eta^6\text{-}C_7H_8)$ is described in the literature (see, e.g., W. A. Herrmann and A. Salzer, *Synthetic Methods of Organometallic and Inorganic Chemistry*, volume 1, Georg Thieme Verlag, New York, 1996, p 129; and Abel et al., *J. Chem. Soc.* (1958) 4559).

Preparation of Tricarbony[tris(isocyanoacetic acid)]Mo(0) (1-b)

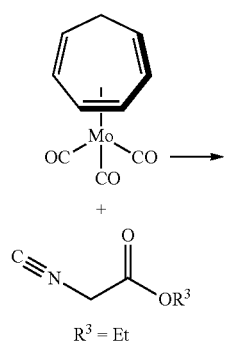

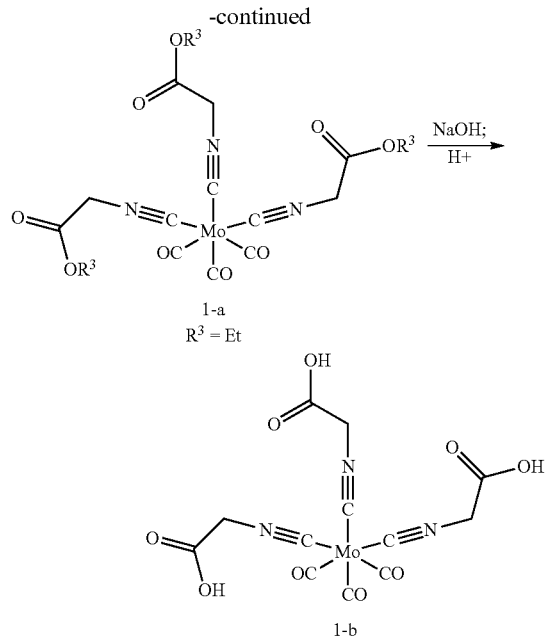

Preparation of tricarbonyl[tris(isocyanoacetic acid ethyl ester)]Mo(0) (1-a): $Mo(CO)_3(\eta^6\text{-}C_7H_8)$ (2.1 g; 7.72 mmol; 272.1117 g/mol) was dissolved in 40 mL of MeOH to give a red, slightly turbid solution. $CNCH_2CO_2Et$ (3 eq.; 2.53 mL; 23.15 mmol; 113.11 g/mol; 1.035 g/mL) was dissolved in 20 mL MeOH and added to the previous solution. The red solution immediately turned darker, greenish, and gradually became lighter. The solution was stirred at room temperature for 45 min, when a TLC analysis (hexane:ethyl acetate 1:3) showed that $(Mo(CO)_3(\eta^6\text{-}C_7H_8))$ had been completely consumed. The mixture was filtered to remove some fine black powder giving a dark red solution that was taken to dryness yielding a dark oil. The oil was immediately loaded onto a silica column equilibrated in hexane. The column was eluted with hexane (approx 1-2 column volumes) then the product was eluted with hexane:ethyl acetate (6:4). TLC analysis of the product fraction showed it to be a mixture of two well separated compounds. The mixture was again chromatographed using the same eluent and collecting smaller fractions. The major product eluted second; it was collected and taken to dryness affording an off-white powder, compound (1-a). $C_{18}H_{21}N_3O_9Mo$ (519.31 g/mol). Yield: 55% (Batch No. 2) and 64% (Batch No. 4).

Characterization of (1-a): Elemental Analysis: Calculated for $C_{18}H_{21}N_3O_9Mo$: % C, 41.63; % H, 4.07; % N, 8.09; Batch No. 2 Found: % C, 41.00; % H, 4.08; % N, 8.24. IR (KBr): Bands (C=O): 1941(s); 1873(s); Bands (C=O): 1749(s); Bands (C≡N): 2181(s); 2135(s). $^1$H-NMR (CDCl$_3$, 400 MHz, rt, δ in ppm): δ=4.37 (s, 2H), 4.27 (q, 2H), 1.32 (t, 3H). $^{13}$C-NMR (CDCl$_3$, 100 MHz, rt, δ in ppm): δ=211.9 (C≡O), 167.72 (CN), 164.87 (C=O), 62.74 (CNCH$_2$CO), 45.53 (CO CH$_2$CH$_3$), 14.15 (COCH$_2$CH$_3$).

Preparation of tricarbonyl[tris(isocyanoacetic acid)]Mo(0) (1-b): Compound (1-a) (0.250 g, 0.48 mmol, 519.31 g/mol) was dissolved in anhydrous THF (20 mL), and an aqueous solution of sodium hydroxide (16 equivalents, 8.0 mmol, 0.32 g, 8 mL) was added dropwise. The solution became turbid and was left stirring at room temperature under nitrogen. After 24 hours, TLC (hexane:ethyl acetate, 6:4) indicated complete consumption of starting material (R$_f$ 0.2). The mixture was concentrated and re-dissolved in water (20 mL). Hydrochloric acid (1 M) was then added dropwise (~6 mL-until pH~3 and beginning of precipitation) and a white precipitate formed. The precipitate was filtered and washed with cold water. The off-white compound was dried in vacuo to provide compound (1-b). $C_{12}H_9O_9N_3Mo$ (435.1583 g/mol). Yield: 100%.

Characterization of (1-b): Elemental Analysis: Calculated for $C_{12}H_9O_9N_3Mo$: % C, 33.12; % H, 2.08; % N, 9.66; Batch No. 2 Found: % C, 32.40; % H, 2.12; % N, 9.86; Batch No. 3 Found: % C, 30.50; % H, 2.12; % N, 9.13; Calculated for $MoC_{12}H_9N_3O_9.(NaCl)_{0.6}$% C, 30.65; % H, 1.93; % N, 8.94. IR (KBr): Bands (C=O): 1941(s); 1849(s); Bands (C=O): 1720(s); Bands (C≡N): 2195(s); 2159(s). $^1$H-NMR ($D_2O$, 400 MHz, rt, δ in ppm): δ=4.52 (s, 2H). $^1$H-NMR ($d^6$-DMSO, 400 MHz, rt, δ in ppm): δ=4.64 (s, 2H). $^{13}$C-NMR ($d^6$-DMSO, 100 MHz, rt, δ in ppm): δ=213.9 (C=O), 166.25 (CN), 159.9 (CO), 45.90 (CNCH$_2$). $^{13}$C-NMR ($d^6$-acetone, 100 MHz, rt, δ in ppm): δ=214.4 (C=O), 167.52 (CN), 163.81 (CO), 46.10 (CNCH$_2$).

Preparation of Tricarbonyl[tris(2-isocyanopropionic acid)]Mo(0) (2-b)

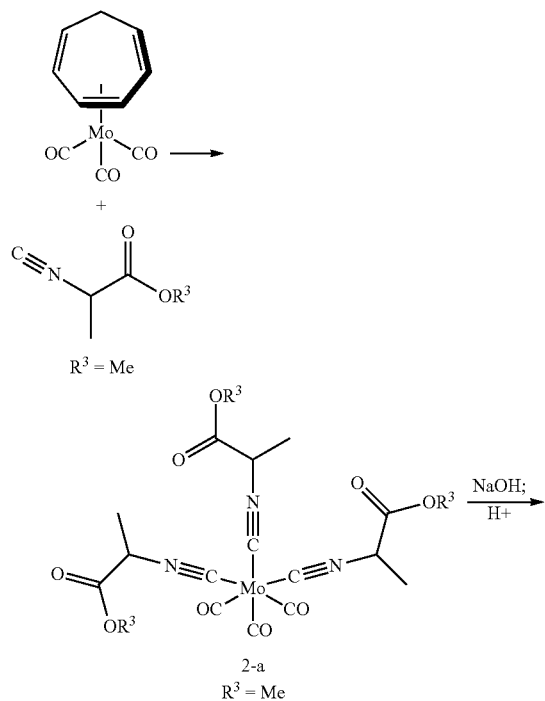

Preparation of tricarbonyl[tris(2-isocyanopropionic acid methyl ester)]Mo(0) (2-a): ($\eta^6$-$C_7H_8$)Mo(CO)$_3$ (0.383 g; 1.41 mmol; 272.11 g/mol) was dissolved in 30 mL of MeOH and CNCH(CH$_3$)CO$_2$Me (3 equiv.; 0.4784 g; 4.23 mmol; 113.12 g/mol), dissolved in 10 mL of MeOH, was slowly added. The dark red suspension turned orange-brown and was stirred at room temperature during 1 h. The solution was taken to dryness, giving an orange oil, which was applied onto a silica column equilibrated in hexane. It was eluted with hexane and then ethyl acetate/hexane 4:6. Fractions were pooled based on TLC analysis. The product solution was taken to dryness giving a green oil, compound (2-a). $C_{18}H_{21}N_3O_9Mo$ (519.3186 g/mol). Yield: 0.3677 g, (50%). Batch No. 2 was prepared analogously giving a yield of 63%.

Characterization of (2-a): IR(CHCl$_3$): Bands (C=O): 1948(s); 1887(br, s); Bands (C=O): 1746(s); Bands (C≡N): 2103(s). $^1$H-NMR (CDCl$_3$, 400 MHz, rt, δ in ppm): δ=4.49 (q, 1H), 3.82 (s, 3H), 1.66 (d, 3H).

Preparation of tricarbonyl[tris(2-isocyanopropionic acid)]Mo(0) (2-b): Compound (2a) (0.3677 g; 7.08×10$^{-4}$ mol; 519.3186 g/mol) was dissolved in 20 mL of THF and placed in an ice bath. NaOH (10 equiv.; 0.283 g; 7.08 mmol; 40 g/mol) was dissolved in 5 mL of H$_2$O and slowly added to the previous solution. The solution was stirred for 4 h while it slowly warmed to room temperature. It was then taken to dryness giving a white powder. The solid was dissolved in water and hydrochloric acid (1 M) was added until the pH reached 1 to provide a white precipitate, compound (2-b) which was collected by filtration and washed with cold water. $C_{15}H_{15}N_3O_9Mo$ (477.2382 g/mol). Yield: 96%.

Characterization of (2-b): Elemental Analysis: Calculated for $C_{15}H_{15}N_3O_9Mo.0.5NaCl$: % C: 35.57; % H: 2.98; % N: 8.30; Batch No. 1 Found: % C, 35.35; % H, 3.19; % N, 8.55. IR (KBr): Bands (C=O): 1920(s); 1867(br, s); Bands (C=O): 1729(s); Bands (C≡N): 2170(s); 2123(s). $^1$H-NMR (CD$_3$COCD$_3$, 400 MHz, rt, δ in ppm): δ=4.78 (q, 1H), 1.67 (d, 3H).

Preparation of Tricarbonyl[tris(2-isocyano-2-methyl-propionic acid methyl ester)]Mo(0) (3-a)

Method A

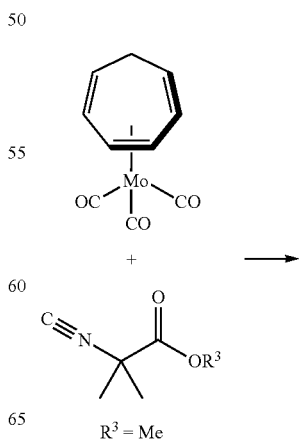

-continued

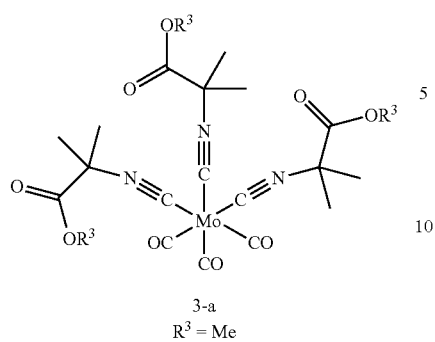

3-a
R³ = Me

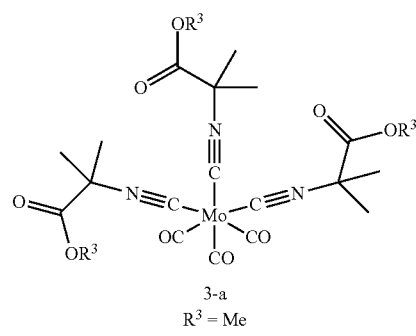

3-a
R³ = Me

Methyl 2-isocyano-2-methylpropanoate (3.068 g; 24.127 mmol; 127.14 g/mol) was dissolved in 65 mL of THF. ($\eta^6$-$C_7H_8$)Mo(CO)$_3$ (⅓ equiv.; 2.2 g; 8.085 mmol; 272.11 g/mol) was slowly added, in portions as a solid. An orange-red, slightly turbid solution was obtained. This was stirred at room temperature (22-23° C.) and 500 rpm. TLC analysis in ethyl acetate:hexane (1:1) after 30 min showed one main spot with Rf 0.65 (revealed with ceric ammonium molybdate), and another small spot with Rf 0.9 that didn't color with ceric ammonium molybdate. After 1 h reaction time, TLC analysis showed only one major spot with Rf 0.65. The solution was concentrated and a precipitate was formed when half of the solvent was evaporated. The solution was further concentrated almost to dryness (ca. 5 mL remaining) and Et$_2$O (45 mL) was added. The resulting precipitate was filtered and washed with 2×15 mL of Et$_2$O to provide a beige powder, compound (3-a). Yield: 4.22 g (93.0%) (MW=561.3939 g/mol).

Characterization of compound (3-a): Elemental Analysis: Calculated for MoC$_{21}$H$_{27}$N$_3$O$_9$: % C, 44.92; % H, 4.85; % N, 7.48. Found: % C, 44.70; % H, 5.05; % N, 7.61. $^1$H-NMR (CDCl$_3$, 400 MHz, rt, δ in ppm; 10 mg/600 μL): δ=3.82 (s, 3H)OC$\underline{H}_3$, 1.68 (s, 6H) C(C$\underline{H}_3$)$_2$. $^{13}$C-NMR (100.6 MHz, CDCl$_3$, rt, δ in ppm, 10 mg/600 μL): 212.66 ($\overline{C}$═O); 170.82 ($\overline{C}$═N); 166.68 ($\underline{C}$═O); 61.16 (C$_{quat}$); 53.52 (O$\underline{C}$H$_3$); 27.81 (2×$\overline{C}$H$_3$). IR (0.4 mg/280 mg KBr): Bands (C═O): 1932(s), 1873(sh), 1860(s); Bands (C═O): 1749 and 1742(m, split); Bands (C═N): 2168(m), 2124 and 2111(m, split). IR (0.5 mg/mL CHCl$_3$): Bands (C═O): 1944(s), 1888(s); Bands (C═O): 1744(m); Bands (C═N): 2152(w), 2090(m).

Method B

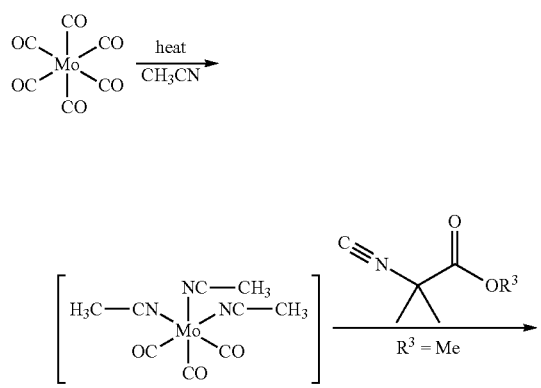

The following alternative preparation was adapted from Achatz et al., *Anorg. Allg. Chem* (2005) 631:2339-2346, where Mo(CO)$_3$(NCMe)$_3$ is formed and used in situ.

Mo(CO)$_6$ (0.6 g; 2.27 mmol; 264 g/mol) was heated to reflux in CH$_3$CN for 20 hours. After cooling to room temperature, 1 g (3.5 eq.) CNC(CH$_3$)$_2$CO$_2$Me was added and the reaction was stirred at room temperature for another 20 hours and at 55° C. for 5 hours. The solvent was evaporated under vacuum and the residue was washed with ethyl acetate/hexane (2:3) and the black residue was chromatographed over silica gel with dichloromethane to give 250 mg of compound (3-a). Yield: 21%.

TABLE 1

Figure 3A:
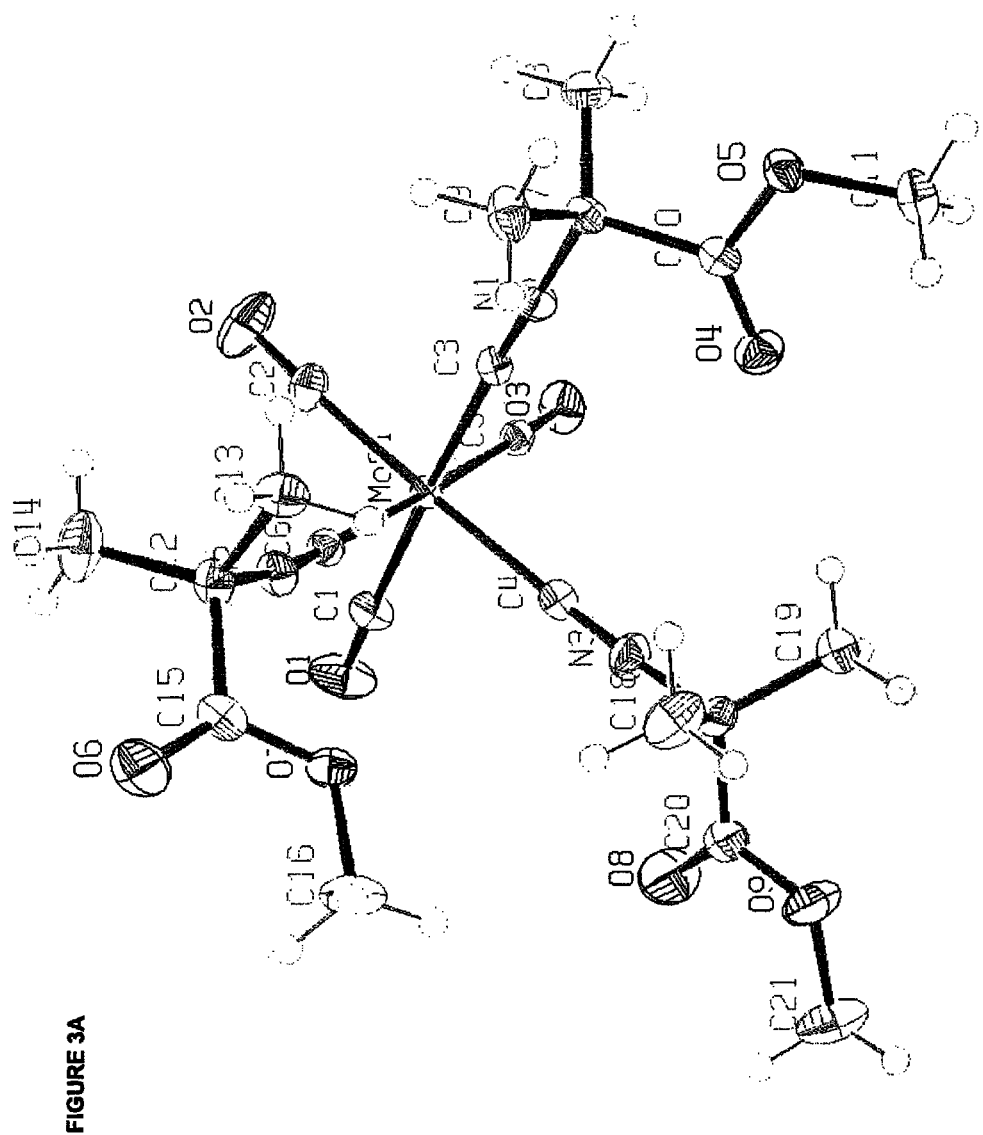
FIGS. 3A-3B.
Figure 3B:
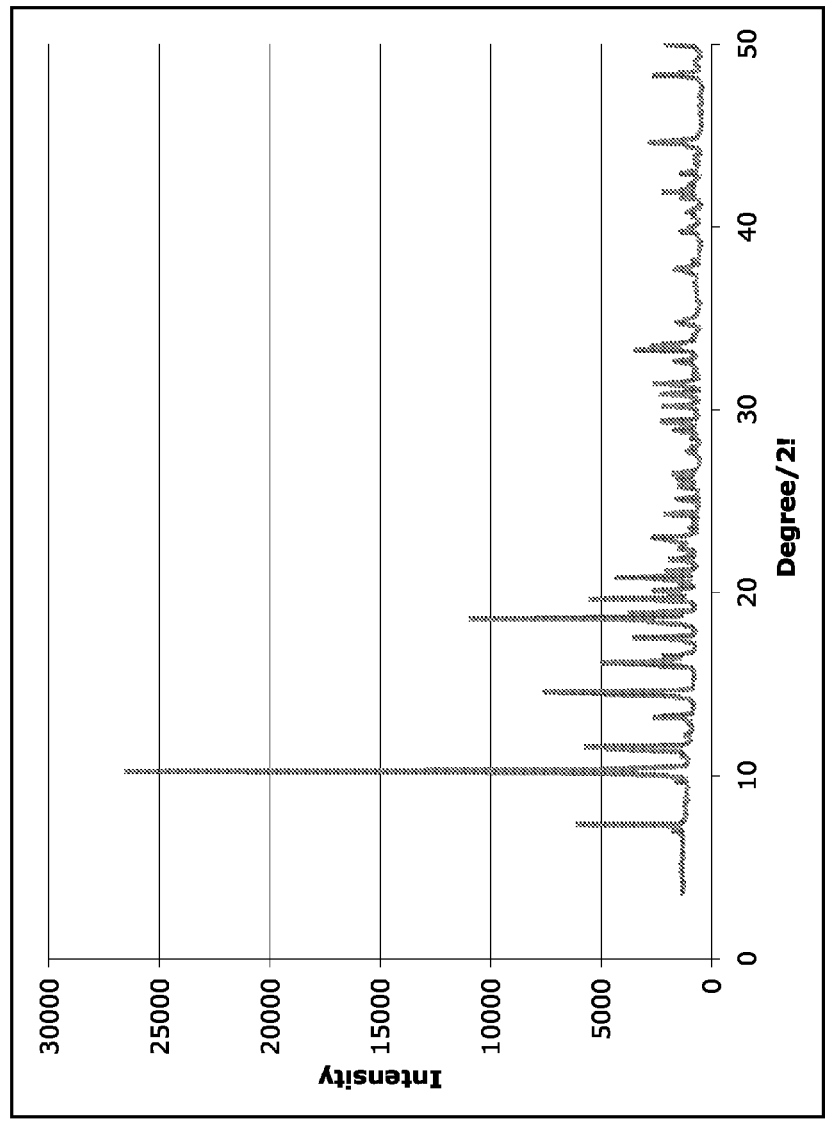

X-ray Powder Diffraction data for Compound 3a
(spectra provided in FIG. 3B)

| Pos. [°2Th.] | Height [cts] | FWHM [°2Th.] | d-spacing [Å] | Rel. Int. [%] | Tip width [°2Th.] |
| --- | --- | --- | --- | --- | --- |
| 7.0301 | 1086.94 | 0.2319 | 12.57423 | 4.97 | 0.2783 |
| 7.3100 | 4729.63 | 0.1181 | 12.09333 | 21.62 | 0.1417 |
| 9.7404 | 842.89 | 0.0634 | 9.08068 | 3.85 | 0.0761 |
| 10.2522 | 21880.08 | 0.1181 | 8.62851 | 100.00 | 0.1417 |
| 10.5961 | 1578.50 | 0.4069 | 8.34923 | 7.21 | 0.4883 |
| 11.1690 | 803.13 | 0.0748 | 7.92216 | 3.67 | 0.0897 |
| 11.5561 | 5718.57 | 0.1949 | 7.65770 | 26.14 | 0.2339 |
| 11.5823 | 4312.47 | 0.2362 | 7.64044 | 19.71 | 0.2834 |
| 11.9561 | 65.64 | 0.0900 | 7.40239 | 0.30 | 0.1080 |
| 12.2441 | 301.11 | 0.1181 | 7.22888 | 1.38 | 0.1417 |
| 12.8761 | 196.44 | 0.0900 | 6.87548 | 0.90 | 0.1080 |
| 13.2278 | 1664.17 | 0.1181 | 6.69341 | 7.61 | 0.1417 |
| 14.1561 | 1221.10 | 0.0010 | 6.25654 | 5.58 | 0.0012 |
| 14.5561 | 14614.87 | 0.1423 | 6.08550 | 66.80 | 0.1707 |
| 14.5913 | 6264.68 | 0.2362 | 6.07086 | 28.63 | 0.2834 |
| 15.8761 | 2170.69 | 0.0010 | 5.58238 | 9.92 | 0.0012 |
| 16.1858 | 4203.96 | 0.1181 | 5.47624 | 19.21 | 0.1417 |
| 16.4267 | 1503.52 | 0.3431 | 5.39646 | 6.87 | 0.4117 |
| 16.5692 | 1233.75 | 0.1181 | 5.35039 | 5.64 | 0.1417 |
| 16.7961 | 918.22 | 0.4154 | 5.27862 | 4.20 | 0.4984 |
| 17.2361 | 836.42 | 0.0010 | 5.14485 | 3.82 | 0.0012 |
| 17.5515 | 2770.11 | 0.1181 | 5.05308 | 12.66 | 0.1417 |
| 18.1161 | 803.92 | 0.0010 | 4.89687 | 3.67 | 0.0012 |
| 18.6117 | 10181.39 | 0.1181 | 4.76756 | 46.53 | 0.1417 |
| 18.9242 | 3006.51 | 0.1181 | 4.68954 | 13.74 | 0.1417 |
| 19.6593 | 4402.52 | 0.1181 | 4.51582 | 20.12 | 0.1417 |
| 20.0361 | 1744.89 | 0.1026 | 4.43174 | 7.97 | 0.1231 |

TABLE 1-continued

X-ray Powder Diffraction data for Compound 3a
(spectra provided in FIG. 3B)

| Pos. [°2Th.] | Height [cts] | FWHM [°2Th.] | d-spacing [Å] | Rel. Int. [%] | Tip width [°2Th.] |
|---|---|---|---|---|---|
| 20.1394 | 1868.29 | 0.1181 | 4.40923 | 8.54 | 0.1417 |
| 20.5782 | 1082.94 | 0.0617 | 4.31262 | 4.95 | 0.0740 |
| 20.5961 | 1956.44 | 0.0010 | 4.31963 | 8.94 | 0.0012 |
| 20.8445 | 3487.36 | 0.1574 | 4.25812 | 15.94 | 0.1889 |
| 21.1916 | 1379.14 | 0.1181 | 4.18917 | 6.30 | 0.1417 |
| 21.8365 | 1274.91 | 0.1181 | 4.06688 | 5.83 | 0.1417 |
| 22.1161 | 358.84 | 0.0900 | 4.01609 | 1.64 | 0.1080 |
| 22.4411 | 804.84 | 0.1574 | 3.95866 | 3.68 | 0.1889 |
| 22.6781 | 928.98 | 0.3323 | 3.91782 | 4.25 | 0.3988 |
| 23.0189 | 2058.35 | 0.1181 | 3.86058 | 9.41 | 0.1417 |
| 23.5656 | 379.02 | 0.1181 | 3.77224 | 1.73 | 0.1417 |
| 23.9315 | 225.32 | 0.1181 | 3.71538 | 1.03 | 0.1417 |
| 24.3088 | 1283.09 | 0.1574 | 3.65856 | 5.86 | 0.1889 |
| 25.1256 | 966.15 | 0.1574 | 3.54145 | 4.42 | 0.1889 |
| 25.8356 | 801.00 | 0.1574 | 3.44572 | 3.66 | 0.1889 |
| 26.2350 | 863.64 | 0.1181 | 3.39415 | 3.95 | 0.1417 |
| 26.5574 | 1002.35 | 0.1181 | 3.35367 | 4.58 | 0.1417 |
| 27.7020 | 511.31 | 0.1574 | 3.21765 | 2.34 | 0.1889 |
| 27.9561 | 352.11 | 0.0900 | 3.18899 | 1.61 | 0.1080 |
| 28.4762 | 368.84 | 0.1574 | 3.13191 | 1.69 | 0.1889 |
| 28.8820 | 800.58 | 0.1574 | 3.08882 | 3.66 | 0.1889 |
| 29.3887 | 1651.43 | 0.1574 | 3.03671 | 7.55 | 0.1889 |
| 29.8361 | 146.46 | 0.0900 | 2.99219 | 0.67 | 0.1080 |
| 30.2165 | 1040.25 | 0.1574 | 2.95537 | 4.75 | 0.1889 |
| 30.8992 | 1213.52 | 0.1574 | 2.89161 | 5.55 | 0.1889 |
| 31.1561 | 969.14 | 0.0010 | 2.86836 | 4.43 | 0.0012 |
| 31.4427 | 1953.63 | 0.1574 | 2.84286 | 8.93 | 0.1889 |
| 31.9903 | 257.05 | 0.1574 | 2.79543 | 1.17 | 0.1889 |
| 32.3561 | 193.07 | 0.0900 | 2.76467 | 0.88 | 0.1080 |
| 32.6777 | 1161.21 | 0.1574 | 2.73818 | 5.31 | 0.1889 |
| 33.3123 | 2979.60 | 0.1181 | 2.68746 | 13.62 | 0.1417 |
| 33.5452 | 2099.09 | 0.5730 | 2.66933 | 9.59 | 0.6876 |
| 33.9961 | 258.12 | 0.0900 | 2.63495 | 1.18 | 0.1080 |
| 34.7439 | 892.15 | 0.2362 | 2.57993 | 4.08 | 0.2834 |
| 34.7961 | 1482.26 | 0.0010 | 2.58258 | 6.77 | 0.0012 |
| 36.1400 | 187.16 | 0.1574 | 2.48340 | 0.86 | 0.1889 |
| 36.9215 | 285.89 | 0.1968 | 2.43262 | 1.31 | 0.2362 |
| 37.5161 | 553.76 | 0.0900 | 2.39542 | 2.53 | 0.1080 |
| 37.7521 | 1047.46 | 0.1574 | 2.38098 | 4.79 | 0.1889 |
| 38.1617 | 310.89 | 0.1574 | 2.35636 | 1.42 | 0.1889 |
| 39.3561 | 135.20 | 0.0900 | 2.28756 | 0.62 | 0.1080 |
| 39.7513 | 928.26 | 0.1181 | 2.26572 | 4.24 | 0.1417 |
| 39.9754 | 618.59 | 0.1181 | 2.25353 | 2.83 | 0.1417 |
| 40.5647 | 358.12 | 0.1574 | 2.22214 | 1.64 | 0.1889 |
| 40.8789 | 527.11 | 0.1574 | 2.20579 | 2.41 | 0.1889 |
| 41.6261 | 857.01 | 0.1181 | 2.16790 | 3.92 | 0.1417 |
| 41.9554 | 1396.25 | 0.1574 | 2.15164 | 6.38 | 0.1889 |
| 42.3427 | 568.09 | 0.1181 | 2.13286 | 2.60 | 0.1417 |
| 42.9455 | 868.03 | 0.1574 | 2.10430 | 3.97 | 0.1889 |
| 43.5161 | 273.05 | 0.0900 | 2.07803 | 1.25 | 0.1080 |
| 43.8132 | 281.04 | 0.1968 | 2.06462 | 1.28 | 0.2362 |
| 44.3961 | 699.17 | 0.0900 | 2.03886 | 3.20 | 0.1080 |
| 44.6649 | 2250.52 | 0.1574 | 2.02721 | 10.29 | 0.1889 |
| 46.1282 | 117.20 | 0.1181 | 1.96625 | 0.54 | 0.1417 |
| 46.5849 | 80.29 | 0.2362 | 1.94803 | 0.37 | 0.2834 |
| 48.3071 | 1791.64 | 0.1440 | 1.88253 | 8.19 | 0.1728 |
| 49.0361 | 1.00 | 0.0900 | 1.85623 | 0.00 | 0.1080 |

Preparation of Tricarbonyl[tris(2-isocyano-2-methyl-propionic acid ethyl ester)]Mo(0) (3-c)

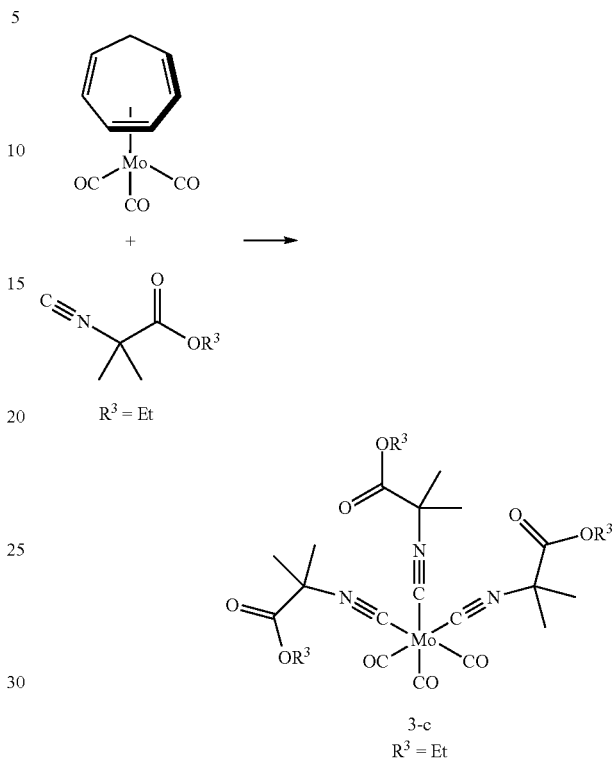

3-c
$R^3$ = Et $(\eta^6\text{-}C_7H_8)Mo(CO)_3$ (0.644 g; 2.37 mmol; 272.11 g/mol) was dissolved in 30 mL of MeOH and $CNC(CH_3)_2CO_2Et$ (3 equiv.; 0.903 g; 6.40 mmol; 141.17 g/mol), dissolved in 10 mL of MeOH was slowly added. The dark red solution turned orange-brown and was stirred at room temperature for 2.5 hours. The solution was concentrated and diethyl ether was added, but no precipitate formed, therefore the solution was evaporated to dryness. IR analysis of the crude product mixture indicated that the desired product was contaminated with $Mo(CO)_4(CNC(CH_3)_2CO_2Et)_2$ (band at 2019 cm$^{-1}$). Therefore the mixture was separated by silica gel column chromatography. The column was first washed with hexane and then eluted with a mixture of hexane and ethyl acetate (8:2) to provide compound (3-c) as a greenish oil. Yield: 0.94 g (73%).

Characterization of compound (3-c): Elemental Analysis: Calculated for $C_{24}H_{33}N_3O_9Mo$: % C, 47.77; % H, 5.51; % N, 6.96. Found: % C, 47.70; % H, 5.20; % N, 6.63. IR (KBr): Bands (C═O): 1939(s); 1868(br, s); Bands (C═O): 1744(s); Bands (C═N): 2154(s); 2104 (s). $^1$H-NMR (CDCl$_3$, 400 MHz, rt, δ in ppm): δ=4.25 (q, 6H), 1.66 (s, 18H), 1.34 (t, 9H).

Preparation of Tricarbonyl[tris(2-isocyano-2-methyl-propionic acid)]Mo(0) (3b)

Following the procedure described by Beck and coworkers (Achatz et al., *Anorg. Allg. Chem* (2005) 631:2339-2346) saponification of compound (3-a) or (3-c) with NaOH followed by protonation with an acid (e.g., HCl or H$_2$SO$_4$) in aqueous solution led to the formation of tricarbonyl[tris(2-isocyano-2-methyl-propionic acid)]Mo(0) (3-b). Compound (3-b) is stable when stored in brown vials at ambient temperature under $N_2$ for over 6 months or more.

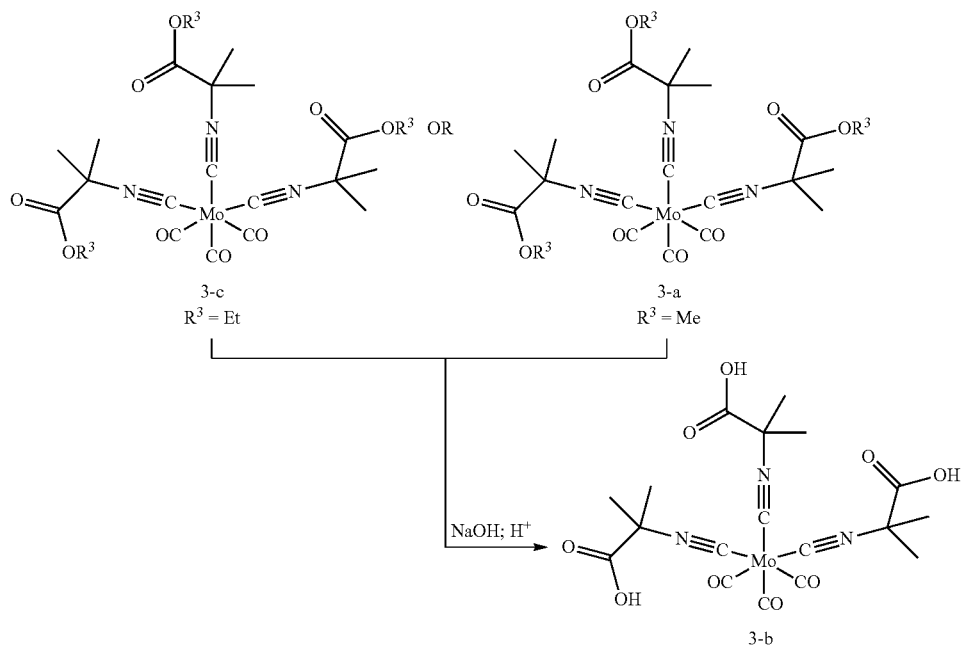

It was observed after the preparation of several batches that two sets of spectroscopic data were obtained for compound (3-b). The Type I product corresponds to the fully protonated tricarboxylic acid complex and the Type II product contains minor amounts of carboxylic acid sodium salt arising from a small degree of deprotonation (variable amounts 0.4-0.6 mol Na per mol Mo). Type II product can be converted into Type I by adding excess acid during the synthesis or through washing with acid at the end of the synthesis. The biological activity of the Type I and Type II products are the same. Type I and Type II products are recognized by the differences in their IR spectra (KBr) and $^{13}C$ NMR spectra. The overall composition and the facial stereochemistry of Compound (3-b) was confirmed by X-ray crystallography.

Preparation of Tricarbonyl[tris(2-isocyano-2-methyl-propionic acid)]Mo(0), (3-b) Type I

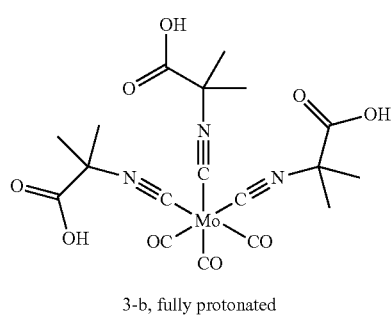

3-b, fully protonated

Method A

Compound (3-a) (1.914 g; 3.41 mmol; 561.3939 g/mol) was dissolved in 36 mL of THF and placed in an ice bath. NaOH (10 equiv.; 1.364 g; 34.1 mmol; 40 g/mol) was dissolved in 9 mL of $H_2O$ and slowly added to the previous yellow solution. A yellow, turbid solution was obtained, which was stirred for 1 hour while it slowly warmed to room temperature. A TLC analysis in hexane:ethyl acetate (1:1) showed only one spot with Rf 0 at the end of this time. The solvents were concentrated until all the THF was gone. Then, 27 mL of water were added, followed by 17.05 mL of 1M $H_2SO_4$ acid. A white precipitate formed, which then turned into a yellow oil. The water was evaporated until a white powder was reformed. After filtration, the pH of the colorless solution was 1. The solid was washed with 5×20 mL portions of water. The pH of the washing solutions was successively 3, 4, 4, 4 and 4. The final washed product was dried under vacuum. After drying at $1.0 \times 10^{-2}$ Torr for 30 h and at $2.0 \times 10^{-5}$ Torr for 9 h the IR spectrum (1.2 mg of compound (3-b) in 840 mg of KBr) and NMR (10 mg/600 μL of acetone-$d^6$) showed the complex was pure. Yield: 1.600 g (90.3%). $C_{18}H_{21}O_9N_3Mo$ (519.31 g/mol).

Characterization of compound (3-b), Type I. Elemental Analysis: Calculated for $C_{18}H_{21}O_9N_3Mo$: % C, 41.63; % H, 4.08; % N, 8.09. Found: C, 41.50; % H, 4.43; % N, 8.31. $^1$H-NMR ($CD_3COCD_3$, 400 MHz, rt, δ in ppm, 10 mg/600 μL): δ=1.71 (s, $CH_3$). $^{13}$C-NMR ($CD_3COCD_3$, 100.6 MHz, rt, δ in ppm, 10 mg/600 μL): 214.65 (C≡O); 171.37 (C≡N); 164.34 (C=O); 62.08 ($C_{quat}$); 27.85 (2×$CH_3$). IR (KBr): Bands (C≡O): 1925(s), 1875(s); 1841(sh), Bands (C=O): 1747(w, sh) and 1719(m), Bands (C≡N): 2157(m), 2110(s). IR($CHCl_3$): Bands (C≡O): 1942(s), 1882(s); Bands (C=O): 1737(w); Bands (C≡N): 2152(w), 2098(m).

Method B

A second method was developed to obtain type I, fully protonated complexes.

Compound (3-a) (1.01 g; 1.800 mmol; 561.3939 g/mol) was dissolved in 20 mL of THF giving a transparent yellow solution. This solution was placed in an ice bath and stirred for about 10 minutes. NaOH (10 equiv.; 0.722 g; 18.00 mmol; 40 g/mol) was dissolved in 5 mL of $H_2O$ (miliQ) and added dropwise. The yellow solution was stirred without removing the ice-bath. The solution became light-yellow and turbid. After 20 minutes, TLC analysis performed in hexane:ethyl acetate (1:1) showed complete consumption of starting material (Rf 0.8, stains blue with ceric ammonium molybdate) and a new spot at the starting point (stains strongly blue with ceric ammonium molybdate). After another hour, Dowex 50WX8-200 ion exchange resin (Ref. 217506; Exchange Capacity 1.7 meq/mL; 6 g) was added and the solution stirred for 10 minutes (the Dowex resin had been activated prior to use by dissolving it in 1M aqueous HCl and stirring for two hours, followed by filtration and washing with water until pH neutral). The Dowex resin was filtered off and the solution evaporated (bath temperature 30° C.) giving a white material and a gummy brown residue (the NMR in acetone showed some THF contamination). The next day, the crude (white material) was washed with water (2×30 ml). The suspension was allowed to rest and then filtered. The final pH of the washing solution was 2.6 (pH electrode). The white powder, compound (3b), Type I product, was dried in vacuum. Yield: 0.66 g (70%).

Characterization of compound (3-b), Type I. Elemental Analysis: Calculated for $C_{18}H_{21}O_9N_3Mo$: % C, 41.63; % H, 4.08; % N, 8.09. Found: % C, 41.30; % H, 4.23; % N, 8.05. $^1$H-NMR ($CD_3COCD_3$, 400 MHz, rt, δ in ppm, 10 mg/600 μL): δ=1.71 (s, $CH_3$). $^{13}$C-NMR ($CD_3COCD_3$, 100.6 MHz, rt, δ in ppm, 10 mg/600 μL): 214.70 (C≡O); 171.46 (C≡N); 164.22 (C=O); 62.10 ($C_{quat}$); 27.86 (2×$CH_3$). IR (KBr): Bands (C≡O): 1924(s), 1871(s); 1840(sh); Bands (C=O): 1747(w, sh) and 1721(m); Bands (C≡N): 2158(m), 2108(s). IR($CHCl_3$): Bands (C≡O): 1941(s), 1882(s); Bands (C=O): 1737(w); Bands (C≡N): 2153(w), 2099(m).

TABLE 2

Figure 4A:
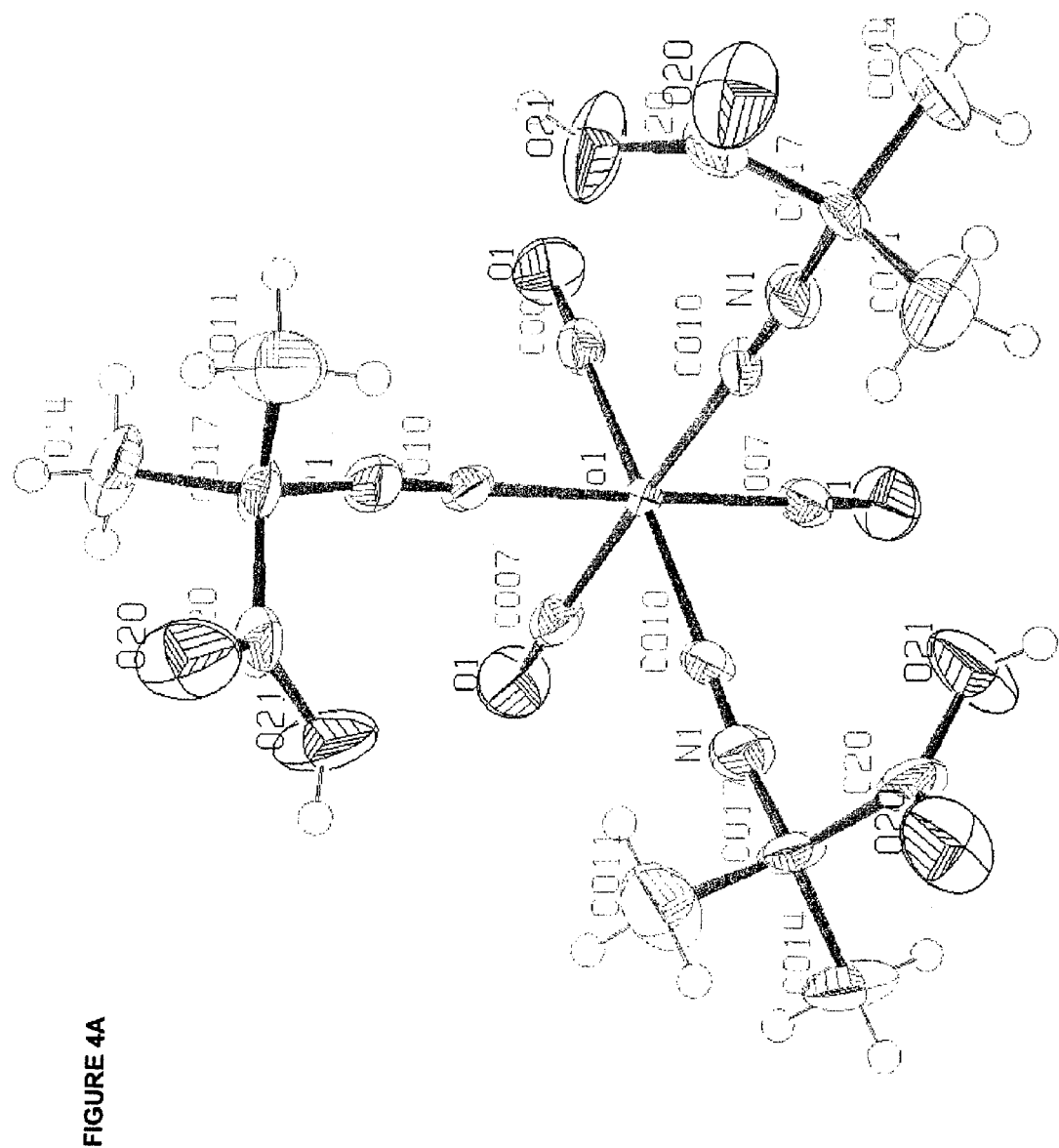
FIG. 4A-4G.
Figure 4B:
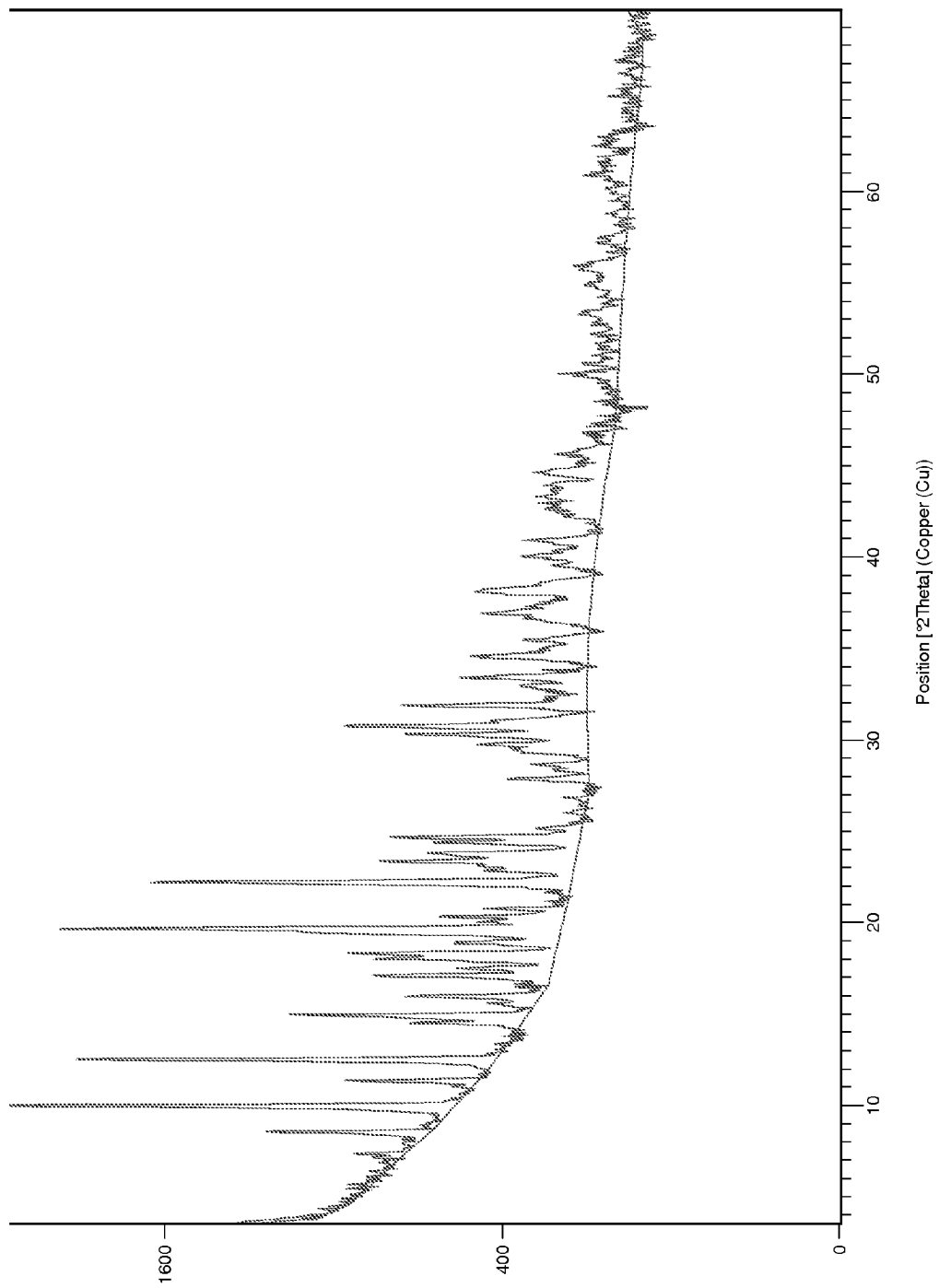

X-ray Powder Diffraction data for Compound 3b, Type I
(spectra provided in FIG. 4B)

| Pos. [°2Th.] | Height [cts] | FWHM [°2Th.] | d-spacing [Å] | Rel. Int. [%] | Tip width [°2Th.] |
|---|---|---|---|---|---|
| 7.3071 | 104.21 | 0.2362 | 12.09818 | 5.15 | 0.2834 |
| 8.5643 | 570.16 | 0.1574 | 10.32490 | 28.16 | 0.1889 |
| 9.9976 | 2025.02 | 0.1181 | 8.84764 | 100.00 | 0.1417 |
| 11.1631 | 225.27 | 0.6884 | 7.92639 | 11.12 | 0.8261 |
| 11.3636 | 403.87 | 0.1574 | 7.78695 | 19.94 | 0.1889 |
| 12.5320 | 1651.83 | 0.1574 | 7.06346 | 81.57 | 0.1889 |
| 14.5147 | 290.27 | 0.1181 | 6.10275 | 14.33 | 0.1417 |
| 14.9564 | 728.89 | 0.1181 | 5.92349 | 35.99 | 0.1417 |
| 15.5593 | 242.82 | 0.1732 | 5.69531 | 11.99 | 0.2078 |
| 15.9707 | 350.89 | 0.1574 | 5.54950 | 17.33 | 0.1889 |
| 17.1217 | 474.25 | 0.1574 | 5.17896 | 23.42 | 0.1889 |
| 17.5108 | 231.68 | 0.1181 | 5.06474 | 11.44 | 0.1417 |
| 18.0265 | 467.34 | 0.1181 | 4.92100 | 23.08 | 0.1417 |
| 18.3523 | 524.18 | 0.1181 | 4.83437 | 25.88 | 0.1417 |
| 18.8952 | 235.57 | 0.1968 | 4.69666 | 11.63 | 0.2362 |
| 19.5631 | 1443.96 | 0.3012 | 4.53781 | 71.31 | 0.3615 |
| 19.6857 | 1861.41 | 0.1574 | 4.50981 | 91.92 | 0.1889 |
| 20.0428 | 332.44 | 0.1856 | 4.43026 | 16.42 | 0.2227 |
| 20.3432 | 299.89 | 0.1181 | 4.36551 | 14.81 | 0.1417 |
| 20.7693 | 181.47 | 0.1181 | 4.27691 | 8.96 | 0.1417 |
| 22.2149 | 1436.61 | 0.1968 | 4.00177 | 70.94 | 0.2362 |
| 22.8270 | 189.65 | 0.1181 | 3.89583 | 9.37 | 0.1417 |
| 23.0031 | 351.89 | 0.0010 | 3.86640 | 17.38 | 0.0012 |
| 23.3512 | 500.66 | 0.1181 | 3.80953 | 24.72 | 0.1417 |
| 23.8140 | 349.40 | 0.1968 | 3.73654 | 17.25 | 0.2362 |
| 24.3728 | 344.81 | 0.1181 | 3.65213 | 17.03 | 0.1417 |
| 24.6863 | 472.11 | 0.1574 | 3.60645 | 23.31 | 0.1889 |
| 25.1231 | 84.73 | 0.0900 | 3.54474 | 4.18 | 0.1080 |
| 26.0031 | 39.50 | 0.0900 | 3.42674 | 1.95 | 0.1080 |
| 27.8772 | 167.00 | 0.1574 | 3.20048 | 8.25 | 0.1889 |
| 28.3631 | 60.99 | 0.0900 | 3.14675 | 3.01 | 0.1080 |
| 28.6635 | 102.42 | 0.1181 | 3.11444 | 5.06 | 0.1417 |
| 29.4031 | 258.48 | 0.1672 | 3.03777 | 12.76 | 0.2006 |
| 29.7607 | 240.64 | 0.1181 | 3.00208 | 11.88 | 0.1417 |

TABLE 2-continued

X-ray Powder Diffraction data for Compound 3b, Type I
(spectra provided in FIG. 4B)

| Pos. [°2Th.] | Height [cts] | FWHM [°2Th.] | d-spacing [Å] | Rel. Int. [%] | Tip width [°2Th.] |
|---|---|---|---|---|---|
| 30.3092 | 448.03 | 0.1574 | 2.94899 | 22.12 | 0.1889 |
| 30.7590 | 639.70 | 0.1968 | 2.90688 | 31.59 | 0.2362 |
| 30.9231 | 375.19 | 0.0010 | 2.89183 | 18.53 | 0.0012 |
| 31.8625 | 407.11 | 0.1574 | 2.80868 | 20.10 | 0.1889 |
| 32.9911 | 132.45 | 0.1574 | 2.71513 | 6.54 | 0.1889 |
| 33.3765 | 242.32 | 0.1574 | 2.68466 | 11.97 | 0.1889 |
| 34.6343 | 209.74 | 0.2755 | 2.58999 | 10.36 | 0.3306 |
| 35.4600 | 133.72 | 0.1181 | 2.53155 | 6.60 | 0.1417 |
| 36.6431 | 131.56 | 0.0900 | 2.45249 | 6.50 | 0.1080 |
| 36.9291 | 234.25 | 0.1181 | 2.43415 | 11.57 | 0.1417 |
| 37.3231 | 128.05 | 0.0900 | 2.40935 | 6.32 | 0.1080 |
| 38.1379 | 245.64 | 0.3149 | 2.35973 | 12.13 | 0.3779 |
| 38.6431 | 89.09 | 0.0900 | 2.33004 | 4.40 | 0.1080 |
| 39.5231 | 72.92 | 0.0900 | 2.28016 | 3.60 | 0.1080 |
| 40.0232 | 133.72 | 0.2362 | 2.25282 | 6.60 | 0.2834 |
| 40.9283 | 148.51 | 0.1181 | 2.20506 | 7.33 | 0.1417 |
| 42.2431 | 68.44 | 0.0900 | 2.13943 | 3.38 | 0.1080 |
| 42.4031 | 76.70 | 0.0900 | 2.13172 | 3.79 | 0.1080 |
| 42.5631 | 62.75 | 0.0900 | 2.12408 | 3.10 | 0.1080 |
| 43.0418 | 90.09 | 0.9446 | 2.10156 | 4.45 | 1.1336 |
| 44.0031 | 98.50 | 0.0900 | 2.05786 | 4.86 | 0.1080 |
| 44.6400 | 144.25 | 0.2755 | 2.02996 | 7.12 | 0.3306 |
| 45.6313 | 75.09 | 0.3936 | 1.98814 | 3.71 | 0.4723 |
| 46.8031 | 22.71 | 0.0900 | 1.94106 | 1.12 | 0.1080 |
| 48.5231 | 37.91 | 0.0900 | 1.87621 | 1.87 | 0.1080 |
| 50.0381 | 82.16 | 0.3149 | 1.82289 | 4.06 | 0.3779 |
| 50.5231 | 54.18 | 0.0900 | 1.80653 | 2.68 | 0.1080 |
| 52.1631 | 26.97 | 0.0900 | 1.75353 | 1.33 | 0.1080 |
| 53.3498 | 62.23 | 0.6298 | 1.71729 | 3.07 | 0.7557 |
| 54.9231 | 56.59 | 0.0900 | 1.67176 | 2.79 | 0.1080 |
| 55.9430 | 69.71 | 0.4723 | 1.64368 | 3.44 | 0.5668 |
| 57.3994 | 34.49 | 0.4723 | 1.60539 | 1.70 | 0.5668 |
| 60.1631 | 33.11 | 0.0900 | 1.53808 | 1.63 | 0.1080 |
| 61.2152 | 49.98 | 0.9446 | 1.51415 | 2.47 | 1.1336 |
| 62.7421 | 35.86 | 0.7680 | 1.47970 | 1.77 | 0.9216 |
| 65.2831 | 2.62 | 0.0900 | 1.42930 | 0.13 | 0.1080 |
| 66.5631 | 19.62 | 0.0900 | 1.40489 | 0.97 | 0.1080 |
| 67.1631 | 26.13 | 0.0900 | 1.39379 | 1.29 | 0.1080 |

Preparation of Tricarbonyl[tris(2-isocyano-2-methyl-propionic acid)]Mo(0), (3-b) Type II

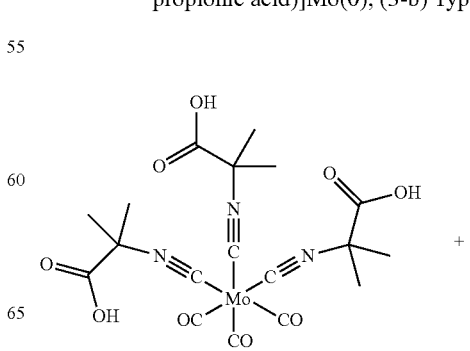

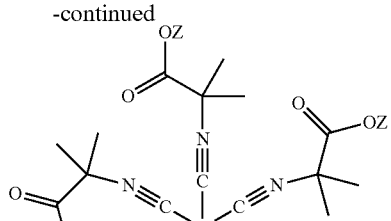

3-b, fully protonated + minor amount
of sodium salt
Z = H or Na, Na: Mo = 0.4-0.6

Compound (3-a) (1.06 g; 1.888 mmol; 561.3939 g/mol) was dissolved in 40 mL of THF and placed in an ice bath. NaOH (10 equiv.; 0.755 g; 18.88 mmol; 40 g/mol) was dissolved in 10 mL of $H_2O$ and added dropwise to the previous solution over 10 min. The light-yellow, turbid solution was stirred for 2 h while it slowly warmed to room temperature, without removing the ice-bath. After 2 h, TLC analysis performed in hexane:ethyl acetate (1:1) showed only hydrolyzed product with Rf=0. The light-yellow, turbid solution was taken to dryness giving a large amount of a white powder. The solid was redissolved in water (10 mL) and 1 M $H_2SO_4$ (9.4 mL) was added dropwise. The solution became blue and had a final pH of 1-2. The solid was filtered and washed with 5×10 mL of water. Each time the solution was stirred for 2 min and allowed to rest. The final pH of the washing solution was between 4 and 5. The off-white powder was dried in vacuum to provide compound (3-b) containing sodium (Type II). Yield: 0.920 g (93.8%).

Characterization of compound (3-b), Type II. Elemental Analysis: Calculated for $C_{18}H_{21}O_9N_3Mo$: % C, 41.63; % H, 4.08; % N, 8.09. Found: C, 40.60; % H, 3.80; % N, 7.82. The compound was further dried in high-vacuum ($2 \times 10^{-5}$ Torr) during 1 week. Found: % C, 41.20; % H, 4.15; % N, 8.24. $^1$H-NMR ($CD_3COCD_3$, 400 MHz, rt, δ in ppm, 10 mg/600 µL): δ=1.68 (s, $CH_3$) $^{13}$C-NMR ($CD_3COCD_3$, 100.6 MHz, rt, δ in ppm, 10 mg/600 µL): 214.93 (C≡O); 172.59 (C≡N); 163.48 (C=O); 62.60 ($C_{quat}$); 27.92 (2×$CH_3$); IR (KBr): Bands (C≡O): 1927(s), 1859(s); Bands (C=O): 1755(m) and 1685(w); Bands (C≡N): 2166(m), 2105 (m). IR($CHCl_3$): Bands (C≡O): 1942(s), 1882(s); Bands (C=O): 1735(w) and 1677(w); Bands (C≡N): 2157(w), 2099(m).

TABLE 3

Figure 4C:
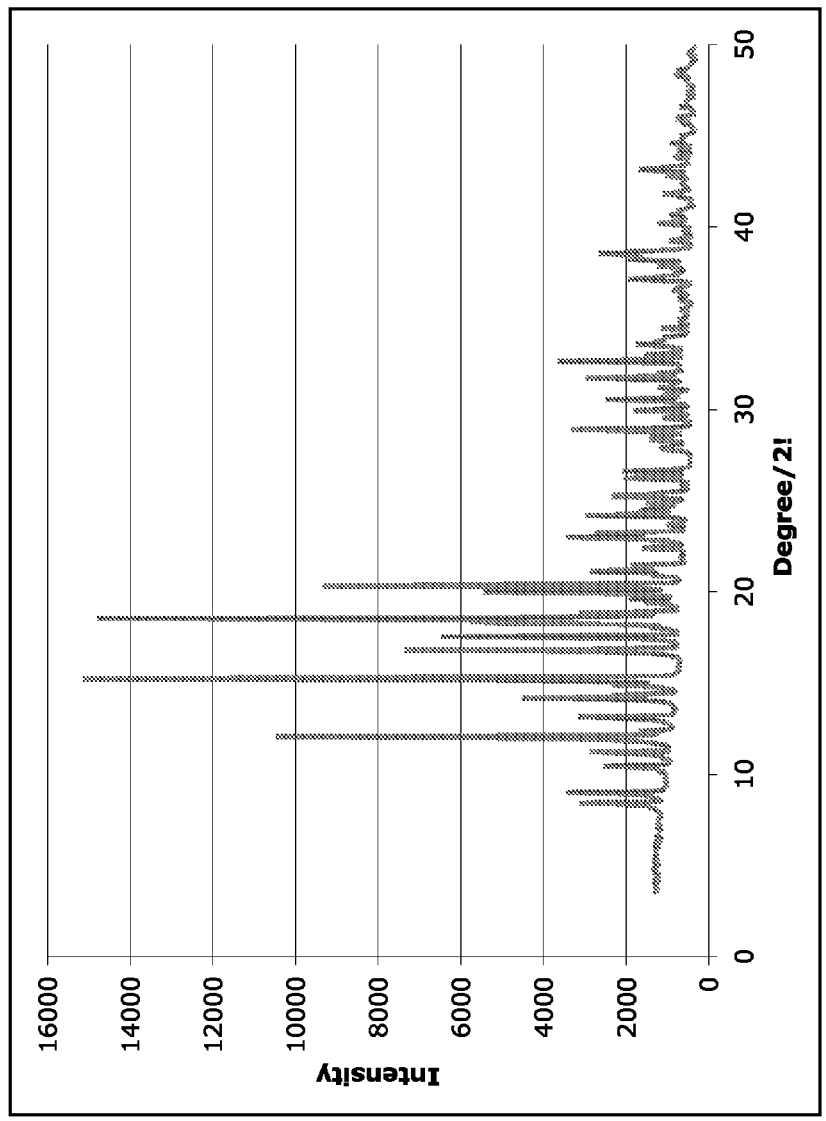

X-ray Powder Diffraction data for Compound 3b, Type II
(spectra provided in FIG. 4C)

| Pos. [°2Th.] | Height [cts] | FWHM [°2Th.] | d-spacing [Å] | Rel. Int. [%] | Tip width [°2Th.] |
|---|---|---|---|---|---|
| 8.4046 | 693.12 | 0.1181 | 10.52069 | 10.77 | 0.1417 |
| 9.0220 | 1116.38 | 0.1181 | 9.80208 | 17.34 | 0.1417 |
| 10.4406 | 897.42 | 0.1181 | 8.47318 | 13.94 | 0.1417 |
| 11.1898 | 718.15 | 0.1181 | 7.90751 | 11.15 | 0.1417 |
| 12.0642 | 4146.69 | 0.1181 | 7.33625 | 64.40 | 0.1417 |
| 12.3598 | 558.34 | 0.1181 | 7.16147 | 8.67 | 0.1417 |
| 12.7161 | 352.12 | 0.0010 | 6.96163 | 5.47 | 0.0012 |
| 13.1525 | 1852.12 | 0.1181 | 6.73158 | 28.77 | 0.1417 |
| 14.1853 | 1751.55 | 0.1181 | 6.24372 | 27.20 | 0.1417 |
| 14.4761 | 855.55 | 0.5774 | 6.11895 | 13.29 | 0.6929 |
| 14.9150 | 1108.39 | 0.0557 | 5.93985 | 17.21 | 0.0668 |
| 15.2754 | 6245.08 | 0.1574 | 5.80052 | 97.00 | 0.1889 |
| 16.8191 | 3219.27 | 0.1181 | 5.27143 | 50.00 | 0.1417 |
| 17.5629 | 2561.96 | 0.1181 | 5.04984 | 39.79 | 0.1417 |
| 18.1561 | 770.77 | 0.0798 | 4.88617 | 11.97 | 0.0957 |
| 18.4106 | 3739.81 | 0.1754 | 4.81919 | 58.08 | 0.2104 |
| 18.5642 | 6438.53 | 0.1181 | 4.77965 | 100.00 | 0.1417 |
| 18.8668 | 1896.91 | 0.1181 | 4.70368 | 29.46 | 0.1417 |
| 19.3886 | 548.12 | 0.1181 | 4.57825 | 8.51 | 0.1417 |
| 19.5770 | 754.05 | 0.0319 | 4.53461 | 11.71 | 0.0383 |
| 19.9962 | 3012.25 | 0.1181 | 4.44048 | 46.78 | 0.1417 |
| 20.3682 | 4161.26 | 0.1181 | 4.36023 | 64.63 | 0.1417 |
| 21.0361 | 758.19 | 0.0842 | 4.22327 | 11.78 | 0.1010 |
| 21.0361 | 758.19 | 0.0842 | 4.22327 | 11.78 | 0.1010 |
| 21.0361 | 758.19 | 0.0842 | 4.22327 | 11.78 | 0.1010 |
| 21.1445 | 1109.60 | 0.1181 | 4.20186 | 17.23 | 0.1417 |
| 21.4743 | 715.52 | 0.1181 | 4.13806 | 11.11 | 0.1417 |
| 22.4230 | 461.94 | 0.1181 | 3.96508 | 7.17 | 0.1417 |
| 22.9853 | 1320.11 | 0.1181 | 3.86934 | 20.50 | 0.1417 |
| 23.2480 | 1361.50 | 0.1181 | 3.82621 | 21.15 | 0.1417 |
| 23.7168 | 251.03 | 0.1574 | 3.75163 | 3.90 | 0.1889 |
| 24.2239 | 1107.55 | 0.1181 | 3.67423 | 17.20 | 0.1417 |
| 24.5635 | 880.09 | 0.0386 | 3.62421 | 13.67 | 0.0463 |
| 24.6166 | 875.68 | 0.0728 | 3.61651 | 13.60 | 0.0874 |
| 24.6285 | 596.28 | 0.1968 | 3.61479 | 9.26 | 0.2362 |
| 25.2742 | 964.10 | 0.1574 | 3.52388 | 14.97 | 0.1889 |
| 25.8361 | 89.65 | 0.0900 | 3.44851 | 1.39 | 0.1080 |
| 26.2646 | 694.73 | 0.1181 | 3.39320 | 10.79 | 0.1417 |
| 26.6375 | 726.26 | 0.1574 | 3.34655 | 11.28 | 0.1889 |
| 27.8654 | 342.90 | 0.1574 | 3.20181 | 5.33 | 0.1889 |
| 28.0361 | 193.62 | 0.0900 | 3.18270 | 3.01 | 0.1080 |
| 28.3296 | 584.86 | 0.1181 | 3.15039 | 9.08 | 0.1417 |
| 28.5032 | 708.22 | 0.0202 | 3.13159 | 11.00 | 0.0242 |
| 28.9163 | 1335.22 | 0.1574 | 3.08779 | 20.74 | 0.1889 |
| 29.5701 | 385.66 | 0.1181 | 3.02099 | 5.99 | 0.1417 |
| 29.9695 | 667.36 | 0.1181 | 2.98164 | 10.37 | 0.1417 |
| 30.5576 | 891.48 | 0.1574 | 2.92558 | 13.85 | 0.1889 |
| 30.9107 | 335.55 | 0.1181 | 2.89296 | 5.21 | 0.1417 |
| 31.2307 | 343.16 | 0.1181 | 2.86405 | 5.33 | 0.1417 |
| 31.4361 | 365.48 | 0.0900 | 2.84580 | 5.68 | 0.1080 |
| 31.7528 | 1213.96 | 0.1574 | 2.81814 | 18.85 | 0.1889 |
| 31.9561 | 222.28 | 0.0900 | 2.80067 | 3.45 | 0.1080 |
| 32.3161 | 162.00 | 0.0900 | 2.77029 | 2.52 | 0.1080 |
| 32.6753 | 1762.53 | 0.1574 | 2.74065 | 27.37 | 0.1889 |
| 33.0260 | 752.80 | 0.0603 | 2.71234 | 11.69 | 0.0723 |
| 33.5161 | 385.22 | 0.0900 | 2.67380 | 5.98 | 0.1080 |
| 33.5408 | 471.86 | 0.1574 | 2.66967 | 7.33 | 0.1889 |
| 33.5961 | 851.84 | 0.0010 | 2.67203 | 13.23 | 0.0012 |
| 33.9812 | 400.50 | 0.1181 | 2.63607 | 6.22 | 0.1417 |
| 34.4694 | 309.84 | 0.1181 | 2.59985 | 4.81 | 0.1417 |
| 34.7561 | 169.83 | 0.0900 | 2.57906 | 2.64 | 0.1080 |
| 35.4745 | 110.00 | 0.1181 | 2.52845 | 1.71 | 0.1417 |
| 36.1065 | 181.14 | 0.1968 | 2.48563 | 2.81 | 0.2362 |
| 36.5241 | 255.60 | 0.2362 | 2.45817 | 3.97 | 0.2834 |
| 37.1576 | 763.34 | 0.1574 | 2.41770 | 11.86 | 0.1889 |
| 37.9056 | 445.34 | 0.1574 | 2.37169 | 6.92 | 0.1889 |
| 38.3937 | 1081.37 | 0.0721 | 2.34265 | 16.80 | 0.0866 |
| 38.6178 | 928.72 | 0.2362 | 2.32957 | 14.42 | 0.2834 |
| 39.2817 | 314.81 | 0.1181 | 2.29172 | 4.89 | 0.1417 |
| 39.7236 | 132.84 | 0.1181 | 2.26723 | 2.06 | 0.1417 |
| 40.2360 | 366.37 | 0.1574 | 2.23953 | 5.69 | 0.1889 |
| 40.6669 | 254.37 | 0.1181 | 2.21679 | 3.95 | 0.1417 |
| 40.8361 | 189.89 | 0.0900 | 2.20800 | 2.95 | 0.1080 |
| 41.6361 | 173.21 | 0.0900 | 2.16741 | 2.69 | 0.1080 |
| 41.8622 | 277.62 | 0.1968 | 2.15622 | 4.31 | 0.2362 |
| 42.3961 | 164.70 | 0.0900 | 2.13030 | 2.56 | 0.1080 |
| 42.5561 | 163.70 | 0.0900 | 2.12266 | 2.54 | 0.1080 |
| 42.8155 | 302.26 | 0.1181 | 2.11039 | 4.69 | 0.1417 |
| 43.1695 | 609.30 | 0.1968 | 2.09390 | 9.46 | 0.2362 |
| 43.8690 | 202.44 | 0.1181 | 2.06213 | 3.14 | 0.1417 |
| 44.2503 | 175.16 | 0.1574 | 2.04524 | 2.72 | 0.1889 |
| 44.6012 | 267.21 | 0.1181 | 2.02996 | 4.15 | 0.1417 |
| 44.9961 | 151.84 | 0.0900 | 2.01306 | 2.36 | 0.1080 |
| 46.0376 | 178.86 | 0.1968 | 1.96991 | 2.78 | 0.2362 |
| 46.6165 | 140.91 | 0.1181 | 1.94678 | 2.19 | 0.1417 |
| 47.4015 | 102.08 | 0.1181 | 1.91636 | 1.59 | 0.1417 |
| 47.8761 | 121.07 | 0.0900 | 1.89847 | 1.88 | 0.1080 |
| 48.3561 | 208.06 | 0.0900 | 1.88074 | 3.23 | 0.1080 |

TABLE 3-continued

X-ray Powder Diffraction data for Compound 3b, Type II
(spectra provided in FIG. 4C)

| Pos. [°2Th.] | Height [cts] | FWHM [°2Th.] | d-spacing [Å] | Rel. Int. [%] | Tip width [°2Th.] |
|---|---|---|---|---|---|
| 48.4788 | 138.59 | 0.5760 | 1.87626 | 2.15 | 0.6912 |
| 48.5961 | 164.94 | 0.0900 | 1.87666 | 2.56 | 0.1080 |

Preparation of Tricarbonyl[tris(lithium 2-isocyanosuccinate)]Mo(0) (4-b)

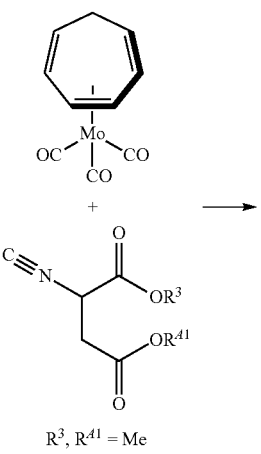

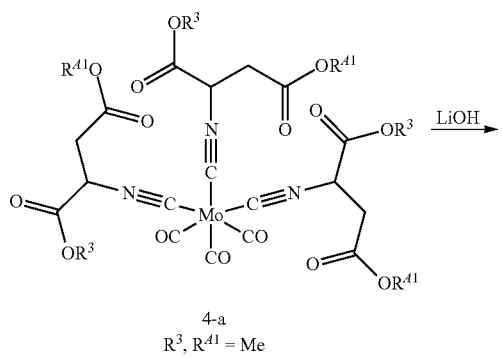

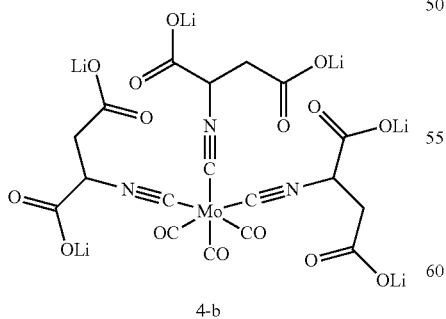

Preparation of tricarbonyl[tris(2-isocyanosuccinate methyl ester)]Mo(0) (4-a): ($\eta^6$-$C_7H_8$)Mo(CO)$_3$ (0.281 g; 1.032 mmol; 272.11 g/mol) was dissolved in 20 mL of MeOH and CNCH(COOMe)CH$_2$COOMe (3 equiv.; 0.5303 g; 3.1 mmol; 171.14 g/mol), dissolved in 10 mL of MeOH was slowly added. The dark-red solution slowly turned orange-brown. The reaction was stopped after 1.5 h and taken to dryness to provide compound (4-a). Yield: 100%. $C_{24}H_{27}N_3O_{15}$Mo (693.4284 g/mol)

Characterization of Compound (4-a): Elemental Analysis: Calculated for MoC$_{24}$H$_{27}$N$_3$O$_{15}$: % C, 41.57; % H, 3.92; % N, 6.06. Found: % C, 41.3; % H, 3.94; % N, 6.06. IR (KBr): Bands (C≡O): 1943(s); 1876(s); Bands (C═O): 1740(s); Bands (C≡N): 2165(sh); 2107(s). $^1$H-NMR (CDCl$_3$, 400 MHz, rt, δ in ppm): δ=4.82 (t, 3H), 3.86 (s, 9H), 3.77 (s, 9H), 3.04 (m, 6H).

Preparation of tricarbonyl[tris(lithium 2-isocyanosuccinate)]Mo(0) (4-b): Compound (4-a) (0.6669 g; 9.62×10$^{-4}$ mol; 693.4224 g/mol) was dissolved in 20 mL of THF at 0° C. LiOH.H$_2$O (6 equiv.; 242 mg; 5.77 mmol), dissolved in 5 mL of H$_2$O also at 0° C. The solution of lithium hydroxide was added, the reaction was kept overnight, warming to room temperature then evaporated to dryness to provide compound (4-b) as the hexylithium salt. Yield of compound (4-b): 100%.

Characterization of compound (4-b): Elemental Analysis: Calculated for MoC$_{18}$H$_9$N$_3$O$_{15}$Li$_6$: % C, 33.53; % H, 1.41; % N, 6.52. Found: % C, 33.42; % H, 3.06; % N, 4.94. IR (KBr): Bands (C≡O): 1944(s); 1872(s); Bands (C═O): 1586(s); Bands (C≡N): 2144(s) $^1$H NMR (D$_2$O, 400 MHz, rt, δ in ppm): δ=4.64-4.60 (m, 3H), 2.85-2.69 (m, 6H).

Preparation of Tricarbonyl[tris(isocyanocyclopropylcarboxylic acid]Mo(0 (5-b)

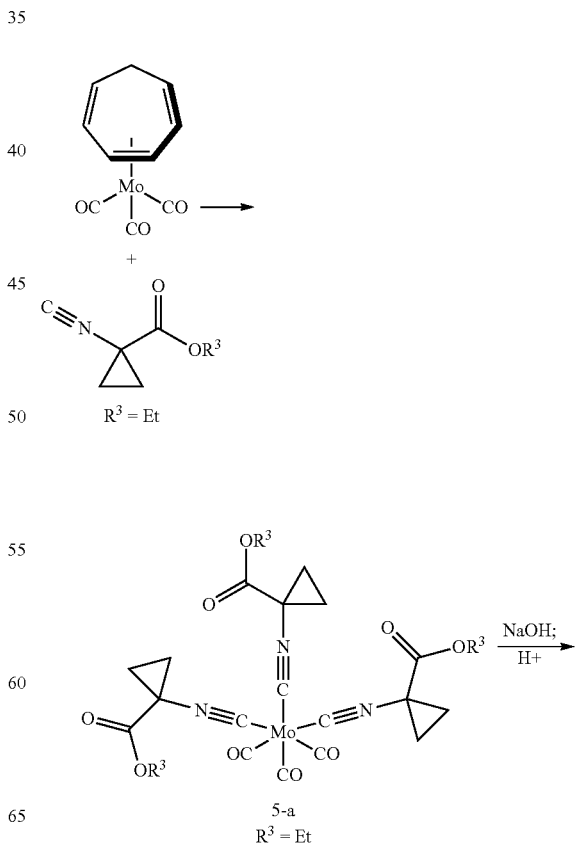

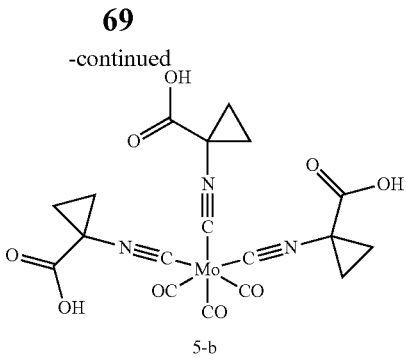

5-b

Preparation of tricarbonyl[tris(isocyanocyclopropylcarboxylic acid ethyl ester)]Mo(0) (5-a): Mo(CO)$_3$(η$^6$-C$_7$H$_8$) (0.521 g; 1.92 mmol; 272.1117 g/mol) was suspended in 25 mL of MeOH to give a red suspension. Ethyl isocyanocyclopropylcarboxylate (3 eq.; 0.8 g; 5.75 mmol; 139.16 g/mol) was dissolved in 20 mL of MeOH and was added slowly to the previous suspension. A light orange solution was immediately obtained. The solution was stirred at room temperature for 1 hour, after which the solvent was concentrated and a white powder started to fall down. The solid, slightly contaminated with traces of an oil, was filtered and washed with 5 mL of MeOH. It was then transferred to an activated silica-gel chromatographic column. Fractions were collected in test tubes and the elution was followed by TLC. The eluent mixture (hexane (7)/ethyl acetate (3)) was always the same, however the first 6 test tubes eluted corresponded to trace mixtures of impurities and were discarded. The clean fractions were gathered and evaporated to dryness to give a green oil. Yield: 54% (0.6194 g).

Characterization for compound (5a): Calculated for C$_{24}$H$_{27}$N$_3$O$_9$Mo: % C, 48.25; % H, 6.24; % N, 7.03. Found: % C, 47.60; % H, 4.80; % N, 7.05. IR (KBr): Bands (C—O): 1942 (s); 1875 (s); Bands (C=O): 1738 (m); Bands (C≡N): 2154 (m); 2106 (s). $^1$H-NMR(C$_6$D$_6$, 400 MHz, rt, δ in ppm): δ=3.86 (q, 2H, OCH$_2$CH$_3$), 1.08 (m, 2H, cycle), 0.97 (t, 3H, OCH$_2$CH$_3$), 0.87 (m, 2H, cycle). $^{13}$C-NMR(C$_6$D$_6$, 100 MHz, rt, δ in ppm): δ=212.5 (C—O), 168.3 (CN), 166.8 (C=O), 62.5 (CCH$_2$CH$_2$), 36.5 (CCH$_2$CH$_2$), 19.3 (COCH$_2$CH$_3$), 14.15 (COCH$_2$CH$_3$).

Preparation of tricarbonyl[tris(isocyanocyclopropylcarboxylic acid)]Mo(0) (5-b): Compound (5-a) (0.619 g, 1.04 mmol, 597.432 g/mol) was dissolved in anhydrous THF (20 mL) and placed in an ice bath. An aqueous solution of sodium hydroxide (10 equivalents, 10.37 mmol, 0.4148 g) in 5 mL of water was added dropwise to the yellow solution. A yellow emulsion was obtained, which stirred for 4 hours while slowly coming to room temperature. THF was evaporated, and when only water was left, 15 mL more of this solvent were added. The solution was filtered to remove traces of a solid, and 5.2 mL of 1M H$_2$SO$_4$ aqueous solution (37 mmol) were added dropwise. After all the acid was added and a brownish oil precipitated, the solution's pH was 2. The solvent was concentrated, more oil separated, and after a certain point the oil turned into a dark yellow powder. It was filtered and washed 4 times with 20 mL of water each (pH 5). The solid was dried under vacuum. Yield: 79% (0.420 g).

Characterization of (5b): Calculated for C$_{18}$H$_{15}$N$_3$O$_9$Mo: % C, 42.12; % H, 2.95; % N, 8.19. Found: % C, 42.40; % H, 3.32; % N, 8.48. IR (KBr): Bands (C=O): 1941 (s); 1874 (s); Bands (C=O): 1705 (m); Bands (C≡N): 2153 (m); 2109 (s). $^1$H-NMR (CD$_3$OD, 400 MHz, rt, δ in ppm): δ=1.66, 1.63 (m, 4H, cycle). $^{13}$C-NMR (CD$_3$OD, 100 MHz, rt, δ in ppm): δ=213.7 (C—O), 171.5 (CN), 164.2 (C=O), 37.2 (CCH$_2$CH$_2$), 20.2 (CCH$_2$CH$_2$).

Example 2

CO-Release Kinetics

The CO release kinetics of Compounds 1b, 2b, 3b, 4b, and 5b was performed in vitro in HEPES buffer (pH 7.4) or in phosphate buffer (pH 7.4) and in the presence of liver microsomes. The quantization of the released CO was performed according to Vreman et al. *Anal. Biochem.* (2005) 341: 280-289 using a Gas Chromatograph with a Reducing Compound Photometer detector (GC-RCP; Peak Laboratories, Mountain View, Calif.), which allows quantifying CO in gas mixtures at concentrations as low as 1-2 parts per billion (ppb).

General Method for the Determination of CO Release in HEPES Buffer

The CO release kinetics of all compounds was evaluated in 50 mM HEPES buffer (pH 7.4) in a sealed 8-mL vial. Stock solutions (5 mM) of the compounds were prepared in PBS buffer (each compound was soluble in PBS after the addition of 3 equivalents of NaOH) and 10 μL were added to 990 μL of 50 mM HEPES buffer (final concentration in buffer was 50 μM). Since light activation can release CO from molybdenum carbonyl compounds, CO release was determined with solutions in closed, clear glass vials kept under light (on the laboratory bench under regular laboratory lighting) or in the dark (wrapped in aluminum foil and kept inside a cardboard box). Gas samples (from 10 μL up to 500 μL) of the vial headspace (7 ml volume) were removed with a gas-tight syringe at 15, 30, 60, 120, 240, 360 min, and 24 hours after start of the incubation. The gas samples were injected into sealed vials containing air (8 mL) for dilution. The entire gas volume of the vials (8 mL) was transferred with carrier gas to the GC-RCP and analyzed for CO. The GC-RCP had been calibrated with gas containing a known amount of CO. The calibration curve had been established starting with gas from a cylinder which contained synthetic air with 30 ppm CO (Linde, Cat. No. 14960013) and preparing dilutions in 8-mL vials as described above.

General Method for the CO Release in the Presence of Liver Microsomes

The CO release kinetics of Compounds 1b, 2b, 3b, 4b, and 5b were also evaluated in the presence of rat or human liver microsomes. In a 8-mL vial, the following reagents were combined:

713 μL of purified water
200 μL of 0.5 M potassium phosphate buffer, pH 7.4
50 μL of NADPH regenerating system solution A (BD, Cat. No. 451220)
10 μL of NADPH regenerating system solution B (BD, Cat. No. 451200)
2 μL of 5 mM solution of the compound in DMSO (10 μM final concentration)

The vials were closed and after mixing, the samples were warmed to 37° C. for 5 minutes before an aliquot (25 μL, 0.5 mg protein content) of rat liver microsomes (BD, Cat. No. 452511) or human liver microsomes (BD, Cat. No. 452161) was added to each vial. In parallel analogous vials with all the reagents except the microsomes were prepared. Due to the light-sensitivity of the molybdenum compounds, the reactions were performed in the dark. The samples were incubated at 37° C. and gas samples of the headspace (from 100 μL to 500 μL) of the vials were removed with a gas-tight syringe after 5, 10, 15, 30, and 60 minutes (in some cases samples were also taken at 1, 2, 3 or 4 minutes) upon microsomes addition. The gas samples were then injected into empty sealed vials (8 mL volume) and the amount of CO present in the vials was measured using GC-RCP.

CO Calibration Curve for the GC-RCP

A calibration curve of CO was established in order to be able to extrapolate the peak areas obtained in the GC-RCP to the known CO concentrations. Different gas volumes of a 30 ppm CO gas bottle (Linde, Cat. No. 14960013) were injected into 8 ml vials. The peak area values obtained in the GC-RCP and the corresponding ppm or pmol of CO in each sample was plotted in a graph. A linear response curve was obtained for CO concentrations of up to 0.857 ppm (or 268 pmol). Above these values the readings of the GC-RCP are not accurate.

Table 4 provides the volume of gas injected from a 30 ppm CO gas bottle (Linde, Cat. No. 14960013) into an 8-mL vial and the corresponding CO concentrations. Values of the CO peak areas from the different samples analyzed in the GC-RCP.

TABLE 4

| Volume from CO bottle (μl) | CO (ppm) | CO (pmol) | Peak area |
|---|---|---|---|
| 0 | 0 | 0 | 4854782 |
| 25 | 0.107 | 33 | 9682321 |
| 50 | 0.214 | 67 | 13791770 |
| 75 | 0.321 | 100 | 19163149 |
| 100 | 0.429 | 134 | 27436859 |
| 200 | 0.857 | 268 | 49579021 |
| 250 | 1.071 | 335 | 1085495 |
| 350 | 1.5 | 469 | 29003989 |

The CO equivalents released at each time point from each compound were determined by the following equation: (CO released (pmol)×number of CO ligands in the molecule)/([CO] in the compound (pmol)). A 1 mL solution of a tricarbonyl compound, at 50 μM concentration contains a total of 150,000 pmol of CO.

CO Release Kinetics of Compound 1b

The CO release kinetics of Compound 1b in 50 mM HEPES (pH 7.4) buffer are presented in FIG. 1A. The half-life of CO release is approximately 4 hours in the dark and about 1 h under light. In 24 hours in 50 mM HEPES buffer, Compound 1b releases 1.6 CO equivalents under light and 1.4 CO equivalents in the dark, respectively.

Figure 1B:
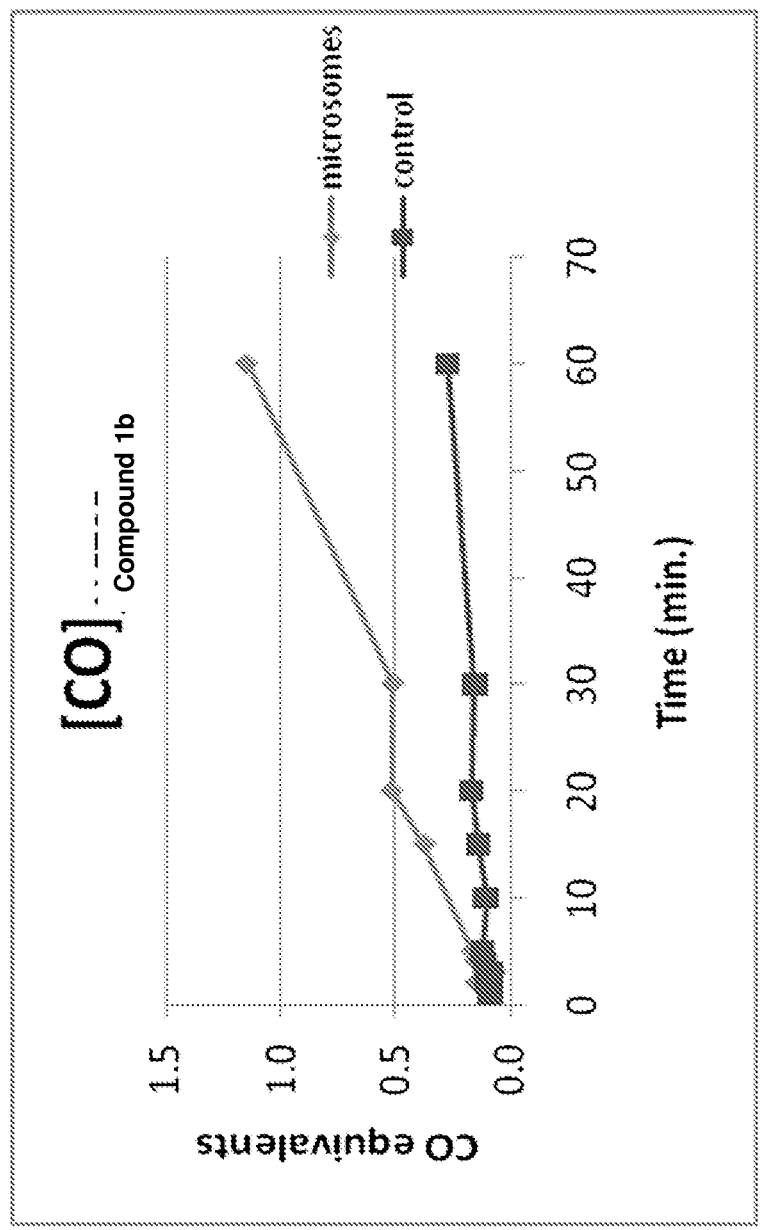

In an in vitro metabolism study of Compound 1b, it was determined that 60% of Compound 1b decayed in a one-hour reaction with liver microsomes. Sixty percent decay could release up to 1.8 molar equivalents of CO. This decay rate is faster than what was observed in pH 7.4 buffer alone, where 0.5 molar equivalents of CO were released in about 4 h. Therefore liver microsomes accelerate the decomposition of the compound. In order to investigate if this accelerated decomposition of Compound 1b in the presence of microsomes was inducing a fast CO release from the compound, the CO release profile of Compound 1b in the presence of liver microsomes was determined. Microsomes were incubated with Compound 1b using closed vials to enable quantitative measurement of the released CO. As a control, Compound 1b was incubated under similar conditions in the absence of microsomes. The results are presented in FIG. 1B and show an increased rate of CO release from Compound 1b in the presence of microsomes after 10 minutes of reaction.

CO Release Kinetics of Compound 2b

Figure 2A:
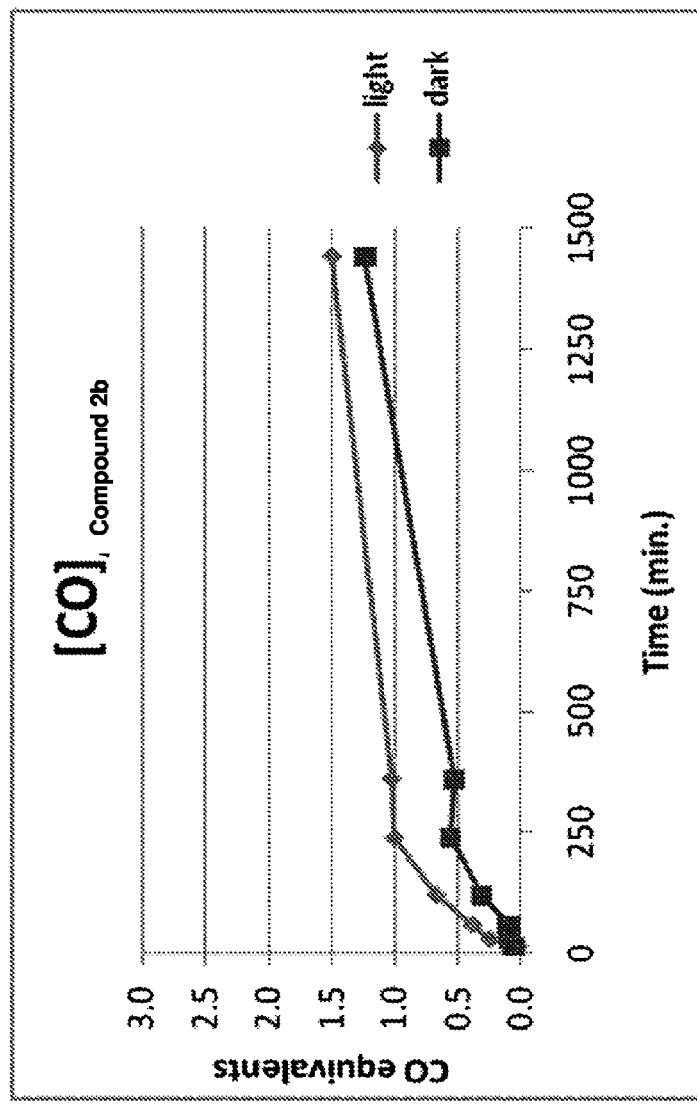
FIGS. 2A-2E.

The CO release kinetics of Compound 2b in 50 mM HEPES (pH 7.4) buffer are presented in FIG. 2A. The half-life of CO release in the case of Compound 2b is approximately 4 hours in the dark but under light it takes about 90 minutes to release 0.5 CO equivalents. After 24 hours incubation in 50 mM HEPES buffer, Compound 2b releases 1.5 CO equivalents under light and 1.2 CO equivalents in the dark, respectively.

Figure 2B:
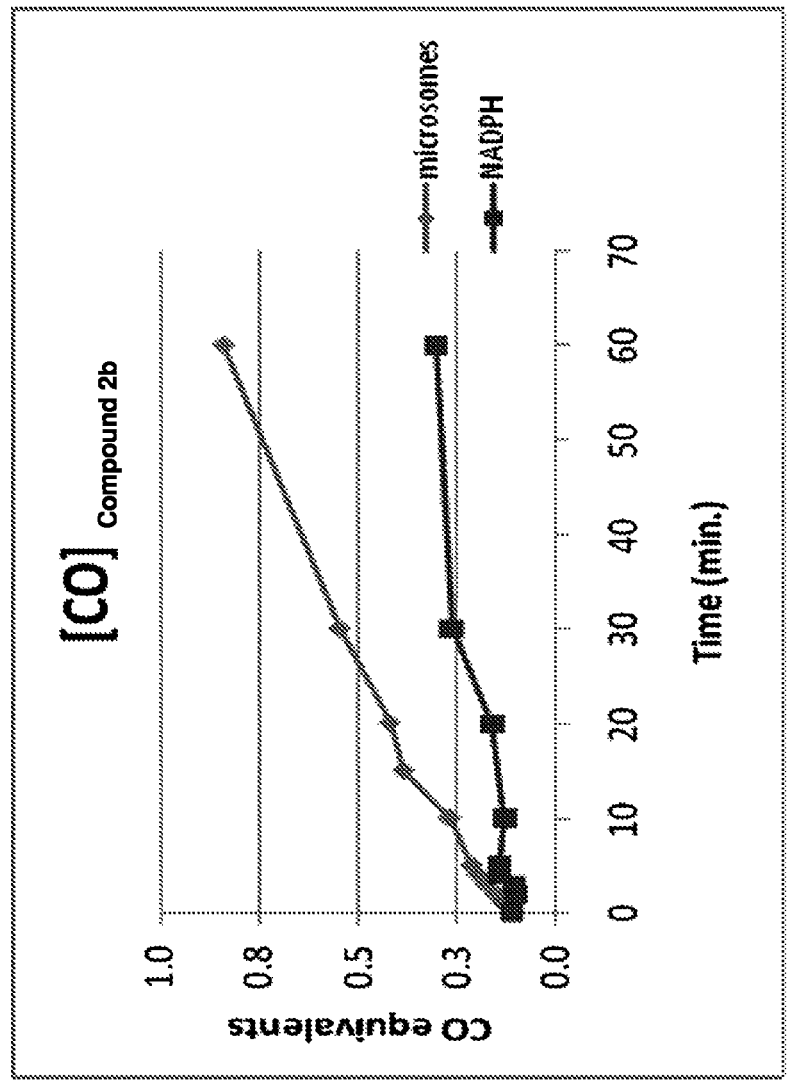

The CO release kinetics of Compound 2b in the presence of rat liver microsomes were also investigated. Microsomes were incubated with Compound 2b using closed vials to enable the quantitative measurement of released CO. As a control, Compound 2b was incubated in similar conditions in the absence of microsomes. The results are presented in FIG. 2B. Microsomes accelerated the decay of Compound 2b.

CO Release Kinetics of Compound 3b

Figure 4D:
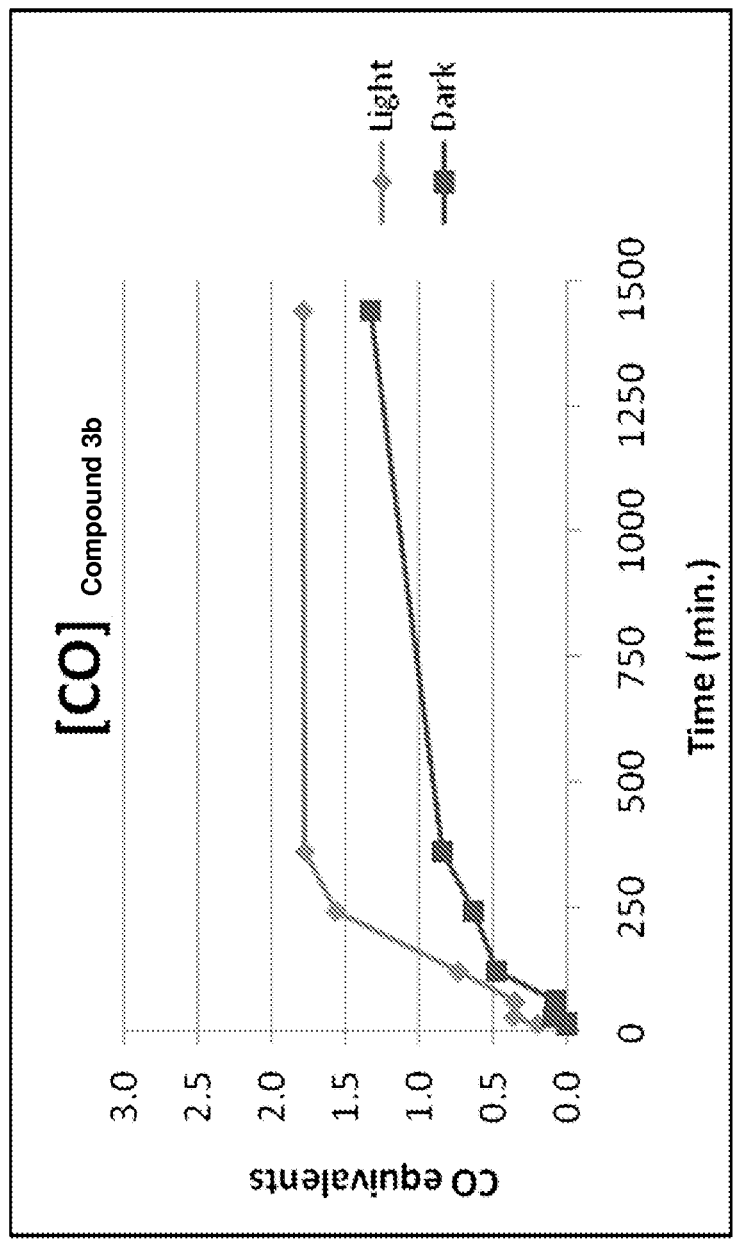

The CO release kinetics of Compound 3b in 50 mM HEPES (pH 7.4) buffer are presented in FIG. 4D. The half-life of CO release is approximately 2 hours in the dark and about 1 h under light. In 24 hours in 50 mM HEPES buffer, Compound 3b releases 1.8 CO equivalents under light and 1.3 CO equivalents in the dark, respectively.

Figure 4E:
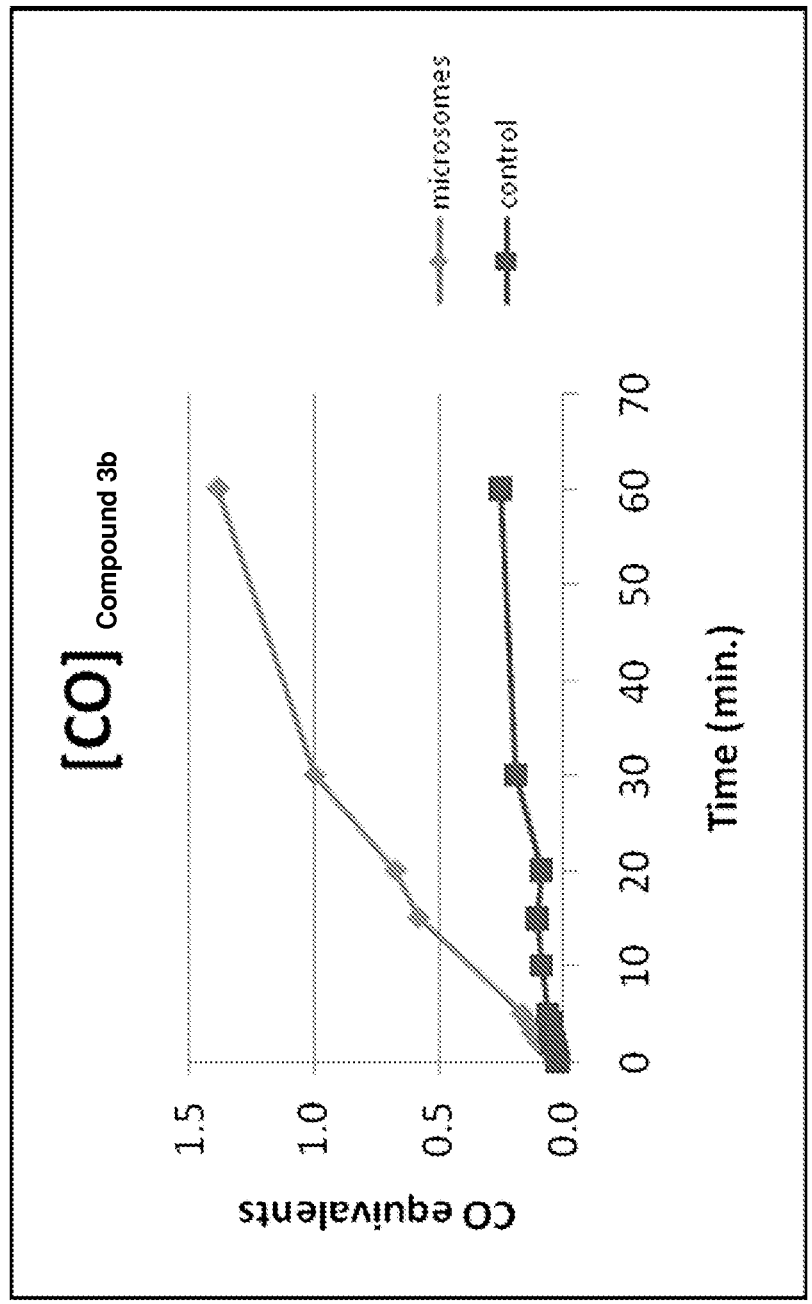

In an in vitro metabolism study of the CO release kinetics of Compound 3b, it was determined that 80% of Compound 3b decayed in 60 minutes incubation with liver microsomes. In order to investigate if this accelerated decomposition of Compound 3b in the presence of microsomes was inducing a faster CO release from the compound, the CO release profile of Compound 3b in the presence of liver microsomes was determined. Microsomes were incubated with Compound 3b using closed vials to enable quantitative measurement of the released CO. As a control, Compound 3b was incubated under similar conditions in the absence of microsomes. The results are presented in FIG. 4E and show an increased rate of CO release from Compound 3b in the presence of microsomes. The initial rate of CO release is 0.0297 CO equivalents (297.22 pmol) per minute in the presence of microsomes and 0.0072 CO equivalents (72.265 pmol) per minute in the absence of microsomes. These results indicate that the initial CO release rate is approximately 4 times faster in the presence of microsomes.

CO Release Kinetics of Compound 4b

Figure 5A:
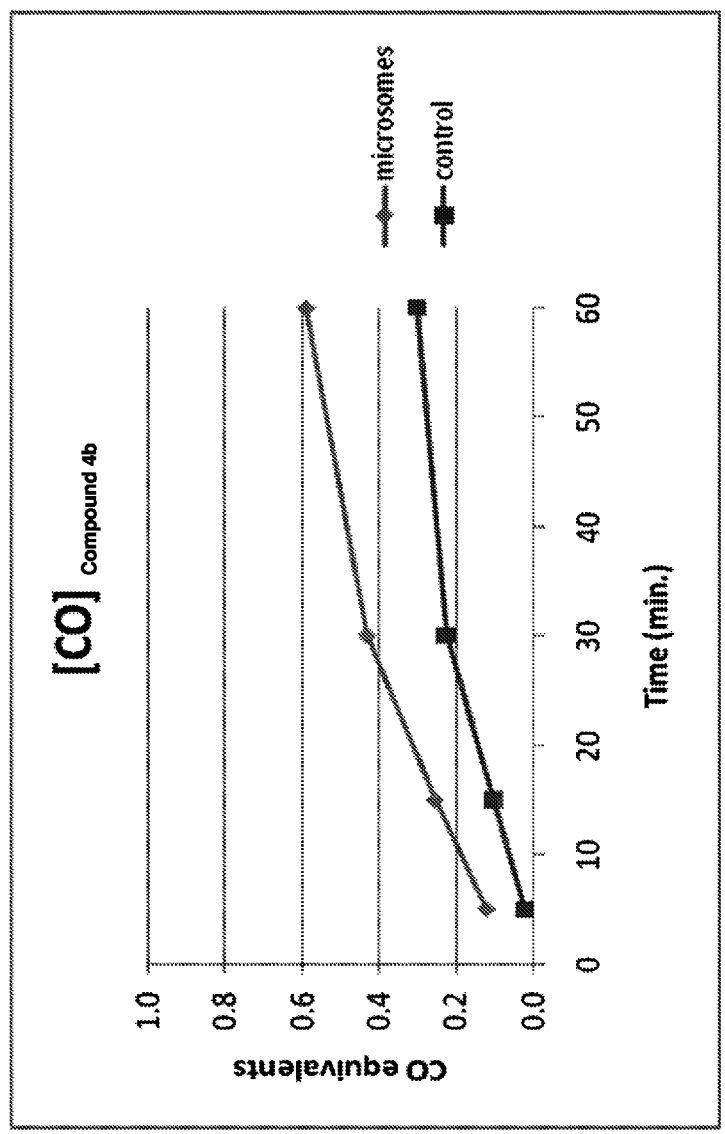
FIGS. 5A-5B.

The CO release kinetics of Compound 4b in 50 mM HEPES (pH 7.4) buffer are presented in FIG. 5A. The stability of compound 4b was determined by measuring the release of CO in vitro in 50 mM Hepes buffer (pH 7.4) using a RCP-equipped GC. Compound 4b concentration was 50 μM. The half-life for CO release is defined as the time necessary to release 0.5 molar equivalents of CO and was found to be about 1 h for compound 4b (in the absence of light). The half-life for CO release was also measured in sheep blood using an oximeter. A concentration of 632.1 μg/mL of compound 4b was used. This concentration corresponds to the calculated Cmax in the mouse for a dose of 50 mg/kg. The half-life for CO release in blood in vitro was found to be about 2.5 hours.

CO Release Kinetics of Compound 5b

Figure 6A:
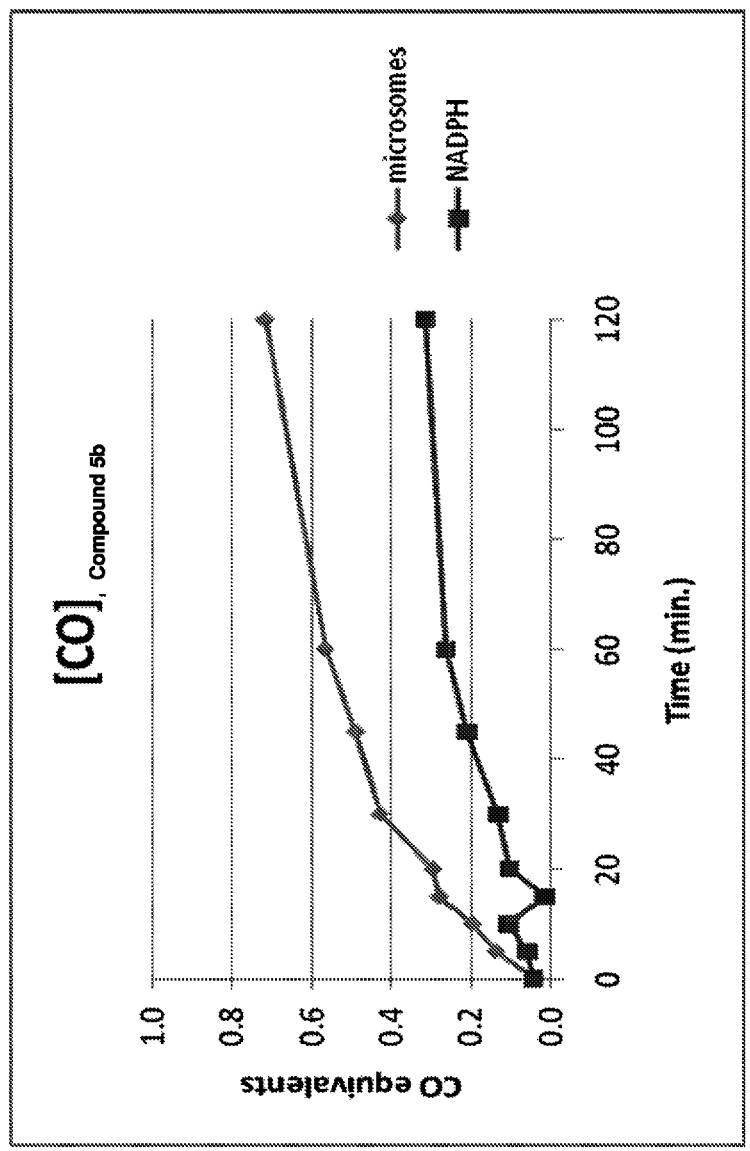
FIGS. 6A-6B.

The CO release kinetics of Compound 5b in 50 mM HEPES (pH 7.4) buffer are presented in FIG. 6A. The stability of compound 5b was determined by measuring the release of CO in vitro in 50 mM Hepes buffer (pH 7.4) using a RCP-equipped GC. Compound 5b concentration was 50 μM. The half-life for CO release is defined as the time necessary to release 0.5 molar equivalents of CO and was found to be 6 h for compound 5b (in the absence of light).

The half-life for CO release was also measured in sheep blood using an oximeter. A concentration of 632.1 μg/mL of compound 5b was used (this concentration corresponds to the calculated Cmax in the mouse for a dose of 50 mg/kg). Compound 5b released 0.12 molar equivalents of CO in 3 hours.

Summary

Table 5 summarizes the CO release half-lives of molybdenum carbonyl isocyano compounds in 50 mM HEPES buffer (pH 7.4) or in potassium phosphate buffer (pH 7.4) in the presence of microsomes. Compound 4b is the least stable, with a half-life of 1 hour for spontaneous CO release in solutions of pH 7.4. Compound 1b and 2b have half-lives of spontaneous CO release of 4 hours.

TABLE 5

| Compound | CO release Half-life in the dark (time to release 0.5CO equivalents) | |
| --- | --- | --- |
| | HEPES buffer (pH 7.4) | Microsomes K-phosphate buffer (pH 7.4) |
| 1b | 4 h | 20 min (1.1CO eq. in 1 h) |
| 2b | 4 h | 30 min. (0.9CO eq. in 1 h) |
| 3b | 2 h | 13 min (1.5CO eq. in 1 h) |
| 4b | 1 h | — |
| 5b | 6 h | — |

The CO release kinetics of these compounds were evaluated in the presence of liver microsomes. For all compounds evaluated, microsomes accelerated the release of CO. These results suggest that the compounds might be activated in vivo by metabolism in the liver. In fact, tissue CO distribution experiments performed in mice showed that the administration of Compound 3b or Compound 2b increased CO levels in the liver, when compared with blood, kidney, heart and lung tissues (see Example 3). However, there was no higher CO accumulation in the liver of animals treated with Compound 1b even though this compound was also activated by microsomes in vitro.

Example 3

Accumulation of Carbon Monoxide (CO) in Tissues after Administration of Carbon-Monoxide Releasing Molecule Carbon monoxide-releasing molecules (CO-RMs) are carriers of carbon monoxide (CO) and can release CO in vivo. CO can bind to hemoglobin in the blood and to various heme proteins in cells. Vreman et al. *Anal Biochem* 341:280-289 describes a method to release CO bound to tissues into the gas phase, and quantify it using GC-RCP chromatography. We applied this methodology to assay CO in various tissues of mice treated with CO-RMs (see Example 2, herein). However, since the CO release method of Vreman (in vitro incubation with sulfosalicylic acid) also releases CO from the CO-RM, the CO released from tissue samples represents CO bound to tissue proteins and CO from CO-RM compound accumulated in tissue. For CO-RM compounds with slow CO release rates in vivo, the CO measured at the earliest sampling point (5 min after CO-RM administration) may therefore mostly be a measure for the tissue distribution of the intact CO-RM.

Methods

The compound was dissolved in PBS and the acids neutralized with 3 eq. NaOH (from a NaOH stock solution 2.5M). The pH was brought down to about 7.5 by adding HCl (from a stock solution 1 M). The compound was then administered i.v. (50 mg/kg in 150 µL) to two CD-1 female mice (Charles River). The mice were warmed for ten minutes under an infrared lamp to facilitate the i.v. administration into a tail vein. Five and twenty minutes after the dosing, the two mice were anesthetized with IsoFluorane, and the blood was collected from the retro-orbital plexus using a Pasteur pipette containing ~20 µL of heparin solution. The animal was opened; the portal vein was cut and the organs were perfused by injecting 10-15 mL of cold PBS in the left ventricle of the heart. Then the heart, kidneys, liver and lung were collected, briefly washed with potassium phosphate buffer, dried with a paper towel and snap frozen in liquid nitrogen. Samples of the freshly collected blood were transferred to AVOXimeter 4000 cuvettes (ITC) to measure the levels of carboxyhemoglobin (COHb), oxyhemoglobin (O2Hb) and methemoglobin (MetHb) using a portable AVOXimeter 4000 CO-oximeter. The results are shown as mean percentage of total hemoglobin species in circulation. The organs and blood were conserved at −20° C. until the CO quantization was done.

Figure 1C:
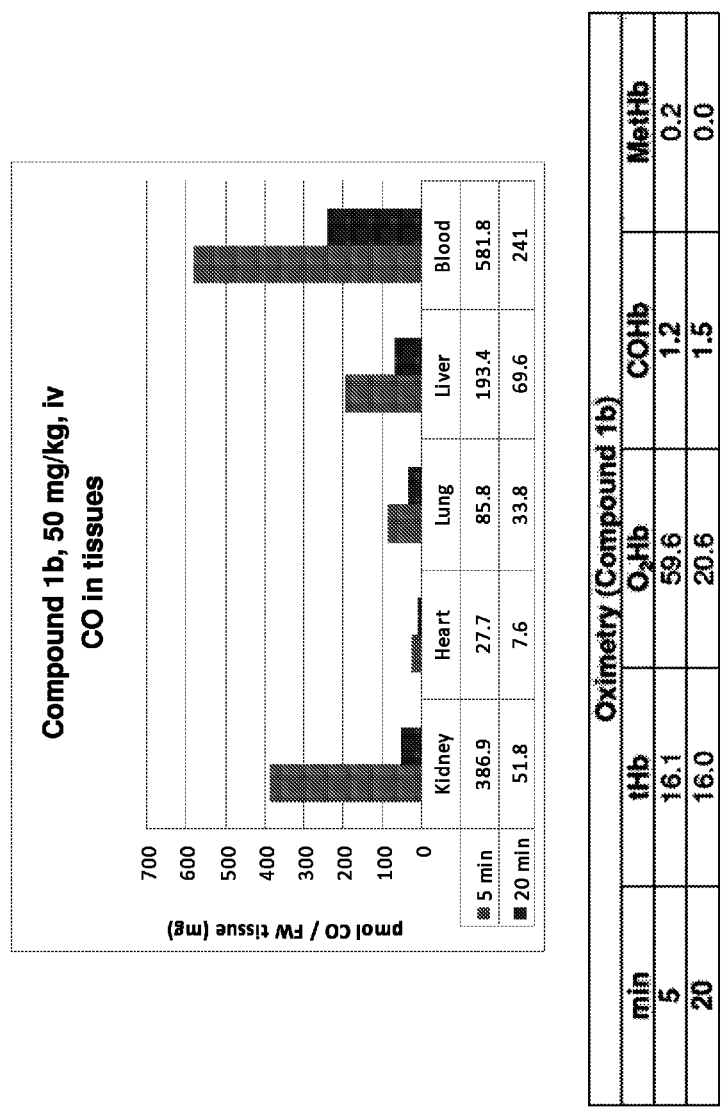
Figure 2C:
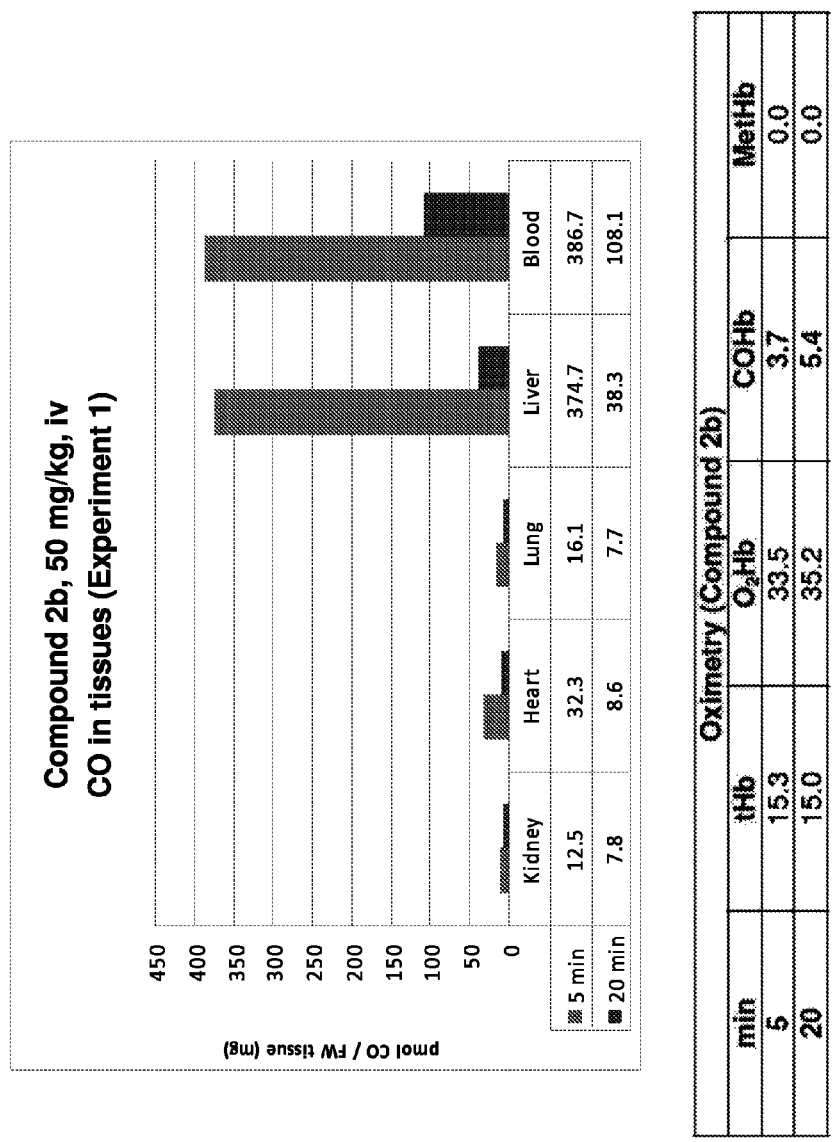
Figure 2D:
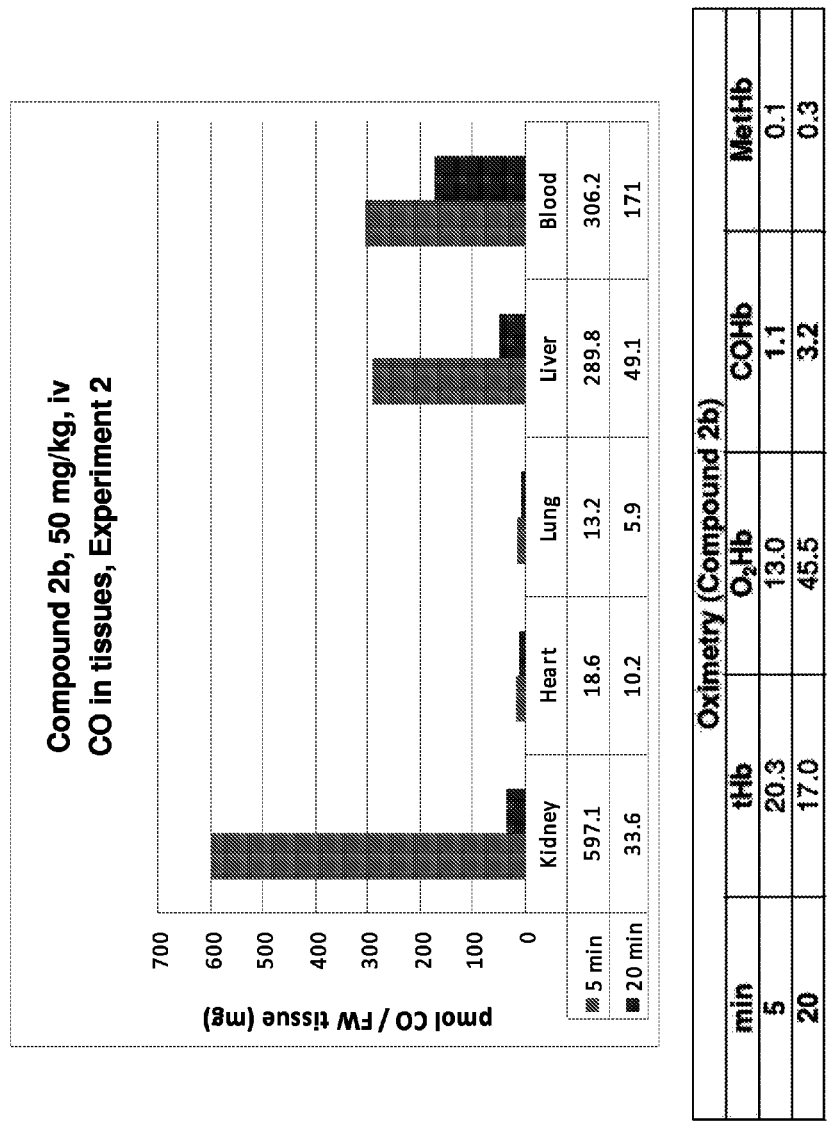
Figure 2E:
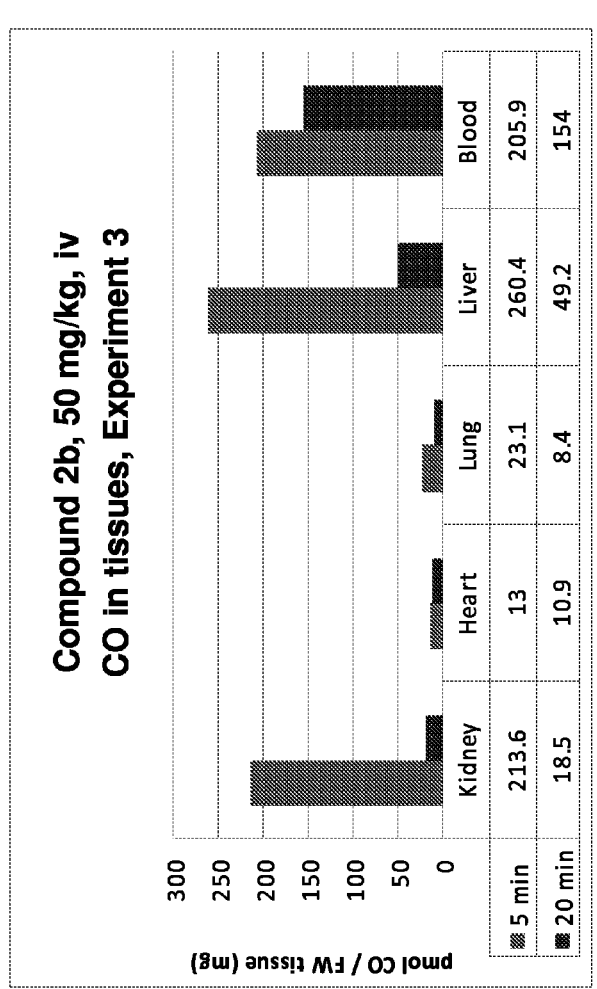
Figure 4F:
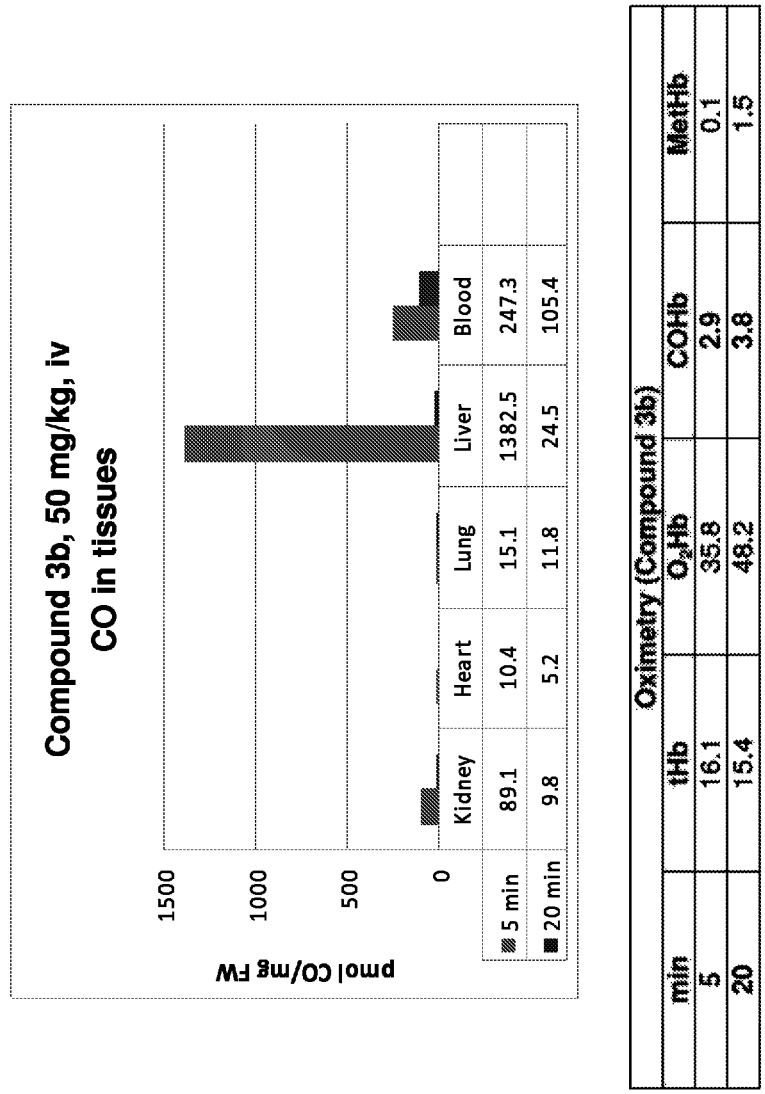
Figure 4G:
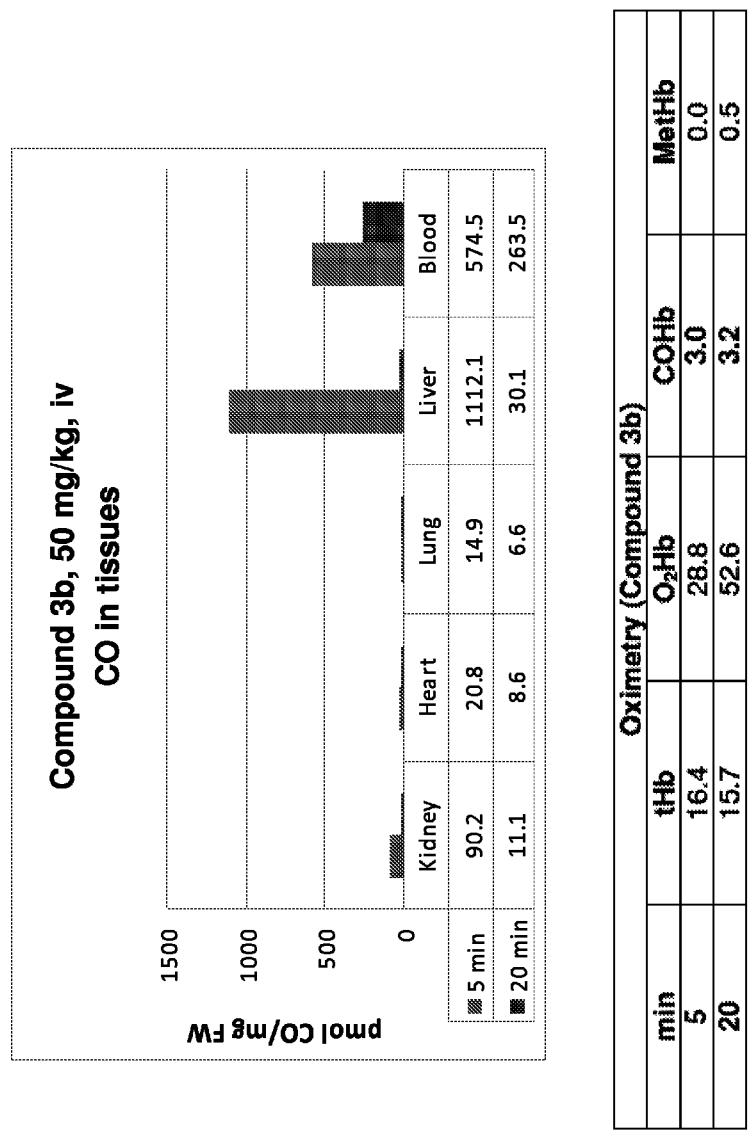
Figure 5B:
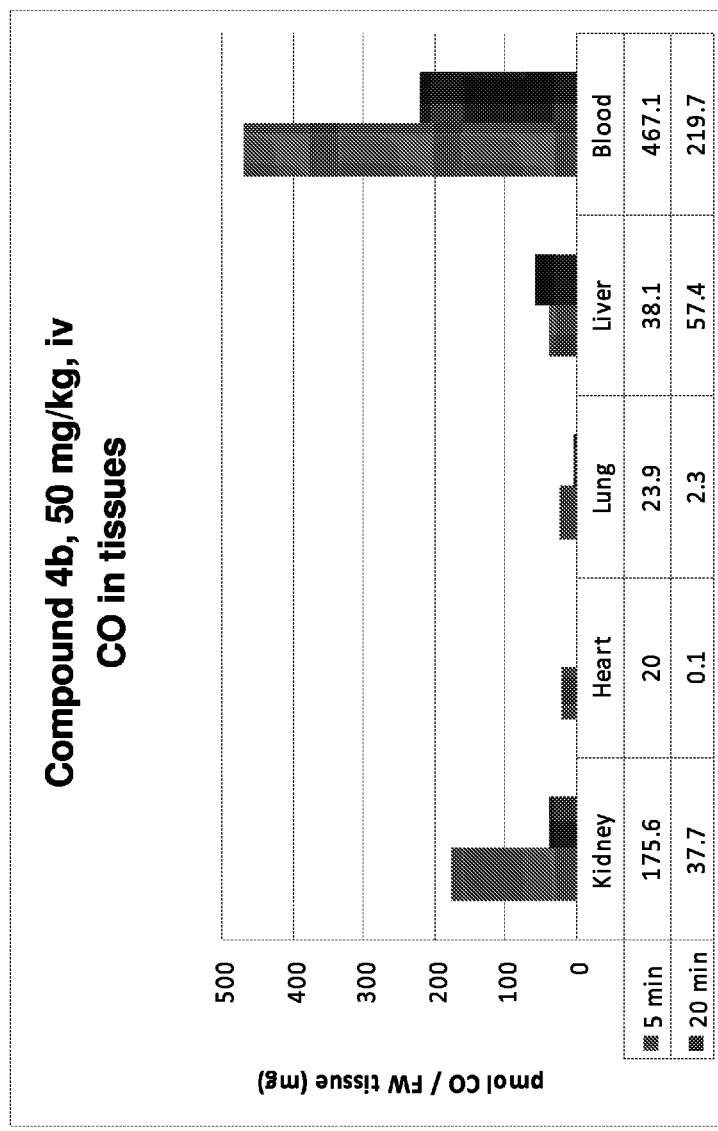
Figure 6B:
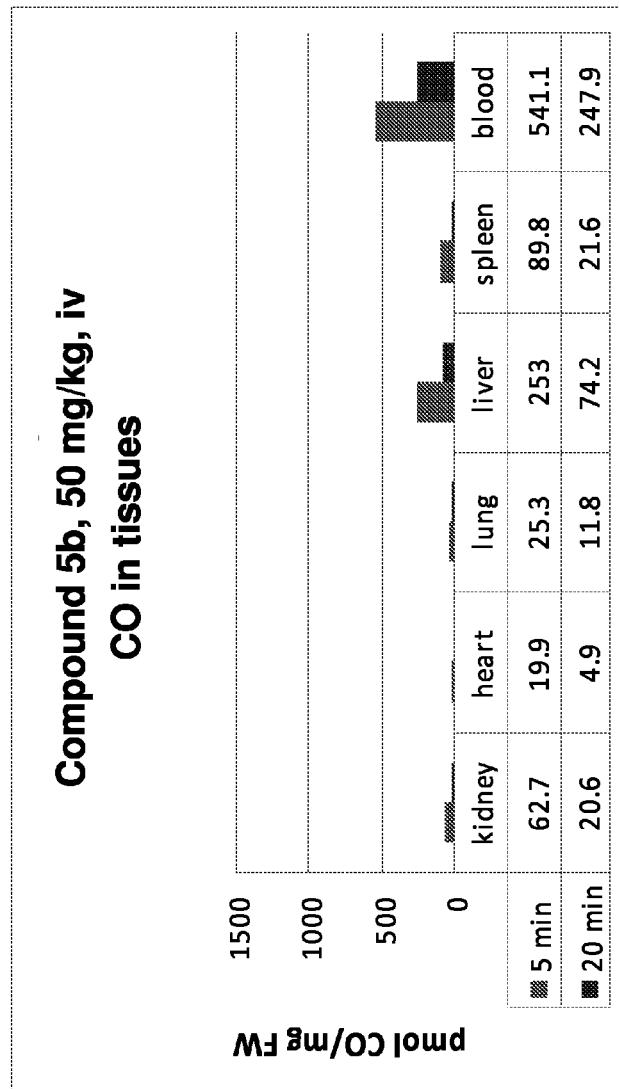

For CO quantization, the protocol described by Vreman et al was followed. The organs were cut into small pieces, which were weighed and 4 volumes of water (a volume corresponding to four times the weight of the tissue sample) were added to each organ sample. The tissues were homogenized using a tissue tearer. Aliquots of homogenate (30 L) were placed into vials to which were added water (25 L) and sulfosalicylic acid (SSA, 5 µL, 30% [wt/vol]) immediately before they were closed with a gas-tight septum cap. The vials were incubated on ice for at least 20 min before being analyzed by GC-RCP (in later experiments, the incubation time was extended to 45 minutes). The amount of CO was calculated using a calibration curve prepared from CO standards. The results for Compound 1b (one experiment, FIG. 1C), Compound 2b (three repeated experiments, FIGS. 2C-2E), Compound 3b (two repeated experiments, FIGS. 4F-4G), Compound 4b (FIG. 5B), and Compound 5b (FIG. 6B), are presented as pmol CO per mg of fresh wet tissue (pmol CO/mg FW). COHb was determined using an oximeter (AVOXimeter 4000, USA).

Results: Tissue CO distribution experiments performed in mice showed that the administration of compound 3b or compound 2b increased CO levels in the liver, when compared with blood, kidney, heart and lung tissues. In contrast, there is no preferential accumulation of CO in the liver of animals treated with compound 1b, relative to other organs, even though this compound was also activated by microsomes in vitro. The results show that Compounds 2b and 3b distribute preferentially to the liver shortly after administration, while compound 1b does not. Interestingly, all these three compounds are decomposed by liver microsomes to liberate CO at relatively similar rates, although somewhat faster in the case of compound 3b. Compound 3b, which has a preferential accumulation in the liver and also a faster CO release rate induced by liver microsome, has a better CO delivery profile to this organ than both 2b and 1b. The latter releases CO faster than 2b but its liver tropism is low enough to fully compromise therapeutic efficacy. Compound 2b strikes an intermediate balance and still retains therapeutic activity although lower than that of Compound 3b. Taken together these two sets of results suggest that the release of CO in the liver is not enough to produce therapeutic action and that some preferential accumulation in the liver is also needed (see below Example 4 "Therapeutic benefit of Compound 3b in APAP-induced acute liver failure (ALF) model").

Example 4

Carbon-Monoxide Releasing Molecules for the Treatment of Liver Disease

Preliminary Safety Studies in Mice

Figure 7:
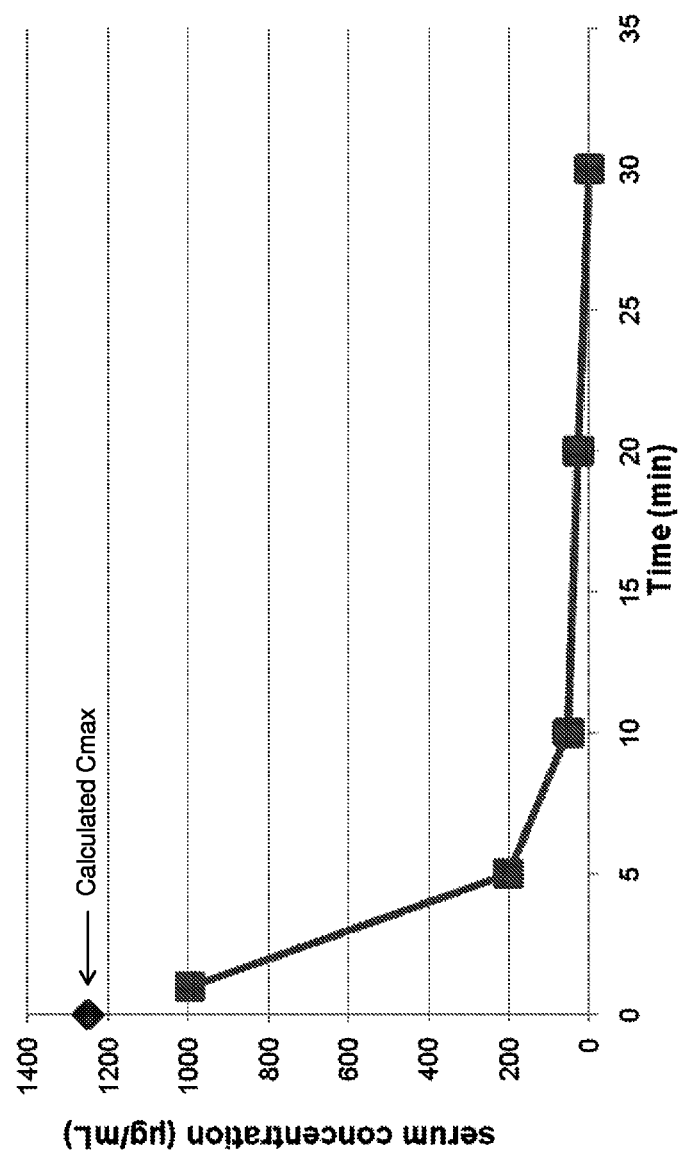
FIG. 7 depicts the pharmacokinetics of Compound 3b in CD-1 mice. Compound 3b was administered intravenously (i.v.), at a dose of 100 mg/kg. Blood samples were collected after 1, 5, 10, 20 and 30 minutes after administration. The concentration of Compound 3b in serum was assayed by HPLC. The experimental curve represents elimination from circulation and decay through CO release.

Preliminary safety studies in mice demonstrated that doses up to 1 g/kg showed no toxicity. FIG. 7 depicts the pharmacokinetics of Compound 3b in CD-1 mice. Compound 3b was administered intravenously (i.v.), at a dose of 100 mg/kg. Blood samples were collected after 1, 5, 10, 20 and 30 minutes after administration. The concentration of Compound 3b in serum was assayed by HPLC. The experimental curve represents elimination from circulation and decay through CO release.

In Vivo Distribution

It was found that Compound 3b rapidly distributes to the liver. Five minutes after i.v. injection of Compound 3b, CO concentration is five times higher in the liver than in blood; twenty minutes later, among the four non-blood tissues assayed, CO concentration is still highest in the liver.

Table 6 provides the CO distribution in blood, heart, liver, lung and kidney following Compound 3b administration at 50 mg/kg by i.p. injection. CO was assayed by GC-RCP, 5 and 20 minutes after administration of the compound. The CO concentration in the several organs is normalized to the amount of CO quantified in the blood (CO concentration as fraction of concentration in blood 50 mg/kg Compound 3b injected i.v. at t=0; CO assayed in tissues by GC at t=5 min and t=20 min).

TABLE 6

|  | 5 min | 20 min |
| --- | --- | --- |
| Blood | 1 | 1 |
| Heart | 0.046 ± 0.012 | 0.072 ± 0.055 |
| Liver | 5.26 ± 3.18 | 0.163 ± 0.062 |
| Lung | 0.049 ± 0.020 | 0.060 ± 0.046 |
| Kidney | 0.419 ± 0.295 | 0.074 ± 0.028 |

Human and Rat Microsomes Accelerate CO Release from Compound 3b

Figure 8:
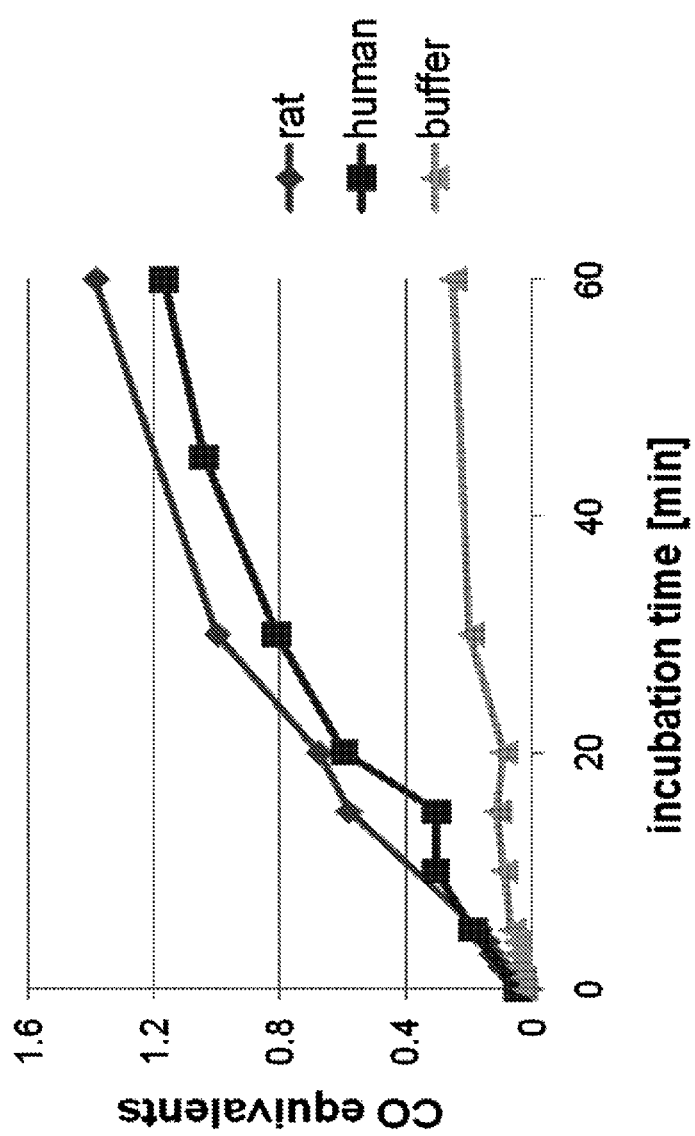
FIG. 8 depicts the amount of CO released from Compound 3b, expressed in equivalents of CO, in phosphate buffer pH 7.4 ("buffer"), phosphate buffer pH 7.4 in the presence of human liver microsomes ("human") or rat liver microsomes ("rat"). The assay was performed in closed vials during 1 hour at 37° C. A gas aliquot was removed from the air space of the vials and CO concentration was determined by GC-RCP at different time points.

FIG. 8 depicts the amount of CO released from Compound 3b, expressed in equivalents of CO, in phosphate buffer pH 7.4 ("buffer"), phosphate buffer pH 7.4 in the presence of human microsomes ("human") or rat microsomes ("rat"). The assay was performed in closed vials during 1 hour at 37° C. A gas aliquot was removed from the air space of the vials and CO concentration was determined by GC-RCP at different time points.

It was found that in pH 7.4 buffer Compound 3b releases 0.25 mol equiv. of CO in 1 hour. It was also found that microsomes accelerate CO release by a factor of about 4.0-5.5. The tissue distribution to the liver and enhanced CO release by liver microsomes suggest specific CO delivery to the liver.

COHb Levels in Compound 3b-Treated Mice

Figure 9:
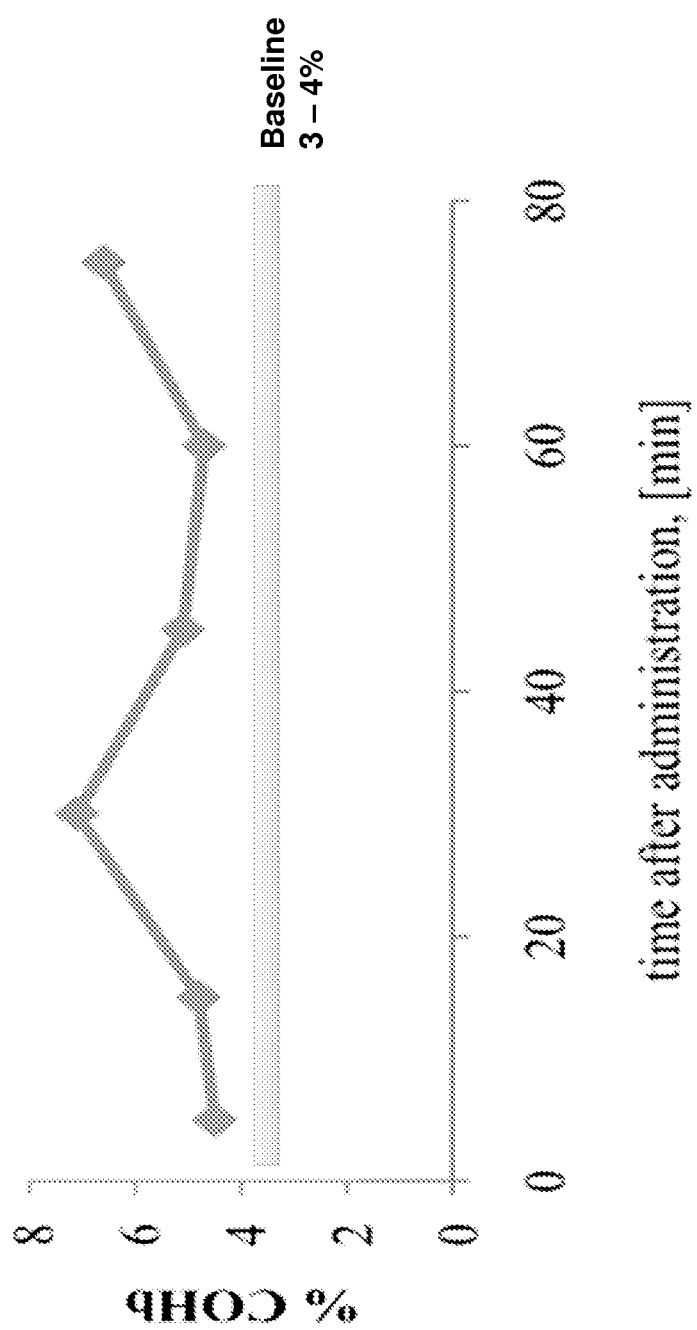
FIG. 9 depicts the percentage of carboxyhemoglobin (CO-Hb) measured in CD-1 female mice following Compound 3b administration at 300 mg/kg, intravenously. The CO-Hb was quantified over 80 min by using an oximeter (Avoximeter 4000 from A-vox Instruments). The base line of CO-Hb measured with this instrument is 3-4%.

FIG. 9 depicts the percentage of carboxyhemoglobin (CO-Hb) measured in CD-1 female mice following Compound 3b administration at 300 mg/kg, intravenously. The CO-Hb was quantified over 80 min by using an oximeter (Avoximeter 4000 from A-vox Instruments). The base line of CO-Hb measured with this instrument is 3-4%. It was found that mice treated i.v with Compound 3b at a dose of 300 mg/kg did not exceed 7.5% COHb in blood and that therapeutic doses of Compound 3b did not cause symptomatic levels of COHb in blood of mice.

Therapeutic Benefit of Compound 3b in APAP-Induced Acute Liver Failure (ALF) Model Compound 3b was studied in a sublethal model for acetaminophen (APAP)-induced Liver Injury.

Figures 10A, 10B:
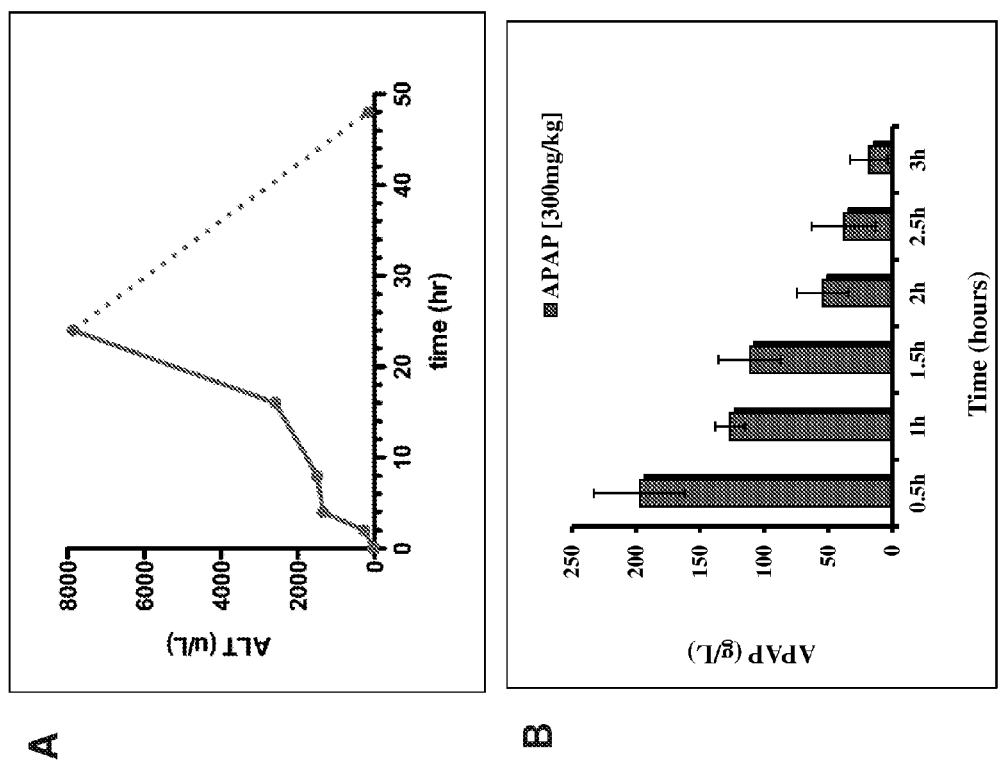
FIGS. 10A-10B depict the kinetics of alanine aminotransferase (ALT) production and clearance.

FIGS. 10A-10B depict the kinetics of alanine aminotransferase (ALT) production and clearance. FIG. 10A depicts the kinetics of ALT production after 300 mg/kg administration of APAP by intraperitoneal (i.p.) injection. ALT is expressed in U/L over time (hours). FIG. 10B depicts the kinetics of APAP clearance after administration of 300 mg/kg by i.p. injection. APAP is expressed in g/L over time (hours).

Figures 11A, 11B:
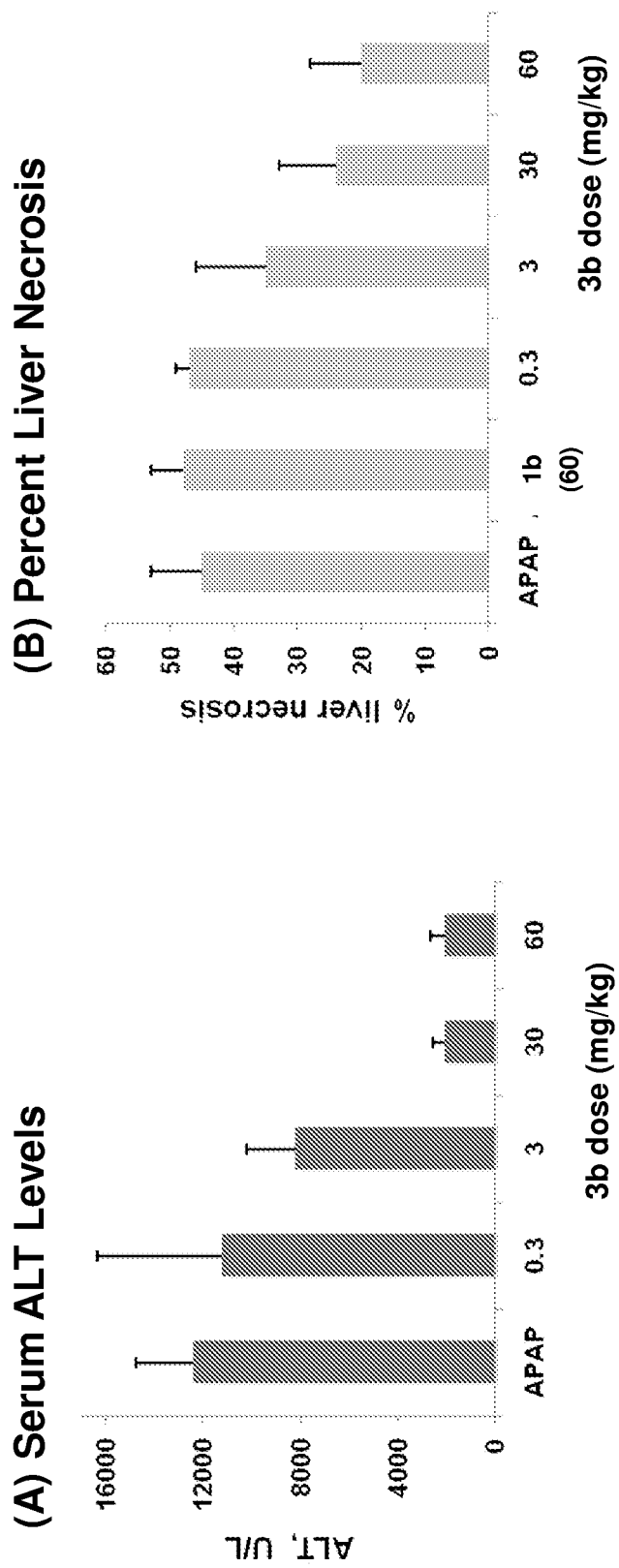
FIGS. 11A-11B.

FIG. 11A depicts the effect of treatment with Compound 3b on serum ALT in an APAP-induced acute liver failure (ALF) model. Male C57BL/6 mice fasted overnight to increase CyP450 activity. ALF was induced in C57Bl/6 male mice with a single dose of acetaminophen (300 mg/kg) by i.p. injection. One hour after APAP injection, the animals were treated with 0.3, 3, 30 or 60 mg/kg doses of Compound 3b. Serum alanine aminotransferase (ALT) was measured 22 h after APAP injection (n=5 mice for each group). FIG. 11B depicts the effect of Compound 3b in the liver damage induced by APAP. ALF was induced in C57Bl/6 male mice with a single dose of acetaminophen (300 mg/kg) by i.p. injection. Compound 3b (0.3, 3, 30, 60 mg/kg) or Compound 1b (60 mg/kg) were administered to mice 1 h after APAP. Twenty-two hours after APAP injection serum ALT was measured (indicated in FIG. 11A), centrilobular sections of mouse livers were cut and stained with hematoxylin and eosin, and the percentage of liver necrosis was determined. The data indicates a dose-dependent reduction of ALT levels of 9% to 83% relative to APAP control, and a dose-dependent reduction of necrosis of 0% to 56% relative to APAP control. The data also indicates that Compound 1b does not reduce necrosis relative to APAP control, even at the highest dose of 60 mg/kg. These data unequivocally show a strong therapeutic activity of Compound 3b in the treatment of the acetaminophen induced ALF and the lack of activity of Compound 1b at similar doses. This difference in therapeutic activity strongly correlates with the profiles of CO delivery to the liver by accumulation and CO release, both of which favor Compound 3b over Compound 1b as discussed in Example 3.

Therapeutic Benefit of Compound 3b at Higher Doses in ALF Model

Compound 3b was also studied to see if there was therapeutic benefit at higher doses. Three groups of 5 mice were treated with 2 doses of compound given at 1 h and 3 h after APAP challenge: (1) Compound 3b, 2×60 mg/kg; (2) Compound 3b, 2×120 mg/kg; and (3) NAC, 2×300 mg/kg, and the effect evaluated 22 h post APAP.

Figures 12A, 12B:
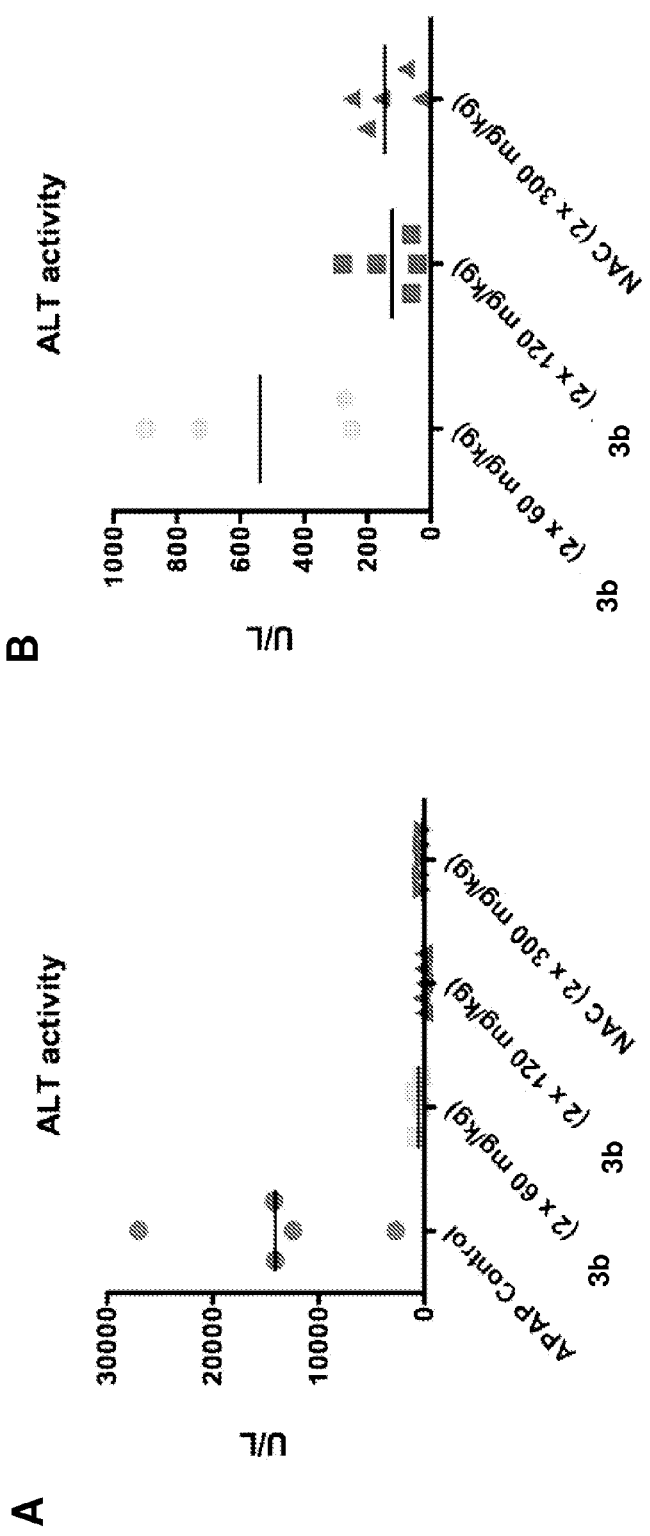
FIGS. 12A-12C.

FIGS. 12A-12B depict the effect of treatment with NAC or Compound 3b on serum ALT in an ALF model. ALF was induced in C57Bl/6 male mice with a single dose of acetaminophen (300 mg/kg) by i.p. injection. Animals were treated with NAC(N-acetyl-cysteine; 300 mg/kg) or Compound 3b (60 or 120 mg/kg) administered at one and three hours after APAP injection. Alanine aminotransferase (ALT) was measured 22 h after APAP injection (n=4 or n=5 mice for each group). FIG. 12B is a zoom of FIG. 12A to help visualize the differences in the treated groups.

Figure 12C:
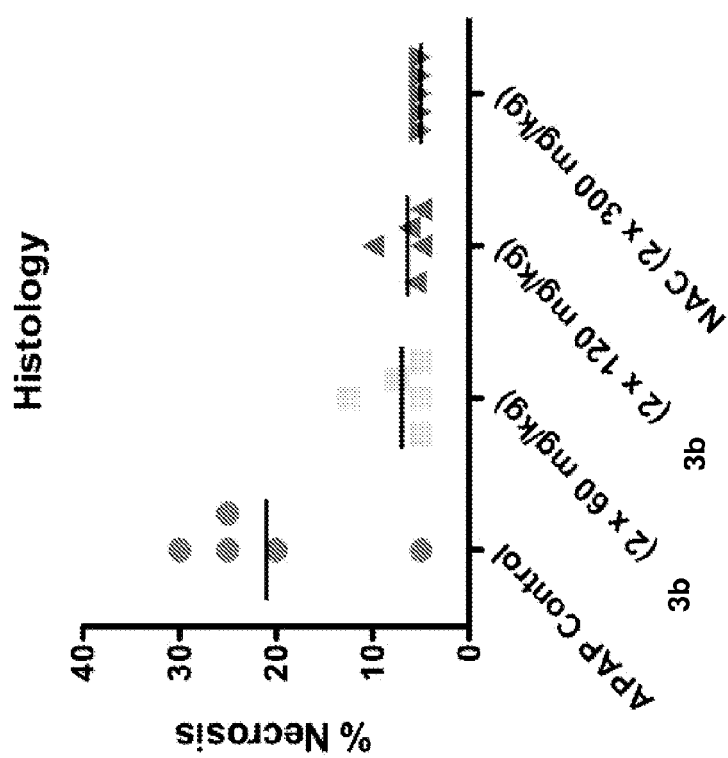

FIG. 12C confirms the results obtained with ALT serum markers (FIGS. 12A-12B), and depicts the effect of treatment with NAC or Compound 3b on liver damage in an APAP-induced ALF model. ALF was induced in C57Bl/6 male mice with a single dose of acetaminophen (300 mg/kg) by i.p. injection. Animals were treated with NAC (300 mg/kg) or Compound 3b (60 or 120 mg/kg) administered at one and three hours after APAP injection. Twenty-two hours after APAP injection, serum ALT was measured (indicated in FIGS. 12A-12B), centrilobular sections of mouse livers were cut and stained with hematoxylin and eosin, and the percentage of liver necrosis was determined.

The results indicate that at both doses used Compound 3b is highly therapeutic, and at 2×120 mg/kg, Compound 3b is as effective as NAC.

Figure 13:
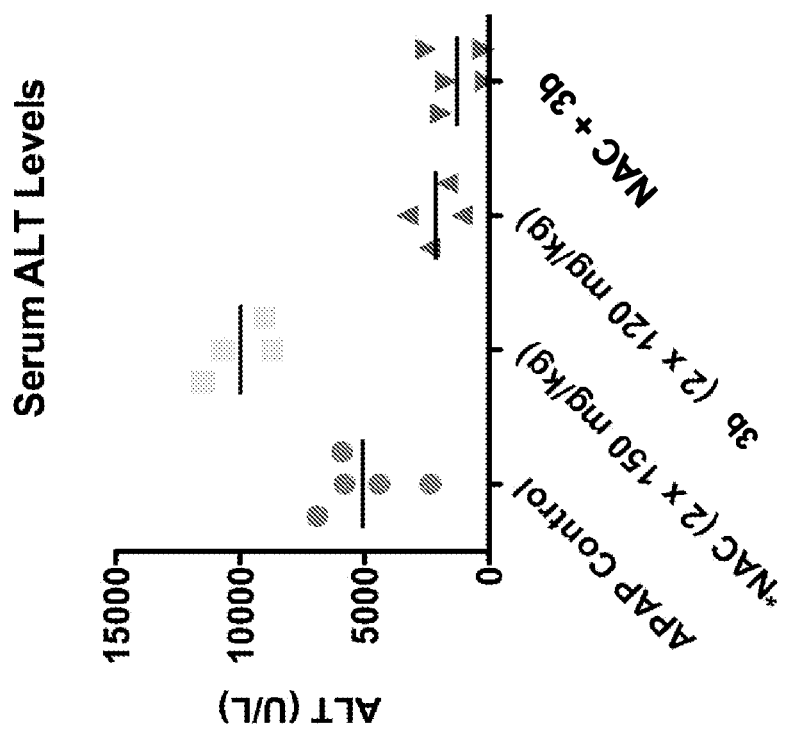
FIG. 13 depicts the effect of treatment with NAC or Compound 3b on serum ALT in an APAP-induced acute liver failure (ALF) model. ALF was induced in C57Bl/6 male mice with a single dose of acetaminophen (300 mg/kg) by i.p. injection. At five hours and seven hours after APAP injection, the animals were treated with NAC (150 mg/kg) or Compound 3b (120 mg/kg) or a combination of both compounds. Alanine aminotransferase (ALT) was measured 22 h after APAP injection (n=4 or n=5 mice for each group).

Dosing Compound 3b Late after APAP Injury in ALF Model is More Effective than Dosing NAC FIG. 13 depicts the effect of treatment with NAC or Compound 3b on serum ALT in an APAP-induced acute liver failure (ALF) model. ALF was induced in C57Bl/6 male mice with a single dose of acetaminophen (300 mg/kg) by i.p. injection. At five hours and seven hours after APAP injection, the animals were treated with NAC (150 mg/kg) or Compound 3b (120 mg/kg) or a combination of both compounds. Alanine aminotransferase (ALT) was measured 22 h after APAP injection (n=4 or n=5 mice for each group). *NAC administration to mice mimics human dose, which is 150 mg/kg (loading dose) over 60 min; 50 mg over 4 hours ($2^{nd}$ dose); 100 mg over 16 hours ($3^{rd}$ dose); for a total of 300 mg over 21 hours.

Figure 14:
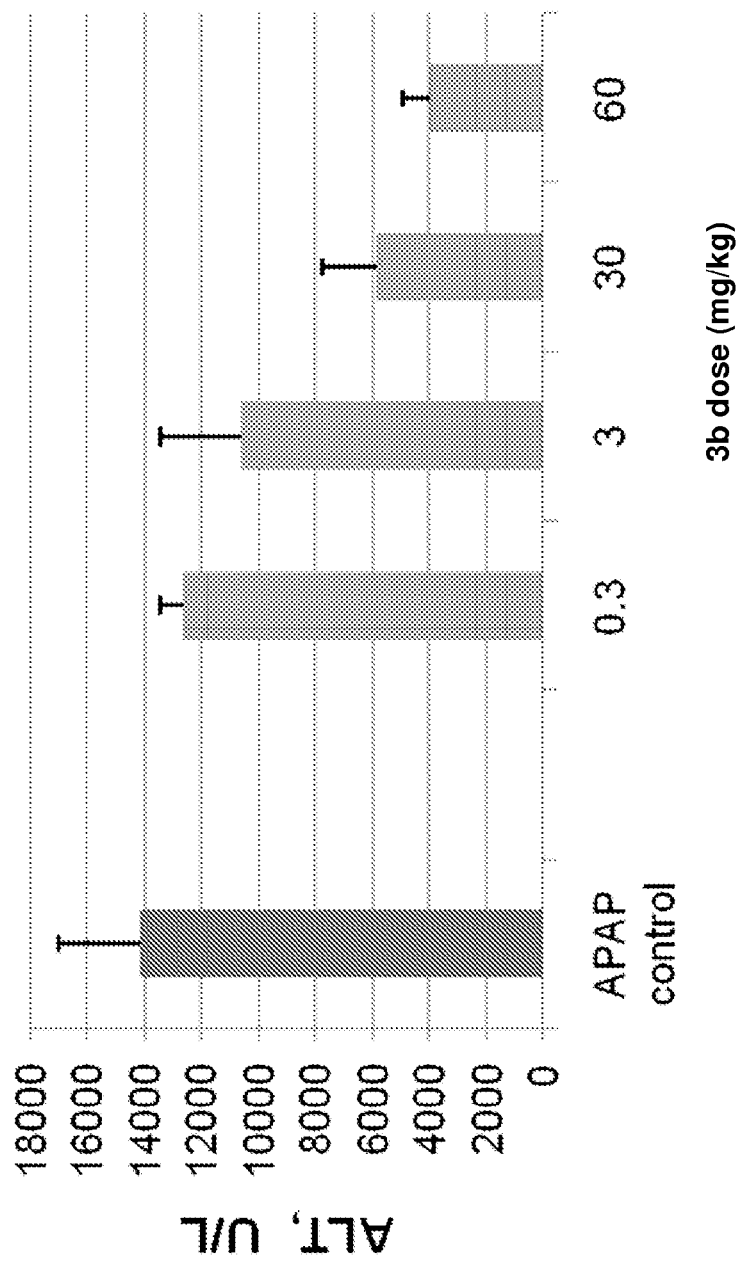
FIG. 14 depicts the effect of late treatment with Compound 3b on serum ALT in ALF model. ALF was induced in C57Bl/6 male mice with a single dose of acetaminophen (300 mg/kg) by i.p. injection. At sixteen hours after APAP injection, the animals were treated with different doses of Compound 3b (0.3, 3, 30 or 60 mg/kg). Alanine aminotransferase (ALT) was measured 22 h after APAP injection (n=4 or n=5 mice for each group).

FIG. 14 depicts the effect of late treatment with Compound 3b on serum ALT in ALF model. ALF was induced in C57Bl/6 male mice with a single dose of acetaminophen (300 mg/kg) by i.p. injection. At sixteen hours after APAP injection, the animals were treated with different doses of Compound 3b (0.3, 3, 30 or 60 mg/kg). Alanine aminotransferase (ALT) was measured 22 h after APAP injection (n=4 or n=5 mice for each group).

It was found that NAC given late after APAP injury is no longer effective and increases serum ALT levels (is toxic). Compound 3b is therapeutic when administered late after APAP injury when NAC has lost activity. Furthermore, NAC does not interfere with the activity of Compound 3b.

It was also found that treatment with a single dose of Compound 3b administered 16 hours after APAP injury produces a dose-dependent therapeutic effect. Serum ALT levels reach maximum at about 22 h post APAP administration, when the measurements were taken, and return to near normal at 48 h post APAP. Thus later treatments in this model are not indicative of drug activity.

Figures 15A, 15B:
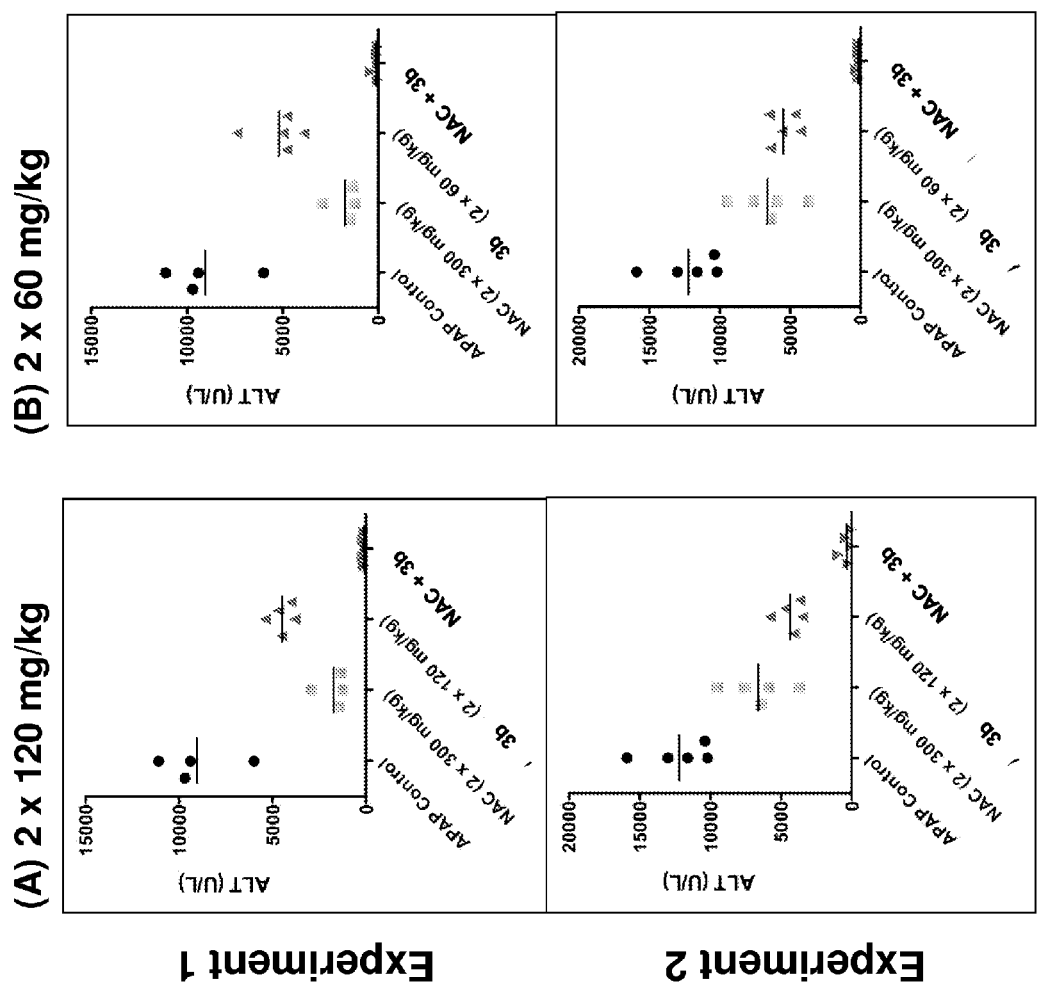
FIGS. 15A-15B depict the effect of combination treatment with NAC and Compound 3b on serum ALT in ALF model. ALF was induced in C57Bl/6 male mice with a single dose of acetaminophen (300 mg/kg) by i.p. injection. NAC (300 mg/kg) and Compound 3b (120 mg/kg, FIG. 15A or 60 mg/kg, FIG. 15B) were administered to mice, separately or in combination, one hour and three hours after APAP injection. Experiments 1 and 2 represent two independent experiments. Alanine aminotransferase (ALT) was measured 22 h after APAP injection (n=4 or n=5 mice for each group).

Dosing Compound 3b Plus NAC Early after APAP Injury Shows Additive Effect in ALF Model FIGS. 15A-15B depict the effect of combination treatment with NAC and Compound 3b on serum ALT in ALF model. ALF was induced in C57Bl/6 male mice with a single dose of acetaminophen (300 mg/kg) by i.p. injection. NAC (300 mg/kg) and Compound 3b (120 mg/kg, FIG. 15A or 60 mg/kg, FIG. 15B) were administered to mice, separately or in combination, one hour and three hours after APAP injection. Experiments 1 and 2 represent two independent experiments. Alanine aminotransferase (ALT) was measured 22 h after APAP injection (n=4 or n=5 mice for each group). The ALT levels and the respective percentage of ALT increase, relative to the increase observed in mice injected with APAP alone, are presented in Table 7.

Table 7 provides the measured ALT levels in mice serum 22 hours after APAP administration and the percentage of ALT increase relative to the increase observed in mice, which were injected with APAP alone.

TABLE 7

| Treatment at 1 h and 3 h post APAP | Measured ALT values (mean ± S.D.) | | % ALT increase relative to increase with APAP alone | |
|---|---|---|---|---|
| | Experiment 1 | Experiment 2 | Experiment 1 | Experiment 2 |
| APAP, 300 mg/kg at t = 0 (no treatment) | 9050 | 12220 | 100 (=9050 ALT U/L) | 100 (=12220 ALT U/L) |
| NAC (2 × 300 mg/kg) | 1745 ± 738 | 6620 ± 2142 | 19.3 ± 8.7 | 54.2 ± 17.5 |
| 3b (2 × 120 mg/kg) | 4480 ± 630 | 4360 ± 926 | 49.5 ± 7.0 | 35.7 ± 7.6 |
| NAC plus 3b (2 × 120 mg/kg) | 123 ± 59 | 352 ± 59 | 1.4 ± 0.6 | 2.9 ± 3.1 |
| 3b (2 × 60 mg/kg) | 5180 ± 1312 | 5500 ± 987 | 57.2 ± 14.5 | 45.0 ± 8.1 |
| NAC plus 3b (2 × 60 mg/kg) | 132 ± 156 | 189 ± 103 | 1.5 ± 1.7 | 1.5 ± 0.8 |

The data provides the experimental serum ALT values for each animal.
Results: 2 × 60 mg/kg Compound 3b is nearly as effective as 2 × 120 mg/kg Compound 3b. The therapeutic effects of NAC and Compound 3b are additive. In combination, the low and higher doses of Compound 3b are equally effective.

Liver Histology Analysis in ALF Model

Figure 16:
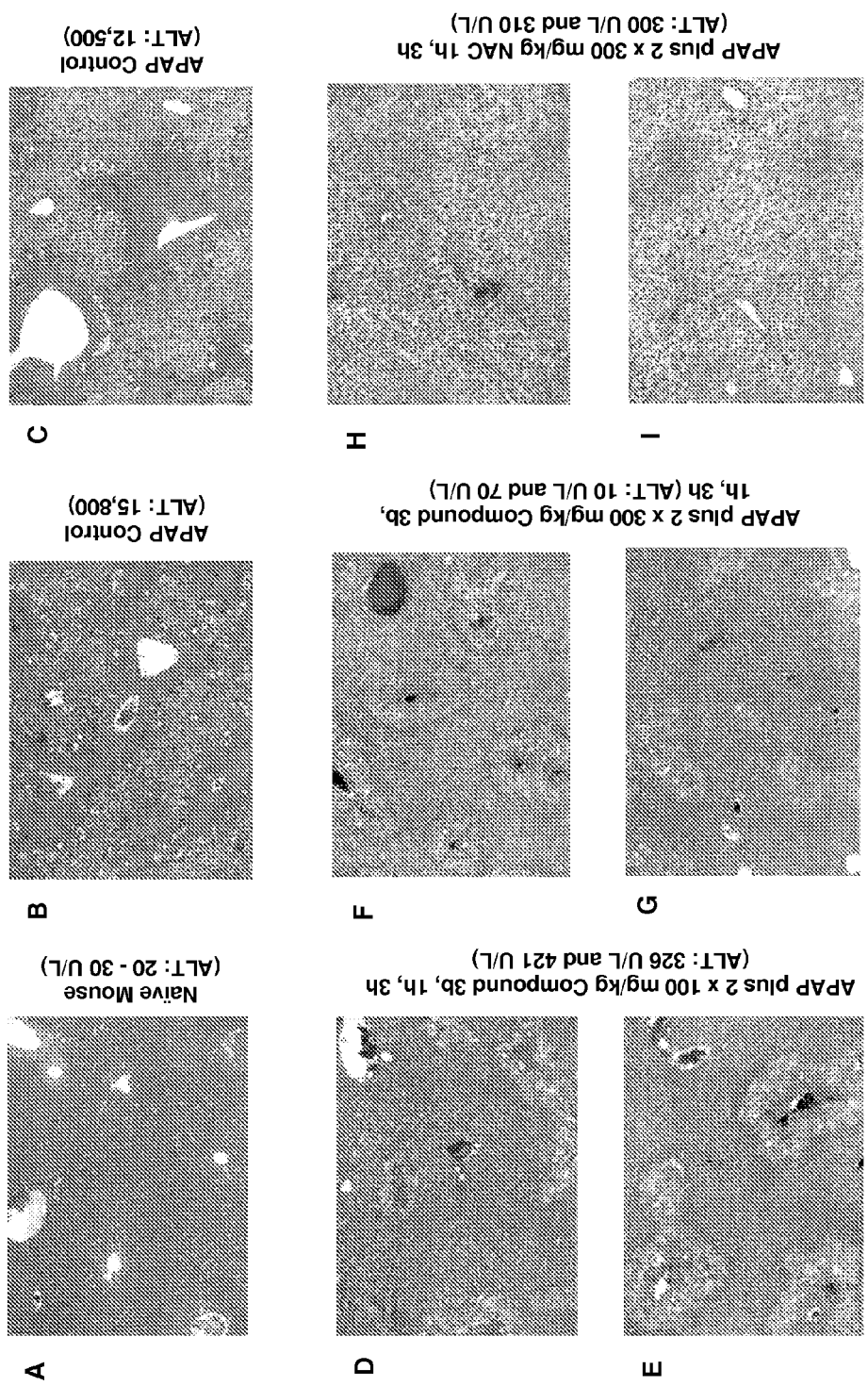
FIG. 16 depicts the effect of NAC and Compound 3b in the liver damage induced by Acetaminophen. ALF was induced in C57Bl/6 male mice with a single dose of acetaminophen (300 mg/kg) by i.p. injection. NAC and Compound 3b were administered at one and three hours after APAP administration. Twenty-two hours after APAP injection, serum ALT was measured and centrilobular sections of mouse livers were cut and stained with hematoxylin and eosin. A: Naïve mouse; B and C: APAP control mouse; D and E: APAP plus Compound 3b 2×100 mg/kg (duplicate experiments); F and G: APAP plus Compound 3b 2×300 mg/kg (duplicate experiments); H and I: APAP plus NAC 2×300 mg/kg (duplicate experiments).

FIG. 16 depicts the effect of NAC and Compound 3b in the liver damage induced by Acetaminophen. ALF was induced in C57Bl/6 male mice with a single dose of acetaminophen (300 mg/kg) by i.p. injection. NAC and Compound 3b were administered at one and three hours after APAP administration. Twenty-two hours after APAP injection, serum ALT was measured and centrilobular sections of mouse livers were cut and stained with hematoxylin and eosin. A: Naïve mouse; B and C: APAP control mouse (duplicate experiment); D and E: APAP plus Compound 3b 2×100 mg/kg (duplicate experiment); F and G: APAP plus Compound 3b 2×300 mg/kg (duplicate experiment); H and I: APAP plus NAC 2×300 mg/kg (duplicate experiment).

Results: a dose of 300 mg/kg acetaminophen causes strong necrosis in the mouse liver. Necrosis is centrilobular and perivascular as described in the literature. Livers from Compound 3b or NAC treated animals have very little if any necrosis. Livers from Compound 3b and NAC treated animals looked different, which suggested to the pathologist different drug mechanisms in this model. Therefore one might expect additivity for the therapeutic effects when NAC and Compound 3b are given in combination.

Hypothesis: NAC given early (<3-5 h) in this model, prevents liver injury by reacting with the toxic acetaminophen metabolite, NAPQI. Compound 3b given early or late (<16 h) accelerates healing by limiting inflammation and promoting regeneration. This hypothesis of the mechanism of action of Compound 3b is supported by the observation that perivascular areas had large numbers of mitotic figures.

Dosing Compound 4b in the ALF Model

Figure 24:
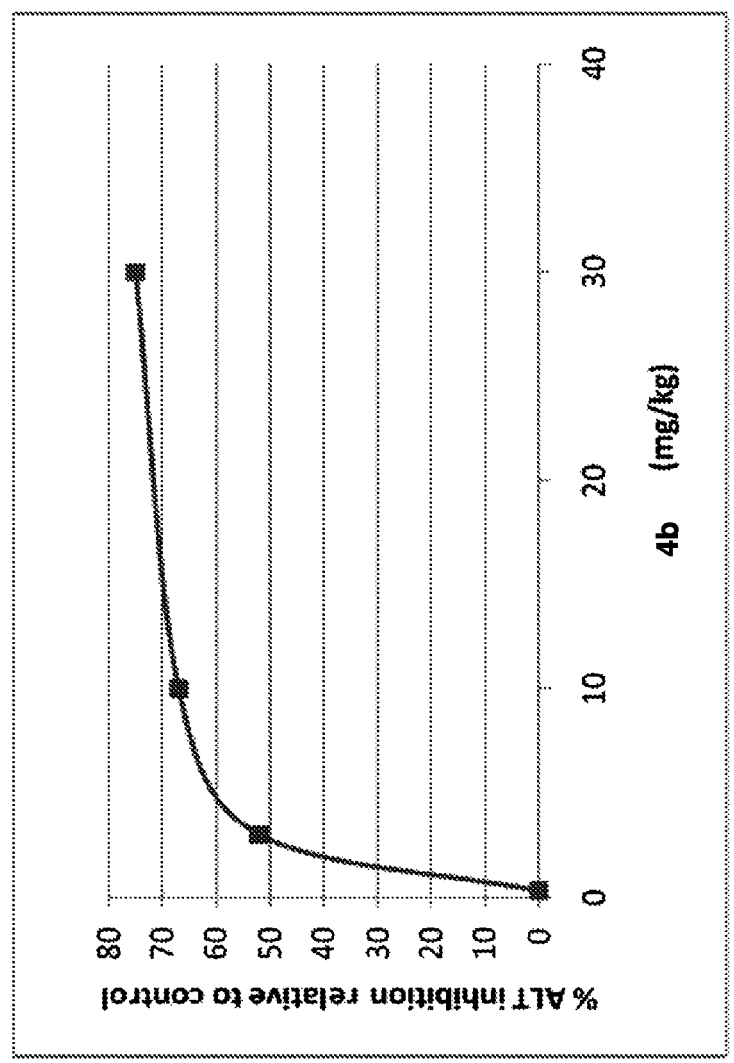
FIG. 24 depicts the effect of Compound 4b in the ALF model in mice, administered (i.p.) at a dose of 0.3, 3, 10 or 30 mg/kg given 3 hours and 5 hours (+3 h, +5 h) after APAP (300 mg/kg) administration. Serum ALT levels were evaluated 22 hours after APAP administration. Compound 4b was able to reduce ALT levels induced by APAP in a dose-dependent manner; at a dose of 30 mg/kg the ALT levels were 75% reduced relative to untreated control animals.

FIG. 24 depicts the effect of Compound 4b in the ALF model in mice, administered (i.p.) at a dose of 0.3, 3, 10 or 30 mg/kg given 3 hours and 5 hours (+3 h, +5 h) after APAP (300 mg/kg) administration. Serum ALT levels were evaluated 22 hours after APAP administration. Compound 4b was able to reduce ALT levels induced by APAP in a dose-dependent manner, at a dose of 30 mg/kg the ALT levels were 75% reduced relative to untreated control animals.

Dosing Compound 5b in the ALF Model

Figure 25:
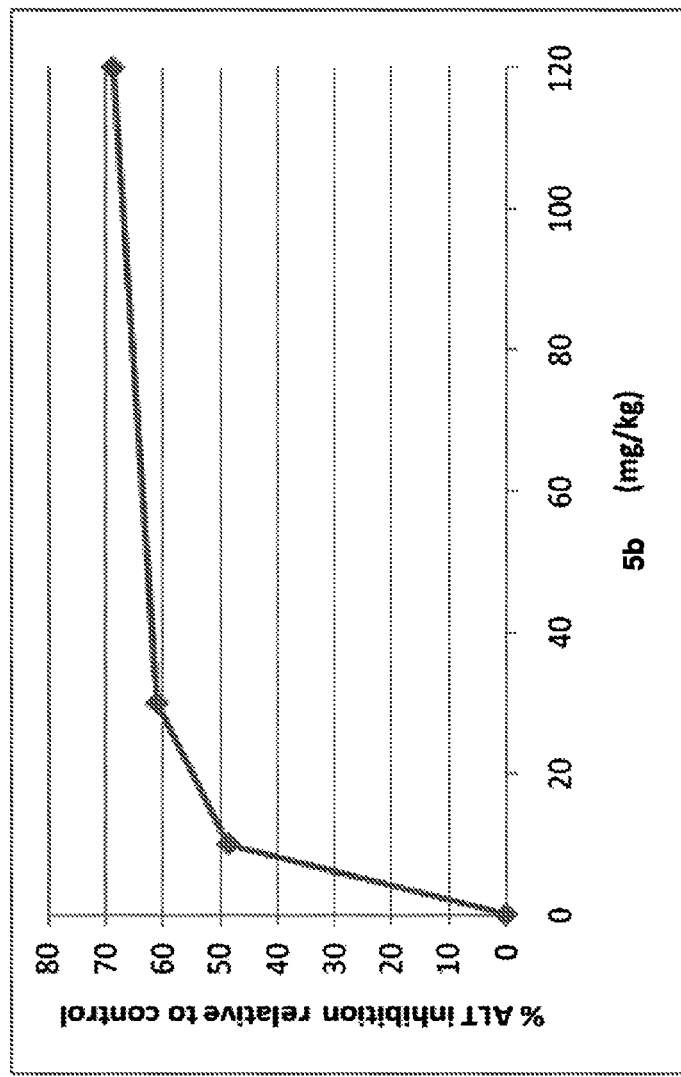
FIG. 25 depicts the effect of Compound 5b in the ALF model in mice, administered (i.p.) at a dose of 10, 30 or 120 mg/kg given 3 hours and 5 hours (+3 h, +5 h) after APAP (300 mg/kg) administration. Serum ALT levels were evaluated 22 hours after APAP administration. Compound 5b was able to reduce ALT levels induced by APAP in a dose-dependent manner; at a dose of 120 mg/kg the ALT levels were 70% reduced relative to untreated control animals.

FIG. 25 depicts the effect of Compound 5b in the ALF model in mice, administered (i.p.) at a dose of 10, 30 or 120 mg/kg given 3 hours and 5 hours (+3 h, +5 h) after APAP (300 mg/kg) administration. Serum ALT levels were evaluated 22 hours after APAP administration. Compound 5b was able to reduce ALT levels induced by APAP in a dose-dependent manner, at a dose of 120 mg/kg the ALT levels were 70% reduced relative to untreated control animals.

Lethal APAP Liver Failure Model

Compound 3b was tested in a lethal APAP liver failure model (see, e.g. Imaeda et al. *J Clin Invest* (2009) 119:305-14).

Male C57BL/6 mice fasted overnight to increase CyP450 activity. APAP dosed i.p. at 500 mg/kg. Survival monitored over 3 to 5 days. Survival in APAP-treated control animals is 40-60% at the end of the experiment.

Figure 17:
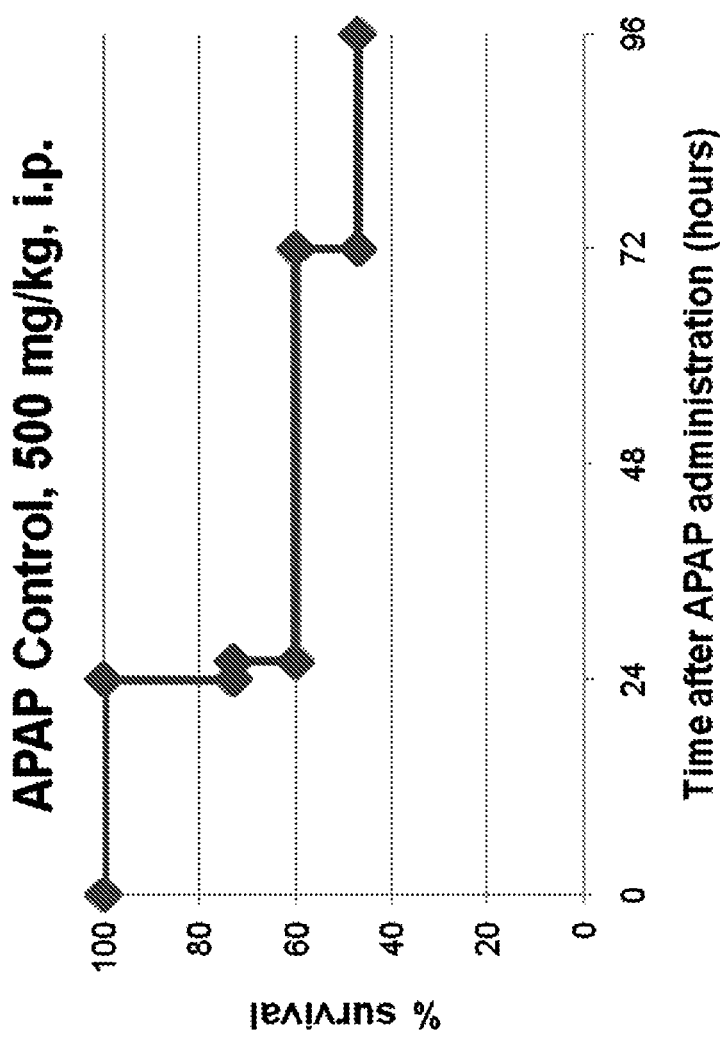
FIG. 17 depicts the survival curve of C57BL/6 mice injected (i.p.) with 500 mg/kg of APAP. Mice were fasted overnight and APAP was administered afterward (n=15). Mice survival was monitored for 4 days.

FIG. 17 depicts the survival curve of C57BL/6 mice injected (i.p.) with 500 mg/kg of APAP. Mice were fasted overnight and APAP was administered afterward (n=15). Mice survival was monitored for 4 days.

Figures 18A, 18B:
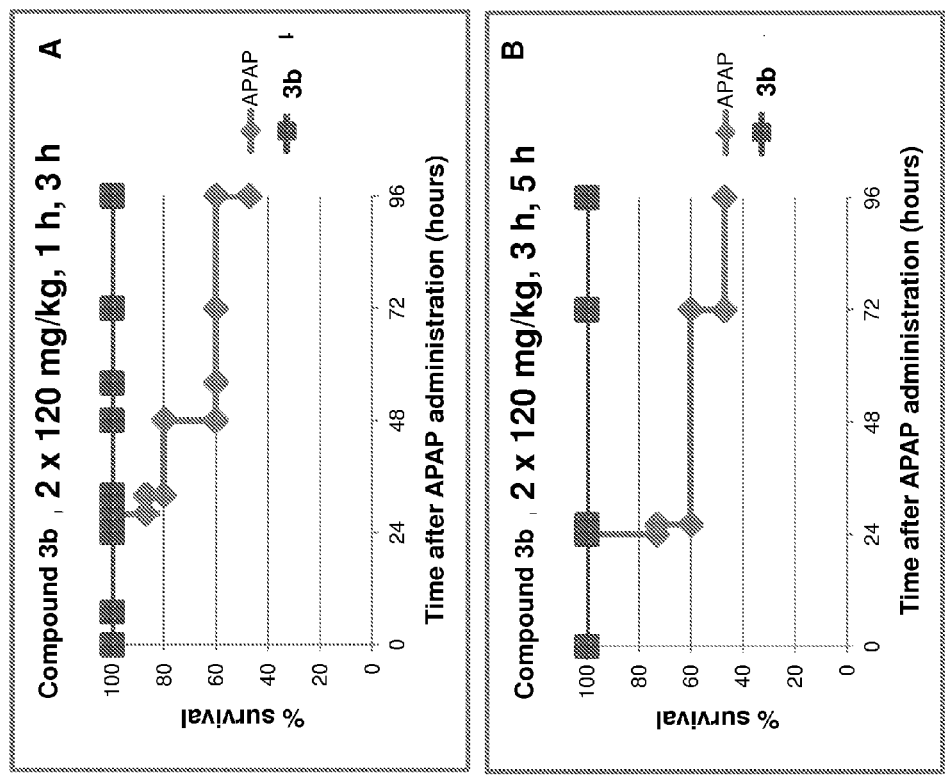
FIGS. 18A-18B depicts the survival curve of C57BL/6 mice injected (i.p.) with 500 mg/kg of APAP and treated with Compound 3b. Mice were fasted overnight and APAP was administered afterward (n=15). Compound 3b was administered at a dose of 120 mg/kg at 1 h and 3 h (A) or at 3 h and 5 h (B) after APAP administration. Mice survival was monitored for 4 days.

FIGS. 18A-18B depicts the survival curve of C57BL/6 mice injected (i.p.) with 500 mg/kg of APAP and treated with Compound 3b. Mice were fasted overnight and APAP was administered afterward (n=15). Compound 3b was administered at a dose of 120 mg/kg at 1 h and 3 h (A) or at 3 h and 5 h (B) after APAP administration. Mice survival was monitored for 4 days.

Figure 19:
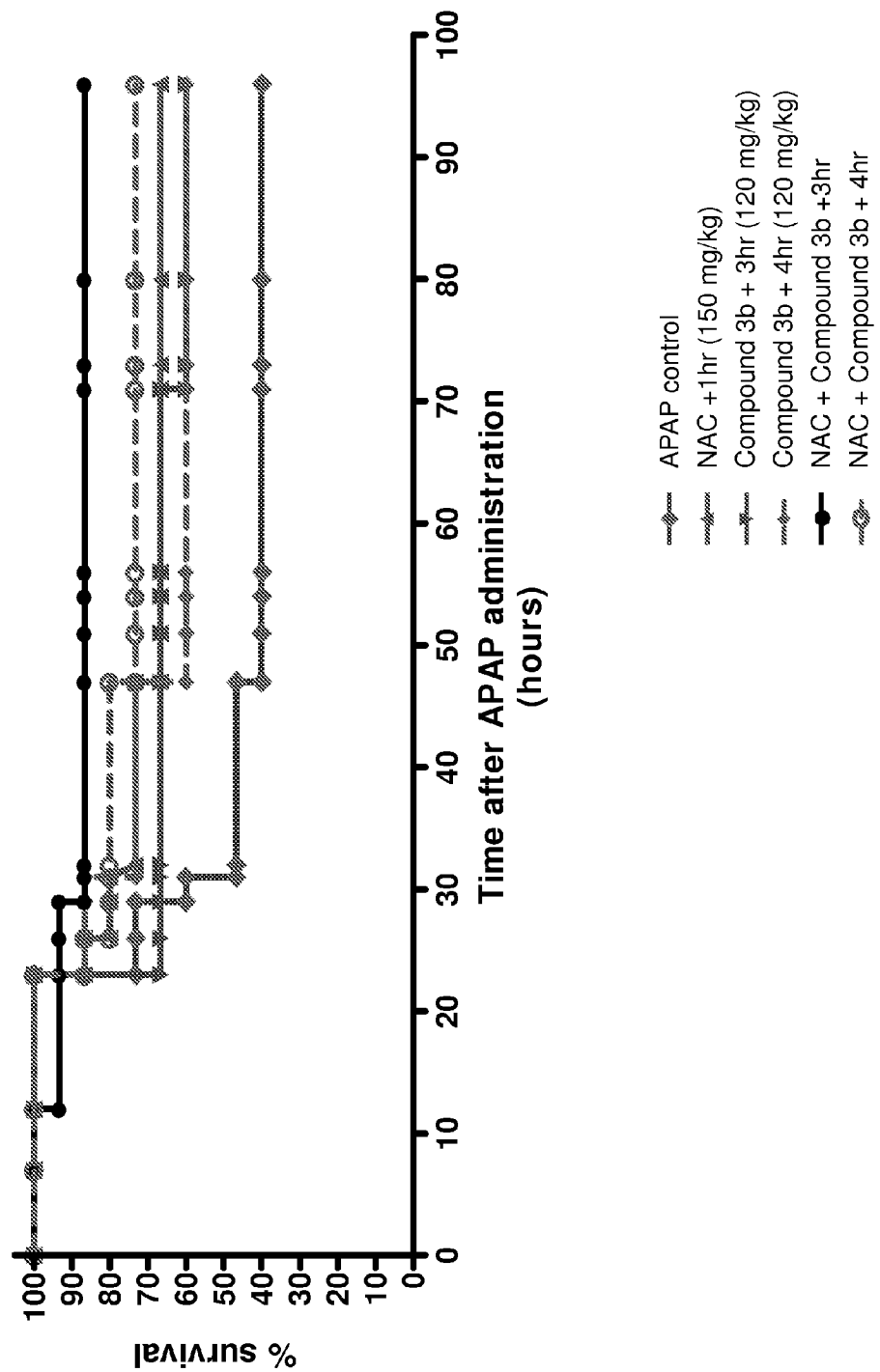
FIG. 19 depicts the survival curve of C57BL/6 mice injected (i.p.) with 500 mg/kg of APAP and treated with Compound 3b, NAC or both administered at different times. Mice were fasted overnight and APAP was administered afterward (n=15). Compound 3b was administered at a dose of 120 mg/kg (ip) at +3 h or +4 h after APAP administration. Another group of mice received NAC (150 mg/kg, ip) at +1 h after APAP. The remaining two groups are administered in NAC+ Compound 3b combination mode; one group of mice was administered with NAC (150 mg/kg, ip) at +1 h plus Compound 3b (120 mg/kg, ip)+3 h and other with Compound 3b (150 mg/kg, ip) at +1 h plus Compound 3b (120 mg/kg, ip)+4 h. Mice survival was monitored for 4 days.

FIG. 19 depicts the survival curve of C57BL/6 mice injected (i.p.) with 500 mg/kg of APAP and treated with Compound 3b and NAC separately and the respective combinations using different administration times. Mice were fasted overnight and APAP was administered afterward (n=15). Compound 3b was administered at a dose of 120 mg/kg (ip) at +3 h or +4 h after APAP administration. Another group of mice received NAC (150 mg/kg, ip) at +1 h after APAP. The remaining two groups are administered in NAC+Compound 3b combination mode; one group of mice was administered with NAC (150 mg/kg, ip) at +1 h plus Compound 3b (120 mg/kg, ip)+3 h and other with Compound 3b (150 mg/kg, ip) at +1 h plus Compound 3b (120 mg/kg, ip)+4 h. Mice survival was monitored for 4 days.

Results: Compound 3B dosed at 2×120 mg/kg, 1 h and 3 h or 3 h and 5 h after APAP administration, causes 100% survival, whereas 53% (8 of 15) of animals die in the APAP control groups. NAC dosed at 2×300 mg/kg using the same schedules effected also 100% survival in both experiments (data not shown). The survival profile of mice treated with APAP and NAC+Compound 3b combinations as described above, is increased compared to individual treatments with NAC or Compound 3b, indicating a possible additive therapeutic effect of these molecules in the ALF model.

Ischemia-Reperfusion Model

Liver ischemia-reperfusion model in C57BL/6 mice. In anesthetized C57BL/6 mice, the hepatic artery and portal vein were clamped for 30 min; 24 h later, serum ALT levels were determined. Compound 3b was dosed i.p. at 30 mg/kg each 1 h before and 1 h after surgery.

Figure 20:
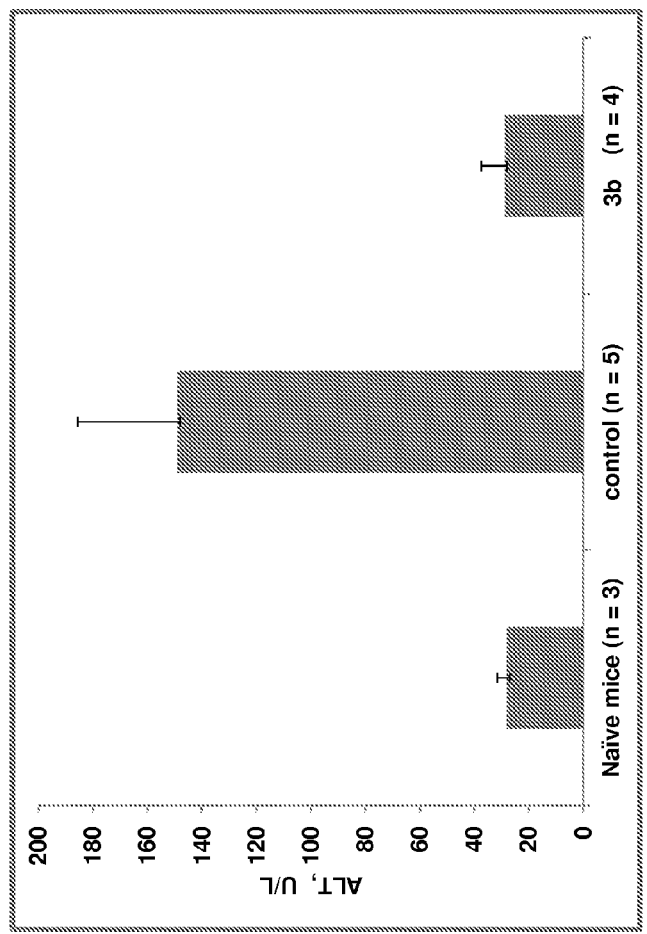
FIG. 20 depicts the effect of Compound 3b in the Ischemia-Reperfusion model. In anesthetized C57BL/6 mice, the hepatic artery and portal vein were clamped for 30 min; 24 h later, serum ALT levels were determined. Compound 3b was administered by i.p. injection at 30 mg/kg, 1 hour before and 1 h after surgery.

FIG. 20 depicts the effect of Compound 3b in the Ischemia-Reperfusion model. In anesthetized C57BL/6 mice, the hepatic artery and portal vein were clamped for 30 min; 24 h later, serum ALT levels were determined. Compound 3b was administered by i.p. injection at 30 mg/kg, 1 hour before and 1 h after surgery.

Results: Compound 3b-treated animals had baseline levels (29 U/L) of serum ALT, whereas untreated control animals had 5-fold (149 U/L) elevated ALT levels. Compound 3b demonstrates prevention of ischemia/reperfusion damage in livers of mice. Compound 3b demonstrates anti-inflammatory activity in the liver.

Ex-Vivo Model of Apoptosis

Figure 21A:
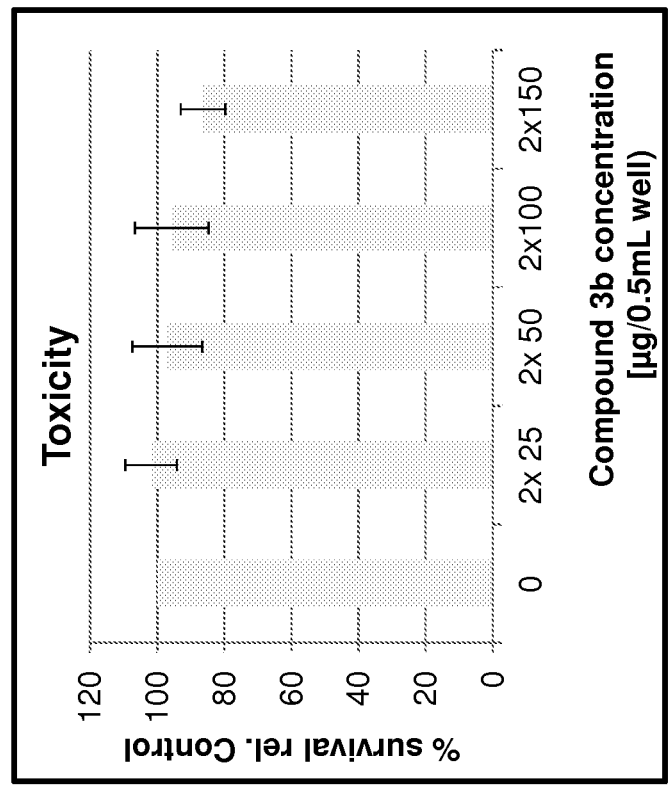
FIGS. 21A-21B depict the effect of Compound 3b in an ex-vivo model of apoptosis. Apoptosis of primary hepatocytes from C57BL/6 mice was induced with Actinomycin D (ActD; 200 ng/mL) and Tumour Necrosis Factor-α (TNF-α; 10 ng/mL). Compound 3b was added to the cultures 1 hour before and 1 hour after the addition of the apoptosis inducers ActD/TNF-α. Compound 3b was tested at concentrations of 25, 50, 100 and 150 µg/0.5 mL well. Hepatocytes survival was determined 24 hours after the addition of the apoptosis inducers.
Figure 21B:
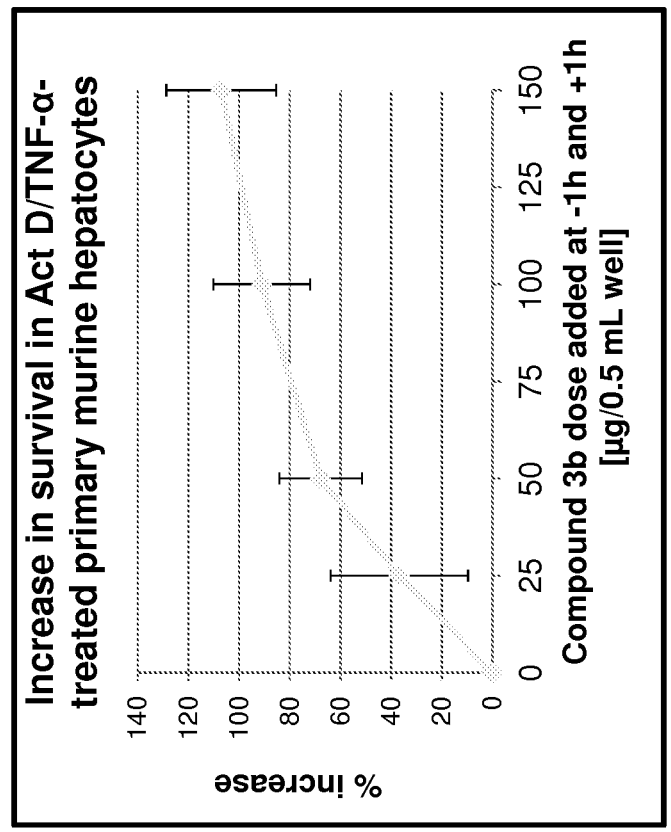

FIGS. 21A-21B depict the effect of Compound 3b in an ex-vivo model of apoptosis. Apoptosis of primary hepatocytes from C57BL/6 mice was induced with Actinomycin D (ActD; 200 ng/mL) and Tumour Necrosis Factor-α (TNF-α; 10 ng/mL). Compound 3b was added to the cultures 1 hour before and 1 hour after the addition of the apoptosis inducers ActD/TNF-α. Compound 3b was tested at concentrations of 25, 50, 100 and 150 µg/0.5 mL well. Hepatocytes survival was determined 24 hours after the addition of the apoptosis inducers. FIG. 21A: Percentage of increase in survival ActD/TNF-α treated cells in the presence of Compound 3b, relative to cells treated with only the apoptosis inducers. FIG. 21B: Toxicity of the Compound 3b doses on murine hepatocytes (not treated with apoptosis inducers). Data are the mean±S.D. of 3-5 independent experiments (3-5 livers from different mice).

Results: Compound 3b has strong anti-apoptotic activity in the liver. ActD/TNF-α treatment alone reduces survival to 24.8±5.5% (n=23; data not shown). Compound 3b also prevents hepatocyte death induced by ActD/TNF-α. It was found that survival of hepatocytes increased in a dose dependent manner, and that this increase is more than 125% at 2×150 µg/0.5 mL well (2×600 µM) treatment with Compound 3b.

Liver Regeneration Model

Liver regeneration in the murine partial hepatectomy model to test for regenerative activity. Model: partial (70%) liver resection in mice and follow rate of regeneration.

Figure 22:
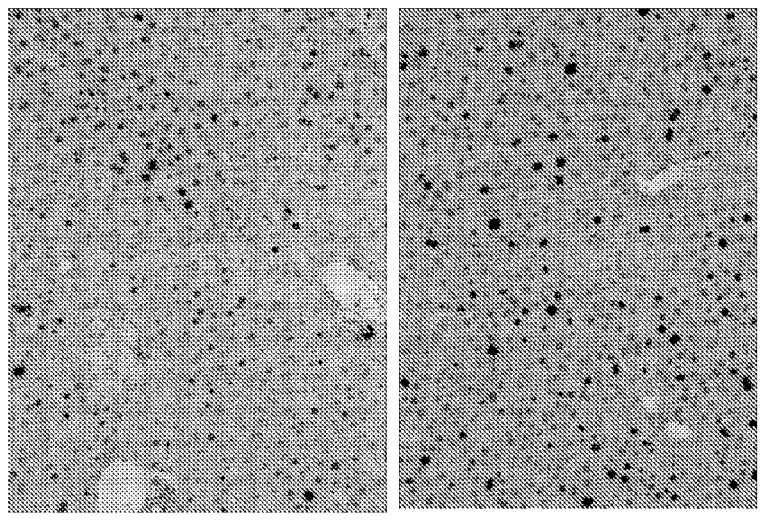
FIG. 22 depicts the effect of Compound 3b in a model of liver regeneration. Animals were anesthetized and 70% of the liver was resected, corresponding to the left and median liver lobes. Compound 3b was administered (2×100 mg/kg) 1 h before and 1 h after surgery. Two days later, animals were sacrificed, livers harvested, weighed, and stained for phosphohistone H3 (PH3, a specific marker for cell division).

FIG. 22 depicts the effect of Compound 3b in a model of liver regeneration. Animals were anesthetized and 70% of the liver was resected, corresponding to the left and median liver lobes. Compound 3b was administered (2×100 mg/kg) 1 h before and 1 h after surgery. Two days later, animals were sacrificed, livers harvested, weighed, and stained for phospho histone H3 (PH3, a specific marker for cell division). The data demonstrates increased mitotic activity of the treated group relative to control.

Results: Liver weight data 48 h after resection hints at faster regeneration with Compound 3b (89% increase in control vs. 102% in Compound 3b-treated animals). Compound 3b increases PH3 staining which indicates that there is an increased frequency of cell division. NAC has no effect and may be detrimental (see, e.g., Yang et al., *Crit. Care* (2009) 13: R55).

TNBS-Induced Colitis Model

Figures 23A, 23B, 23C:
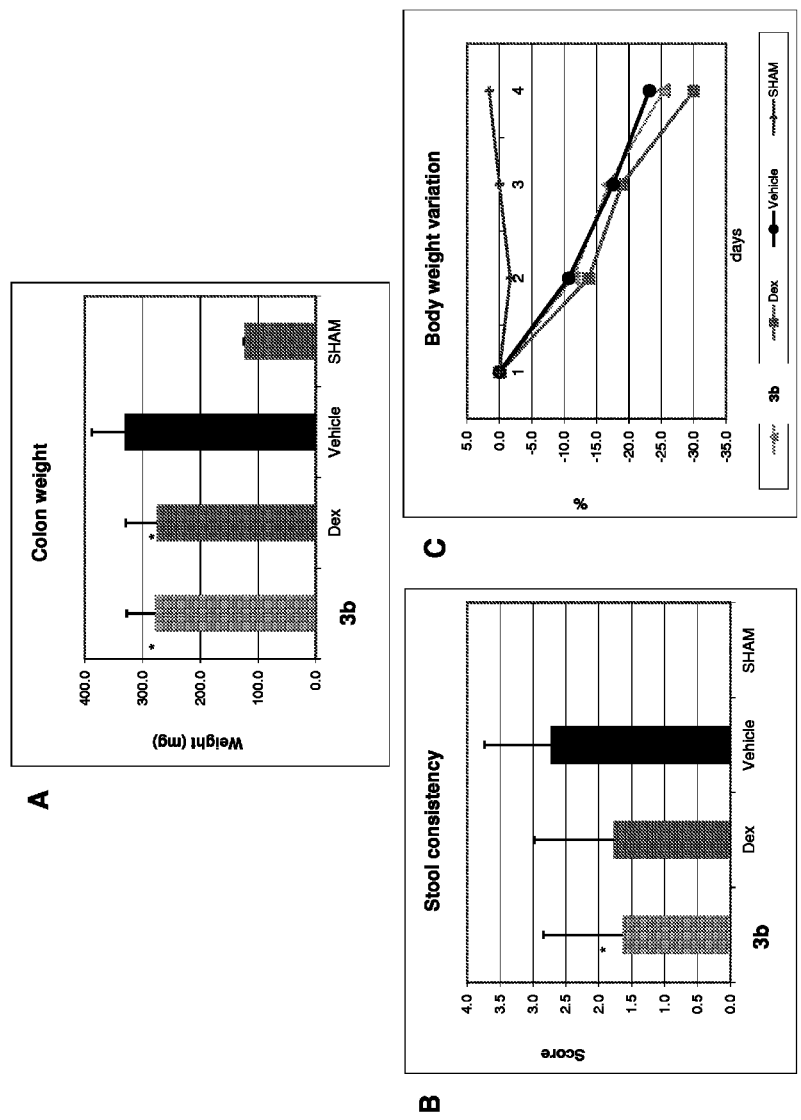
FIGS. 23A-23C depict the effect of Compound 3b in a model of TNBS (2,4,6-trinitrobenzenesulfonic acid) induced colitis. Colitis was induced in Balb/C mice by a single intra-colonic administration of 100 ml of 40% ethanol containing 4 mg of TNBS. Dexamethasone (Dex; 0.3 mg/kg), Compound 3b (120 mg/kg) or its vehicle were administered daily for 3 consecutive days starting from 1 hour before colitis induction (day 1). On day 4 after colitis induction, mice were sacrificed, colon was isolated, cleaned and a 7 cm segment of the distal colon was resected and weighed (FIG. 23A). Stool consistency was determined using the score: 0, well-formed pellets; 1, loose stool; 2, liquid stool or bloody stool (FIG. 23B). Animals were weighed throughout the entire study (FIG. 23C).

FIGS. 23A-23C depict the effect of Compound 3b in a model of TNBS induced colitis. Colitis was induced in Balb/C mice by a single intracolonic administration of 100 ml of 40% ethanol containing 4 mg of TNBS (2,4,6-trinitrobenzenesulfonic acid). Dexamethasone (Dex; 0.3 mg/kg), Compound 3b (120 mg/kg) or its vehicle were administered daily for 3 consecutive days starting from 1 hour before colitis induction (day 1). On day 4 after colitis induction, mice were sacrificed, colon was isolated, cleaned and a 7 cm segment of the distal colon was resected and weighed (FIG. 23A). Stool consistency was determined using the score: 0, well-formed pellets; 1, loose stool; 2, liquid stool or bloody stool (FIG. 23B). Animals were weighed through out the entire study (FIG. 23C).

Other Embodiments

All patents, patent applications, and literature references cited herein are incorporated herein by reference.

The foregoing has been a description of certain non-limiting embodiments of the disclosure. Those of ordinary skill in the art will appreciate that various changes and modifications to this description may be made without departing from the spirit or scope of the present disclosure, as defined in the following claims.

What is claimed is:

1. A compound of Formula:

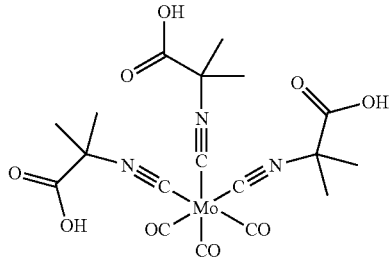

or a salt, ester, amide, solvate, or hydrate thereof, or a combination thereof.

2. A pharmaceutical composition comprising a compound of claim 1, or a salt, ester, amide, solvate, or hydrate thereof, or a combination thereof, and a pharmaceutically acceptable excipient.

3. A method of preparing a compound of claim 1, the method comprising reacting a molybdenum tri-CO complex with an isocyanide of the formula:

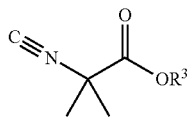

wherein
each instance of $R^3$ is independently $C_{1-6}$alkyl;
form an ester compound of the formula below:

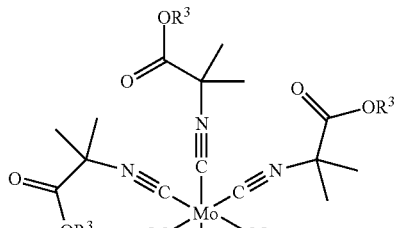

or a solvate or hydrate thereof, or a combination thereof; and hydrolyzing the ester compound to form a compound of the formula below:

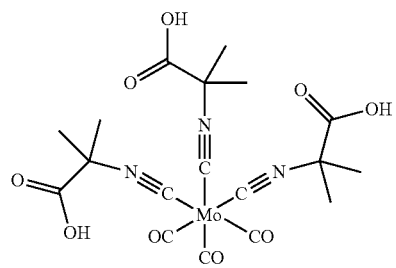

or a salt, solvate, or hydrate, or a combination thereof.

4. A compound of the Formula (II):

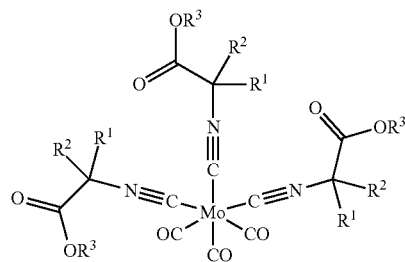

(II)

or a salt, solvate or hydrate thereof, or a combination thereof;
wherein:
each instance of $R^1$ and $R^2$ is —$CH_3$; and
each instance of $R^3$ is independently $C_{1-6}$ alkyl.

5. A compound of the Formula (III):

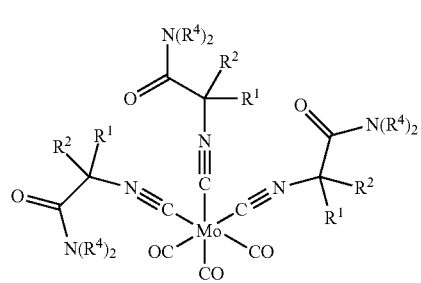

(III)

or a salt, solvate or hydrate thereof, or a combination thereof;
wherein:
each instance of $R^1$ and $R^2$ is —$CH_3$; and
each instance of $R^4$ is independently hydrogen or $C_{1-6}$alkyl.

* * * * *